US008506967B2

(12) United States Patent
Smith et al.

(10) Patent No.: US 8,506,967 B2
(45) **Date of Patent: *Aug. 13, 2013**

(54) FUNCTIONAL INFLUENZA VIRUS LIKE PARTICLES (VLPS)

(75) Inventors: Gale Smith, Rockville, MD (US); Rick Bright, Washington, DC (US); Peter M. Pushko, Rockville, MD (US); Jinyou Zhang, Plainsboro, NJ (US); Kutub Mahmood, Cupertino, CA (US)

(73) Assignee: Novavax, Inc., Rockville, MD (US)

(*) Notice: Subject to any disclaimer, the term of this patent is extended or adjusted under 35 U.S.C. 154(b) by 839 days.

This patent is subject to a terminal disclaimer.

(21) Appl. No.: 12/340,186

(22) Filed: Dec. 19, 2008
(Under 37 CFR 1.47)

(65) Prior Publication Data

US 2010/0129401 A1 May 27, 2010

Related U.S. Application Data

(63) Continuation-in-part of application No. 11/582,540, filed on Oct. 18, 2006, now Pat. No. 8,080,255, which is a continuation-in-part of application No. 10/617,569, filed on Jul. 11, 2003.

(60) Provisional application No. 61/015,440, filed on Dec. 20, 2007, provisional application No. 60/727,513, filed on Oct. 18, 2005, provisional application No. 60/780,847, filed on Mar. 10, 2006, provisional application No. 60/800,006, filed on May 15, 2006, provisional application No. 60/831,196, filed on Jul. 17, 2006, provisional application No. 60/832,116, filed on Jul. 21, 2006, provisional application No. 60/845,495, filed on Sep. 19, 2006.

(51) Int. Cl.
*A61K 39/145* (2006.01)

(52) U.S. Cl.
USPC .................. 424/210.1; 424/209.1; 424/206.1; 424/205.1

(58) Field of Classification Search
None
See application file for complete search history.

(56) References Cited

U.S. PATENT DOCUMENTS

| | | | |
|---|---|---|---|
| 4,552,758 | A | 11/1985 | Murphy et al. |
| 6,649,372 | B1 | 11/2003 | Palese et al. |
| 7,556,940 | B2 | 7/2009 | Galarza et al. |
| 7,763,450 | B2 | 7/2010 | Robinson et al. |
| 8,080,255 | B2 | 12/2011 | Smith et al. |
| 2003/0035814 | A1 | 2/2003 | Kawaoka et al. |
| 2005/0009008 | A1 | 1/2005 | Robinson et al. |
| 2006/0263804 | A1 | 11/2006 | Robinson et al. |
| 2007/0184526 | A1 | 8/2007 | Smith et al. |

FOREIGN PATENT DOCUMENTS

| | | | |
|---|---|---|---|
| EP | 0870508 | A1 | 10/1998 |
| EP | 1644037 | B1 | 12/2011 |
| WO | WO 96/10633 | A1 | 4/1996 |
| WO | WO 96/37624 | A1 | 11/1996 |
| WO | WO 02/00885 | A2 | 1/2002 |
| WO | WO 2005/020889 | A2 | 3/2005 |

OTHER PUBLICATIONS

Ali et. al., "Influenza Virus Assembly: Effect of Influenza Virus Glycoproteins on the Membrane Association of M1 Protein," J. Virol. 74:8709-8719 (2000).

Avalos et al., "Association of Influenza Virus NP and M1 Proteins with Cellular Cytoskeletal Elements in Influenza Virus-Infected Cells," J. Virol. 71:2947-2958 (1997).

Bender et al., "Characterization of the Surface Proteins of Influenza A (H5N1) Viruses Isolated from Humans in 1997-1998," Virology 254:115-123 (1999).

Berglund et al., "Immunization with Recombinant Semlike Forest Virus induces Protection Against Influenza Challenge in Mice," Vaccine 17:497-507 (1999).

Bright et al., "Cross-Clade Protective Immune Responses to Influenza Viruses with H5N1 HA and NA Elicited by art influenza Virus-Like Particle," PLOS One, Public Library of Science 3:1501 (2008).

Bucher et al., "M Protein (M1) of Influenza Virus: Antigenic Analysis and Intracellular Localization with Monoclonal Antibodies," J. Virol. 63:3622-3633 (1989).

Bullido et al., "Several Protein Regions Contribute to Determine the Nuclear and Cytoplasmic Localization of the Influenza A Virus Nucleoprotein," J. Gen. Virol. 81:135-142 (2000).

Castrucci et al., "Reverse Genetics System for Generation of an Influenza A Virus Mutant Containing a Deletion of the Carboxyl-Terminal Residue of M2 Protein," J. Virol. 69:2725-2728 (1995).

Chambers et al., "A single dose of killed Mycobacterium bovis BCG in a novel class of adjuvant (Novasome™) protects guinea pigs from lethal tuberculosis," Vaccine 22:1063-1071 (2004).

Chen et al., "Avian flu: H5N1 virus outbreak in migratory waterfowl," Nature 436:191-192 (2005).

Chen et al., "Comparison of the ability of viral protein-expressing plasmid DNAs to protect against influenza," Vaccine 16:1544-1549 (1998).

Chen et al., "Enhanced protection against a lethal influenza virus challenge by immunization with both hemagglutinin- and neuraminidase-expressing DNAs," Vaccine 17:653-659 (1999).

Chen et al., "The Evolution of H5N1 Influenza Viruses in Ducks in Southern China," Proc. Natl. Acad. Sci. USA 101:10452-10457 (2004).

Cox and Coulter. "Adjuvants—A Classification and Review of Their Modes of Action," Vaccine 15:248-256 (1997).

(Continued)

*Primary Examiner* — Mary E Mosher
*Assistant Examiner* — Myron Hill
(74) *Attorney, Agent, or Firm* — Cooley LLP

(57) ABSTRACT

The present invention discloses and claims virus like particles (VLPs) that express and/or contains seasonal influenza virus proteins, avian influenza virus proteins and/or influenza virus proteins from viruses with pandemic potential. The invention includes vector constructs comprising said proteins, cells comprising said constructs, formulations and vaccines comprising VLPs of the inventions. The invention also includes methods of making and administrating VLPs to vertebrates, including methods of inducing substantial immunity to either seasonal and avian influenza, or at least one symptom thereof.

19 Claims, 41 Drawing Sheets

(56) References Cited

OTHER PUBLICATIONS

Crawford et al., "Baculovirus-Derived Hemagglutinin Vaccines Protect Against Lethal Influenza Infections by Avian H5 and H7 Subtypes," Vaccine 17:2265-2274 (1999).
Crowther et al., "Three-Dimensional Structure of Hepatitis B. Virus Core Particles Determined by Electron Cryomicroscopy," Cell 77:943-950 (1994).
Das et al., "Structural basis for suppression of a host antoviral response by influenza A virus," Proc. Natl. Acad. Sci. USA 105:13093-13098 (2008).
Database UniProt [Online] Oct. 1, 2004, Hongbo Z et al.: "Matrix protein 1" XP002526328 retrieved from http://www.uniprot.org/uniprot/Q6B3P4 Database accession No. Q6B3P4.
Database UniProt [Online] Jul. 11, 2006, Hoffmann E et al.: "Hemagglutinin" XP002526332 retrieved from http://www.uniprot.org/uniprot/Q195D4 Database accession No. Q195D4.
Database UniProt [Online] Sep. 13, 2005, Chen H et al.: "Neuramidase" XP002526329 retrieved from http://www.uniprot.org/uniprot/Q4FB59 Database accession No. Q4FB59.
Database UniProt [Online] Aug. 16, 2004, Li KS et al.: "Hemagglutinin" XP002526330 retrieved from http://www.uniprot.org/uniprot/Q6DQ47 Database accession No. Q6DQ47.
Database UniProt Oct. 25, 2004, Li KS et al.: "Neuramidase" XP002526331 retrieved from http://www.uniprot.org/uniprot/Q6DPH6 Database accession No. Q6DPH6.
Elster et al., "Influenza Virus MI Protein Binds to RNA Through Its Nuclear Localization Signal", J. Gen. Virol. 78:1589-1956 (1997).
Enami and Enami, "Influenza Virus Hemagglutinin and Neuraminidase Glycoproteins Stimulate the Membrane Association of the Matrix Protein," J. Virol. 70:6653-6657 (1996).
Fodor et al., "Rescue of Influenza A Virus from Recombinant DNA," J. Virol. 73:9679-9682 (1999).
Galarza et al., "Virus-Like Particle (VLP) Conferred Complete Protection Against a Lethal Influenza Virus Challenge," Viral Immunol. 18:244-251 (2005).
Galarza et al., "Virus-Like Particle Vaccine Conferred Complete Protection Against a Lethal Influenza Virus Challenge," Viral Immunol. 18:365-372 (2005).
Germann et al., "Mitigation Strategies for Pandemic Influenza in the United States," Proc. Natl. Acad. Sci. USA 103:5935-5940 (2006).
Gómez-Puertas et al., "Efficient Formation of Influenza Virus-Like Particles: Dependence on the Expression Levels of Viral Prottins," J. Gen. Virol. 80:1635-1645 (1999).
Gómez-Puertas et al., "Influenza Virus Matrix Protein is the Major Driving Force in Virus Budding," J. Virol. 74:11538-11547 (2000).
Gupta et al., "Adjuvant properties of non-phospholipid liposomes (Novasomes) in experimental animals for human vaccine antigens," Vaccine 14(3):219-225 (1996).
Heiduschat, "Supplementary European Search Report," 12 pages, from EP Appl. No. 06826264.1, European Patent Office, Munich, Germany (mailed May 28, 2009).
Hoffmann et al., "A DNA Transfection System for Generation of Influenza A Virus from Eight Plasmids," Proc. Natl. Acad. Sci. USA 97:6108-6113 (2000).
Huylebroeck et al., "High-level transient expression of influenza virus proteins from a series of SV40 late and early replacement vectors," Gene 66:163-181 (1988).
Johansson, "Immunization with Influenza A Virus Hemagglutinin and Neuraminidase Produced in Recobinant Baculovirus Results in a Balanced and Broadened Immune Response Superior to Conventional Vaccine," Vaccine 17:2073-2080 (1999).
Kretzschmar et al., "Membrane Association of Influenza Virus Matrix Protein Does Not Require Specific Hydrophobic Domains or the Viral Glycoproteins," Virol. 220:37-45 (1996).
Kuroda et al., "Expression of the Influenza virus Haemagglutinin in Insect Cells by a Baculovirus Vector," The EMBO J. 5:1359-1365 (1986).
Lakey et al., "Recombinant Baculovirus Influenza A Hemagglutinin Vaccines are Well Tolerated and Immunogenic in Healthy Adults, Concise Communications" J. Infect. Dis. 174:838-841 (1996).
Latham and Galarza, "Formation of Wild-Type and Chimeric Influenza Virus-Like Particles Following Simultaneous Expression of Only Four Structural Proteins," J. Virol. 75:6154-6165 (2001).
Li et al., "Chimeric Influenza Virus Induces Neutralizing Antibodies and Cytotoxic T Cells Against Human Immunodeficiency Virus Type 1," J. Virol. 67:6659-6666 (1993).
Li et al., "Genesis of a highly pathogenic and potentially pandemic H5N1 influenza virus in eastern Asia," Nature 430:209-213 (2004).
Li et al., "Recombinant Influenza A Virus Vaccines for the Pathogenic Human A/Hong Kong/97 (H5N1 Viruses)," J. Infect. Dis. 179:1132-1138 (1999).
Logrippo, "Investigations of the use of beta-propiolactone in virus inactivation," Ann. N.Y. Acad. Sci. 83:578-594 (1960).
Lyles et al. "Subunit Interactions of Vesicular Stomatitis Virus Envelope Glycoprotein Stablilized by Binding to Viral Matrix Protein," J. Virol. 66:349-358 (1992).
Matassov et al., "A Novel intranasal Virus-Like Particle (VLP) Vaccine Designed to Protect against the Pandemic 1918 Influenza A Virus (H1N1)," Viral Immunol. 20:441-452 (2007).
Mena et al., "Rescue of a Synthetic Chloramphenicol Acetyltransferase RNA into Influenza Virus-Like Particles Obtained from Recombinant Plasmids," J. Virol. 70:5016-5024 (1996).
Murphy and Webster, Orthomyxoviruses, Fields Virology, Third Edition, vol. 1, pp. 1397-1445 (1996).
Neumann et al., "An Improved Reverse Genetics System for Influenza A Virus Generation and its Implications for Vaccine Production," Proc. Natl. Acad. Sci. 102:16825-16829 (2005).
Neumann et al., "Generation of Influenza A Viruses Entirely from Cloned cDNAs," Proc. Natl. Acad. Sci. USA 96:935-9350 (1999).
Neumann et al., "Plasmid-Driven Formation of Influenza Virus-Like Particles," J. Virol. 74:547-551 (2000).
Olsen et al., "Immunogenicity and Efficacy of Baculovirus-Expressed and DNA-Based Equine Influenza Virus Hemagglutinin Vaccines in Mice," Vaccine 15:1149-1156 (1997).
Palese "Making Better Influenza Vaccines?" Emerg. Infect Dis. 12:61-65 (2006).
Park, Man-Seong, et al., "Engineered Viral Vaccine Constructs with Dual Specificity: Avian Influenza and Newcastle Disease," Proc. Natl. Acad. Sci. 103:8203-8208 (2006).
Pattnaik et al., "Formation of Influenza Virus particles Lacking Hemagglutinin on the Viral Envelope," J. Virol. 60:994-1001 (1986).
Peiris et al., "Cocirculation of Avian H-N2 and Contemporary "Human" H3N2 Influenza A Viruses in Pigs in Southeastern China: Potential for Genetic Reassortment?" J. Virol. 75:9679-9686 (2001).
Piedra et al., "Herd Immunity in Adults Against Influenza-Related Illnesses with use of the Trivalent-Live Attenuated Influenza Vaccine (CAIV-T) in Children," Vaccine 23:1540-1548 (2005).
Pleschka et al., "A Plasmid-Based Reverse Genetics System for Influenza A Virus," J. Virol. 70:4188-4192 (1996).
Pumpens and Grens, "Artificial Genes for Chimeric Virus-Like Particles," Artificial DNA (Khudyakov, Y.E., and Fields, H.A., Eds.) pp. 249-327. CRC Press, New York (2003).
Pushko et al., "Influenza Virus-Like Particles Comprised of the HA, NA, and M1 proteins of H9N2 Influenza Virus Induce Protective Immune Responses in BALB/c Mice," Vaccine 23:5751-5759 (2005).
Pushko et al., "Replicon-Helper Systems from Attenuated Venezuelan Equine Encephalitis Virus: Expression of Heterologous Genes in Vitro and Immunization Against Heterologous Pathogens in Vivo," Virology 239:389-401 (1997).
Saito et al., "Characterization of a human H9N2 influenza virus isolated in Hong Kong," Vaccine 20:125-133 (2001).
Slepushkin et al., "Protection of Mice Against Influenza A Virus Challenge by Vaccination With Baculovirus-Expressed M2 Protein," Vaccine 13:1399-1402 (1995).
St. Angelo et al., "Two of the Three Influenza Viral Polymerase Proteins Expressed by Using Baculovirus Vectors Form a Complex in Insect Cells," J. Virol. 61:361-365 (1987).
Tobita et al., "Spontaneous Excretion of Virus from MDCK Cells Persistently Infected with Influenza Virus A/PR/8/34," J. Gen. Virol. 78:563-566 (1997).

Treanor et al., "Evaluation of a Recombinant Hemagglutinin Expressed in Insect Cells as an Influenza Vaccine in Young an Elderly Adults," J. Infec. Dis. 173:1467-1470 (1996).
Treanor et al., "Safety and Immunogenicity of an Inactivated Subvirion Influenza A (H5N1) Vaccine," N. Engl. J. Med. 354:1343-1351 (2006).
Tsuji et al, "Recombinant Sindbis Viruses Expressing a Cytotoxic T-Lymphocyte Epitope of a Malaria Parasite or of Influenza Virus Elicit Protection Against the Corresponding Pathogen in Mice," J. Virol. 72:6907-6910 (1998).
Ulmer et al., "Heterologous Protection Against Influenza by Injection of DNA Encoding a Viral Protein," Science 259:1745-1749 (1993).
Ulmer et al., "Protective CD4+ and CD8+ T cells against Influenza Virus Induced by Vaccination with Nucleoprotein DNA," J. Virol. 72:5648-5653 (1998).
Watanabe et al., "Immunogenicity and Protective Efficacy of Replication-Incompetent Influenza Virus-Like Particles," J. Virol. 76:767-773 (2002).
Wiebke, "Supplementary European Search Report," 6 pages, from EP Appl. No. 04786052.3, European Patent Office, Munich, Germany (mailed Mar. 26, 2008).
Wiebke, "Communication pursuant to Article 94(3) EPC," 7 pages, from EP Appl. No. 04786052.3, European Patent Office, Munich, Germany (mailed Sep. 15, 2008).
Wiebke, "Communication pursuant to Article 94(3) EPC," 4 pages, from EP Appl. No. 04786052,3, European Patent Office, Munich, Germany (mailed Mar. 19, 2010).
Wood et al., "Preparation of Vaccines Against H5N1 Influenza," Vaccine 20:S84-S87 (2002).
Yasuda et al., "Growth Control of Influenza A Virus by MI Protein: Analysis of Transfectant Viruses Carrying the Chimeric M Gene," J. Virol. 68:8141-8146 (1994).
Ye et al., "Nucleus-Targeting Domain of the Matrix Protein (MI) of Influenza Virus," J. Virol. 69:1964-1970 (1995).
Zhang and Lamb, "Characterization of the Membrane Association of the Influenza Virus Matrix Protein in Living Cells," Virol. 225:255-266 (1996).
Zhao et al., "The M1 and NP Proteins of Influenza A Virus Form Homo- but not Heterooligomeric Complexes when Coexpressed in BHK-21 Cells," J. Gen. Virol. 79:2435-2446 (1998).
Zhou et al., "Generation of Cytotoxic and Humoral Immune-Responses by Non-replicative Recombinant Semlike Forest Virus," Proc. Natl. Acad. Sci. USA 92:3009-3013 (1995).
Smith et al., U.S. Appl. No. 12/558,844, filed Sep. 14, 2009.
NCBI Accession No. CY014173, "Influenza A virus (A/Indonesia/5/2005 (H5N1)) segment 7 sequence," 3 pages (available Aug. 30, 2006).
Belser et al., "The ferret as a model organism to study influenza A virus infection," Dis. Model. Mech. 4(5):575-579 (2011).
Itamura, "Development of influenza vaccines against newly emerging A/H5N1 virus," Nippon Rinsho 58:255-264 (2000).
Ottolini et al,. "The cotton rat provides a useful small-animal model for the study of influenza virus pathogenesis," J. Gen. Virol. 86(Pt 10):2823-2830 (2005).
Park et al., "The M2 Ectodomain Is Important for Its Incorporation into Influenza A Virions," J. Virol. 72(3):2449-2455 (1998).
Unknown, Rinsho to Kenkyuu 81:1899-1903 (2004).
Watanabe et al., "Influenza A Virus Can Undergo Multiple Cycles of Replication without M2 Ion Channel Activity," J. Virol. 75(12):5656-5662 (2001).
"Section 1. Past Achievements and Future Needs," Vaccines, Vaccination and the Immune Response, pp. 1-45, by Gordon Ada, Alistair Ramsay (1997).
Bucher et al., "Incorporation of Influenza Virus M-Protein into Liposomes," J. Virol. 36:586-590 (1980).
Ebel, Search Report and Written Opinion, 9 pages, from Singapore Patent Appl. No. 200701731-2 (mailed Feb. 25, 2010).
Gregoriadis et al., "Vaccine Entrapment in Liposomes," Methods 19:156-162 (1999).
Matsuda, "Notice of Reasons for Rejection," 3 pages, Japan Patent Appl. No. 2006-518925, with 4 pages translation (mailed Mar. 17, 2010).
Nerome et al., "Development of a new type of influenza subunit vaccine made by muramyldipeptide-liposome: enhancement of humoral and cellular immune responses," Vaccine 8:503-509 (1990).
Peradze et al., "Anti-influenza prophylactic formulations," 1986, Moscow, Meditsina, pp. 218-225.
Smith et al., U.S. Appl. No. 12/832,657, filed Jul. 8, 2010.
The Patent Office of the People's Republic of China, "The Decision of Final Rejection of the Application," 4 pages, from China Patent Appl. No. 200480026152.3 (issued May 20, 2010).
Welsh, "Examiner's first report on patent application No. 2004268510," 3 pages, from Australian Patent Appl. No. 2004268510 (dated Feb. 5, 2010).
Wiebke, "European Search Report," 8 pages, from EP Appl. No. 10010286.2, European Patent Office, Munich, Germany (mailed May 23, 2011).
Zitzow et al., "Pathogenesis of Avian Influenza A (H5N1) Viruses in Ferrets," J. Virol. 76(9):4420-4439 (2002).

```
ATGAATCCAAATCAAAAGATAATAGCACTTGGCTCTGTTTCTATAACTATTGCGACAATATG
TTTACTCATGCAGATTGCCATCTTAGCAACGACTATGACACTACATTTCAATGAATGTACCA
ACCCATCGAACAATCAAGCAGTGCCATGTGAACCAATCATAATAGAAAGGAACATAACAGAG
ATAGTGCATTTGAATAATACTACCATAGAGAAGGAAAGTTGTCCTAAAGTAGCAGAATACAA
GAATTGGTCAAAACCGCAATGTCAAATTACAGGGTTCGCCCCTTTCTCCAAGGACAACTCAA
TTAGGCTTTCTGCAGGCGGGGATATTTGGGTGACAAGAGAACCTTATGTATCGTGCGGTCTT
GGTAAATGTTACCAATTTGCACTTGGGCAGGGAACCACTTTGAACAACAAACACTCAAATGG
CACAATACATGATAGGAGTCCCCATAGAACCCTTTTAATGAACGAGTTGGGTGTTCCATTTC
ATTTGGGAACCAAACAAGTGTGCATAGCATGGTCCAGCTCAAGCTGCCATGATGGGAAGGCA
TGGTTACATGTTTGTGTCACTGGGGATGATAGAAATGCGACTGCTAGCATCATTTATGATGG
GATGCTTACCGACAGTATTGGTTCATGGTCTAAGAACATCCTCAGAACTCAGGAGTCAGAAT
GCGTTTGCATCAATGGAACTTGTACAGTAGTAATGACTGATGGAAGTGCATCAGGAAGGGCT
GATACTAAAATACTATTCATTAGAGAAGGGAAAATTGTCCACATTGGTCCACTGTCAGGAAG
TGCTCAGCATGTGGAGGAATGCTCCTGTTACCCCCGGTATCCAGAAGTTAGATGTGTTTGCA
GAGACAATTGGAAGGGCTCCAATAGACCCGTGCTATATATAAATGTGGCAGATTATAGTGTT
GATTCTAGTTATGTGTGCTCAGGACTTGTTGGCGACACACCAAGAAATGACGATAGCTCCAG
CAGCAGTAACTGCAGGGATCCTAATAACGAGAGAGGGGGCCCAGGAGTGAAAGGGTGGGCCT
TTGACAATGGAAATGATGTTTGGATGGGACGAACAATCAAGAAAGATTCGCGCTCTGGTTAT
GAGACTTTCAGGGTCGTTGGTGGTTGGACTACGGCTAATTCCAAGTCACAAATAAATAGGCA
AGTCATAGTTGACAGTGATAACTGGTCTGGGTATTCTGGTATATTCTCTGTTGAAGGAAAAA
CCTGCATCAACAGGTGTTTTTATGTGGAGTTGATAAGAGGGAGACCACAGGAGACCAGAGTA
TGGTGGACTTCAAATAGCATCATTGTATTTTGTGGAACTTCAGGTACCTATGGAACAGGCTC
ATGGCCCGATGGAGCGAATATCAATTTCATGTCTATATAA
```

FIGURE 1

```
ATGGAAACAATATCACTAATAACTATACTACTAGTAGTAACAGCAAGCAATGCAGATAAAAT
CTGCATCGGCCACCAGTCAACAAACTCCACAGAAACTGTGGACACGCTAACAGAAACCAATG
TTCCTGTGACACATGCCAAAGAATTGCTCCACACAGAGCATAATGGAATGCTGTGTGCAACA
AGCCTGGGACATCCCCTCATTCTAGACACATGCACTATTGAAGGACTAGTCTATGGCAACCC
TTCTTGTGACCTGCTGTTGGGAGGAAGAGAATGGTCCTACATCGTCGAAAGATCATCAGCTG
TAAATGGAACGTGTTACCCTGGGAATGTAGAAAACCTAGAGGAACTCAGGACACTTTTTAGT
TCCGCTAGTTCCTACCAAAGAATCCAAATCTTCCCAGACACAACCTGGAATGTGACTTACAC
TGGAACAAGCAGAGCATGTTCAGGTTCATTCTACAGGAGTATGAGATGGCTGACTCAAAAGA
GCGGTTTTTACCCTGTTCAAGACGCCCAATACACAAATAACAGGGGAAAGAGCATTCTTTTC
GTGTGGGGCATACATCACCCACCCACCTATACCGAGCAAACAAATTTGTACATAAGAAACGA
CACAACAACAAGCGTGACAACAGAAGATTTGAATAGGACCTTCAAACCAGTGATAGGGCCAA
GGCCCCTTGTCAATGGTCTGCAGGGAAGAATTGATTATTATTGGTCGGTACTAAAACCAGGC
CAAACATTGCGAGTACGATCCAATGGGAATCTAATTGCTCCATGGTATGGACACGTTCTTTC
AGGAGGGAGCCATGGAAGAATCCTGAAGACTGATTTAAAAGGTGGTAATTGTGTAGTGCAAT
GTCAGACTGAAAAAGGTGGCTTAAACAGTACATTGCCATTCCACAATATCAGTAAATATGCA
TTTGGAACCTGCCCCAAATATGTAAGAGTTAATAGTCTCAAACTGGCAGTCGGTCTGAGGAA
CGTGCCTGCTAGATCAAGTAGAGGACTATTTGGAGCCATAGCTGGATTCATAGAAGGAGGTT
GGCCAGGACTAGTCGCTGGCTGGTATGGTTTCCAGCATTCAAATGATCAAGGGGTTGGTATG
GCTGCAGATAGGGATTCAACTCAAAAGGCAATTGATAAAATAACATCCAAGGTGAATAATAT
AGTCGACAAGATGAACAAGCAATATGAAATAATTGATCATGAATTCAGTGAGGTTGAAACTA
GACTCAATATGATCAATAATAAGATTGATGACCAAATACAAGACGTATGGGCATATAATGCA
GAATTGCTAGTACTACTTGAAAATCAAAAAACACTCGATGAGCATGATGCGAACGTGAACAA
TCTATATAACAAGGTGAAGAGGGCACTGGGCTCCAATGCTATGGAAGATGGGAAAGGCTGTT
TCGAGCTATACCATAAATGTGATGATCAGTGCATGGAAACAATTCGGAACGGGACCTATAAT
AGGAGAAAGTATAGAGAGGAATCAAGACTAGAAAGGCAGAAAATAGAGGGGTTAAGCTGGA
ATCTGAGGGAACTTACAAAATCCTCACCATTTATTCGACTGTCGCCTCATCTCTTGTGCTTG
CAATGGGGTTTGCTGCCTTCCTGTTCTGGGCCATGTCCAATGGATCTTGCAGATGCAACATT
TGTATATAA
```

FIGURE 2

```
ATGAGTCTTCTAACCGAGGTCGAAACGTACGTTCTCTCTATCATCCCATCAGGCCCCCTCAA
AGCCGAGATCGCGCAGAGACTTGAGGATGTTTTGCAGGGAAGAACACAGATCTTGAGGCTC
TCATGGAATGGCTAAAGACAAGACCAATCCTGTCACCTCTGACTAAGGGGATTTTAGGGTTT
GTGTTCACGCTCACCGTGCCCAGTGAGCGAGGACTGCAGCGTAGACGATTTGTCCAAAATGC
CCTAAATGGGAATGGAGACCCAAACAACATGGACAGGGCAGTTAAACTATACAAGAAGCTGA
AGAGGGAAATGACATTCCATGGAGCAAAGGAAGTTGCACTCAGTTACTCAACTGGTGCGCTT
GCCAGTTGCATGGGTCTCATATACAACCGGATGGGAACAGTGACCACAGAAGTGGCTCTTGG
CCTAGTATGTGCCACTTGTGAACAGATTGCTGATGCCCAACATCGGTCCCACAGGCAGATGG
CGACTACCACCAACCCACTAATCAGGCATGAGAACAGAATGGTACTAGCCAGCACTACGGCT
AAGGCCATGGAGCAGATGGCTGGATCAAGTGAGCAGGCAGCAGAAGCCATGGAAGTCGCAAG
TCAGGCTAGGCAAATGGTGCAGGCTATGAGGACAATTGGGACTCACCCTAGTTCCAGTGCAG
GTCTAAAAGATGATCTTATTGAAAATTTGCAGGCTTACCAGAAACGGATGGGAGTGCAAATG
CAGAGATTCAAGTGA
```

FIGURE 3

(A)
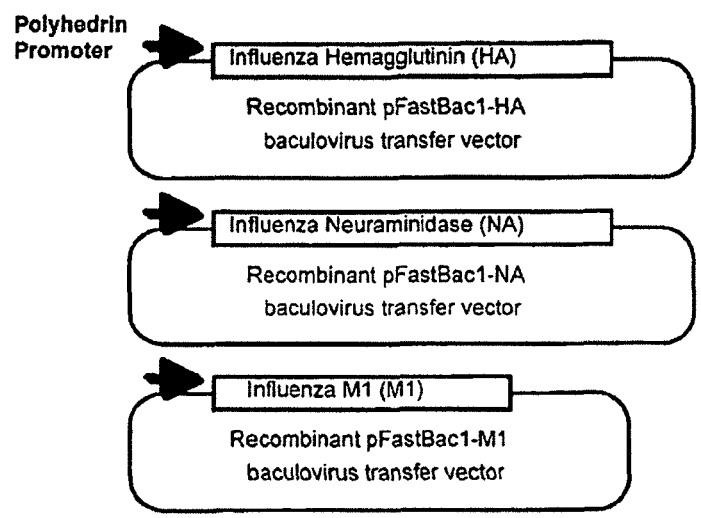
(B)
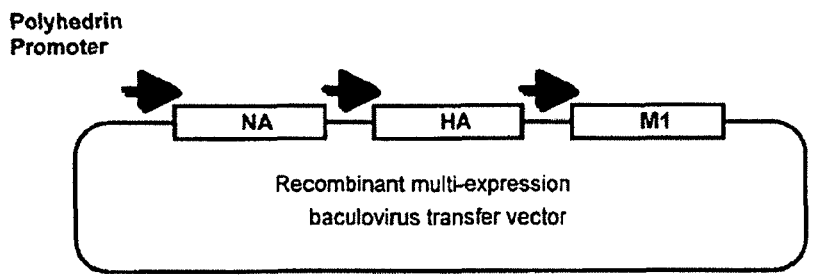
FIGURE 4

(A)  1 2 3 4 5 6 7 8 9 10 11 12 13 14 M
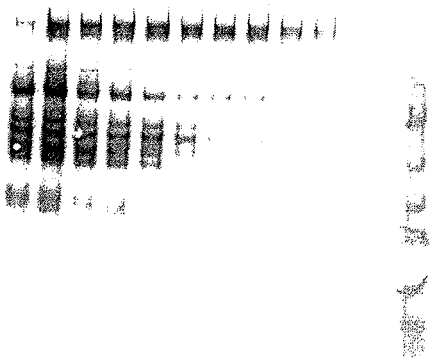
(B)  1 2 3 4 5 6 7 8 9 10 11 12 13 14 M
(C)  1 2 3 4 5 6 7 8 9 10 11 12 13 14 M
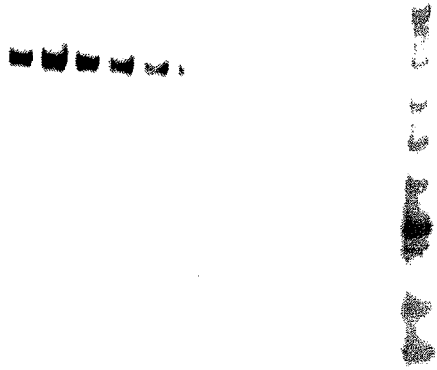
FIGURE 7

Table X. Hemagglutinin-Inhibition Titer-Ferrets

| Vaccine | H3N2 | | | H1N1 |
|---|---|---|---|---|
| | CA/04 | Fuj/02 | Wuh

Extreme Dose Sparing
Intramuscular-H5N1 Vietnam/1203/2003 VLP

HI titer to A/Fujian/411/2002 (H3N2) after intranasal inoculation with H3H2 VLPs

FIGURE 30 B

HI titer to A/Panama/2007/99 (H3N2) after intranasal inoculation with H3H2 VLPs

HI titer to A/Wyoming/3/03 (H3N2) after intranasal inoculation with H3H2 VLPs

FIGURE 30 F

HI titer to A/New York/55/2004 (H3N2) after intramuscular inoculation with H3H2 VLPs

FIGURE 30 G

HI titer to A/New York/55/2004 (H3N2) after intranasal inoculation with H3H2 VLPs

FIGURE 30 H

SEQUENCE LISTING

```
<160> NUMBER OF SEQ ID NOS: 60

<210> SEQ ID NO 1
<211> LENGTH: 1404
<212> TYPE: DNA
<213> ORGANISM: Influenza virus

<400> SEQUENCE: 1
atgaatccaa atcaaaagat aatagcactt ggctctgttt ctataactat tgcgacaata      60
tgtttactca tgcagattgc catcttagca acgactatga cactacattt caatgaatgt     120
accaacccat cgaacaatca agcagtgcca tgtgaaccaa tcataataga aggaacata      180 acagagatag tgcatttgaa taatactacc atagagaagg aaagttgtcc taaagtagca     240
gaatacaaga attggtcaaa accgcaatgt caaattacag ggttcgcccc tttctccaag     300
gacaactcaa ttaggctttc tgcaggcggg gatatttggg tgacaagaga accttatgta     360
tcgtgcggtc ttggtaaatg ttaccaattt gcacttgggc agggaaccac tttgaacaac     420
aaacactcaa atggcacaat acatgatagg agtccccata gaacccttt aatgaacgag      480 ttgggtgttc catttcattt gggaaccaaa caagtgtgca tagcatggtc cagctcaagc     540
tgccatgatg gaggcatg gttacatgtt tgtgtcactg gggatgatag aaatgcgact      600
gctagcatca tttatgatgg gatgcttacc gacagtattg gttcatggtc taagaacatc     660
ctcagaactc aggagtcaga atgcgtttgc atcaatggaa cttgtacagt agtaatgact     720
gatggaagtg catcaggaag ggctgatact aaaatactat tcattagaga agggaaaatt     780
gtccacattg gtccactgtc aggaagtgct cagcatgtgg aggaatgctc ctgttacccc     840
cggtatccag aagttagatg tgtttgcaga gacaattgga agggctccaa tagacccgtg     900
ctatatataa atgtggcaga ttatagtgtt gattctagtt atgtgtgctc aggacttgtt     960
ggcgacacac aagaaatga cgatagctcc agcagcagta actgcaggga tcctaataac    1020
gagagagggg gcccaggagt gaagggtgg gcctttgaca atggaaatga tgtttggatg    1080
ggacgaacaa tcaagaaaga ttcgcgctct ggttatgaga ctttcagggt cgttggtggt    1140
tggactacgg ctaattccaa gtcacaaata aataggcaag tcatagttga cagtgataac    1200
tggtctgggt attctggtat attctctgtt gaaggaaaaa cctgcatcaa caggtgtttt    1260
tatgtggagt tgataagagg gagaccacag gagaccagag tatggtggac ttcaaatagc    1320
atcattgtat tttgtggaac ttcaggtacc tatggaacag gctcatggcc cgatggagcg    1380
aatatcaatt tcatgtctat ataa                                           1404

<210> SEQ ID NO 2
<211> LENGTH: 1683
<212> TYPE: DNA
<213> ORGANISM: Influenza virus

<400> SEQUENCE: 2
atggaaacaa tatcactaat aactatacta ctagtagtaa cagcaagcaa tgcagataaa       60
```

| | |
|---|---|
| atctgcatcg gccaccagtc aacaaactcc acagaaactg tggacacgct aacagaaacc | 120 |
| aatgttcctg tgacacatgc caaagaattg ctccacacag agcataatgg aatgctgtgt | 180 |
| gcaacaagcc tgggacatcc cctcattcta gacacatgca ctattgaagg actagtctat | 240 |
| ggcaacccct cttgtgacct gctgttggga ggaagagaat ggtcctacat cgtcgaaaga | 300 |
| tcatcagctg taaatggaac gtgttaccct gggaatgtag aaaacctaga ggaactcagg | 360 |
| acactttta gttccgctag ttcctaccaa agaatccaaa tcttcccaga cacaacctgg | 420 |
| aatgtgactt acactggaac aagcagagca tgttcaggtt cattctacag gagtatgaga | 480 |
| tggctgactc aaaagagcgg ttttacccct gttcaagacg cccaatacac aaataacagg | 540 |
| ggaaagagca ttctttcgt gtggggcata catcacccac ccacctatac cgagcaaaca | 600 |
| aatttgtaca taagaaacga cacaacaaca agcgtgacaa cagaagattt gaataggacc | 660 |
| ttcaaaccag tgatagggcc aaggccccct gtcaatggtc tgcagggaag aattgattat | 720 |
| tattggtcgg tactaaaacc aggccaaaca ttgcgagtac gatccaatgg gaatctaatt | 780 |
| gctccatggt atggacacgt tctttcagga gggagccatg gaagaatcct gaagactgat | 840 |
| ttaaaaggtg gtaattgtgt agtgcaatgt cagactgaaa aaggtggctt aaacagtaca | 900 |
| ttgccattcc acaatatcag taaatatgca tttggaacct gccccaaata tgtaagagtt | 960 |
| aatagtctca aactggcagt cggtctgagg aacgtgcctg ctagatcaag taggacta | 1020 |
| tttggagcca tagctggatt catagaagga ggttggccag gactagtcgc tggctggtat | 1080 |
| ggtttccagc attcaaatga tcaaggggtt ggtatggctg cagataggga ttcaactcaa | 1140 |
| aaggcaattg ataaaataac atccaaggtg aataatatag tcgacaagat gaacaagcaa | 1200 |
| tatgaaataa ttgatcatga attcagtgag gttgaaacta gactcaatat gatcaataat | 1260 |
| aagattgatg accaaataca agacgtatgg gcatataatg cagaattgct agtactactt | 1320 |
| gaaaatcaaa aaacactcga tgagcatgat gcgaacgtga acaatctata taacaaggtg | 1380 |
| aagagggcac tgggctccaa tgctatggaa gatgggaaag ctgtttcga gctataccat | 1440 |
| aaatgtgatg atcagtgcat ggaaacaatt cggaacggga cctataatag agaaagtgat | 1500 |
| agagaggaat caagactaga aaggcagaaa atagaggggg ttaagctgga atctgaggga | 1560 |
| acttacaaaa tcctcaccat ttattcgact gtcgcctcat ctcttgtgct tgcaatgggg | 1620 |
| tttgctgcct tcctgttctg gccatgtcc aatggatctt gcagatgcaa catttgtata | 1680 |
| taa | 1683 |

<210> SEQ ID NO 3
<211> LENGTH: 759
<212> TYPE: DNA
<213> ORGANISM: Influenza virus

<400> SEQUENCE: 3

| | |
|---|---|
| atgagtcttc taaccgaggt cgaaacgtac gttctctcta tcatcccatc aggccccctc | 60 |
| aaagccgaga tcgcgcagag acttgaggat gtttttgcag ggaagaacac agatcttgag | 120 |
| gctctcatgg aatggctaaa gacaagacca atcctgtcac ctctgactaa ggggattta | 180 |
| gggtttgtgt tcacgctcac cgtgcccagt gagcgaggac tgcagcgtag acgatttgtc | 240 |
| caaaatgccc taaatgggaa tggagaccca acaacatgg acaggcagt taaactatac | 300 |
| aagaagctga gagggaaat gacattccat ggagcaaagg aagttgcact cagttactca | 360 |
| actggtgcgc ttgccagttg catgggtctc atatacaacc ggatgggaac agtgaccaca | 420 |
| gaagtggctc ttggcctagt atgtgccact tgtgaacaga ttgctgatgc ccaacatcgg | 480 |

```
tcccacaggc agatggcgac taccaccaac ccactaatca ggcatgagaa cagaatggta    540
ctagccagca ctacggctaa ggccatggag cagatggctg gatcaagtga gcaggcagca    600
gaagccatgg aagtcgcaag tcaggctagg caaatggtgc aggctatgag gacaattggg    660
actcaccctc gttccagtgc aggtctaaaa gatgatctta ttgaaaattt gcaggcttac    720
cagaaacgga tgggagtgca aatgcagaga ttcaagtga                          759
```

```
<210> SEQ ID NO 4
<211> LENGTH: 31
<212> TYPE: DNA
<213> ORGANISM: Influenza virus

<400> SEQUENCE: 4
aacggtccga tggagaaaat agtgcttctt c                                  31

<210> SEQ ID NO 5
<211> LENGTH: 33
<212> TYPE: DNA
<213> ORGANISM: Influenza virus

<400> SEQUENCE: 5
aaagctttta aatgcaaatt ctgcattgta acg                                33

<210> SEQ ID NO 6
<211> LENGTH: 32
<212> TYPE: DNA
<213> ORGANISM: Influenza virus

<400> SEQUENCE: 6
aacggtccga tgaatccaaa tcagaagata at                                 32

<210> SEQ ID NO 7
<211> LENGTH: 32
<212> TYPE: DNA
<213> ORGANISM: Influenza virus

<400> SEQUENCE: 7
aaagcttcta cttgtcaatg gtgaatggca ac                                 32

<210> SEQ ID NO 8
<211> LENGTH: 30
<212> TYPE: DNA
<213> ORGANISM: Influenza virus

<400> SEQUENCE: 8
aacggtccga tgagtcttct aaccgaggtc                                    30

<210> SEQ ID NO 9
<211> LENGTH: 31
<212> TYPE: DNA
<213> ORGANISM: Influenza virus

<400> SEQUENCE: 9
aaagctttca cttgaatcgc tgcatctgca c                                  31

<210> SEQ ID NO 10
<211> LENGTH: 1707
<212> TYPE: DNA
<213> ORGANISM: Influenza virus

<400> SEQUENCE: 10
atggagaaaa tagtgcttct tcttgcaata gtcagtcttg ttaaaagtga tcagatttgc    60
```

```
attggttacc atgcaaacaa ttcaacagag caggttgaca caatcatgga aaagaacgtt    120
actgttacac atgcccaaga catactggaa aagacacaca acgggaagct ctgcgatcta    180
gatggagtga agcctctaat tttaagagat tgtagtgtag ctggatggct cctcgggaac    240
ccaatgtgtg acgaattcat caatgtaccg gaatggtctt acatagtgga aaggccaat     300 ccaaccaatg acctctgtta cccagggagt tcaacgact atgaagaact gaaacaccta     360
ttgagcagaa taaccatttt tgagaaaatt caaatcatcc ccaaaagttc ttggtccgat    420
catgaagcct catcaggagt gagctcagca tgtccatacc tgggaagtcc ctccttttt     480 agaaatgtgg tatggcttat caaaaagaac agtacatacc caacaataaa gaaaagctac    540
aataatacca accaagaaga tcttttggta ctgtggggaa ttcaccatcc taatgatgcg    600
gcagagcaga caaggctata tcaaaaccca accacctata tttccattgg gacatcaaca    660
ctaaaccaga gattggtacc aaaaatagct actagatcca agtaaacgg caaagtgga     720 aggatggagt tcttctggac aattttaaaa cctaatgatg caatcaactt cgagagtaat    780
ggaaatttca ttgctccaga atatgcatac aaaattgtca agaaggggga ctcagcaatt    840
atgaaaagtg aattggaata tggtaactgc aacaccaagt gtcaaactcc aatgggggcg    900
ataaactcta gtatgccatt ccacaacata caccctctca ccatcgggga atgccccaaa    960
tatgtgaaat caaacagatt agtccttgca cagggctca gaaatagccc tcaaagagag    1020
agcagaagaa aaagagagg actatttgga gctatagcag gttttatga gggaggatgg    1080 cagggaatgg tagatggttg gtatgggtac accatagca atgagcaggg gagtgggtac    1140
gctgcagaca agaatccac tcaaaaggca atagatggag tcaccaataa ggtcaactca    1200
atcattgaca aaatgaacac tcagtttgag gccgttggaa gggaatttaa taacttagaa    1260
aggagaatag agaatttaaa caagaagatg gaagacgggt ttctagatgt ctggacttat    1320
aatgccgaac ttctggttct catggaaaat gagagaactc tagactttca tgactcaaat    1380
gttaagaacc tctacgacaa ggtccgacta cagcttaggg ataatgcaaa ggagctgggt    1440
aacggttgtt tcgagttcta tcacaaatgt gataatgaat gtatggaaag tataagaaac    1500
ggaacgtaca actatccgca gtattcagaa gaagcaagat taaaaagaga ggaaataagt    1560
ggggtaaaat tggaatcaat aggaacttac caaatactgt caatttattc aacagtggcg    1620
agttccctag cactggcaat catgatggct ggtctatctt tatggatgtg ctccaatgga    1680
tcgttacaat gcagaatttg catttaa                                        1707

<210> SEQ ID NO 11
<211> LENGTH: 1350
<212> TYPE: DNA
<213> ORGANISM: Influenza virus

<400> SEQUENCE: 11
atgaatccaa atcagaagat aataaccatt ggatcaatct gtatggtaat tggaatagtt     60
agcttaatgt tacaaattgg gaacatgatc tcaatatggg tcagtcattc aattcagaca    120
gggaatcaac accaagctga atcaatcagc aatactaacc ctcttactga aaagctgtg     180 gcttcagtaa cattagcggg caattcatct ctttgcccca ttagaggatg ggctgtacac    240
agtaaggaca acaatataag gatcggttcc aaggggatg tgtttgttat tagagagccg    300
ttcatctcat gctcccacct ggaatgcaga actttcttct tgactcaggg agccttgctg    360
aatgacaagc actccaacgg gactgtcaaa gacagaagcc ctcacagaac attaatgagt    420
tgtcctgtgg gtgaggctcc ctctccatat aactcaaggt ttgagtctgt tgcttggtca    480
```

```
gcaagtgctt gccatgatgg caccagttgg ttgacaattg gaatttctgg cccagacaat    540
gaggctgtgg ctgtattgaa atacaatggc ataataacag acactatcaa gagttggagg    600
aacaacatac tgagaactca agagtctgaa tgtgcatgtg taaatggctc ttgctttact    660
gtaatgactg atggaccaag tgatgggcag gcatcatata agatcttcaa aatggaaaaa    720
ggaaaagtgg tcaaatcagt cgaattggat gctcctaatt atcactatga ggaatgctcc    780
tgttatcctg atgccggcga aatcacatgt gtttgcaggg ataattggca tggctcaaat    840
aggccatggg tatcttttca tcaaaatttg gagtatcaaa taggatatat atgcagtgga    900
gttttcggag acaatccacg ccccaatgat ggaacaggta gttgtggccc gatgtcccct    960 aacgggcat atgggtaaa agggttttca tttaaatacg gcaatggtgt ttggatcggg    1020
agaaccaaaa gcactaattc caggagcggc tttgaaatga tttgggatcc aaatgggtgg    1080
actggaacgg acagtagctt ttcagtgaaa caagatatag tagcaataac tgattggtca    1140
ggatatagcg ggagttttgt ccagcatcca gaactgacag gattagattg cataagacct    1200
tgtttctggg ttgagttaat cagagggcgg cccaaagaga gcacaatttg gactagtggg    1260
agcagcatat cttttgtgg tgtaaatagt gacactgtga gttggtcttg ccagacggt    1320 gctgagttgc cattcaccat tgacaagtag                                     1350
```

<210> SEQ ID NO 12
<211> LENGTH: 759
<212> TYPE: DNA
<213> ORGANISM: Influenza virus

<400> SEQUENCE: 12

```
atgagtcttc taaccgaggt cgaaacgtac gttctctcta tcatcccgtc aggccccctc     60
aaagccgaga tcgcgcagaa acttgaagat gtctttgcag gaaagaacac cgatctcgag    120
gctctcatgg agtggctaaa gacaagacca atcctgtcac ctctgactaa agggattttg    180
ggatttgtat tcacgctcac cgtgcccagt gagcgaggac tgcagcgtag acgctttgtc    240
cagaatgccc taaatggaaa tggagatcca aataatatgg ataggggcagt taagctatat    300 aagaagctga aaagagaaat aacattccat ggggctaaag aggtttcact cagctactca    360
accggtgcac ttgccagttg catgggtctc atatacaaca ggatgggaac ggtgactacg    420
gaagtggctt ttggcctagt gtgtgccact tgtgagcaga ttgcagattc acagcatcgg    480
tctcacaggc agatggcaac tatcaccaac ccactaatca ggcatgaaaa cagaatggtg    540
ctggccagca ctacagctaa ggctatggag cagatggcgg gatcaagtga gcaggcagcg    600
gaagccatgg aggtcgctaa tcaggctagg cagatggtgc aggcaatgag gacaattgga    660
actcatccta actctagtgc tggtctgaga gataatcttc ttgaaaattt gcaggcctac    720
cagaaacgaa tgggagtgca gatgcagcga ttcaagtga                            759
```

<210> SEQ ID NO 13
<211> LENGTH: 30
<212> TYPE: DNA
<213> ORGANISM: Influenza virus

<400> SEQUENCE: 13

```
aggatccatg aagactatca ttgctttgag                                       30
```

<210> SEQ ID NO 14
<211> LENGTH: 32
<212> TYPE: DNA
<213> ORGANISM: Influenza virus

```
<400> SEQUENCE: 14
aggtacctca aatgcaaatg ttgcacctaa tg                                 32

<210> SEQ ID NO 15
<211> LENGTH: 72
<212> TYPE: DNA
<213> ORGANISM: Influenza virus

<400> SEQUENCE: 15
ggggacaagt ttgtacaaaa aagcaggctt agaaggagat agaaccatga atccaaatca  60
aaagataata ac                                                      72

<210> SEQ ID NO 16
<211> LENGTH: 57
<212> TYPE: DNA
<213> ORGANISM: Influenza virus

<400> SEQUENCE: 16
ggggaccact ttgtacaaga aagctgggtc ctatataggc atgagattga tgtccgc     57

<210> SEQ ID NO 17
<211> LENGTH: 38
<212> TYPE: DNA
<213> ORGANISM: Influenza virus

<400> SEQUENCE: 17
aaagaattca tgagtcttct aaccgaggtc gaaacgta                          38

<210> SEQ ID NO 18
<211> LENGTH: 38
<212> TYPE: DNA
<213> ORGANISM: Influenza virus

<400> SEQUENCE: 18
aaattcgaat tactccagct ctatgctgac aaaatgac                          38

<210> SEQ ID NO 19
<211> LENGTH: 57
<212> TYPE: DNA
<213> ORGANISM: Influenza virus

<400> SEQUENCE: 19
agaatcatga gtcttctaac cgaggtcgaa acgcctatca gaaacgaatg ggggtgc     57

<210> SEQ ID NO 20
<211> LENGTH: 38
<212> TYPE: DNA
<213> ORGANISM: Influenza virus

<400> SEQUENCE: 20
aaattcgaat tactccagct ctatgctgac aaaatgac                          38

<210> SEQ ID NO 21
<211> LENGTH: 30
<212> TYPE: DNA
<213> ORGANISM: Influenza virus

<400> SEQUENCE: 21
agaattcatg gcgtcccaag gcaccaaacg                                   30

<210> SEQ ID NO 22
<211> LENGTH: 50
```

```
<212> TYPE: DNA
<213> ORGANISM: Influenza virus

<400> SEQUENCE: 22
agcggccgct taattgtcgt actcctctgc attgtctccg aagaaataag         50

<210> SEQ ID NO 23
<211> LENGTH: 35
<212> TYPE: DNA
<213> ORGANISM: Influenza virus

<400> SEQUENCE: 23
agaattcatg aaggcaataa ttgtactact catgg                          35

<210> SEQ ID NO 24
<211> LENGTH: 47
<212> TYPE: DNA
<213> ORGANISM: Influenza virus

<400> SEQUENCE: 24
agcggccgct tatagacaga tggagcaaga aacattgtct ctggaga             47

<210> SEQ ID NO 25
<211> LENGTH: 31
<212> TYPE: DNA
<213> ORGANISM: Influenza virus

<400> SEQUENCE: 25
agaattcatg ctaccttcaa ctatacaaac g                              31

<210> SEQ ID NO 26
<211> LENGTH: 40
<212> TYPE: DNA
<213> ORGANISM: Influenza virus

<400> SEQUENCE: 26
agcggccgct tacagagcca tatcaacacc tgtgacagtg                     40

<210> SEQ ID NO 27
<211> LENGTH: 568
<212> TYPE: PRT
<213> ORGANISM: Unknown
<220> FEATURE:
<223> OTHER INFORMATION: Vac2-hac-opt

<400> SEQUENCE: 27

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
        115                 120                 125
```

Lys Ile Gln Ile Ile Pro Lys Ser Ser Trp Ser Asp His Glu Ala Ser
            130                 135                 140

Ser Gly Val Ser Ser Ala Cys Pro Tyr Leu Gly Ser Pro Ser Phe Phe
145                 150                 155                 160

Arg Asn Val Val Trp Leu Ile Lys Lys Asn Ser Thr Tyr Pro Thr Ile
                165                 170                 175

Lys Lys Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Ile Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Ser Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Ile Arg Asn Gly Thr Tyr Asn Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
    530                 535                 540

Leu Ala Ile Met Met Ala Gly Leu Ser Leu Trp Met Cys Ser Asn Gly

Ser Leu Gln Cys Arg Ile Cys Ile
545                 550                 555                 560
                565

<210> SEQ ID NO 28
<211> LENGTH: 572
<212> TYPE: PRT
<213> ORGANISM: Unknown
<220> FEATURE:
<223> OTHER INFORMATION: Vac2-hac-spc-opt

<400> SEQUENCE: 28

Met Pro Leu Tyr Lys Leu Leu Asn Val Leu Trp Leu Val Ala Val Ser
1               5                   10                  15

Asn Ala Ile Pro Asp Gln Ile Cys Ile Gly Tyr His Ala Asn Asn Ser
            20                  25                  30

Thr Glu Gln Val Asp Thr Ile Met Glu Lys Asn Val Thr Val Thr His
        35                  40                  45

Ala Gln Asp Ile Leu Glu Lys Thr His Asn Gly Lys Leu Cys Asp Leu
    50                  55                  60

Asp Gly Val Lys Pro Leu Ile Leu Arg Asp Cys Ser Val Ala Gly Trp
65                  70                  75                  80

Leu Leu Gly Asn Pro Met Cys Asp Glu Phe Ile Asn Val Pro Glu Trp
                85                  90                  95

Ser Tyr Ile Val Glu Lys Ala Asn Pro Thr Asn Asp Leu Cys Tyr Pro
            100                 105                 110

Gly Ser Phe Asn Asp Tyr Glu Glu Leu Lys His Leu Leu Ser Arg Ile
        115                 120                 125

Asn His Phe Glu Lys Ile Gln Ile Ile Pro Lys Ser Ser Trp Ser Asp
    130                 135                 140

His Glu Ala Ser Ser Gly Val Ser Ser Ala Cys Pro Tyr Leu Gly Ser
145                 150                 155                 160

Pro Ser Phe Phe Arg Asn Val Val Trp Leu Ile Lys Lys Asn Ser Thr
                165                 170                 175

Tyr Pro Thr Ile Lys Lys Ser Tyr Asn Asn Thr Asn Gln Glu Asp Leu
            180                 185                 190

Leu Val Leu Trp Gly Ile His His Pro Asn Asp Ala Ala Glu Gln Thr
        195                 200                 205

Arg Leu Tyr Gln Asn Pro Thr Thr Tyr Ile Ser Ile Gly Thr Ser Thr
    210                 215                 220

Leu Asn Gln Arg Leu Val Pro Lys Ile Ala Thr Arg Ser Lys Val Asn
225                 230                 235                 240

Gly Gln Ser Gly Arg Met Glu Phe Phe Trp Thr Ile Leu Lys Pro Asn
                245                 250                 255

Asp Ala Ile Asn Phe Glu Ser Asn Gly Asn Phe Ile Ala Pro Glu Tyr
            260                 265                 270

Ala Tyr Lys Ile Val Lys Lys Gly Asp Ser Ala Ile Met Lys Ser Glu
        275                 280                 285

Leu Glu Tyr Gly Asn Cys Asn Thr Lys Cys Gln Thr Pro Met Gly Ala
    290                 295                 300

Ile Asn Ser Ser Met Pro Phe His Asn Ile His Pro Leu Thr Ile Gly
305                 310                 315                 320

Glu Cys Pro Lys Tyr Val Lys Ser Asn Arg Leu Val Leu Ala Thr Gly
                325                 330                 335

Leu Arg Asn Ser Pro Gln Arg Glu Ser Arg Arg Lys Lys Arg Gly Leu
            340                 345                 350

```
Phe Gly Ala Ile Ala Gly Phe Ile Glu Gly Gly Trp Gln Gly Met Val
            355                 360                 365
Asp Gly Trp Tyr Gly Tyr His His Ser Asn Glu Gln Gly Ser Gly Tyr
        370                 375                 380
Ala Ala Asp Lys Glu Ser Thr Gln Lys Ala Ile Asp Gly Val Thr Asn
385                 390                 395                 400
Lys Val Asn Ser Ile Ile Asp Lys Met Asn Thr Gln Phe Glu Ala Val
            405                 410                 415
Gly Arg Glu Phe Asn Asn Leu Glu Arg Arg Ile Glu Asn Leu Asn Lys
        420                 425                 430
Lys Met Glu Asp Gly Phe Leu Asp Val Trp Thr Tyr Asn Ala Glu Leu
    435                 440                 445
Leu Val Leu Met Glu Asn Glu Arg Thr Leu Asp Phe His Asp Ser Asn
        450                 455                 460
Val Lys Asn Leu Tyr Asp Lys Val Arg Leu Gln Leu Arg Asp Asn Ala
465                 470                 475                 480
Lys Glu Leu Gly Asn Gly Cys Phe Glu Phe Tyr His Lys Cys Asp Asn
            485                 490                 495
Glu Cys Met Glu Ser Ile Arg Asn Gly Thr Tyr Asn Tyr Pro Gln Tyr
        500                 505                 510
Ser Glu Glu Ala Arg Leu Lys Arg Glu Glu Ile Ser Gly Val Lys Leu
    515                 520                 525
Glu Ser Ile Gly Thr Tyr Gln Ile Leu Ser Ile Tyr Ser Thr Val Ala
        530                 535                 540
Ser Ser Leu Ala Leu Ala Ile Met Met Ala Gly Leu Ser Leu Trp Met
545                 550                 555                 560
Cys Ser Asn Gly Ser Leu Gln Cys Arg Ile Cys Ile
            565                 570

<210> SEQ ID NO 29
<211> LENGTH: 570
<212> TYPE: PRT
<213> ORGANISM: Unknown
<220> FEATURE:
<223> OTHER INFORMATION: Vac2-hac-sph9-opt

<400> SEQUENCE: 29

Met Glu Thr Ile Ser Leu Ile Thr Ile Leu Leu Val Val Thr Ala Ser
1               5                   10                  15
Asn Ala Asp Gln Ile Cys Ile Gly Tyr His Ala Asn Asn Ser Thr Glu
            20                  25                  30
Gln Val Asp Thr Ile Met Glu Lys Asn Val Thr Val Thr His Ala Gln
        35                  40                  45
Asp Ile Leu Glu Lys Thr His Asn Gly Lys Leu Cys Asp Leu Asp Gly
    50                  55                  60
Val Lys Pro Leu Ile Leu Arg Asp Cys Ser Val Ala Gly Trp Leu Leu
65                  70                  75                  80
Gly Asn Pro Met Cys Asp Glu Phe Ile Asn Val Pro Glu Trp Ser Tyr
                85                  90                  95
Ile Val Glu Lys Ala Asn Pro Thr Asn Asp Leu Cys Tyr Pro Gly Ser
            100                 105                 110
Phe Asn Asp Tyr Glu Glu Leu Lys His Leu Leu Ser Arg Ile Asn His
        115                 120                 125
Phe Glu Lys Ile Gln Ile Ile Pro Lys Ser Ser Trp Ser Asp His Glu
    130                 135                 140
```

-continued

```
Ala Ser Ser Gly Val Ser Ser Ala Cys Pro Tyr Leu Gly Ser Pro Ser
145                 150                 155                 160

Phe Phe Arg Asn Val Val Trp Leu Ile Lys Asn Ser Thr Tyr Pro
            165                 170                 175

Thr Ile Lys Lys Ser Tyr Asn Asn Thr Asn Gln Glu Asp Leu Leu Val
            180                 185                 190

Leu Trp Gly Ile His His Pro Asn Asp Ala Ala Glu Gln Thr Arg Leu
            195                 200                 205

Tyr Gln Asn Pro Thr Thr Tyr Ile Ser Ile Gly Thr Ser Thr Leu Asn
            210                 215                 220

Gln Arg Leu Val Pro Lys Ile Ala Thr Arg Ser Lys Val Asn Gly Gln
225                 230                 235                 240

Ser Gly Arg Met Glu Phe Phe Trp Thr Ile Leu Lys Pro Asn Asp Ala
                245                 250                 255

Ile Asn Phe Glu Ser Asn Gly Asn Phe Ile Ala Pro Glu Tyr Ala Tyr
                260                 265                 270

Lys Ile Val Lys Lys Gly Asp Ser Ala Ile Met Lys Ser Glu Leu Glu
            275                 280                 285

Tyr Gly Asn Cys Asn Thr Lys Cys Gln Thr Pro Met Gly Ala Ile Asn
            290                 295                 300

Ser Ser Met Pro Phe His Asn Ile His Pro Leu Thr Ile Gly Glu Cys
305                 310                 315                 320

Pro Lys Tyr Val Lys Ser Asn Arg Leu Val Leu Ala Thr Gly Leu Arg
                325                 330                 335

Asn Ser Pro Gln Arg Glu Ser Arg Lys Lys Arg Gly Leu Phe Gly
                340                 345                 350

Ala Ile Ala Gly Phe Ile Glu Gly Gly Trp Gln Gly Met Val Asp Gly
            355                 360                 365

Trp Tyr Gly Tyr His His Ser Asn Glu Gln Gly Ser Gly Tyr Ala Ala
            370                 375                 380

Asp Lys Glu Ser Thr Gln Lys Ala Ile Asp Gly Val Thr Asn Lys Val
385                 390                 395                 400

Asn Ser Ile Ile Asp Lys Met Asn Thr Gln Phe Glu Ala Val Gly Arg
                405                 410                 415

Glu Phe Asn Asn Leu Glu Arg Arg Ile Glu Asn Leu Asn Lys Lys Met
                420                 425                 430

Glu Asp Gly Phe Leu Asp Val Trp Thr Tyr Asn Ala Glu Leu Leu Val
            435                 440                 445

Leu Met Glu Asn Glu Arg Thr Leu Asp Phe His Asp Ser Asn Val Lys
450                 455                 460

Asn Leu Tyr Asp Lys Val Arg Leu Gln Leu Arg Asp Asn Ala Lys Glu
465                 470                 475                 480

Leu Gly Asn Gly Cys Phe Glu Phe Tyr His Lys Cys Asp Asn Glu Cys
            485                 490                 495

Met Glu Ser Ile Arg Asn Gly Thr Tyr Asn Tyr Pro Gln Tyr Ser Glu
                500                 505                 510

Glu Ala Arg Leu Lys Arg Glu Glu Ile Ser Gly Val Lys Leu Glu Ser
            515                 520                 525

Ile Gly Thr Tyr Gln Ile Leu Ser Ile Tyr Ser Thr Val Ala Ser Ser
            530                 535                 540

Leu Ala Leu Ala Ile Met Met Ala Gly Leu Ser Leu Trp Met Cys Ser
545                 550                 555                 560

Asn Gly Ser Leu Gln Cys Arg Ile Cys Ile
                565                 570
```

<210> SEQ ID NO 30
<211> LENGTH: 564
<212> TYPE: PRT
<213> ORGANISM: Unknown
<220> FEATURE:
<223> OTHER INFORMATION: Vac2-hac-cs-opt

<400> SEQUENCE: 30

```
Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Leu Gly Ser Pro Ser Phe Phe
145                 150                 155                 160

Arg Asn Val Val Trp Leu Ile Lys Lys Asn Ser Thr Tyr Pro Thr Ile
                165                 170                 175

Lys Lys Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Ile Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Ser Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365
```

```
Ser Asn Glu Gln Gly Ser Gly Tyr Ala Ala Asp Lys Glu Ser Thr Gln
            370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
                420                 425                 430

Val Trp Thr Tyr Asn Ala Glu Leu Leu Val Leu Met Glu Asn Glu Arg
            435                 440                 445

Thr Leu Asp Phe His Asp Ser Asn Val Lys Asn Leu Tyr Asp Lys Val
            450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Ile Arg Asn
                485                 490                 495

Gly Thr Tyr Asn Tyr Pro Gln Tyr Ser Glu Ala Arg Leu Lys Arg
            500                 505                 510

Glu Glu Ile Ser Gly Val Lys Leu Glu Ser Ile Gly Thr Tyr Gln Ile
            515                 520                 525

Leu Ser Ile Tyr Ser Thr Val Ala Ser Ser Leu Ala Leu Ala Ile Met
            530                 535                 540

Met Ala Gly Leu Ser Leu Trp Met Cys Ser Asn Gly Ser Leu Gln Cys
545                 550                 555                 560

Arg Ile Cys Ile

<210> SEQ ID NO 31
<211> LENGTH: 449
<212> TYPE: PRT
<213> ORGANISM: Unknown
<220> FEATURE:
<223> OTHER INFORMATION: Vac2-naj-opt

<400> SEQUENCE: 31

Met Asn Pro Asn Gln Lys Ile Ile Thr Ile Gly Ser Ile Cys Met Val
1               5                   10                  15

Ile Gly Ile Val Ser Leu Met Leu Gln Ile Gly Asn Met Ile Ser Ile
                20                  25                  30

Trp Val Ser His Ser Ile Gln Thr Gly Asn Gln His Gln Ala Glu Ser
            35                  40                  45

Ile Ser Asn Thr Asn Pro Leu Thr Glu Lys Ala Val Ala Ser Val Thr
50                  55                  60

Leu Ala Gly Asn Ser Ser Leu Cys Pro Ile Arg Gly Trp Ala Val His
65                  70                  75                  80

Ser Lys Asp Asn Asn Ile Arg Ile Gly Ser Lys Gly Asp Val Phe Val
                85                  90                  95

Ile Arg Glu Pro Phe Ile Ser Cys Ser His Leu Glu Cys Arg Thr Phe
                100                 105                 110

Phe Leu Thr Gln Gly Ala Leu Leu Asn Asp Lys His Ser Asn Gly Thr
            115                 120                 125

Val Lys Asp Arg Ser Pro His Arg Thr Leu Met Ser Cys Pro Val Gly
130                 135                 140

Glu Ala Pro Ser Pro Tyr Asn Ser Arg Phe Glu Ser Val Ala Trp Ser
145                 150                 155                 160

Ala Ser Ala Cys His Asp Gly Thr Ser Trp Leu Thr Ile Gly Ile Ser
                165                 170                 175
```

```
Gly Pro Asp Asn Glu Ala Val Ala Val Leu Lys Tyr Asn Gly Ile Ile
            180                 185                 190

Thr Asp Thr Ile Lys Ser Trp Arg Asn Asn Ile Leu Arg Thr Gln Glu
        195                 200                 205

Ser Glu Cys Ala Cys Val Asn Gly Ser Cys Phe Thr Val Met Thr Asp
210                 215                 220

Gly Pro Ser Asp Gly Gln Ala Ser Tyr Lys Ile Phe Lys Met Glu Lys
225                 230                 235                 240

Gly Lys Val Val Lys Ser Val Glu Leu Asp Ala Pro Asn Tyr His Tyr
                245                 250                 255

Glu Glu Cys Ser Cys Tyr Pro Asp Ala Gly Glu Ile Thr Cys Val Cys
            260                 265                 270

Arg Asp Asn Trp His Gly Ser Asn Arg Pro Trp Val Ser Phe Asn Gln
        275                 280                 285

Asn Leu Glu Tyr Gln Ile Gly Tyr Ile Cys Ser Gly Val Phe Gly Asp
290                 295                 300

Asn Pro Arg Pro Asn Asp Gly Thr Gly Ser Cys Gly Pro Met Ser Pro
305                 310                 315                 320

Asn Gly Ala Tyr Gly Val Lys Gly Phe Ser Phe Lys Tyr Gly Asn Gly
                325                 330                 335

Val Trp Ile Gly Arg Thr Lys Ser Thr Asn Ser Arg Ser Gly Phe Glu
            340                 345                 350

Met Ile Trp Asp Pro Asn Gly Trp Thr Gly Thr Asp Ser Ser Phe Ser
        355                 360                 365

Val Lys Gln Asp Ile Val Ala Ile Thr Asp Trp Ser Gly Tyr Ser Gly
370                 375                 380

Ser Phe Val Gln His Pro Glu Leu Thr Gly Leu Asp Cys Ile Arg Pro
385                 390                 395                 400

Cys Phe Trp Val Glu Leu Ile Arg Gly Arg Pro Lys Glu Ser Thr Ile
                405                 410                 415

Trp Thr Ser Gly Ser Ser Ile Ser Phe Cys Gly Val Asn Ser Asp Thr
            420                 425                 430

Val Ser Trp Ser Trp Pro Asp Gly Ala Glu Leu Pro Phe Thr Ile Asp
        435                 440                 445

Lys

<210> SEQ ID NO 32
<211> LENGTH: 252
<212> TYPE: PRT
<213> ORGANISM: Unknown
<220> FEATURE:
<223> OTHER INFORMATION: Vac2-mc-opt

<400> SEQUENCE: 32

Met Ser Leu Leu Thr Glu Val Glu Thr Tyr Val Leu Ser Ile Ile Pro
1               5                   10                  15

Ser Gly Pro Leu Lys Ala Glu Ile Ala Gln Lys Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Arg Ala
```

85 90 95

Val Lys Leu Tyr Lys Lys Leu Lys Arg Glu Ile Thr Phe His Gly Ala
100 105 110

Lys Glu Val Ser Leu Ser Tyr Ser Thr Gly Ala Leu Ala Ser Cys Met
115 120 125

Gly Leu Ile Tyr Asn Arg Met Gly Thr Val Thr Thr Glu Val Ala Phe
130 135 140

Gly Leu Val Cys Ala Thr Cys Glu Gln Ile Ala Asp Ser Gln His Arg
145 150 155 160

Ser His Arg Gln Met Ala Thr Ile Thr Asn Pro Leu Ile Arg His Glu
165 170 175

Asn Arg Met Val Leu Ala Ser Thr Thr Ala Lys Ala Met Glu Gln Met
180 185 190

Ala Gly Ser Ser Glu Gln Ala Ala Glu Ala Met Glu Val Ala Asn Gln
195 200 205

Ala Arg Gln Met Val Gln Ala Met Arg Thr Ile Gly Thr His Pro Asn
210 215 220

Ser Ser Ala Gly Leu Arg Asp Asn Leu Leu Glu Asn Leu Gln Ala Tyr
225 230 235 240

Gln Lys Arg Met Gly Val Gln Met Gln Arg Phe Lys
245 250

<210> SEQ ID NO 33
<211> LENGTH: 564
<212> TYPE: PRT
<213> ORGANISM: Unknown
<220> FEATURE:
<223> OTHER INFORMATION: VN1203-ha-cs-opt

<400> SEQUENCE: 33

Met Glu Lys Ile Val Leu Leu Phe Ala Ile Val Ser Leu Val Lys Ser
1 5 10 15

Asp Gln Ile Cys Ile Gly Tyr His Ala Asn Asn Ser Thr Glu Gln Val
20 25 30

Asp Thr Ile Met Glu Lys Asn Val Thr Val Thr His Ala Gln Asp Ile
35 40 45

Leu Glu Lys Thr His Asn Gly Lys Leu Cys Asp Leu Asp Gly Val Lys
50 55 60

Pro Leu Ile Leu Arg Asp Cys Ser Val Ala Gly Trp Leu Leu Gly Asn
65 70 75 80

Pro Met Cys Asp Glu Phe Ile Asn Val Pro Glu Trp Ser Tyr Ile Val
85 90 95

Glu Lys Ala Asn Pro Ala Asn Asp Leu Cys Tyr Pro Gly Asp Phe Asn
100 105 110

Asp Tyr Glu Glu Leu Lys His Leu Leu Ser Arg Ile Asn His Phe Glu
115 120 125

Lys Ile Gln Ile Ile Pro Lys Asn Ser Trp Ser Ser His Glu Ala Ser
130 135 140

Leu Gly Val Ser Ser Ala Cys Pro Tyr Gln Gly Lys Ser Ser Phe Phe
145 150 155 160

Arg Asn Val Val Trp Leu Ile Lys Lys Asn Asn Ala Tyr Pro Thr Ile
165 170 175

Lys Arg Ser Tyr Asn Asn Thr Asn Gln Glu Asp Leu Leu Val Leu Trp
180 185 190

Gly Ile His His Pro Asn Asp Ala Ala Glu Gln Thr Arg Leu Tyr Gln
195 200 205

Asn Pro Thr Thr Tyr Ile Ser Val Gly Thr Ser Thr Leu Asn Gln Arg
        210                 215                 220

Leu Val Pro Lys Ile Ala Thr Arg Ser Lys Val Asn Gly Gln Asn Gly
225                 230                 235                 240

Arg Met Glu Phe Phe Trp Thr Ile Leu Lys Pro Asn Asp Ala Ile Asn
            245                 250                 255

Phe Glu Ser Asn Gly Asn Phe Ile Ala Pro Glu Tyr Ala Tyr Lys Ile
        260                 265                 270

Val Lys Lys Gly Asp Ser Ala Ile Met Lys Ser Glu Leu Glu Tyr Gly
    275                 280                 285

Asn Cys Asn Thr Lys Cys Gln Thr Pro Met Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Gln Tyr Ser Glu Glu Ala Arg Leu Lys Arg
            500                 505                 510

Glu Glu Ile Ser Gly Val Lys Leu Glu Ser Ile Gly Thr Tyr Gln Ile
        515                 520                 525

Leu Ser Ile Tyr Ser Thr Val Ala Ser Ser Leu Ala Leu Ala Ile Met
530                 535                 540

Val Ala Gly Leu Ser Leu Trp Met Cys Ser Asn Gly Ser Leu Gln Cys
545                 550                 555                 560

Arg Ile Cys Ile

<210> SEQ ID NO 34
<211> LENGTH: 572
<212> TYPE: PRT
<213> ORGANISM: Unknown
<220> FEATURE:
<223> OTHER INFORMATION: VN1203-ha-spc-opt

<400> SEQUENCE: 34

Met Pro Leu Tyr Lys Leu Leu Asn Val Leu Trp Le

-continued

```
1               5                   10                  15
Asn Ala Ile Pro Asp Gln Ile Cys Ile Gly Tyr His Ala Asn Asn Ser
                20                  25                  30

Thr Glu Gln Val Asp Thr Ile Met Glu Lys Asn Val Thr Val Thr His
                35                  40                  45

Ala Gln Asp Ile Leu Glu Lys Thr His Asn Gly Lys Leu Cys Asp Leu
    50                  55                  60

Asp Gly Val Lys Pro Leu Ile Leu Arg Asp Cys Ser Val Ala Gly Trp
65                  70                  75                  80

Leu Leu Gly Asn Pro Met Cys Asp Glu Phe Ile Asn Val Pro Glu Trp
                85                  90                  95

Ser Tyr Ile Val Glu Lys Ala Asn Pro Ala Asn Asp Leu Cys Tyr Pro
                100                 105                 110

Gly Asp Phe Asn Asp Tyr Glu Glu Leu Lys His Leu Leu Ser Arg Ile
                115                 120                 125

Asn His Phe Glu Lys Ile Gln Ile Ile Pro Lys Asn Ser Trp Ser Ser
                130                 135                 140

His Glu Ala Ser Leu Gly Val Ser Ser Ala Cys Pro Tyr Gln Gly Lys
145                 150                 155                 160

Ser Ser Phe Phe Arg Asn Val Val Trp Leu Ile Lys Lys Asn Asn Ala
                165                 170                 175

Tyr Pro Thr Ile Lys Arg Ser Tyr Asn Asn Thr Asn Gln Glu Asp Leu
                180                 185                 190

Leu Val Leu Trp Gly Ile His His Pro Asn Asp Ala Ala Glu Gln Thr
                195                 200                 205

Arg Leu Tyr Gln Asn Pro Thr Thr Tyr Ile Ser Val Gly Thr Ser Thr
    210                 215                 220

Leu Asn Gln Arg Leu Val Pro Lys Ile Ala Thr Arg Ser Lys Val Asn
225                 230                 235                 240

Gly Gln Asn Gly Arg Met Glu Phe Phe Trp Thr Ile Leu Lys Pro Asn
                245                 250                 255

Asp Ala Ile Asn Phe Glu Ser Asn Gly Asn Phe Ile Ala Pro Glu Tyr
                260                 265                 270

Ala Tyr Lys Ile Val Lys Lys Gly Asp Ser Ala Ile Met Lys Ser Glu
                275                 280                 285

Leu Glu Tyr Gly Asn Cys Asn Thr Lys Cys Gln Thr Pro Met Gly Ala
                290                 295                 300

Ile Asn Ser Ser Met Pro Phe His Asn Ile His Pro Leu Thr Ile Gly
305                 310                 315                 320

Glu Cys Pro Lys Tyr Val Lys Ser Asn Arg Leu Val Leu Ala Thr Gly
                325                 330                 335

Leu Arg Asn Ser Pro Gln Arg Glu Arg Arg Lys Lys Arg Gly Leu
                340                 345                 350

Phe Gly Ala Ile Ala Gly Phe Ile Glu Gly Gly Trp Gln Gly Met Val
                355                 360                 365

Asp Gly Trp Tyr Gly Tyr His His Ser Asn Glu Gln Gly Ser Gly Tyr
                370                 375                 380

Ala Ala Asp Lys Glu Ser Thr Gln Lys Ala Ile Asp Gly Val Thr Asn
385                 390                 395                 400

Lys Val Asn Ser Ile Ile Asp Lys Met Asn Thr Gln Phe Glu Ala Val
                405                 410                 415

Gly Arg Glu Phe Asn Asn Leu Glu Arg Arg Ile Glu Asn Leu Asn Lys
                420                 425                 430
```

Lys Met Glu Asp Gly Phe Leu Asp Val Trp Thr Tyr Asn Ala Glu Leu
              435                 440                 445

Leu Val Leu Met Glu Asn Glu Arg Thr Leu Asp Phe His Asp Ser Asn
450                 455                 460

Val Lys Asn Leu Tyr Asp Lys Val Arg Leu Gln Leu Arg Asp Asn Ala
465                 470                 475                 480

Lys Glu Leu Gly Asn Gly Cys Phe Glu Phe Tyr His Lys Cys Asp Asn
              485                 490                 495

Glu Cys Met Glu Ser Val Arg Asn Gly Thr Tyr Asp Tyr Pro Gln Tyr
              500                 505                 510

Ser Glu Glu Ala Arg Leu Lys Arg Glu Glu Ile Ser Gly Val Lys Leu
              515                 520                 525

Glu Ser Ile Gly Thr Tyr Gln Ile Leu Ser Ile Tyr Ser Thr Val Ala
              530                 535                 540

Ser Ser Leu Ala Leu Ala Ile Met Val Ala Gly Leu Ser Leu Trp Met
545                 550                 555                 560

Cys Ser Asn Gly Ser Leu Gln Cys Arg Ile Cys Ile
              565                 570

<210> SEQ ID NO 35
<211> LENGTH: 570
<212> TYPE: PRT
<213> ORGANISM: Unknown
<220> FEATURE:
<223> OTHER INFORMATION: VN1203-ha-sph9-opt

<400> SEQUENCE: 35

Met Glu Thr Ile Ser Leu Ile Thr Ile Leu Leu Val Val Thr Ala Ser
1               5                   10                  15

Asn Ala Asp Gln Ile Cys Ile Gly Tyr His Ala Asn Asn Ser Thr Glu
                20                  25                  30

Gln Val Asp Thr Ile Met Glu Lys Asn Val Thr Val Thr His Ala Gln
            35                  40                  45

Asp Ile Leu Glu Lys Thr His Asn Gly Lys Leu Cys Asp Leu Asp Gly
        50                  55                  60

Val Lys Pro Leu Ile Leu Arg Asp Cys Ser Val Ala Gly Trp Leu Leu
65                  70                  75                  80

Gly Asn Pro Met Cys Asp Glu Phe Ile Asn Val Pro Glu Trp Ser Tyr
                85                  90                  95

Ile Val Glu Lys Ala Asn Pro Ala Asn Asp Leu Cys Tyr Pro Gly Asp
            100                 105                 110

Phe Asn Asp Tyr Glu Glu Leu Lys His Leu Leu Ser Arg Ile Asn His
        115                 120                 125

Phe Glu Lys Ile Gln Ile Ile Pro Lys Asn Ser Trp Ser Ser His Glu
130                 135                 140

Ala Ser Leu Gly Val Ser Ser Ala Cys Pro Tyr Gln Gly Lys Ser Ser
145                 150                 155                 160

Phe Phe Arg Asn Val Val Trp Leu Ile Lys Lys Asn Asn Ala Tyr Pro
                165                 170                 175

Thr Ile Lys Arg Ser Tyr Asn Asn Thr Asn Gln Glu Asp Leu Leu Val
            180                 185                 190

Leu Trp Gly Ile His His Pro Asn Asp Ala Ala Glu Gln Thr Arg Leu
        195                 200                 205

Tyr Gln Asn Pro Thr Thr Tyr Ile Ser Val Gly Thr Ser Thr Leu Asn
    210                 215                 220

Gln Arg Leu Val Pro Lys Ile Ala Thr Arg Ser Lys Val Asn Gly Gln

```
            225                 230                 235                 240
Asn Gly Arg Met Glu Phe Phe Trp Thr Ile Leu Lys Pro Asn Asp Ala
                245                 250                 255
Ile Asn Phe Glu Ser Asn Gly Asn Phe Ile Ala Pro Glu Tyr Ala Tyr
            260                 265                 270
Lys Ile Val Lys Lys Gly Asp Ser Ala Ile Met Lys Ser Glu Leu Glu
        275                 280                 285
Tyr Gly Asn Cys Asn Thr Lys Cys Gln Thr Pro Met Gly Ala Ile Asn
    290                 295                 300
Ser Ser Met Pro Phe His Asn Ile His Pro Leu Thr Ile Gly Glu Cys
305                 310                 315                 320
Pro Lys Tyr Val Lys Ser Asn Arg Leu Val Leu Ala Thr Gly Leu Arg
                325                 330                 335
Asn Ser Pro Gln Arg Glu Arg Arg Lys Lys Arg Gly Leu Phe Gly
            340                 345                 350
Ala Ile Ala Gly Phe Ile Glu Gly Gly Trp Gln Gly Met Val Asp Gly
        355                 360                 365
Trp Tyr Gly Tyr His His Ser Asn Glu Gln Gly Ser Gly Tyr Ala Ala
    370                 375                 380
Asp Lys Glu Ser Thr Gln Lys Ala Ile Asp Gly Val Thr Asn Lys Val
385                 390                 395                 400
Asn Ser Ile Ile Asp Lys Met Asn Thr Gln Phe Glu Ala Val Gly Arg
                405                 410                 415
Glu Phe Asn Asn Leu Glu Arg Arg Ile Glu Asn Leu Asn Lys Lys Met
            420                 425                 430
Glu Asp Gly Phe Leu Asp Val Trp Thr Tyr Asn Ala Glu Leu Leu Val
        435                 440                 445
Leu Met Glu Asn Glu Arg Thr Leu Asp Phe His Asp Ser Asn Val Lys
    450                 455                 460
Asn Leu Tyr Asp Lys Val Arg Leu Gln Leu Arg Asp Asn Ala Lys Glu
465                 470                 475                 480
Leu Gly Asn Gly Cys Phe Glu Phe Tyr His Lys Cys Asp Asn Glu Cys
                485                 490                 495
Met Glu Ser Val Arg Asn Gly Thr Tyr Asp Tyr Pro Gln Tyr Ser Glu
            500                 505                 510
Glu Ala Arg Leu Lys Arg Glu Glu Ile Ser Gly Val Lys Leu Glu Ser
        515                 520                 525
Ile Gly Thr Tyr Gln Ile Leu Ser Ile Tyr Ser Thr Val Ala Ser Ser
    530                 535                 540
Leu Ala Leu Ala Ile Met Val Ala Gly Leu Ser Leu Trp Met Cys Ser
545                 550                 555                 560
Asn Gly Ser Leu Gln Cys Arg Ile Cys Ile
                565                 570

<210> SEQ ID NO 36
<211> LENGTH: 1707
<212> TYPE: DNA
<213> ORGANISM: Influenza virus

<400> SEQUENCE: 36
atggagaaaa tagtgcttct ttttgcaata gtcagtcttg ttaaaagtga tcagatttgc      60
attggttacc atgcaaacaa ctcgacagag caggttgaca caataatgga aaagaacgtt     120
actgttacac atgcccaaga catactggaa aagaaacaca cgggaagct ctgcgatcta     180 gatggagtga agcctctaat tttgagagat tgtagcgtag ctggatggct cctcggaaac     240
```

```
ccaatgtgtg acgaattcat caatgtgccg gaatggtctt acatagtgga gaaggccaat      300
ccagtcaatg acctctgtta cccaggggat ttcaatgact atgaagaatt gaaacaccta      360
ttgagcagaa taaccatttt tgagaaaatt cagatcatcc ccaaaagttc ttggtccagt      420
catgaagcct cattaggggt gagctcagca tgtccatacc agggaaagtc ctcctttttc      480
agaaatgtgg tatggcttat caaaaagaac agtacatacc caacaataaa gaggagctac      540
aataatacca accaagaaga tcttttggta ctgtgggga ttcaccatcc taatgatgcg       600
gcagagcaga caaagctcta tcaaaaccca accacctata tttccgttgg acatcaaca      660 ctaaaccaga gattggtacc aagaatagct actagatcca agtaaacgg gcaaagtgga      720 aggatgggagt tcttctggac aattttaaag ccgaatgatg caatcaactt cgagagtaat     780
ggaaatttca ttgctccaga atatgcatac aaaattgtca agaaggggga ctcaacaatt     840
atgaaaagtg aattggaata tggtaactgc aacaccaagt gtcaaactcc aatggggcg     900 ataaactcta gcatgccatt ccacaatata caccctctca ccattgggga atgccccaaa    960
tatgtgaaat caaacagatt agtccttgcg actgggctca gaaatagccc tcaaagagag   1020
agaagaagaa aaaagagagg attatttgga gctatagcag gttttataga gggaggatgg    1080
cagggaatgg tagatggttg gtatgggtac caccatagca atgagcaggg gagtgggtac    1140
gctgcagaca agaatccact caaaaggca atagatggag tcaccaataa ggtcaactcg    1200
atcattgaca aaatgaacac tcagtttgag gccgttggaa gggaatttaa caacttagaa     1260
aggagaatag agaattttaaa caagaagatg gaagacggg tcctagatgt ctggacttat    1320
aatgctgaac ttctggttct catggaaaat gagagaactc tagactttca tgactcaaat    1380
gtcaagaacc tttacgacaa ggtccgacta cagcttaggg ataatgcaaa ggagctgggt    1440
aacggttgtt tcgagttcta tcataaatgt gataatgaat gtatggaaag tgtaagaaat    1500
ggaacgtatg actacccgca gtattcagaa gaagcgagac taaaaagaga ggaaataagt    1560
ggagtaaaat tggaatcaat aggaatttac caaatactgt caatttattc tacagtggcg    1620
agttccctag cactggcaat catggtagct ggtctatcct tatggatgtg ctccaatgga     1680
tcgttacaat gcagaatttg catttaa                                         1707
```

<210> SEQ ID NO 37
<211> LENGTH: 1750
<212> TYPE: DNA
<213> ORGANISM: Influenza virus

<400> SEQUENCE: 37

```
agtgtgatgg atatctgcag aattcgccct taggcgcgcc atggagaaaa tagtgcttct      60
ttttgcaata gtcagtcttg ttaaaagtga tcagatttgc attggttacc atgcaaacaa     120
ctcgacagag caggttgaca caataatgga aaagaacgtt actgttacac atgcccaaga     180
catactggaa aagaaacaca cgggaagct ctgcgatcta gatggagtga agcctctaat     240
tttgagagat tgtagcgtag ctggatggcc cctcggaaac ccaatgtgtg acgaattcat     300
caatgtgccg gaatggtctt acatagtgga gaaggccaat ccagtcaatg acctctgtta    360
cccaggggat ttcaatgact atgaagaatt gaaacaccta ttgagcagaa taaccatttt    420
tgagaaaatt cagatcatcc ccaaaagttc ttggtccagt catgaagcct cattaggggt    480
gagctcagca tgtccatacc agggaaagtc ctcctttttc agaaatgtgg tatggcttat    540
caaaaagaac agtacatacc caacaataaa gaggagctac aataatacca accaagaaga    600
tcttttggta ctgtgggga ttcaccatcc taatgatgcg gcagagcaga caaagctcta    660
```

| | |
|---|---|
| tcaaaaccca accacctata tttccgttgg gacatcaaca ctaaaccaga gattggtacc | 720 |
| aagaatagct actagatcca aagtaaacgg gcaaagtgga aggatggagt tcttctggac | 780 |
| aattttaaag ccgaatgatg caatcaactt cgagagtaat ggaaatttca ttgctccaga | 840 |
| atatgcatac aaaattgtca agaaagggga ctcaacaatt atgaaaagtg aattggaata | 900 |
| tggtaactgc aacaccaagt gtcaaactcc aatgggggcg ataaactcta gcatgccatt | 960 |
| ccacaatata caccctctca ccattgggga atgccccaaa tatgtgaaat caaacagatt | 1020 |
| agtccttgcg actgggctca gaaatagccc tcaaagagag agaagaagaa aaagagagg | 1080 |
| attatttgga gctatagcag gttttataga gggaggatgg cagggaatgg tagatggttg | 1140 |
| gtatgggtac caccatagca atgagcaggg gagtgggtac gctgcagaca agaatccac | 1200 |
| tcaaaaggca atagatggag tcaccaataa ggtcaactcg atcattgaca aaatgaacac | 1260 |
| tcagtttgag gccgtggaa gggaatttaa caacttagaa aggagaatag agaatttaaa | 1320 |
| caagaagatg gaagacgggt tcctagatgt ctggacttat aatgctgaac ttctggttct | 1380 |
| catggaaaat gagagaactc tagactttca tgactcaaat gtcaagaacc tttacgacaa | 1440 |
| ggtccgacta cagcttaggg ataatgcaaa ggagctgggg aacggttgtt tcgagttcta | 1500 |
| tcataaatgt gataatgaat gtatggaaag tgtaagaaat ggaacgtatg actacccgca | 1560 |
| gtattcagaa gaagcgagac taaaagaga ggaaataagt ggagtaaaat ggaatcaat | 1620 |
| aggaatttac caaatactgt caatttattc tacagtggcg agttccctag cactggcaat | 1680 |
| catggtagct ggtctatcct tatggatgtg ctccaatggg tcgttacaat gcagaatttg | 1740 |
| catttaagcg | 1750 |

<210> SEQ ID NO 38
<211> LENGTH: 1350
<212> TYPE: DNA
<213> ORGANISM: Influenza virus

<400> SEQUENCE: 38

| | |
|---|---|
| atgaatccaa atcagaagat aataaccatc ggatcaatct gtatggtaac tggaatagtt | 60 |
| agcttaatgt tacaaattgg gaacatgatc tcaatatggg tcagtcattc aattcacaca | 120 |
| gggaatcaac accaatctga accaatcagc aatactaatt ttcttactga gaaagctgtg | 180 |
| gcttcagtaa aattagcggg caattcatct ctttgcccca ttaacggatg gctgtatac | 240 |
| agtaaggaca cagtataag gatcggttcc aaggggatg tgtttgttat aagagagccg | 300 |
| ttcatctcat gctcccactt ggaatgcaga actttctttt tgactcaggg agccttgctg | 360 |
| aatgacaagc actccaatgg gactgtcaaa gacagaagcc ctcacagaac attaatgagt | 420 |
| tgtcctgtgg gtgaggctcc ctccccatat aactcaaggt ttgagtctgt tgcttggtca | 480 |
| gcaagtgctt gccatgatgg caccagttgg ttgacgattg gaatttctgg cccagacaat | 540 |
| ggggctgtgg ctgtattgaa atacaatggc ataataacag acactatcaa gagttggagg | 600 |
| aacaacatac tgagaactca agagtctgaa tgtgcatgtg taaatggctc ttgctttact | 660 |
| gtaatgactg acggaccaag taatggtcag gcatcacata gatcttcaa aatggaaaaa | 720 |
| gggaaagtgg ttaaatcagt cgaattggat gctcctaatt atcactatga ggaatgctcc | 780 |
| tgttatccta atgccggaga atcacatgt gtgtgcaggg ataattggca tggctcaaat | 840 |
| cggccatggg tatctttcaa tcaaaatttg gagtatcaaa taggatatat atgcagtgga | 900 |
| gttttcggag acaatccacg ccccaatgat ggaacaggta ttgtggtcc ggtgtcctct | 960 |
| aacgggggcat atggggtaaa agggttttca tttaaatacg gcaatggtgt ctggatcggg | 1020 |

| | |
|---|---:|
| agaaccaaaa gcactaattc caggagcggc tttgaaatga tttgggatcc aaatgggtgg | 1080 |
| actgaaacgg acagtagctt ttcagtgaaa caagatatcg tagcaataac tgattggtca | 1140 |
| ggatatagcg ggagttttgt ccagcatcca gaactgacag gactagattg cataagacct | 1200 |
| tgtttctggg ttgagttgat cagagggcgg cccaaagaga gcacaatttg gactagtggg | 1260 |
| agcagcatat cttttttgtgg tgtaaatagt gacactgtgg gttggtcttg gccagacggt | 1320 |
| gccgagttgc cattcaccat tgacaagtag | 1350 |

<210> SEQ ID NO 39
<211> LENGTH: 1400
<212> TYPE: DNA
<213> ORGANISM: Influenza virus

<400> SEQUENCE: 39

| | |
|---|---:|
| ccgggatgaa tccaaatcag aagataataa ccatcggatc aatctgtatg gtaactggaa | 60 |
| tagttagctt aatgttacaa attgggaaca tgatctcaat atgggtcagt cattcaattc | 120 |
| acacagggaa tcaacaccaa tctgaaccaa tcagcaatac taattttctt actgagaaag | 180 |
| ctgtggcttc agtaaaatta gcgggcaatt catctctttg ccccattaac ggatgggctg | 240 |
| tatacagtaa ggacaacagt ataaggatcg gttccaaggg ggatgtgttt gttataagag | 300 |
| agccgttcat ctcatgctcc cacttggaat gcagaacttt cttttgact cagggagcct | 360 |
| cgctgaatga caagcactcc aatgggactg tcaaagacag aagccctcac agaacattaa | 420 |
| tgagttgtcc tgtgggtgag gctccctccc catataactc aaggtttgag tctgttgctt | 480 |
| ggtcagcaag tgcttgccat gatggcacca gttggttgac gattggaatt tctggcccag | 540 |
| acaatggggt gtggctgta ttgaaataca atggcataat aacagacact atcaagagtt | 600 |
| ggaggaacaa catactgaga actcaagagt ctgaatgtgc atgtgtaaat ggctcttgct | 660 |
| ttactgtaat gactgacgga ccaagtaatg gtcaggcatc acataagatc ttcaaaatgg | 720 |
| aaaaagggaa agtggttaaa tcagtcgaat ggatgctcc taattatcac tatgaggaat | 780 |
| gctcctgtta tcctaatgcc ggagaaatca catgtgtgtg cagggataat tggcatggct | 840 |
| caaatcggcc atgggtatct ttcaatcaaa atttggagta tcaaatagga tatatatgca | 900 |
| gtggagtttt cggagacaat ccacgcccca atgatggaac aggtagttgt ggtccggtgt | 960 |
| cctctaacgg ggcatatggg gtaaaagggt tttcatttaa atacggcaat ggtgtctgga | 1020 |
| tcgggagaac caaaagcact aattccagga gcggctttga aatgatttgg gatccaaatg | 1080 |
| ggtggactga aacggacagt agcttttcag tgaaacaaga tatcgtagca ataactgatt | 1140 |
| ggtcaggata tagcgggagt tttgtccagc atccagaact gacaggacta gattgcataa | 1200 |
| gaccttgttt ctgggttgag ttgatcagag ggcggcccaa agagagcaca atttggacta | 1260 |
| gtgggagcag catatctttt tgtgtgtaa atagtgacac tgtgggttgg tcttggccag | 1320 |
| acggtgctga gttgccattc accattgaca gtagggggcc ctcgagtaag ggcgaattcc | 1380 |
| agcacactgg cggccgttac | 1400 |

<210> SEQ ID NO 40
<211> LENGTH: 759
<212> TYPE: DNA
<213> ORGANISM: Influenza virus

<400> SEQUENCE: 40

| | |
|---|---:|
| atgagtcttc taaccgaggt cgaaacgtac gttctctcta tcatcccgtc aggccccctc | 60 |
| aaagccgaga tcgcacagaa acttgaagat gtctttgcag gaaagaacac cgatctcgag | 120 |

-continued

```
gctctcatgg agtggctaaa gacaagacca atcctgtcac ctctgactaa agggattttg      180
ggatttgtat tcacgctcac cgtgcccagt gagcgaggac tgcagcgtag acgctttgtc      240
cagaatgccc taaatggaaa tggagatcca aataatatgg atagggcagt taagctatat      300
aagaagctga aaagagaaat aacattccat ggggctaagg aggtcgcact cagctactca      360
accggtgcac ttgccagttg catgggtctc atatacaaca ggatgggaac ggtgactacg      420
gaagtggctt ttggcctagt gtgtgccact tgtgagcaga ttgcagattc acagcatcgg      480
tctcacagac agatggcaac tatcaccaac ccactaatca gacatgagaa cagaatggtg      540
ctggccagca ctacagctaa ggctatggag cagatggcgg gatcaagtga gcaggcagcg      600
gaagccatgg agatcgctaa tcaggctagg cagatggtgc aggcaatgag gcaattgggg      660
actcatccta actctagtgc tggtctgaga gataatcttc ttgaaaattt gcaggcctac      720
cagaaacgaa tgggagtgca gatgcagcga ttcaagtga                            759

<210> SEQ ID NO 41
<211> LENGTH: 793
<212> TYPE: DNA
<213> ORGANISM: Influenza virus

<400> SEQUENCE: 41
atatctgcag aattcgccct tagaattcga cgtcatgagt cttctaaccg aggtcgaaac       60
gtacgttctc tctatcatcc cgtcaggccc cctcaaagcc gagatcgcac agaaacttga      120
agatgtcttt gcaggaaaga acaccgatct cgaggctctc atggagtggc taaagacaag      180
accaatcctg tcacctctga ctaaagggat tttgggattt gtattcacgc tcaccgtgcc      240
cagtgagcga ggactgcagc gtagacgctt tgtccagaat gccctaaatg gaaatggaga      300
tccaaataat atggataggg cagttaagct atataagaag ctgaaaagag aaataacatt      360
ccatggggct aaggaggtcg cactcagcta ctcaaccggt gcacttgcca gttgcatggg      420
tctcatatac aacaggatgg gaacggtgac tacggaagtg gcttttggcc tagtgtgtgc      480
cacttgtgag cagattgcag attcacagca tcggtctcac agacagatgg caactatcac      540
caacccacta atcagacatg agaacagaat ggtgctggcc agcactacag ctaaggctat      600
ggagcagatg gcgggatcaa gtgagcaggc agcggaagcc atggagatcg ctaatcaggc      660
taggcagatg gtgcaggcaa tgaggacaat tggggactcat cctaactcta gtgctggtct      720
gagagataat cttcttgaaa atttgcaggc ctaccagaaa cgaatgggag tgcagatgca      780
gcgattcaag tga                                                        793

<210> SEQ ID NO 42
<211> LENGTH: 1740
<212> TYPE: DNA
<213> ORGANISM: Artificial sequence
<220> FEATURE:
<223> OTHER INFORMATION: Influenza HA gene optimized for expression in
      insect cell expression system

<400> SEQUENCE: 42
ggtaccggat ccgccaccat ggagaagatc gtgctgctgc tggctatcgt gtccctggtg       60
aagtccgacc agatctgcat cggttaccac gctaacaact ccaccgagca ggtggacacc      120
atcatggaga agaacgtcac cgtgacccac gctcaggaca tcctcgaaaa gacccacaac      180
ggcaagctgt gcgacctgga cggtgtcaag ccccctgatc ctgcgtgactg ctccgtggct      240 ggttggctgc tgggtaaccc catgtgcgac gagttcatca acgtgcccga gtggtcctac      300
```

```
                                    -continued atcgtggaga aggctaaccc caccaacgac ctgtgctacc ccggttcctt caacgactac    360
gaggagctga agcacctgct gtcccgtatc aaccacttcg agaagatcca gatcatcccc    420
aagtcctctt ggtccgacca cgaggcttcc tccggtgtct cctccgcttg cccctacctg    480 ggttcccccct ccttcttccg taacgtggtg tggctgatca agaagaactc cacctacccc    540
accatcaaga agtcctacaa caacaccaac caggaggacc tgctggtcct gtggggtatc    600
caccacccca cgacgctgc cgagcagacc cgtctgtacc agaacccac cacctacatc    660 tccatcggca cctccaccct gaaccagcgt ctggtgccca gatcgctac ccgttccaag    720 gtgaacggcc agtccggtcg tatggagttc ttctggacca ccctgaagcc taacgacgct    780
atcaacttcg agtccaacgg caacttcatc gctcccgagt acgcttacaa gatcgtgaag    840
aagggcgact ccgctatcat gaagtccgag ctggagtacg gtaactgcaa caccaagtgc    900 cagacccca tgggtgctat caactcctcc atgcccttcc acaacatcca ccccctgacc    960 atcgcgagt gccccaagta cgtgaagtcc aacgtctgg tgctggctac cggtctgcgt   1020 aactccccc agcgcgagtc ccgtcgtaag aagcgtggtc tgttcggcgc tatcgctggt   1080
ttcatcgagg gcggttggca gggcatggtg acggatggt acggttacca ccactctaac   1140
gagcagggtt ccggttacgc tgctgacaag gagtccaccc agaaggctat cgacggcgtc   1200
accaacaagg tgaactccat catcgacaag atgaacaccc agttcgaggc tgtgggtcgt   1260
gagttcaaca acctcgagcg tcgtatcgag aacctgaaca agaagatgga ggacggtttc   1320
ctggacgtgt ggacctacaa cgccgagctg ctggtgctga tggagaacga gcgtacctg   1380 gacttccacg actccaacgt gaagaacctg tacgacaagg tccgcctgca gctgcgtgac   1440
aacgctaagg agctgggtaa cggttgcttc gagttctacc acaagtgcga caacgagtgc   1500
atggagtcca tccgtaacgg cacctacaac taccccccagt actccgagga ggctcgtctg   1560
aagcgtgagg agatctccgg cgtgaagctc gagtccatcg gaacctacca gatcctgtcc   1620
atctactcca ccgtggcttc ctccctggct ctggctatca tgatggctgg tctgtccctg   1680
tggatgtgct ccaacggttc cctgcagtgc cgtatctgca tctaatgaaa gcttgagctc   1740
```

<210> SEQ ID NO 43
<211> LENGTH: 568
<212> TYPE: PRT
<213> ORGANISM: Influenza virus
<400> SEQUENCE: 43

```
Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
        115                 120                 125
```

-continued

```
Lys Ile Gln Ile Ile Pro Lys Ser Ser Trp Ser Asp His Glu Ala Ser
            130                 135                 140

Ser Gly Val Ser Ser Ala Cys Pro Tyr Leu Gly Ser Pro Ser Phe Phe
145                 150                 155                 160

Arg Asn Val Val Trp Leu Ile Lys Lys Asn Ser Thr Tyr Pro Thr Ile
                165                 170                 175

Lys Lys Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
            195                 200                 205

Asn Pro Thr Thr Tyr Ile Ser Ile Gly Thr Ser Thr Leu Asn Gln Arg
210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
                260                 265                 270

Val Lys Lys Gly Asp Ser Ala Ile Met Lys Ser Glu Leu Glu Tyr Gly
            275                 280                 285

Asn Cys Asn Thr Lys Cys Gln Thr Pro Met Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Ser Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
            355                 360                 365

Gly Tyr His His Ser Asn Glu Gln Gly Ser Gly Tyr Ala Ala Asp Lys
        370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
            435                 440                 445

Glu Asn Glu Arg Thr Leu Asp Phe His Asp Ser Asn Val Lys Asn Leu
        450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Ile Arg Asn Gly Thr Tyr Asn Tyr Pro Gln Tyr Ser Glu Glu Ala
            500                 505                 510

Arg Leu Lys Arg Glu Glu Ile Ser Gly Val Lys Leu Glu Ser Ile Gly
            515                 520                 525

Thr Tyr Gln Ile Leu Ser Ile Tyr Ser Thr Val Ala Ser Ser Leu Ala
        530                 535                 540

Leu Ala Ile Met Met Ala Gly Leu Ser Leu Trp Met Cys Ser Asn Gly
545                 550                 555                 560
```

Ser Leu Gln Cys Arg Ile Cys Ile
            565

<210> SEQ ID NO 44
<211> LENGTH: 1716
<212> TYPE: DNA
<213> ORGANISM: Artificial Sequence
<220> FEATURE:
<223> OTHER INFORMATION: Influenza HA gene optimized for expression in
      insect cell expression system

<400> SEQUENCE: 44

```
ggatccgcca ccatggagaa gatcgtgctg ctgctggcta tcgtgtccct ggtgaagtcc      60
gaccagatct gcatcggtta ccacgctaac aactccaccg agcaggtgga caccatcatg     120
gagaagaacg tcaccgtgac ccacgctcag gacatcctcg aaaagaccca caacggcaag     180
ctgtgcgacc tggacggtgt caagcccctg atcctgcgtg actgctccgt ggctggttgg     240
ctgctgggta accccatgtg cgacgagttc atcaacgtgc ccgagtggtc ctacatcgtg     300
gagaaggcta accccaccaa cgacctgtgc taccccggtt ccttcaacga ctacgaggag     360
ctgaagcacc tgctgtcccg tatcaaccac ttcgagaaga tccagatcat ccccaagtcc     420
tcttggtccg accacgaggc ttcctccggt gtctcctccg cttgccccta cctgggttcc     480
ccctccttct ccgtaacgt ggtgtggctg atcaagaaga ctccaccta ccccaccatc      540
aagaagtcct acaacaacac caaccaggag gacctgctgg tcctgtgggg tatccaccac     600
cccaacgacg ctgccgagca gacccgtctg taccagaacc ccaccaccta catctccatc     660
ggcacctcca ccctgaacca gcgtctggtg cccaagatcg ctacccgttc aaggtgaac      720
ggccagtccg tcgtatgga gttcttctgg accatcctga gcctaacga cgctatcaac      780
ttcgagtcca acggcaactt catcgctccc gagtacgctt acaagatcgt gaagaagggc     840
gactccgcta tcatgaagtc cgagctggag tacggtaact gcaacaccaa gtgccagacc     900
cccatgggtg ctatcaactc ctccatgccc ttccacaaca tccacccct gaccatcggc      960
gagtgcccca gtacgtgaa gtccaaccgt ctggtgctgg ctaccggtct gcgtaactcc    1020
ccccagcgcg agtcccgtgg tctgttcggc gctatcgctg gtttcatcga gggcggttgg    1080
cagggcatgg tggacggatg gtacggttac caccactcta acgagcaggg ttccggttac    1140
gctgctgaca aggagtccac ccagaaggct atcgacggcg tcaccaacaa ggtgaactcc    1200
atcatcgaca gatgaacac ccagttcgag gctgtgggtc gtgagttcaa caacctcgag     1260
cgtcgtatcg agaacctgaa caagaagatg gaggacggtt tcctggacgt gtggacctac    1320
aacgccgagc tgctggtgct gatggagaac gagcgtaccc tggacttcca cgactccaac    1380
gtgaagaacc tgtacgacaa ggtccgcctg cagctgcgtg acaacgctaa ggagctgggt    1440
aacggttgct tcgagttcta ccacaagtgc gacaacgagt gcatggagtc catccgtaac    1500
ggcacctaca actaccccca gtactccgag gaggctcgtc tgaagcgtga ggagatctcc    1560
ggcgtgaagc tcgagtccat cggaacctac cagatcctgt ccatctactc caccgtggct    1620
tcctccctgg ctctggctat catgatggct ggtctgtccc tgtggatgtg ctccaacggt    1680
tccctgcagt gccgtatctg catctaatga aagctt                              1716
```

<210> SEQ ID NO 45
<211> LENGTH: 564
<212> TYPE: PRT
<213> ORGANISM: Influenza virus

<400> SEQUENCE: 45

```
Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Leu Gly Ser Pro Ser Phe Phe
145                 150                 155                 160

Arg Asn Val Val Trp Leu Ile Lys Lys Asn Ser Thr Tyr Pro Thr Ile
                165                 170                 175

Lys Lys Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Ile Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
    275                 280                 285

Asn Cys Asn Thr Lys Cys Gln Thr Pro Met Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
            325                 330                 335

Pro Gln Arg Glu Ser Arg Gly Leu Phe Gly Ala Ile Ala Gly Phe Ile
        340                 345                 350

Glu Gly Gly Trp Gln Gly Met Val Asp Gly Trp Tyr Gly Tyr His His
    355                 360                 365

Ser Asn Glu Gln Gly Ser Gly Tyr Ala Ala Asp Lys Glu Ser Thr Gln
        370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
```

420             425             430
Val Trp Thr Tyr Asn Ala Glu Leu Leu Val Leu Met Glu Asn Glu Arg
            435                 440                 445

Thr Leu Asp Phe His Asp Ser Asn Val Lys Asn Leu Tyr Asp Lys Val
        450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Ile Arg Asn
                485                 490                 495

Gly Thr Tyr Asn Tyr Pro Gln Tyr Ser Glu Glu Ala Arg Leu Lys Arg
            500                 505                 510

Glu Glu Ile Ser Gly Val Lys Leu Glu Ser Ile Gly Thr Tyr Gln Ile
        515                 520                 525

Leu Ser Ile Tyr Ser Thr Val Ala Ser Ser Leu Ala Leu Ala Ile Met
        530                 535                 540

Met Ala Gly Leu Ser Leu Trp Met Cys Ser Asn Gly Ser Leu Gln Cys
545                 550                 555                 560

Arg Ile Cys Ile

<210> SEQ ID NO 46
<211> LENGTH: 1383
<212> TYPE: DNA
<213> ORGANISM: Artificial Sequence
<220> FEATURE:
<223> OTHER INFORMATION: Influenza NA gene optimized for expression in
      insect cell expression system

<400> SEQUENCE: 46

```
ggtaccggat ccgccaccat gaaccccaac cagaagatca tcaccatcgg ctccatctgc     60
atggtgatcg gtatcgtgtc cctgatgctg cagatcggta acatgatctc catctgggtg    120
tcccactcca tccagaccgg taaccagcac caggctgagt ccatctccaa caccaacccc    180
ctgaccgaga aggctgtggc ttccgtgacc ctggctggta actcctccct gtgccccatc    240
cgtggttggg ctgtgcactc caaggacaac aacatccgca tcggttccaa gggtgacgtg    300
ttcgtgatcc gtgagccctt catctcctgc tcccacctcg agtgccgtac cttcttcctg    360
acccaaggtg ctctgctgaa cgacaagcac tccaacggca ccgtgaagga ccgttccccc    420
caccgtaccc tgatgtcctg cccgtgggc gaggctccct ccccctacaa ctcccgtttc    480
gagtccgtgg cttggtccgc ttccgcttgc cacgacggca cctcttggct gaccatcggt    540
atctccggtc ccgacaacga ggctgtcgct gtgctgaagt acaacggcat catcaccgac    600
accatcaagt cctggcgtaa caacatcctg cgtacccagg agtccgagtg cgcttgcgtg    660
aacggttcct gcttcaccgt gatgaccgac ggtcccccg acggccaggc ttcctacaag    720
atcttcaaga tggagaaggg caaggtggtg aagtccgtgg agctggacgc tcccaactac    780
cactacgagg agtgctcttg ctacccgac gctggcgaga tcacctgcgt gtgccgtgac    840
aactggcacg gttccaaccg tccctgggtg tccttcaacc agaacctcga gtaccagatc    900
ggttacatct gctccggcgt gttcggtgac aaccccgtc ccaacgacgg aaccggttcc    960
tgcggtccca tgtcccccaa cggtgcttac ggtgtcaagg cttctccctt caagtacggt   1020
aacggtgtct ggatcggtcg taccaagtcc accaactccc gctccggttt cgagatgatc   1080
tgggacccca acggttggac cggcaccgac tcttccttct ccgtgaagca ggacatcgtg   1140
gctatcaccg actggtccgg ttactccggt tccttcgtgc agcaccccga gctgaccggt   1200
ctggactgca ttcgtccctg cttctgggtg agctgatcc gtggtcgtcc caaggagtcc   1260
```

-continued

```
accatctgga cctccggctc ctccatctct ttctgcggtg tgaactccga caccgtgtcc    1320
tggtcctggc ccgacggtgc cgagctgccc ttcaccatcg acaagtaatg aaagcttgag    1380
ctc                                                                  1383
```

<210> SEQ ID NO 47
<211> LENGTH: 449
<212> TYPE: PRT
<213> ORGANISM: Influenza virus

<400> SEQUENCE: 47

```
Met Asn Pro Asn Gln Lys Ile Ile Thr Ile Gly Ser Ile Cys Met Val
1               5                   10                  15

Ile Gly Ile Val Ser Leu Met Leu Gln Ile Gly Asn Met Ile Ser Ile
            20                  25                  30

Trp Val Ser His Ser Ile Gln Thr Gly Asn Gln His Gln Ala Glu Ser
        35                  40                  45

Ile Ser Asn Thr Asn Pro Leu Thr Glu Lys Ala Val Ala Ser Val Thr
    50                  55                  60

Leu Ala Gly Asn Ser Ser Leu Cys Pro Ile Arg Gly Trp Ala Val His
65                  70                  75                  80

Ser Lys Asp Asn Asn Ile Arg Ile Gly Ser Lys Gly Asp Val Phe Val
                85                  90                  95

Ile Arg Glu Pro Phe Ile Ser Cys Ser His Leu Glu Cys Arg Thr Phe
            100                 105                 110

Phe Leu Thr Gln Gly Ala Leu Leu Asn Asp Lys His Ser Asn Gly Thr
        115                 120                 125

Val Lys Asp Arg Ser Pro His Arg Thr Leu Met Ser Cys Pro Val Gly
    130                 135                 140

Glu Ala Pro Ser Pro Tyr Asn Ser Arg Phe Glu Ser Val Ala Trp Ser
145                 150                 155                 160

Ala Ser Ala Cys His Asp Gly Thr Ser Trp Leu Thr Ile Gly Ile Ser
                165                 170                 175

Gly Pro Asp Asn Glu Ala Val Ala Val Leu Lys Tyr Asn Gly Ile Ile
            180                 185                 190

Thr Asp Thr Ile Lys Ser Trp Arg Asn Asn Ile Leu Arg Thr Gln Glu
        195                 200                 205

Ser Glu Cys Ala Cys Val Asn Gly Ser Cys Phe Thr Val Met Thr Asp
    210                 215                 220

Gly Pro Ser Asp Gly Gln Ala Ser Tyr Lys Ile Phe Lys Met Glu Lys
225                 230                 235                 240

Gly Lys Val Val Lys Ser Val Glu Leu Asp Ala Pro Asn Tyr His Tyr
                245                 250                 255

Glu Glu Cys Ser Cys Tyr Pro Asp Ala Gly Glu Ile Thr Cys Val Cys
            260                 265                 270

Arg Asp Asn Trp His Gly Ser Asn Arg Pro Trp Val Ser Phe Asn Gln
        275                 280                 285

Asn Leu Glu Tyr Gln Ile Gly Tyr Ile Cys Ser Gly Val Phe Gly Asp
    290                 295                 300

Asn Pro Arg Pro Asn Asp Gly Thr Gly Ser Cys Gly Pro Met Ser Pro
305                 310                 315                 320

Asn Gly Ala Tyr Gly Val Lys Gly Phe Ser Phe Lys Tyr Gly Asn Gly
                325                 330                 335

Val Trp Ile Gly Arg Thr Lys Ser Thr Asn Ser Arg Ser Gly Phe Glu
            340                 345                 350
```

```
Met Ile Trp Asp Pro Asn Gly Trp Thr Gly Thr Asp Ser Ser Phe Ser
            355                 360                 365

Val Lys Gln Asp Ile Val Ala Ile Thr Asp Trp Ser Gly Tyr Ser Gly
        370                 375                 380

Ser Phe Val Gln His Pro Glu Leu Thr Gly Leu Asp Cys Ile Arg Pro
385                 390                 395                 400

Cys Phe Trp Val Glu Leu Ile Arg Gly Arg Pro Lys Glu Ser Thr Ile
                405                 410                 415

Trp Thr Ser Gly Ser Ser Ile Ser Phe Cys Gly Val Asn Ser Asp Thr
            420                 425                 430

Val Ser Trp Ser Trp Pro Asp Gly Ala Glu Leu Pro Phe Thr Ile Asp
            435                 440                 445

Lys
```

<210> SEQ ID NO 48
<211> LENGTH: 792
<212> TYPE: DNA
<213> ORGANISM: Artificial Sequence
<220> FEATURE:
<223> OTHER INFORMATION: Influenza M1 gene optimized for expression in
      insect cell expression system

<400> SEQUENCE: 48

```
ggtaccggat ccgccaccat gtccctgctg accgaggtgg agacctacgt gctgtccatc      60
atcccctccg gtcctctgaa ggctgagatc gctcagaagc tcgaggacgt tttcgctggc     120
aagaacaccg acctcgaggc tctgatggag tggctcaaga cccgtcccat cctgtccccc     180
ctgaccaagg gtatcctggg tttcgtgttc accctgaccg tgccctccga gcgtggtctg     240
cagcgtcgtc gtttcgtgca gaacgctctg aacggtaacg tgaccccaa caacatggac     300
cgtgctgtga gctgtacaa gaagctgaag cgcgagatca ccttccacgg tgctaaggag     360
gtgtccctgt cctactccac cggtgctctg gctagctgca tgggcctgat ctacaaccgt     420
atgggcaccg tgaccaccga ggtggccttc ggtctggtct cgctacctg cgagcagatc     480
gctgactccc agcaccgttc ccaccgtcag atggctacca tcaccaaccc cctgatccgt     540
cacgagaacc gtatggtgct ggcttccacc accgctaagg ctatggagca gatggctggt     600
tcctccgagc aggctgctga ggccatggag gtggccaacc aggctcgtca gatggtgcag     660
gctatgcgta ccatcggcac ccaccccaac tcctccgctg gtctgcgtga caacctgctc     720
gagaacctgc aggcttacca gaagcgtatg ggagtccaga tgcagcgctt caagtaatga     780
aagcttgagc tc                                                         792
```

<210> SEQ ID NO 49
<211> LENGTH: 252
<212> TYPE: PRT
<213> ORGANISM: Influenza virus

<400> SEQUENCE: 49

```
Met Ser Leu Leu Thr Glu Val Glu Thr Tyr Val Leu Ser Ile Ile Pro
  1               5                  10                  15

Ser Gly Pro Leu Lys Ala Glu Ile Ala Gln Lys Leu Glu Asp Val Phe
             20                  25                  30

Ala Gly Lys Asn Thr Asp Leu Glu Ala Leu Met Glu Trp Leu Lys Thr
         35                  40                  45

Arg Pro Ile Leu Ser Pro Leu Thr Lys Gly Ile Leu Gly Phe Val Phe
     50                  55                  60
```

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Arg Ala
                85                  90                  95

Val Lys Leu Tyr Lys Lys Leu Lys Arg Glu Ile Thr Phe His Gly Ala
            100                 105                 110

Lys Glu Val Ser Leu Ser Tyr Ser Thr Gly Ala Leu Ala Ser Cys Met
        115                 120                 125

Gly Leu Ile Tyr Asn Arg Met Gly Thr Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Ala Thr Ile Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Asn Gln
        195                 200                 205

Ala Arg Gln Met Val Gln Ala Met Arg Thr Ile Gly Thr His Pro Asn
    210                 215                 220

Ser Ser Ala Gly Leu Arg Asp Asn Leu Leu Glu Asn Leu Gln Ala Tyr
225                 230                 235                 240

Gln Lys Arg Met Gly Val Gln Met Gln Arg Phe Lys
                245                 250

<210> SEQ ID NO 50
<211> LENGTH: 1736
<212> TYPE: DNA
<213> ORGANISM: Artificial Sequence
<220> FEATURE:
<223> OTHER INFORMATION: Influenza HA gene optimized for expression in
      insect cell expression system

<400> SEQUENCE: 50
ggtaccggat ccctcgagat ggagaagatc gtgctgctgc tggctatcgt gtccctggtg      60
aagtccgacc agatctgcat cggttaccac gctaacaact ccaccgagca ggtggacacc    120
atcatggaga gaacgtcac cgtgacccac gctcaggaca tcctggaaaa gacccacaac    180
ggcaagctgt gcgacctgga cggtgtcaag cccctgatcc tgcgtgactg ctccgtggct    240
ggttggctgc tgggtaaccc catgtgcgac gagttcatca acgtgcccga gtggtcctac    300
atcgtggaga aggctaaccc cgctaacgac ctgtgctacc cggtaacttc aacgactac     360 gaggagctga agcacctgct gtcccgtatc aaccacttcg agaagatcca gatcatcccc   420
aagtcctctt ggtccgacca cgaggcttcc tccggtgtct cctccgcttg cccataccag    480
ggcaccccat ctttcttccg taacgtggtg tggctgatca agaagaacaa cacctacccc   540
accatcaagc gttcctacaa caacaccaac caggaggacc tgctgatcct gtggggtatc    600
caccactcca cgacgctgc cgagcagacc aagctgtacc agaacccac cacctacatc      660 tccgtgggca cctccaccct gaaccagcgt ctggtgccca gatcgctac ccgttccaag     720 gtgaacggcc agtccggtcg tatggacttc ttctggacca tcctgaagcc taacgacgct   780
atcaacttcg agtccaacgg caacttcatc gctcccgagt acgcttacaa gatcgtgaag    840
aagggcgact ccgctatcgt caagtccgag gtggagtacg gtaactgcaa caccaagtgc    900 cagacccccca tcggtgctat caactcctcc atgcccttcc acaacatcca ccccctgacc    960
atcggcgagt gccccaagta cgtgaagtcc aacaagctgg tgctggctac cggtctgcgt   1020

-continued

```
aactcccccc tgcgtgagcg tggtctgttc ggcgctatcg ctggtttcat cgagggcggt   1080
tggcagggca tggtggacgg ttggtacggt taccaccaca gcaacgagca gggttccggt   1140
tacgctgctg acaaggagtc cacccagaag gctatcgacg gcgtcaccaa caaggtgaac   1200
tccatcatcg acaagatgaa cacccagttc gaggctgtgg gtcgtgagtt caacaacctg   1260
gagcgtcgta tcgagaacct gaacaagaag atggaggacg gtttcctgga cgtgtggacc   1320
tacaacgccg agctgctggt gctgatggag aacgagcgta ccctggactt ccacgactct   1380
aacgtgaaga acctgtacga caaggtccgc ctgcagctgc gtgacaacgc taaggagctg   1440
ggtaacggtt gcttcgagtt ctaccacaag tgcgacaacg agtgcatgga gtccgtgcgt   1500
aacggcacct acgactaccc ccagtactcc gaggaggctc gtctgaagcg tgaggagatc   1560
tccggcgtga agctggagtc catcggcacc taccagatct gtccatcta ctccaccgtg   1620 gcttcctccc tggctctggc tatcatggtg gctggtctgt ccctgtggat gtgctccaac   1680
ggttccctgc agtgccgtat ctgcatctaa taatgaggcg cgccaagctt gagctc       1736
```

<210> SEQ ID NO 51
<211> LENGTH: 563
<212> TYPE: PRT
<213> ORGANISM: Influenza virus

<400> SEQUENCE: 51

```
Met Glu Lys Ile Val Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Gln Gly Thr Pro Ser Phe Phe
145                 150                 155                 160

Arg Asn Val Val Trp Leu Ile Lys Lys Asn Asn Thr Tyr Pro Thr Ile
                165                 170                 175

Lys Arg Ser Tyr Asn Asn Thr Asn Gln Glu Asp Leu Leu Ile Leu Trp
            180                 185                 190

Gly Ile His His Ser Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Asp Phe Phe Trp Thr Ile Leu Lys Pro Asn Asp Ala Ile Asn
                245                 250                 255
```

| | | | | | | | | | | | |
|---|---|---|---|---|---|---|---|---|---|---|---|
|Phe|Glu|Ser|Asn|Gly|Asn|Phe|Ile|Ala|Pro|Glu|Tyr|Ala|Tyr|Lys|Ile|
| | |260| | | |265| | | |270| |

Val Lys Lys Gly Asp Ser Ala Ile Val Lys Ser Glu Val Glu Tyr Gly
            275                 280                 285

Asn Cys Asn Thr Lys Cys Gln Thr Pro Ile Gly Ala Ile Asn Ser Ser
        290                 295                 300

Met Pro Phe His Asn Ile His Pro Leu Thr Ile Gly Glu Cys Pro Lys
305                 310                 315                 320

Tyr Val Lys Ser Asn Lys Leu Val Leu Ala Thr Gly Leu Arg Asn Ser
                325                 330                 335

Pro Leu Arg Glu Arg Gly Leu Phe Gly Ala Ile Ala Gly Phe Ile Glu
            340                 345                 350

Gly Gly Trp Gln Gly Met Val Asp Gly Trp Tyr Gly Tyr His His Ser
        355                 360                 365

Asn Glu Gln Gly Ser Gly Tyr Ala Ala Asp Lys Glu Ser Thr Gln Lys
    370                 375                 380

Ala Ile Asp Gly Val Thr Asn Lys Val Asn Ser Ile Ile Asp Lys Met
385                 390                 395                 400

Asn Thr Gln Phe Glu Ala Val Gly Arg Glu Phe Asn Asn Leu Glu Arg
                405                 410                 415

Arg Ile Glu Asn Leu Asn Lys Lys Met Glu Asp Gly Phe Leu Asp Val
            420                 425                 430

Trp Thr Tyr Asn Ala Glu Leu Leu Val Leu Met Glu Asn Glu Arg Thr
        435                 440                 445

Leu Asp Phe His Asp Ser Asn Val Lys Asn Leu Tyr Asp Lys Val Arg
    450                 455                 460

Leu Gln Leu Arg Asp Asn Ala Lys Glu Leu Gly Asn Gly Cys Phe Glu
465                 470                 475                 480

Phe Tyr His Lys Cys Asp Asn Glu Cys Met Glu Ser Val Arg Asn Gly
                485                 490                 495

Thr Tyr Asp Tyr Pro Gln Tyr Ser Glu Glu Ala Arg Leu Lys Arg Glu
            500                 505                 510

Glu Ile Ser Gly Val Lys Leu Glu Ser Ile Gly Thr Tyr Gln Ile Leu
        515                 520                 525

Ser Ile Tyr Ser Thr Val Ala Ser Ser Leu Ala Leu Ala Ile Met Val
    530                 535                 540

Ala Gly Leu Ser Leu Trp Met Cys Ser Asn Gly Ser Leu Gln Cys Arg
545                 550                 555                 560

Ile Cys Ile

<210> SEQ ID NO 52
<211> LENGTH: 1738
<212> TYPE: DNA
<213> ORGANISM: Artificial Sequence
<220> FEATURE:
<223> OTHER INFORMATION: Influenza HA gene optimized for expression in
      insect cell expression system

<400> SEQUENCE: 52
cgggcgcgga gcggccgcat ggagaagatc gtgctgctgc tggctatcgt gtctctggtc      60
aagtccgacc agatctgcat cggttaccac gctaacaact ccaccgagca ggtggacacc     120
atcatggaga agaacgtcac cgtgacccac gctcaggaca tcctcgaaaa gacccacaac     180
ggcaagctgt gcgacctgga cggcgtgaag cccctgatcc tgcgtgactg ctccgtggct     240
ggttggctgc tgggtaaccc catgtgcgac gagttcctca acgtgcccga gtggtcctac     300

```
atcgtggaga agatcaaccc cgctaacgac ctgtgctacc ccggtaactt caacgactac    360
gaggagctga agcacctgct gtcccgtatc aaccacttcg agaagatcca gatcatcccc    420
aagtcctctt ggtccgacca cgaggcttcc tccggtgtct cctccgcttg cccataccag    480
ggccgttctt ccttcttccg caacgtggtg tggctgatca agaagaacaa cgcctacccc    540
accatcaagc gttcctacaa caacaccaac caggaggacc tgctggtcct gtggggtatc    600
caccacccca cgacgctgc cgagcagacc cgtctgtacc agaacccac cacctacatc       660 tccgtgggca cctctaccct gaaccagcgt ctggtgccca gatcgctac ccgttccaag      720 gtgaacggcc agtccggtcg tatggagttc ttctggacca tcctgaagcc taacgacgct    780
atcaacttcg agtccaacgg caacttcatc gctcccgaga acgcttacaa gatcgtgaag    840
aagggcgact ccaccatcat gaagtccgag ctggagtacg gcaactgcaa cactaagtgc    900 cagacccca tcggtgctat caactcctcc atgcccttcc acaacatcca cccctgact      960 atcggcgagt gccccaagta cgtgaagtcc aacgtctgg tgctggctac cggtctgcgt    1020
aactcccccc agatcgagac tcgtggtctg ttcggcgcta tcgctggttt catcgagggc   1080
ggttggcagg gcatggtgga cggttggtac ggttaccacc actctaacga gcagggttcc   1140
ggttacgctg ctgacaagga gtctacccag aaggctatcg acggcgtcac caacaaggtg   1200
aactccatca tcgacaagat gaacacccag ttcgaggctg tgggtcgtga gttcaacaac   1260
ctcgaacgtc gtatcgagaa cctgaacaag aagatggagg acggtttcct ggacgtgtgg   1320
acctacaacg ccgagctgct ggtgctgatg gagaacgagc gtaccctgga cttccacgac   1380
tccaacgtga agaacctgta cgacaaggtc cgcctgcagc tgcgtgacaa cgctaaggag   1440
ctgggtaacg gttgcttcga gttctaccac cgttgcgaca acgagtgcat ggagtccgtg   1500
cgtaacggca cctacgacta ccccagtac tccgaggagg ctcgtctgaa gcgtgaggag   1560
atctccggtg tcaagctcga atccatcgga acctaccaga tcctgtccat ctactccacc   1620
gtggcttcct ccctggctct ggctatcatg gtggctggtc tgtccctgtg gatgtgctcc   1680
aacggttccc tgcagtgccg tatctgcatc taataatgag gcgcgccaag cttgtcga       1738
```

<210> SEQ ID NO 53
<211> LENGTH: 564
<212> TYPE: PRT
<213> ORGANISM: Influenza virus

<400> SEQUENCE: 53

```
Met Glu Lys Ile Val Leu Leu Leu Ala Ile Val Ser Leu Val Lys Ser
  1               5                  10                  15

Asp Gln Ile Cys Ile Gly Tyr His Ala Asn Asn Ser Thr Glu Gln Val
             20                  25                  30

Asp Thr Ile Met Glu Lys Asn Val Thr Val Thr His Ala Gln Asp Ile
         35                  40                  45

Leu Glu Lys Thr His Asn Gly Lys Leu Cys Asp Leu Asp Gly Val Lys
     50                  55                  60

Pro Leu Ile Leu Arg Asp Cys Ser Val Ala Gly Trp Leu Leu Gly Asn
 65                  70                  75                  80

Pro Met Cys Asp Glu Phe Leu Asn Val Pro Glu Trp Ser Tyr Ile Val
                 85                  90                  95

Glu Lys Ile Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125
```

-continued

```
Lys Ile Gln Ile Ile Pro Lys Ser Ser Trp Ser Asp His Glu Ala Ser
            130                 135                 140

Ser Gly Val Ser Ser Ala Cys Pro Tyr Gln Gly Arg Ser Ser Phe Phe
145                 150                 155                 160

Arg Asn Val Val Trp Leu Ile Lys Lys Asn Asn Ala Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
            195                 200                 205

Asn Pro Thr Thr Tyr Ile Ser Val Gly Thr Ser Thr Leu Asn Gln Arg
210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Asn Ala Tyr Lys Ile
            260                 265                 270

Val Lys Lys Gly Asp Ser Thr Ile Met Lys Ser Glu Leu Glu Tyr Gly
            275                 280                 285

Asn Cys Asn Thr Lys Cys Gln Thr Pro Ile Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Ile Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
            355                 360                 365

Ser Asn Glu Gln Gly Ser Gly Tyr Ala Ala Asp Lys Glu Ser Thr Gln
370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
            435                 440                 445

Thr Leu Asp Phe His Asp Ser Asn Val Lys Asn Leu Tyr Asp Lys Val
450                 455                 460

Arg Leu Gln Leu Arg Asp Asn Ala Lys Glu Leu Gly Asn Gly Cys Phe
465                 470                 475                 480

Glu Phe Tyr His Arg Cys Asp Asn Glu Cys Met Glu Ser Val Arg Asn
                485                 490                 495

Gly Thr Tyr Asp Tyr Pro Gln Tyr Ser Glu Glu Ala Arg Leu Lys Arg
            500                 505                 510

Glu Glu Ile Ser Gly Val Lys Leu Glu Ser Ile Gly Thr Tyr Gln Ile
            515                 520                 525

Leu Ser Ile Tyr Ser Thr Val Ala Ser Ser Leu Ala Leu Ala Ile Met
530                 535                 540

Val Ala Gly Leu Ser Leu Trp Met Cys Ser Asn Gly Ser Leu Gln Cys
```

```
                    545                 550                 555                 560

Arg Ile Cys Ile

<210> SEQ ID NO 54
<211> LENGTH: 1422
<212> TYPE: DNA
<213> ORGANISM: Artificial Sequence
<220> FEATURE:
<223> OTHER INFORMATION: Influenza NA gene optimized for expression in
      insect cell expression system

<400> SEQUENCE: 54
accgtcccac catcgggcgc ggatccctcg agatgaaccc caaccagaag atcatcacca      60
tcggctccat ctgcatggtg atcggtatcg tgtccctgat gctgcagatc ggtaacatga     120
tctccatctg ggtgtcccac tccatccaga ccggtaacca gcgtcaggcc gagcccatct     180
ccaacaccaa gttcctcacc gagaaggctg tggcttccgt gaccctggct ggtaactcct     240
ccctgtgccc catctccggt tgggctgtgt actccaagga caactccatc cgtatcggtt     300
cccgtggtga cgtgttcgtg atccgtgagc ccttcatctc ctgctcccac ctcgaatgcc     360
gtaccttctt cctgacccag ggtgctctgc tgaacgacaa gcactccaac ggcaccgtga     420
aggaccgttc cccccaccgt accctgatgt cctgccccgt gggcgaggct ccctccccct     480
acaactcccg tttcgagtcc gtggcttggt ccgcttccgc ttgccacgac ggcacctctt     540
ggctgaccat cggtatctcc ggtcccgaca cggtgctgt ggctgtgctg aagtacaacg     600
gcatcatcac cgacaccatc aagtcctggc gtaacaacat cctgcgtacc caagagtccg     660
agtgcgcttg cgtgaacggt tcctgcttca ccgtgatgac cgacggtccc tccaacggcc     720
aggcttccta caagatcttc aagatggaga agggcaaggt ggtgaagtcc gtggagctgg     780
acgctcccaa ctaccactac gaggagtgct cttgctaccc cgacgctggc gagatcacct     840
gcgtgtgccg tgacaactgg cacggttcca accgtccctg gtgtccttc aaccagaacc     900 tcgaatacca gatcggttac atctgctccg gcgtgttcgg tgacaacccc cgtcccaacg     960
acggaaccgg ttcctgcggt cccgtgtccc caacggtgc ttacggtgtc aagggcttct    1020
ccttcaagta cggtaacggt gtctggatcg gtcgtaccaa gtccaccaac tcccgctccg    1080
gtttcgagat gatctgggac cccaacggtt ggaccggcac cgactcttcc ttctccgtga    1140
agcaggacat cgtggctatc accgactggt ccggttactc cggttccttc gtgcagcacc    1200
ccgagctgac cggtctggac tgtatccgtc cctgcttctg ggtggagctg atccgtggtc    1260
gtcccaagga gtccaccatc tggacctccg gctcctccat ctctttctgc ggtgtgaact    1320
ccgacaccgt gtcctggtcc tggcccgacg gtgccgagct gcccttcacc atcgacaagt    1380
aataatgaat cgatttgtcg agaagtacta gaggatcata at                      1422

<210> SEQ ID NO 55
<211> LENGTH: 449
<212> TYPE: PRT
<213> ORGANISM: Influenza virus

<400> SEQUENCE: 55

Met Asn Pro Asn Gln Lys Ile Ile Thr Ile Gly Ser Ile Cys Met Val
1               5                   10                  15

Ile Gly Ile Val Ser Leu Met Leu Gln Ile Gly Asn Met Ile Ser Ile
                20                  25                  30

Trp Val Ser His Ser Ile Gln Thr Gly Asn Gln Arg Gln Ala Glu Pro
            35                  40                  45

Ile Ser Asn Thr Lys Phe Leu Thr Glu Lys Ala Val Ala Ser Val Thr
```

```
            50                  55                  60
Leu Ala Gly Asn Ser Ser Leu Cys Pro Ile Ser Gly Trp Ala Val Tyr
 65                  70                  75                  80

Ser Lys Asp Asn Ser Ile Arg Ile Gly Ser Arg Gly Asp Val Phe Val
                 85                  90                  95

Ile Arg Glu Pro Phe Ile Ser Cys Ser His Leu Glu Cys Arg Thr Phe
                100                 105                 110

Phe Leu Thr Gln Gly Ala Leu Leu Asn Asp Lys His Ser Asn Gly Thr
            115                 120                 125

Val Lys Asp Arg Ser Pro His Arg Thr Leu Met Ser Cys Pro Val Gly
130                 135                 140

Glu Ala Pro Ser Pro Tyr Asn Ser Arg Phe Glu Ser Val Ala Trp Ser
145                 150                 155                 160

Ala Ser Ala Cys His Asp Gly Thr Ser Trp Leu Thr Ile Gly Ile Ser
                165                 170                 175

Gly Pro Asp Asn Gly Ala Val Ala Val Leu Lys Tyr Asn Gly Ile Ile
                180                 185                 190

Thr Asp Thr Ile Lys Ser Trp Arg Asn Asn Ile Leu Arg Thr Gln Glu
            195                 200                 205

Ser Glu Cys Ala Cys Val Asn Gly Ser Cys Phe Thr Val Met Thr Asp
210                 215                 220

Gly Pro Ser Asn Gly Gln Ala Ser Tyr Lys Ile Phe Lys Met Glu Lys
225                 230                 235                 240

Gly Lys Val Val Lys Ser Val Glu Leu Asp Ala Pro Asn Tyr His Tyr
                245                 250                 255

Glu Glu Cys Ser Cys Tyr Pro Asp Ala Gly Glu Ile Thr Cys Val Cys
                260                 265                 270

Arg Asp Asn Trp His Gly Ser Asn Arg Pro Trp Val Ser Phe Asn Gln
            275                 280                 285

Asn Leu Glu Tyr Gln Ile Gly Tyr Ile Cys Ser Gly Val Phe Gly Asp
            290                 295                 300

Asn Pro Arg Pro Asn Asp Gly Thr Gly Ser Cys Gly Pro Val Ser Pro
305                 310                 315                 320

Asn Gly Ala Tyr Gly Val Lys Gly Phe Ser Phe Lys Tyr Gly Asn Gly
                325                 330                 335

Val Trp Ile Gly Arg Thr Lys Ser Thr Asn Ser Arg Ser Gly Phe Glu
            340                 345                 350

Met Ile Trp Asp Pro Asn Gly Trp Thr Gly Thr Asp Ser Ser Phe Ser
            355                 360                 365

Val Lys Gln Asp Ile Val Ala Ile Thr Asp Trp Ser Gly Tyr Ser Gly
370                 375                 380

Ser Phe Val Gln His Pro Glu Leu Thr Gly Leu Asp Cys Ile Arg Pro
385                 390                 395                 400

Cys Phe Trp Val Glu Leu Ile Arg Gly Arg Pro Lys Glu Ser Thr Ile
                405                 410                 415

Trp Thr Ser Gly Ser Ser Ile Ser Phe Cys Gly Val Asn Ser Asp Thr
            420                 425                 430

Val Ser Trp Ser Trp Pro Asp Gly Ala Glu Leu Pro Phe Thr Ile Asp
            435                 440                 445

Lys

<210> SEQ ID NO 56
<211> LENGTH: 1750
<212> TYPE: DNA
```

<213> ORGANISM: Influenza virus

<400> SEQUENCE: 56

```
attcgccctt aacggtccga tggaga

-continued

```
Leu Glu Lys Thr His Asn Gly Lys Leu Cys Asp Leu Asp Gly Val Lys
     50                  55                  60

Pro Leu Ile Leu Arg Asp Cys Ser Val Ala Gly Trp Leu Leu Gly Asn
 65                  70                  75                  80

Pro Met Cys Asp Glu Phe Ile Asn Val Pro Glu Trp Ser Tyr Ile Val
                 85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
130                 135                 140

Ser Gly Val Ser Ser Ala Cys Pro Tyr Leu Gly Ser Pro Ser Phe Phe
145                 150                 155                 160

Arg Asn Val Val Trp Leu Ile Lys Lys Asn Ser Thr Tyr Pro Thr Ile
                165                 170                 175

Lys Lys Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Ile Gly Thr Ser Thr Leu Asn Gln Arg
210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Ser Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
370                 375                 380

Glu Ser Thr Gln Lys Ala Met Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
450                 455                 460

Tyr Asp Lys Val Arg Leu Gln Leu Arg Asp Asn Ala Lys Glu Leu Gly
```

```
                      465                 470                 475                 480
Asn Gly Cys Phe Glu Phe Tyr His Lys Cys Asp Asn Glu Cys Met Glu
                485                 490                 495

Ser Ile Arg Asn Gly Thr Cys Asn Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
    530                 535                 540

Leu Ala Ile Met Met Ala Gly Leu Ser Leu Trp Met Cys Ser Asn Gly
545                 550                 555                 560

Ser Leu Gln Cys Arg Ile Cys Ile
                565

<210> SEQ ID NO 58
<211> LENGTH: 568
<212> TYPE: PRT
<213> ORGANISM: Influenza virus

<400> SEQUENCE: 58

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Leu Gly Ser Pro Ser Phe Phe
145                 150                 155                 160

Arg Asn Val Val Trp Leu Ile Lys Lys Asn Ser Thr Tyr Pro Thr Ile
                165                 170                 175

Lys Lys Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Ile Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
```

```
                  275                 280                 285
Asn Cys Asn Thr Lys Cys Gln Thr Pro Met Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
            325                 330                 335

Pro Gln Arg Glu Ser Arg Arg Lys Lys Arg Gly Leu Phe Gly Ala Ile
        340                 345                 350

Ala Gly Phe Ile Glu Gly Gly Trp Gln Gly Met Val Asp Gly Trp Tyr
    355                 360                 365

Gly Tyr His His Ser Asn Glu Gln Gly Ser Gly Tyr Ala Ala Asp Lys
370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Ile Arg Asn Gly Thr Tyr Asn Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
    530                 535                 540

Leu Ala Ile Met Met Ala Gly Leu Ser Leu Trp Met Cys Ser Asn Gly
545                 550                 555                 560

Ser Leu Gln Cys Arg Ile Cys Ile
                565

<210> SEQ ID NO 59
<211> LENGTH: 5
<212> TYPE: PRT
<213> ORGANISM: Influenza virus

<400> SEQUENCE: 59

Arg Arg Arg Lys Arg
1               5

<210> SEQ ID NO 60
<211> LENGTH: 4
<212> TYPE: PRT
<213> ORGANISM: Artificial Sequence
<220> FEATURE:
<223> OTHER INFORMATION: Mutated HA cleavage site

<400> SEQUENCE: 60

Arg Glu Ser Arg
1
```

FUNCTIONAL INFLUENZA VIRUS LIKE PARTICLES (VLPS)

CROSS REFERENCE TO RELATED APPLICATIONS

This application claims priority under 35 U.S.C. §119(e) to U.S. Ser. No. 61/015,440 filed on Dec. 20, 2007, and also claims priority under 35 U.S.C. §120 as a continuation-in-part of U.S. Ser. No. 11/582,540, filed Oct. 18, 2006 now U.S. Pat. No. 8,080,255, which claims priority to U.S. Ser. Nos. 60/727,513, filed Oct. 18, 2005; 60/780,847, filed Mar. 10, 2006; 60/800,006, filed May 15, 2006; 60/831,196, filed Jul. 17, 2006; 60/832,116, filed Jul. 21, 2006, and 60/845,495, filed Sep. 19, 2006, and which also is a continuation-in-part of Ser. No. 10/617,569, filed Jul. 11, 2003, all of which are incorporated herein by reference in their entireties for all proposes.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: NOVV_029_01US_SeqList.ST25.txt, date recorded: Aug. 10, 2009, file size 120 kilobytes).

BACKGROUND OF INVENTION

Influenza virus is a member of Orthomyxoviridae family (for review, see Murphy and Webster, 1996). There are three subtypes of influenza viruses designated A, B, and C. The influenza virion contains a segmented negative-sense RNA genome. The influenza virion includes the following proteins: hemagglutinin (HA), neuraminidase (NA), matrix (M1), proton ion-channel protein (M2), nucleoprotein (NP), polymerase basic protein 1 (PB1), polymerase basic protein 2 (PB2), polymerase acidic protein (PA), and nonstructural protein 2 (NS2) proteins. The HA, NA, M1, and M2 are membrane associated, whereas NP, PB1, PB2, PA, and NS2 are nucleocapsid associated proteins. The NS1 is the only nonstructural protein not associated with virion particles but specific for influenza-infected cells. The M1 protein is the most abundant protein in influenza particles. The HA and NA proteins are envelope glycoproteins, responsible for virus attachment and penetration of the viral particles into the cell, and the sources of the major immunodominant epitopes for virus neutralization and protective immunity. Both HA and NA proteins are considered the most important components for prophylactic influenza vaccines.

Influenza virus infection is initiated by the attachment of the virion surface HA protein to a sialic acid-containing cellular receptor (glycoproteins and glycolipids). The NA protein mediates processing of the sialic acid receptor, and virus penetration into the cell depends on HA-dependent receptor-mediated endocytosis. In the acidic confines of internalized endosomes containing an influenza virion, the HA protein undergoes conformational changes that lead to fusion of viral and host cell membranes followed by virus uncoating and M2-mediated release of M1 proteins from nucleocapsid-associated ribonucleoproteins (RNPs), which migrate into the cell nucleus for viral RNA synthesis. Antibodies to HA molecule can prevent virus infection by neutralizing virus infectivity, whereas antibodies to NA proteins mediate their effect on the early steps of viral replication.

Inactivated influenza A and B virus vaccines are licensed currently as trivalent vaccines for parenteral administration. These trivalent vaccines are produced as monovalent bulk in the allantoic cavity of embryonated chick eggs, purified by rate zonal centrifugation or column chromatography, inactivated with formalin or β-propiolactone, and formulated as a blend of the two strains of type A and the type B strain of influenza viruses in circulation among the human population for a given year. The available commercial influenza vaccines are whole virus (WV) or subvirion (SV; split or purified surface antigen) virus vaccines. The WV vaccine contains intact, inactivated virions. SV vaccines treated with solvents such as tri-n-butyl phosphate (Flu-Shield, Wyeth-Lederle) contain nearly all of the viral structural proteins and some of the viral envelopes. SV vaccines solubilized with Triton X-100 (Fluzone, Sanofi-Aventis; Fluvirin, Novartis) contain aggregates of HA monomers, NA, and NP principally, although residual amounts of other viral structural proteins are present. A live attenuated cold-adapted virus vaccine (FluMist, MedImmune) was granted marketing approval recently by the FDA for commercial usage as an intranasally delivered vaccine indicated for active immunization and the prevention of disease caused by influenza A and B viruses in healthy children and adolescents, 5-17 years of age and healthy adults 18-49 years of age.

Several recombinant products have been developed as recombinant influenza vaccine candidates. These approaches have focused on the expression, production, and purification of influenza virus type A HA and NA proteins, including expression of these proteins using baculovirus infected insect cells (Crawford et al, 1999; Johansson, 1999; Treanor et al., 1996), viral vectors (Pushko et al., 1997; Berglund et al., 1999), and DNA vaccine constructs (Olsen et al., 1997).

Crawford et al. (1999) demonstrated that influenza HA expressed in baculovirus infected insect cells is capable of preventing lethal influenza disease caused by avian H5 and H7 influenza subtypes. At the same time, another group demonstrated that baculovirus-expressed influenza HA and NA proteins induce immune responses in animals superior to those induced by a conventional vaccine (Johansson et al., 1999). Immunogenicity and efficacy of baculovirus-expressed hemagglutinin of equine influenza virus was compared to a homologous DNA vaccine candidate (Olsen et al., 1997). Taken together, the data demonstrated that a high degree of protection against influenza virus challenge can be induced with recombinant HA or NA proteins, using various experimental approaches and in different animal models.

Lakey et al. (1996) showed that a baculovirus-derived influenza HA vaccine was well-tolerated and immunogenic in human volunteers in a Phase I dose escalation safety study. However, results from Phase II studies conducted at several clinical sites in human volunteers vaccinated with several doses of influenza vaccines comprised of HA and/or NA proteins indicated that the recombinant subunit protein vaccines did not elicit protective immunity [G. Smith, Protein Sciences; M. Perdue, USDA, Personal Communications]. These results indicated that conformational epitopes displayed on the surface of HA and NA peplomers of infectious virions were important in the elicitation of neutralizing antibodies and protective immunity.

Regarding the inclusion of other influenza proteins in recombinant influenza vaccine candidates, a number of studies have been carried out, including the experiments involving influenza nucleoprotein, NP, alone or in combination with M1 protein (Ulmer et al., 1993; Ulmer et al., 1998; Zhou et al., 1995; Tsui et al., 1998). These vaccine candidates, which were composed of quasi-invariant inner virion proteins, elicited a broad spectrum immunity that was primarily cellular (both CD4+ and CD8+ memory T cells). These experiments involved the use of the DNA or viral genetic vectors. Relatively large amounts of injected DNA were needed, as results from experiments with lower doses of DNA indicated little or no protection (Chen et al., 1998). Hence, further preclinical and clinical research may be required to evaluate whether such DNA-based approaches involving influenza NP and M1 are safe, effective, and persistent.

Recently, in an attempt to develop more effective vaccines for influenza, particulate proteins were used as carriers of influenza M2 protein epitopes. The rationale for development of an M2-based vaccine was that in animal studies protective immunity against influenza was elicited by M2 proteins (Slepushkin et al., 1995). Neirynck et al. (1999) used a 23-aa long M2 transmembrane domain as an amino terminal fusion partner with the hepatitis B virus core antigen (HBcAg) to expose the M2 epitope(s) on the surface of HBcAg capsid-like particles. However, in spite of the fact that both full-length M2 protein and M2-HBcAg VLP induced detectable antibodies and protection in mice, it was unlikely that future influenza vaccines would be based exclusively on the M2 protein, as the M2 protein was present at low copy number per virion, was weakly antigenic, was unable to elicit antibodies that bound free influenza virions, and was unable to block virus attachment to cell receptors (i.e. virus neutralization).

Since previous research has shown that the surface influenza glycoproteins, HA and NA, are the primary targets for elicitation of protective immunity against influenza virus and that M1 provides a conserved target for cellular immunity to influenza, a new vaccine candidate may include these viral antigens as a protein macromolecular particle, such as viruslike particles (VLPs). Further, the particle with these influenza antigens may display conformational epitopes that elicit neutralizing antibodies to multiple strains of influenza viruses.

Several studies have demonstrated that recombinant influenza proteins could self-assemble into VLPs in cell culture using mammalian expression plasmids or baculovirus vectors (Gomez-Puertas et al., 1999; Neumann et al., 2000; Latham and Galarza, 2001). Gomez-Puertas et al. (1999) demonstrated that efficient formation of influenza VLP depends on the expression levels of viral proteins. Neumann et al. (2000) established a mammalian expression plasmid-based system for generating infectious influenza virus-like particles entirely from cloned cDNAs. Latham and Galarza (2001) reported the formation of influenza VLPs in insect cells infected with recombinant baculovirus co-expressing HA, NA, M1, and M2 genes. These studies demonstrated that influenza virion proteins may self-assemble upon co-expression in eukaryotic cells.

SUMMARY OF INVENTION

The present invention provides for a vaccine comprising an influenza VLP, wherein said VLP comprises influenza M1, HA and NA proteins, wherein said vaccine induces substantial immunity to influenza virus infection in an animal susceptible to influenza. In one embodiment, said M1 protein is derived from a different influenza virus strain as compared to the HA and NA proteins. In another embodiment, said HA and/or NA exhibit hemagglutinin activity and/or neuraminidase activity, respectfully. In another embodiment, said influenza VLP comprises seasonal influenza virus HA and NA proteins. In another embodiment, said influenza VLP comprises avian influenza HA and NA proteins.

The present invention also provides for a method of inducing substantial immunity to influenza virus infection in an animal susceptible to influenza, comprising administering at least one effective dose of the vaccine comprising an influenza VLP. In one embodiment, said method comprises administering to an animal said influenza VLP orally, intradermally, intranasally, intramusclarly, intraperitoneally, intravenously, or subcutaneously.

The present invention also provides for a method of formulating a vaccine that induces substantial immunity to influenza virus infection to an animal susceptible to influenza, comprising adding to said formulation an effective dose of an influenza VLP, wherein said VLP comprises influenza M1, HA and NA proteins, wherein said vaccine induces substantial immunity to influenza virus infection to said animal. In one embodiment, said VLP consists essentially of influenza M1; HA and NA proteins. In another embodiment, said VLP consists of influenza M1, HA and NA proteins.

The present invention also provides for a virus like particle (VLP) comprising an influenza virus M1 protein and influenza virus H5 and N1 hemagglutinin and neuraminidase proteins. In one embodiment said M1 protein is derived from a different influenza virus strain as compared to the H5 and N1 proteins. In one embodiment, said H5 or N1 are from a H5N1 Glade 1 influenza virus. In another embodiment, said H5 and N1 are from a H5N1 Glade 2 influenza virus.

The invention also provides a macromolecular protein structure containing (a) a first influenza virus M1 protein and (b) an additional structural protein, which may include a second or more influenza virus M1 protein; a first, second or more influenza virus HA protein; a first, second, or more influenza virus NA protein; and a first, second, or more influenza virus M2 protein. If the additional structural protein is not from a second or more influenza virus M1 protein, then both or all members of the group, e.g., first and second influenza M2 virus proteins are included. As such, there is provided a functional influenza protein structure, including a subviral particle, VLP, or capsomer structure, or a portion thereof, a vaccine, a multivalent vaccine, and mixtures thereof consisting essentially of influenza virus structural proteins produced by the method of the invention. In a particularly preferred embodiment, the influenza macromolecular protein structure includes influenza virus HA, NA, and M1 proteins that are the expression products of influenza virus genes cloned as synthetic fragments from a wild type virus.

The macromolecular protein structure may also include an additional structural protein, for example, a nucleoprotein (NP), membrane proteins from species other than noninfluenza viruses and a membrane protein from a non-influenza source, which are derived from avian or mammalian origins and different subtypes of influenza virus, including subtype A and B influenza viruses. The invention may include a chimeric macromolecular protein structure, which includes a portion of at least one protein having a moiety not produced by influenza virus.

Prevention of influenza may be accomplished by providing a macromolecular protein structure that may be self-assembled in a host cell from a recombinant construct. The macromolecular protein structure of the invention has the ability to self-assemble into homotypic or heterotypic viruslike particles (VLPs) that display conformational epitopes on HA and NA proteins, which elicit neutralizing antibodies that are protective. The composition may be a vaccine composition, which also contains a carrier or diluent and/or an adjuvant. The functional influenza VLPs elicit neutralizing antibodies against one or more strains or types of influenza virus depending on whether the functional influenza VLPs contain HA and/or NA proteins from one or more viral strains or types. The vaccine may include influenza virus proteins that are wild type influenza virus proteins. Preferably, the structural proteins containing the influenza VLP, or a portion of thereof, may be derived from the various strains of wild type influenza viruses. The influenza vaccines may be administered to humans or animals to elicit protective immunity against one or more strains or types of influenza virus.

The macromolecular protein structures of the invention may exhibit hemagglutinin activity and/or neuraminidase activity.

The invention provides a method for producing a VLP derived from influenza by constructing a recombinant construct that encodes influenza structural genes, including M1, HA, and at least one structural protein derived from influenza virus. A recombinant construct is used to transfect, infect, or transform a suitable host cell with the recombinant baculovirus. The host cell is cultured under conditions which permit the expression of M1, HA and at least one structural protein derived from influenza virus and the VLP is formed in the host cell. The infected cell media containing a functional influenza VLP is harvested and the VLP is purified. The invention also features an additional step of co-transfecting, co-infecting or co-transforming the host cell with a second recombinant construct which encodes a second influenza protein, thereby incorporating the second influenza protein within the VLP. Such structural proteins may be derived from influenza virus, including NA, M2, and NP, and at least one structural protein is derived from avian or mammalian origins. The structural protein may be a subtype A and B influenza viruses. According to the invention, the host cell may be a eukaryotic cell. In addition, the VLP may be a chimeric VLP.

The invention also features a method of formulating a drug substance containing an influenza VLP by introducing recombinant constructs encoding influenza viral genes into host cells and allowing self-assembly of the recombinant influenza viral proteins into a functional homotypic or heterotypic VLP in cells. The influenza VLP is isolated and purified and a drug substance is formulated containing the influenza VLP. The drug substance may further include an adjuvant. In addition, the invention provides a method for formulating a drug product, by mixing such a drug substance containing an influenza VLP with a lipid vesicle, i.e., a non-ionic lipid vesicle. Thus, functional homotypic or heterotypic VLPs may bud as enveloped particles from the infected cells. The budded influenza VLPs may be isolated and purified by ultracentrifugation or column chromatography as drug substances and formulated alone or with adjuvants such as Novasomes®, a product of Novavax, Inc., as drug products such as vaccines. Novasomes®, which provide an enhanced immunological effect, are further described in U.S. Pat. No. 4,911,928, which is incorporated herein by reference.

The invention provides a method for detecting humoral immunity to influenza virus infection in a vertebrate by providing a test reagent including an effective antibody-detecting amount of influenza virus protein having at least one conformational epitope of an influenza virus macromolecular structure. The test reagent is contacted with a sample of bodily fluid from a vertebrate to be examined for influenza virus infection. Influenza virus specific antibodies contained in the sample are allowed to bind to the conformational epitope of an influenza virus macromolecular structure to form antigen-antibody complexes. The complexes are separated from unbound complexes and contacted with a detectably labeled immunoglobulin-binding agent. The amount of the detectably labeled immunoglobulin-binding agent that is bound to the complexes is determined.

Influenza virus may be detected in a specimen from an animal or human suspected of being infected with the virus by providing antibodies, which have a detectable signal producing label, or are attached to a detectably labeled reagent, having specificity to at least one conformational epitope of the particle of the influenza virus. The specimen is contacted with antibodies and the antibodies are allowed to bind to the influenza virus. The presence of influenza virus in the specimen is determined by means of the detectable label.

The invention provides methods for treatment, prevention, and generating a protective immune response by administering to a vertebrate an effective amount of the composition of the invention.

Alternatively, the influenza VLP drug substance may be formulated as laboratory reagents used for influenza virus structure studies and clinical diagnostic assays. The invention also provides a kit for treating influenza virus by administering an effective amount of a composition of the invention and directions for use.

The invention also provides for a VLP comprising HA, NA and M1 proteins derived from an avian influenza virus which can cause morbidity or mortality in a vertebrate. In one embodiment, said HA, NA and M1 proteins are derived from an avian influenza type A virus. In another embodiment the HA is selected from the group consisting of H1, H2, H3, H4, H5, H6, H7, H8, H9, H10, H11, H12, H13, H14, H15 and H16 and the NA is selected from the group consisting of N1, N2, N3, N4, N5, N6, N7, N8 and N9. In a further embodiment, said HA and NA proteins are 1-15 and N1, respectively. In another embodiment, said HA and NA proteins are H9 and N2, respectively. In another embodiment, said HA and/or NA exhibits hemagglutinin activity and/or neuraminidase activity, respectfully. In one embodiment, the VLP consists essentially of HA, NA and M1 proteins, i.e., these are substantially the only influenza proteins in the VLP.

The invention also provides for a method of producing a VLP, comprising transfecting vectors encoding avian influenza virus proteins into a suitable host cell and expressing said avian influenza virus proteins under condition that allow VLPs to be formed. In one embodiment, this method involves transfecting a host cell with recombinant DNA molecules that encode only the HA, NA and M1 influenza proteins.

The invention also comprises an antigenic formulation comprising a VLP comprising HA, NA and M1 proteins derived from an avian influenza virus which can cause morbidity or mortality in a vertebrate. In another embodiment, the HA is selected from the group consisting of H1, H2, H3, H4, H5, H6, H7, H8, H9, H10, H11, H12, H13, H14, H15 and H16 and the NA is selected from the group consisting of N1, N2, N3, N4, N5, N6, N7, N8 and N9. In a further embodiment, said HA and NA proteins are H5 and N1, respectively. In another embodiment, said HA and NA proteins are H9 and N2, respectively. In a further embodiment, said antigenic formulation is administered to the subject orally, intradermally, intranasally, intramusclarly, intraperitoneally, intravenously, or subcutaneously.

The invention further provides for a method of vaccinating a vertebrate against avian influenza virus comprising administering to said vertebrate a protection-inducing amount of a VLP comprising HA, NA and M1 proteins derived from an avian influenza virus.

This invention also comprises a method of inducing substantial immunity to influenza virus infection or at least one symptom thereof in a subject, comprising administering at least one effective dose of an influenza VLP. In one embodiment, said VLP consists essentially of HA, NA and M1. In another embodiment, said VLP comprises influenza proteins, wherein said influenza proteins consist of HA, NA and M1. In another embodiment, said HA and/or NA exhibits hemagglutinin activity and/or neuraminidase activity, respectfully.

This invention also comprises a method of inducing substantial immunity to influenza virus infection or at least one symptom thereof in a subject, comprising administering at least one effective dose of an avian influenza VLP. In one embodiment, said influenza VLP consists essentially of avian HA, NA and M1. In another embodiment, said influenza VLP comprises influenza proteins, wherein said influenza proteins consist of avian HA, NA and M1.

This invention further comprises a method of inducing substantial immunity to influenza virus infection or at least one symptom thereof in a subject, comprising administering at least one effective dose of a seasonal influenza VLP. In one embodiment, said influenza VLP consists essentially of seasonal HA, NA and M1. In another embodiment, said influenza VLP comprises influenza proteins, wherein said influenza proteins consist of seasonal HA, NA and M1.

This invention further comprises a method of inducing substantial immunity to influenza virus infection or at least one symptom thereof in a subject, comprising administering at least one effective dose of at least one seasonal influenza VLP. In one embodiment, said influenza VLP comprises seasonal influenza HA, NA and M1. In another embodiment, said influenza VLP consists essentially of seasonal influenza HA, NA and M1.

This invention further comprises a method of inducing a substantially protective antibody response to influenza virus infection or at least one symptom thereof in a subject, comprising administering at least one effective dose of an influenza VLP.

This invention comprises a method of inducing a substantially protective cellular immune response to influenza virus infection or at least one symptom thereof in a subject, comprising administering at least one effective dose of an influenza VLP.

This invention further comprises a method of formulating a vaccine that induces substantial immunity to influenza virus infection or at least one symptom thereof to a subject, comprising adding to said formulation an effective dose of an influenza VLP. In one embodiment, said substantial immunity to influenza virus infection or at least one symptom thereof is delivered in one dose. In another embodiment, said substantial immunity to influenza virus infection or at least one symptom thereof is delivered in multiple doses.

This invention further comprises a vaccine comprising an influenza VLP, wherein said vaccine induces substantial immunity to influenza virus infection or at least one symptom thereof when administered to a subject. In one embodiment, said influenza VLP is an avian influenza VLP. In another embodiment, said influenza VLP is a seasonal influenza VLP.

This invention further comprises an antigenic formulation comprising an influenza VLP, wherein said vaccine induces substantial immunity to influenza virus infection or at least one symptom thereof when administered to a subject. In one embodiment, said influenza VLP is an avian influenza VLP. In another embodiment, said influenza VLP is a seasonal influenza VLP.

BRIEF DESCRIPTION OF THE DRAWINGS

FIG. 1 depicts the nucleotide sequence of avian influenza A/Hong Kong/1073/99 (H9N2) virus neuraminidase (NA) gene (SEQ ID NO:1).

FIG. 2 depicts the nucleotide sequence of avian influenza A/Hong Kong/1073/99 (H9N2) virus hemagglutinin (HA) gene (SEQ ID NO:2).

FIG. 3 depicts the nucleotide sequence of avian influenza A/Hong Kong/1073/99 (H9N2) virus matrix protein M1 (M1) gene (SEQ ID NO:3).

FIG. 4 depicts the transfer vectors for construction of recombinant baculoviruses for expression of avian influenza A/Hong Kong/1073/99 (H9N2) HA, NA, and M1 proteins. FIG. 4A depicts a transfer vector for expression of individual genes and FIG. 4B depicts the transfer vector for multi-expression of the genes.

FIG. 7 depicts the detection of influenza virus protein by gel filtration chromatography. The antibodies used in the Western blot analyses are as follows: (A) rabbit anti-H9N2; (b) murine anti-M1 mAb; and (C) murine anti-BACgp64.

FIG. 12A depicts sera from BALB/c mice immunized with recombinant VLPs comprised of HA, NA, and M1 proteins from avian influenza virus type A/H9N2/Hong Kong/1073/99. FIG. 12B depicts sera from New Zealand white rabbits immunized with inactivated avian influenza virus type A H9N2 were reacted with Western blots containing inactivated avian influenza virus type A H9N2 (lanes 1 and 3) or cold-adapted avian influenza virus type A H9N2 (lanes 2 and 4).

FIG. 23 depicts serum hemagglutinin inhibition (HI) responses from serum pulled on days 21 and 42 from ferrets after administration of different strains of H3N2 VLPs.

FIG. 24 depicts anti-HA Antibody (Endpoint Dilution Titer) of mice inoculated intramuscularly with H5N1 (Vietnam/1203/2003) VLPs at low doses.

FIG. 29 depicts virus shedding in nasal washes of ferret inoculated with H9N2 VLP vaccine and subsequently challenged intranasally with H9N2 virus.

DETAILED DESCRIPTION OF THE INVENTION

Figure 5:
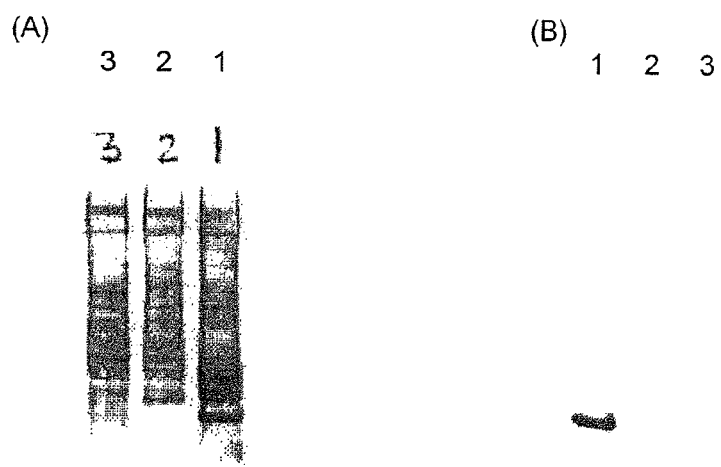
FIG. 5 depicts the expression of avian influenza A/Hong Kong/1073/99 (H9N2) virus HA, NA, and M1 proteins in Sf-9S cells.

As used herein, the term "baculovirus," also known as baculoviridae, refers to a family of enveloped DNA viruses of arthropods, members of which may be used as expression vectors for producing recombinant proteins in insert cell cultures. The virion contains one or more rod-shaped nucleocapsids containing a molecule of circular supercoiled double-stranded DNA (Mr $54\times10^6$-$154\times10^6$). The virus used as a vector is generally *Autographa californica* nuclear polyhedrosis virus (NVP). Expression of introduced genes is under the control of the strong promoter that normally regulates expression of the polyhedron protein component of the large nuclear inclusion in which the viruses are embedded in the infected cells.

As used herein, the term "derived from" refers to the origin or source, and may include naturally occurring, recombinant, unpurified, or purified molecules. The proteins and molecules of the present invention may be derived from influenza or non-influenza molecules.

As used herein the term "first" influenza virus protein, i.e., a first influenza virus M1 protein, refers to a protein, such as M1, HA, NA, and M2, that is derived from a particular strain of influenza virus. The strain or type of the first influenza virus differs from the strain or type of the second influenza virus protein. Thus, "second" influenza virus protein, i.e., the second influenza virus M1 protein, refers to a protein, such as M1, HA, NA, and M2, that is derived from a second strain of influenza virus, which is a different strain or type than the first influenza virus protein.

As used herein, the term "hemagglutinin activity" refers to the ability of HA-containing proteins, VLPs, or portions thereof to bind and agglutinate red blood cells (erythrocytes).

As used herein, the term "neuraminidase activity" refers to the enzymatic activity of NA-containing proteins, VLPs, or portions thereof to cleave sialic acid residues from substrates including proteins such as fetuin.

As used herein, the term "heterotypic" refers to one or more different types or strains of virus.

As used herein, the term "homotypic" refers to one type or strain of virus.

As used herein, the term "macromolecular protein structure" refers to the construction or arrangement of one or more proteins.

As used herein, the term "multivalent" vaccine refers to a vaccine against multiple types or strains of influenza virus.

As used herein, the term "non-influenza" refers to a protein or molecule that is not derived from influenza virus.

As used herein, the term "vaccine" refers to a preparation of dead or weakened pathogens, or of derived antigenic determinants, that is used to induce formation of antibodies or immunity against the pathogen. A vaccine is given to provide immunity to the disease, for example, influenza, which is caused by influenza viruses. The present invention provides vaccine compositions that are immunogenic and provide protection. In addition, the term "vaccine" also refers to a suspension or solution of an immunogen (e.g. VLP) that is administered to a vertebrate to produce protective immunity, i.e., immunity that reduces the severity of disease associated with infection.

As used herein the term "substantial immunity" refers to an immune response in which when VLPs of the invention are administered to a vertebrate there is an induction of the immune system in said vertebrate which results in the prevention of influenza infection, amelioration of influenza infection or reduction of at least one symptom related to influenza virus infection in said vertebrate. Substantial immunity may also refer to a haemagglutination inhibition (HI) titer of $\geq 40$ in a mammal wherein the VLPs of the invention have been administered and have induced an immune response.

As used herein the term "adjuvant" refers to a compound that, when used in combination with a specific immunogen (e.g. a VLP) in a formulation, augments or otherwise alters or modifies the resultant immune response. Modification of the immune response includes intensification or broadening the specificity of either or both antibody and cellular immune responses. Modification of the immune response can also mean decreasing or suppressing certain antigen-specific immune responses.

As used herein the term "immune stimulator" refers to a compound that enhances an immune response via the body's own chemical messengers (cytokines). These molecules comprise various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc. The immune stimulator molecules can be administered in the same formulation as the influenza VLPs, or can be administered separately. Either the protein or an expression vector encoding the protein can be administered to produce an immunostimulatory effect.

As used herein an "effective dose" generally refers to that amount of the VLP of the invention sufficient to induce immunity, to prevent and/or ameliorate influenza virus infection or to reduce at least one symptom of influenza infection and/or to enhance the efficacy of another dose of a VLP. An effective dose may refer to the amount of the VLP sufficient to delay or minimize the onset of an influenza infection. An effective dose may also refer to the amount of the VLP that provides a therapeutic benefit in the treatment or management of influenza infection. Further, an effective dose is the amount with respect to the VLPs of the invention alone, or in combination with other therapies, that provides a therapeutic benefit in the treatment or management of an influenza viral infection. An effective dose may also be the amount sufficient to enhance a subject's (e.g., a human's) own immune response against a subsequent exposure to influenza virus. Levels of immunity can be monitored, e.g., by measuring amounts of neutralizing secretory and/or serum antibodies, e.g., by plaque neutralization, complement fixation, enzyme-linked immunosorbent, or microneutralization assay. In the case of a vaccine, an "effective dose" is one that prevents disease or reduces the severity of symptoms.

As used herein the term "avian influenza virus" refers to influenza viruses found chiefly in birds but that can also infect humans or other animals. In some instances, avian influenza viruses may be transmitted or spread from one human to another. An avian influenza virus that infects humans has the potential to cause an influenza pandemic, i.e., morbidity and/or mortality in humans. A pandemic occurs when a new strain of influenza virus (a virus in which human have no natural immunity) emerges, spreading beyond individual localities, possibly around the globe, and infecting many humans at once.

As used herein the term "seasonal influenza virus" refers to the influenza viral strains that have been determined to be passing within the human population for a given influenza season based on epidemiological surveys conducted by National Influenza Centers worldwide. These epidemiological studies, and some isolated influenza viruses, are sent to one of four World Health Organization (WHO) reference laboratories, one of which is at the Centers for Disease Control and Prevention (CDC) in Atlanta for detailed testing. These laboratories test how well antibodies made to the current vaccine react to the circulating virus and new flu viruses. This information, along with information about flu activity, is summarized and presented to an advisory committee of the U.S. Food and Drug Administration (FDA) and at a WHO meeting. These meetings result in the selection of three viruses (two subtypes of influenza A viruses and one influenza B virus) to go into flu vaccines for the following fall and winter. The selection occurs in February for the northern hemisphere and in September for the southern hemisphere. Usually, one or two of the three virus strains in the vaccine changes each year.

As used herein the term "substantially protective antibody response" refers to an immune response mediated by antibodies against an influenza virus, which is exhibited by a vertebrate (e.g., a human), that prevents or ameliorates influenza infection or reduces at least one symptom thereof. VLPs of the invention can stimulate the production of antibodies that, for example, neutralizing antibodies that block influenza viruses from entering cells, blocks replication of said influenza virus by binding to the virus, and/or protect host cells from infection and destruction.

As used herein the term "substantially protective cellular response" refers to an immune response that is mediated by T-lymphocytes and/or other white blood cells against influenza virus, exhibited by a vertebrate (e.g., a human), that prevents or ameliorates influenza infection or reduces at least one symptom thereof. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

As used herein the term "substantial immunity in a population-wide basis" refers to immunity as a result of VLPs of the invention administered to individuals in a population. The immunity in said individual in said population results in the prevention, amelioration of influenza infection, or reduction of at least one symptom related to influenza virus infection in said individual, and prevents the spread of said influenza virus to others in the population. The term population is defined as group of individuals (e.g. schoolchildren, elderly, healthy individuals etc.) and may comprise a geographic area (e.g. specific cities, schools, neighborhoods, workplace, country, state, etc.).

As use herein, the term "antigenic formulation" or "antigenic composition" refers to a preparation which, when administered to a vertebrate, especially a bird or a mammal, will induce an immune response.

As use herein, the term "vertebrate" or "subject" or "patient" refers to any member of the subphylum cordata, including, without limitation, humans and other primates, including non-human primates such as chimpanzees and other apes and monkey species. Farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like are also non-limiting examples. The terms "mammals" and "animals" are included in this definition. Both adult and newborn individuals are intended to be covered.

Influenza remains a pervasive public health concern despite the availability of specific inactivated virus vaccines that are 60-80% effective under optimal conditions. When these vaccines are effective, illness is usually averted by preventing viral infection. Vaccine failure can occur as a result of accumulated antigenic differences (antigenic shift and antigenic drift). For example, avian influenza virus type A H9N2 co-circulated with human influenza virus type A Sydney/97 (H3N2) in pigs and led to genetic reassortment and emergence of new strains of human influenza virus with pandemic potential (Peiris et al., 2001). In the event of such antigenic shift, it is unlikely that current vaccines would provide adequate protection.

Another reason for the paucity of influenza vaccine programs is the relatively short persistence of immunity elicited by the current vaccines. Further inadequacy of influenza control measures reflects restricted use of current vaccines because of vaccine reactogenicity and side effects in young children, elderly, and people with allergies to components of eggs, which are used in manufacturing of commercially licensed inactivated virus influenza vaccines.

Additionally, inactivated influenza virus vaccines often lack or contain altered HA and NA conformational epitopes, which elicit neutralizing antibodies and play a major role in protection against disease. Thus, inactivated viral vaccines, as well as some recombinant monomeric influenza subunit protein vaccines, deliver inadequate protection. On the other hand, macromolecular protein structures, such as capsomers, subviral particles, and/or VLPs, include multiple copies of native proteins exhibiting conformational epitopes, which are advantageous for optimal vaccine immunogenicity.

The present invention describes the cloning of avian influenza A/Hong Kong/1073/99 (H9N2) virus HA, NA, and M1 genes into a single baculovirus expression vector alone or in tandem and production of influenza vaccine candidates or reagents comprised of recombinant influenza structural proteins that self-assemble into functional and immunogenic homotypic macromolecular protein structures, including subviral influenza particles and influenza VLP, in baculovirus-infected insect cells.

The present invention describes the cloning of human influenza A/Sydney/5/97 and A/Fujian/411/2002 (H3N2) virus HA, NA, M1, M2, and NP genes into baculovirus expression vectors and production influenza vaccine candidates or reagents comprised of influenza structural proteins that self-assemble into functional and immunogenic homotypic macromolecular protein structures, including subviral influenza particles and influenza VLP, in baculovirus-infected insect cells.

In addition, the instant invention describes the cloning of the HA gene of human influenza A/Sydney/5/97 and A/Fujian/411/2002 (H3N2) virus and the HA, NA, and M1 genes of avian influenza A/Hong Kong/1073/99 (H9N2) into a single baculovirus expression vector in tandem and production influenza vaccine candidates or reagents comprised of influenza structural proteins that self-assemble into functional and immunogenic heterotypic macromolecular protein structures, including subviral influenza particles and influenza VLP, in baculovirus-infected insect cells.

VLPs of the Invention

Influenza VLPs of the invention are useful for preparing vaccines against influenza viruses. One important feature of this system is the ability to replace the surface glycoproteins with different subtypes of HA and/or NA or other viral proteins, thus, allowing updating of new influenza antigenic variants every year or to prepare for an influenza pandemic. As antigenic variants of these glycoproteins are identified, the VLPs can be updated to include these new variants (e.g. for seasonal influenza vaccines). In addition, surface glycoproteins from potentially pandemic viruses, such as H5N1, or other HA, NA combinations with pandemic potential could be incorporated into VLPs without concern of releasing genes that had not circulated in humans for several decades. This is because the VLPs are not infectious, do not replicate and cannot cause disease. Thus, this system allows for creating a new candidate influenza vaccine every year and/or an influenza pandemic vaccine whenever it is necessary.

There are 16 different hemagglutinin (HA) and 9 different neuraminidase (NA) all of which have been found among wild birds. Wild birds are the primary natural reservoir for all types of influenza A viruses and are thought to be the source of all types of influenza A viruses in all other vertebrates. These subtypes differ because of changes in the hemagglutinin (HA) and neuraminidase (NA) on their surface. Many different combinations of HA and NA proteins are possible. Each combination represents a different type of influenza A virus. In addition, each type can be further classified into strains based on different mutations found in each of its 8 genes.

All known types of influenza A viruses can be found in birds. Usually avian influenza viruses do not infect humans. However, some avian influenza viruses develop genetic variations associated with the capability of crossing the species barrier. Such a virus is capable of causing a pandemic because humans have no natural immunity to the virus and can easily spread from person to person. In 1997, avian influenza virus jumped from a bird to a human in Hong Kong during an outbreak of bird flu in poultry. This virus was identified as influenza virus H5N1. The virus caused severe respiratory illness in 18 people, six of whom died. Since that time, many more cases of known H5N1 infections have occurred among humans worldwide; approximately half of those people have died.

Thus, the present invention encompasses the cloning of HA, NA and M1 nucleotides from avian influenza viruses, influenza viruses with pandemic potential and/or seasonal influenza viruses into expression vectors. The present invention also describes the production of influenza vaccine candidates or reagents comprised of influenza proteins that self-assemble into functional VLPs. All combinations of viral proteins must be co-expressed with a M1 nucleotide.

VLPs of the invention consist or comprise influenza HA, NA and M1 proteins. In one embodiment, said VLP comprises a HA from an avian, pandemic and/or seasonal influenza virus and a NA from an avian, pandemic and/or seasonal influenza virus, wherein said HA is selected from the group consisting of H1, H2, H3, H4, H5, H6, H,7 H8, H9, H10, H11, H12, H13, H14, H15 and H16 and said NA is selected from the group consisting of N1, N2, N3, N4, N5, N6, N7, N8 and N9. In another embodiment, the invention comprises a VLP that consists essentially of HA, NA and M1. Said HA and NA can be from the above list of HA and NA. These VLPs may comprise additional influenza proteins and/or protein contaminates in negligible concentrations. In another embodiment, said influenza VLP comprises influenza proteins, wherein said influenza proteins consist of HA, NA and M1 proteins. These VLPs contain HA, NA and M1 and may contain additional cellular constituents such as cellular proteins, baculovirus proteins, lipids, carbohydrates etc., but do not contain additional influenza proteins (other than fragments of M1, HA and/or NA). In another embodiment, the HA and/or the NA may exhibit hemagglutinin activity and/or neuraminidase activity, respectively, when expressed on the surface of VLPs.

In another embodiment, said VLP comprises HA and NA of the H5N1 virus and a M1 protein (the M1 protein may or may not be from the same viral strain). In another embodiment, said VLP consists essentially of HA, NA of the H5N1 virus and a M1 protein. These VLPs may comprise additional influenza proteins and/or protein contaminates in negligible concentrations. In a further embodiment, said VLP consists of HA, NA of the H5N1 virus and a M1 protein. In another embodiment, said influenza VLP comprises influenza proteins, wherein said influenza proteins consist of H5, N1 and M1 proteins. These VLPs contain H5, N9 and M1 and may contain additional cellular constituents such as cellular proteins, baculovirus proteins, lipids, carbohydrates etc., but do not contain additional influenza proteins (other than fragments of M1, H5 and/or N1). In another embodiment, the H5 and/or the N1 may exhibit hemagglutinin activity and/or neuraminidase activity, respectively, when expressed on the surface of VLPs.

In another embodiment, said VLP comprises the HA and NA of the H9N2 virus, and a M1 protein. In another embodiment, said VLP consists essentially of the HA and NA of the H9N2 virus, and a M1 protein. These VLPs may comprise additional influenza proteins and/or protein contaminates in negligible concentrations. In another embodiment, said VLP consists of the HA and NA of the H9N2 virus, and a M1 protein. In another embodiment, said influenza VLP comprises influenza proteins, wherein said influenza proteins consist of H9, N2 and M1 proteins. These VLPs contain H9, N2 and M1 and may contain additional cellular constituents such as cellular proteins, baculovirus proteins, lipids, carbohydrates etc., but do not contain additional influenza proteins (other than fragments of M1, H9 and/or N2). In another embodiment, the H9 and/or the N2 may exhibit hemagglutinin activity and/or neuraminidase activity, respectively, when expressed on the surface of VLPs.

In another embodiment, said VLP comprises the HA and NA from an influenza B virus, and a M1 protein. Influenza B viruses are usually found only in humans. Unlike influenza A viruses, these viruses are not classified according to subtype. Influenza B viruses can cause morbidity and mortality among humans, but in general are associated with less severe epidemics than influenza A viruses. In another embodiment, said VLP consists essentially of the HA and NA of the influenza B virus, and a M1 protein. These VLPs may comprise additional influenza proteins and/or protein contaminates in negligible concentrations. In another embodiment, said influenza VLP comprises influenza proteins, wherein said influenza proteins consist of HA, NA and M1 proteins. These VLPs contain HA, NA and M1 and may contain additional cellular constituents such as cellular proteins, baculovirus proteins, lipids, carbohydrates etc., but do not contain additional influenza proteins (other than fragments of M1, HA and/or NA). In another embodiment, said VLP consists of the HA and NA of the influenza B virus, and a M1 protein. In another embodiment, the HA and/or the NA may exhibit hemagglutinin activity and/or neuraminidase activity, respectively, when expressed on the surface of VLPs.

The invention also encompasses variants of the said influenza proteins expressed on or in the VLPs of the invention. The variants may contain alterations in the amino acid sequences of the constituent proteins. The term "variant" with respect to a polypeptide refers to an amino acid sequence that is altered by one or more amino acids with respect to a reference sequence. The variant can have "conservative" changes, wherein a substituted amino acid has similar structural or chemical properties, e.g., replacement of leucine with isoleucine. Alternatively, a variant can have "nonconservative" changes, e.g., replacement of a glycine with a tryptophan. Analogous minor variations can also include amino acid deletion or insertion, or both. Guidance in determining which amino acid residues can be substituted, inserted, or deleted without eliminating biological or immunological activity can be found using computer programs well known in the art, for example, DNASTAR software.

Natural variants can occur due to antigenic drifts. Antigenic drifts are small changes in the viral proteins that happen continually over time. Thus, a person infected with a particular flu virus strain develops antibody against that virus, as newer virus strains appear, the antibodies against the older strains no longer recognize the newer virus and reinfection can occur. This is why there is a new vaccine for influenza each season. In addition, some changes in an influenza virus can cause influenza virus to cross species. For example, some avian influenza viruses developed genetic variations associated with the capability of crossing the species barrier. Such a virus is capable of causing a pandemic because people have no natural immunity to the virus and the virus can easily spread from person to person. These naturally occurring variations of the influenza proteins are an embodiment of the invention.

General texts which describe molecular biological techniques, which are applicable to the present invention, such as cloning, mutation, cell culture and the like, include Berger and Kimmel, Guide to Molecular Cloning Techniques, Methods in Enzymology volume 152 Academic Press, Inc., San Diego, Calif. (Berger); Sambrook et al., Molecular Cloning—A Laboratory Manual (3rd Ed.), Vol. 1-3, Cold Spring Harbor Laboratory, Cold Spring Harbor, N.Y., 2000 ("Sambrook") and Current Protocols in Molecular Biology, F. M. Ausubel et al., eds., Current Protocols, a joint venture between Greene Publishing Associates, Inc. and John Wiley & Sons, Inc., ("Ausubel"). These texts describe mutagenesis, the use of vectors, promoters and many other relevant topics related to, e.g., the cloning and mutation of HA and/or NA molecules, etc. Thus, the invention also encompasses using known methods of protein engineering and recombinant DNA technology to improve or alter the characteristics of the influenza proteins expressed on or in the VLPs of the invention. Various types of mutagenesis can be used to produce and/or isolate variant HA, NA and/or M1 molecules and/or to further modify/mutate the polypeptides of the invention. They include but are not limited to site-directed, random point mutagenesis, homologous recombination (DNA shuffling), mutagenesis using uracil containing templates, oligonucleotide-directed mutagenesis, phosphorothioate-modified DNA mutagenesis, mutagenesis using gapped duplex DNA or the like. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the present invention. In one embodiment, mutagenesis can be guided by known information of the naturally occurring molecule or altered or mutated naturally occurring molecule, e.g., sequence, sequence comparisons, physical properties, crystal structure or the like.

The invention further comprises influenza protein variants which show substantial biological activity, e.g., able to elicit an effective antibody response when expressed on or in a VLP. Such variants include deletions, insertions, inversions, repeats, and substitutions selected according to general rules known in the art so as have little effect on activity.

Methods of cloning said influenza proteins are known in the art. For example, the influenza gene encoding a specific influenza protein can be isolated by RT-PCR from polyadenylated mRNA extracted from cells which had been infected with an influenza virus. The resulting product gene can be cloned as a DNA insert into a vector. The term "vector" refers to the means by which a nucleic acid can be propagated and/or transferred between organisms, cells, or cellular components. Vectors include plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. In many, but not all, common embodiments, the vectors of the present invention are plasmids or bacmids.

Thus, the invention comprises nucleotides which encode the HA, NA and/or M1 influenza proteins cloned into an expression vector which can be expressed in a cell which induces the formation of VLPs. An "expression vector" is a vector, such as a plasmid that is capable of promoting expression, as well as replication of a nucleic acid incorporated therein. Typically, the nucleic acid to be expressed is "operably linked" to a promoter and/or enhancer, and is subject to transcription regulatory control by the promoter and/or enhancer. In one embodiment, said nucleotides that encode for HA from an avian, pandemic and/or seasonal influenza virus is selected from the group consisting of H1, H2, H3, H4, H5, H6, H7, H8, H9, H10, H11, H12, H13, H14, H15 and H16. In another embodiment, said nucleotides that encode for NA from an avian, pandemic and/or seasonal influenza virus, is selected from the group consisting of N1, N2, N3, N4, N5, N6, N7, N8 and N9. In another embodiment, said vector comprises nucleotides that encode the HA, NA and/or M1 influenza protein. In another embodiment, said vector consists of nucleotides that encodes the HA, NA and M1 influenza protein. A preferred expression vector is a baculovirus vector. After the nucleotides encoding said influenza proteins have been cloned said nucleotides can be further manipulated. For example, a person with skill in the art can mutate specific bases in the coding region to produce variants. The variants may contain alterations in the coding regions, non-coding regions, or both. Such variants may increase the immunogenicity of an influenza protein or remove a splice site from a protein or RNA. For example, in one embodiment, the donor and acceptor splicing sites on the influenza M protein (full length) are mutated to prevent splicing of the M mRNA into M1 and M2 transcripts. In another embodiment the HA is engineered to remove or mutate the cleavage site. For example, wild type H5 HA has a cleavage site that contains multiple basic amino acids (RRRKR, SEQ ID NO: 59). This wild type sequence makes the HA more susceptible to multiple ubiquitous proteases that may be present in host or system expression these HAs. In one embodiment, removing these amino acids can reduce the susceptibility of the HA to various proteases. In another embodiment, the cleavage site can be mutated to remove the cleavage site (e.g. mutate to RESR, SEQ ID NO: 60).

The invention also utilizes nucleic acid and polypeptides which encode NA, HA and M1. In one embodiment, an influenza NA nucleic acid or protein is at least 85%, 90%, 95%, 96%, 97%, 98% or 99% identical to SEQ ID NOs 1, 11, 31, 32, 39, 38, 46, 47, 54 or 55. In another embodiment, an influenza HA nucleic acid or protein is at least 85%, 90%, 95%, 96%, 97%, 98% or 99% identical to SEQ ID NOs 2, 10, 56, 57, 58, 27, 28, 29, 30, 37, 36, 33, 34, 35, 42, 43, 44, 45, 50, 51, 52, or 53. In another embodiment, an influenza M1 nucleic acid or protein is at least 85%, 90%, 95%, 96%, 97%, 98% or 99% identical to SEQ ID NOs 12, 40, 41, 48 or 49.

In some embodiments, mutations containing alterations which produce silent substitutions, additions, or deletions, but do not alter the properties or activities of the encoded protein or how the proteins are made. Nucleotide variants can be produced for a variety of reasons, e.g., to optimize codon expression for a particular host (change codons in the human mRNA to those preferred by insect cells such as Sf9 cells). See U.S. patent publication 2005/0118191, herein incorporated by reference in its entirety for all purposes. Examples of optimized codon sequences of the invention are disclosed below (e.g. SEQ ID 42, 44, 46, 48, 50, 52, and 54).

In addition, the nucleotides can be sequenced to ensure that the correct coding regions were cloned and do not contain any unwanted mutations. The nucleotides can be subcloned into an expression vector (e.g. baculovirus) for expression in any cell. The above is only one example of how the influenza viral proteins can be cloned. A person with skill in the art understands that additional methods are available and are possible.

The invention also provides for constructs and/or vectors that comprise avian, pandemic and/or seasonal nucleotides which encode for influenza virus structural genes, including NA, M1 and/or HA. The vector may be, for example, a phage, plasmid, viral, or retroviral vector. The constructs and/or vectors that encodes avian, pandemic and/or seasonal influenza virus structural genes, including NA, M1 and/or HA should be operatively linked to an appropriate promoter, such as the AcMNPV polyhedrin promoter (or other baculovirus), phage lambda PL promoter, the *E. coli* lac, phoA and tac promoters, the SV40 early and late promoters, and promoters of retroviral LTRs are non-limiting examples. Other suitable promoters will be known to the skilled artisan depending on the host cell and/or the rate of expression desired. The expression constructs will further contain sites for transcription initiation, termination, and, in the transcribed region, a ribosome binding site for translation. The coding portion of the transcripts expressed by the constructs will preferably include a translation initiating codon at the beginning and a termination codon appropriately positioned at the end of the polypeptide to be translated.

The expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Among vectors preferred are virus vectors, such as baculovirus, poxvirus (e.g., vaccinia virus, avipox virus, canarypox virus, fowlpox virus, raccoonpox virus, swinepox virus, etc.), adenovirus (e.g., canine adenovirus), herpesvirus, and retrovirus. Other vectors that can be used with the invention comprise vectors for use in bacteria, which comprise pQE70, pQE60 and pQE-9, pBluescript vectors, Phagescript vectors, pNHSA, pNH16a, pNH18A, pNH46A, ptrc99a, pKK223-3, pKK233-3, pDR540, pRIT5. Among preferred eukaryotic vectors are pFastBac1 pWINEO, pSV2CAT, pOG44, pXT1 and pSG, pSVK3, pBPV, pMSG, and pSVL. Other suitable vectors will be readily apparent to the skilled artisan. In one embodiment, said vector that comprises nucleotides encoding for avian, pandemic and/or seasonal influenza virus structural genes, including HA, M1 and/or NA, is pFastBac. In another embodiment, said vector that comprises an insert that consists of nucleotides encoding for avian, pandemic and/or seasonal influenza virus structural genes, comprises HA, M1 and NA, is pFastBac.

Next, the recombinant vector can be transfected, infected, or transformed into a suitable host cell. Thus, the invention provides for host cells which comprise a vector (or vectors) that contain nucleic acids which code for HA, M1 and/or NA and permit the expression of HA, M1 and/or NA in said host cell under conditions which allow the formation of VLPs.

In one embodiment, the recombinant constructs mentioned above could be used to transfect, infect, or transform and can express HA, NA and M1 influenza proteins in eukaryotic cells and/or prokaryotic cells. Among eukaryotic host cells are yeast, insect, avian, plant, *C. elegans* (or nematode) and mammalian host cells. Non limiting examples of insect cells are, *Spodoptera frugiperda* (Sf) cells, e.g. Sf9, Sf21, *Trichoplusia ni* cells, e.g. High Five cells, and *Drosophila* S2 cells. Examples of fungi (including yeast) host cells are *S. cerevisiae, Kluyveromyces lactis* (K lactis), species of *Candida* including *C. albicans* and *C. glabrata, Aspergillus nidulans, Schizosaccharomyces pombe* (*S. pombe*), *Pichia pastoris*, and *Yarrowia lipolytica*. Examples of mammalian cells are COS cells, baby hamster kidney cells, mouse L cells, LNCaP cells, Chinese hamster ovary (CHO) cells, human embryonic kidney (HEK) cells, and African green monkey cells, CV1 cells, HeLa cells, MDCK cells, Vero and Hep-2 cells. *Xenopus laevis* oocytes, or other cells of amphibian origin, may also be used. Prokaryotic host cells include bacterial cells, for example, *E. coli, B. subtilis*, and mycobacteria.

Vectors, e.g., vectors comprising HA, NA and/or M1 polynucleotides, can be transfected into host cells according to methods well known in the art. For example, introducing nucleic acids into eukaryotic cells can be by calcium phosphate co-precipitation, electroporation, microinjection, lipofection, and transfection employing polyamine transfection reagents. In one embodiment, the said vector is a recombinant baculovirus. In another embodiment, said recombinant baculovirus is transfected into a eukaryotic cell. In a preferred embodiment, said cell is an insect cell. In another embodiment, said insect cell is a Sf9 cell.

In another embodiment, said vector and/or host cell comprise nucleotides which encode an avian, pandemic and/or seasonal influenza virus HA protein selected from the group consisting of H1, H2, H3, H4, H5, H6, H7, H8, H9, H10, H11, H12, H13, H14, H15 and H16. In another embodiment, said vector and/or host cells comprise nucleotides which encode an NA protein which is selected from the group consisting of N1, N2, N3, N4, N5, N6, N7, N8 and N9. In another embodiment, said vector and/or host cell comprises influenza HA, M1 and/or NA. In another embodiment, said vector and/or host cell consists essentially of HA, M1 and/or NA. In a further embodiment, said vector and/or host cell consists of influenza protein comprising HA, M1 and NA. These vector and/or host cell contain HA, NA and M1 and may contain additional cellular constituents such as cellular proteins, baculovirus proteins, lipids, carbohydrates etc., but do not contain additional influenza proteins (other than fragments of M1, HA and/or NA). In another embodiment, said nucleotides encode for an HA and/or the NA that exhibits hemagglutinin activity and/or neuraminidase activity, respectively, when expressed on the surface of VLPs.

This invention also provides for constructs and methods that will increase the efficiency of VLPs production. For example, removing cleavage sites from proteins in order to increase protein expression (see above). Other method comprises the addition of leader sequences to the HA, NA and/or M1 protein for more efficient transporting. For example, a heterologous signal sequence can be fused to the HA, NA and/or M1 influenza protein. In one embodiment, the signal sequence can be derived from the gene of an insect cell and fused to the influenza HA protein (for expression in insect cells). In another embodiment, the signal peptide is the chitinase signal sequence, which works efficiently in baculovirus expression systems. In other embodiment, interchanging leader sequences between influenza proteins can provide better protein transport. For example, it has been shown that H5 hemagglutinin is less efficient at being transported to the surface of particles. H9 hemagglutinins, however, targets the surface and is integrated into the surface more efficiently. Thus, in one embodiment, the H9 leader sequence is fused to the H5 protein.

Another method to increase efficiency of VLP production is to codon optimize the nucleotides that encode HA, NA and/or M1 proteins for a specific cell type. For example, codon optimizing nucleic acids for expression in Sf9 cell (see U.S. patent publication 2005/0118191, herein incorporated by reference in its entirety for all purposes). Examples of optimized codon sequences for Sf9 cells are disclosed below (e.g. SEQ ID 42, 44, 46, 48, 50, 52, and 54). In one embodiment, the nucleic acid sequence of codon optimized influenza protein is at least 85%, 90%, 95%, 96, 97, 98, or 99% to any one of SEQ ID Nos. 42, 44, 46, 48, 50, 52, and 54.

The invention also provides for methods of producing VLPs, said methods comprising expressing an avian, pandemic and/or seasonal influenza proteins under conditions that allow VLP formation. Depending on the expression system and host cell selected, the VLPs are produced by growing host cells transformed by an expression vector under conditions whereby the recombinant proteins are expressed and VLPs are formed. The selection of the appropriate growth conditions is within the skill or a person with skill of one of ordinary skill in the art.

Methods to grow cells engineered to produce VLPs of the invention include, but are not limited to, batch, batch-fed, continuous and perfusion cell culture techniques. Cell culture means the growth and propagation of cells in a bioreactor (a fermentation chamber) where cells propagate and express protein (e.g. recombinant proteins) for purification and isolation. Typically, cell culture is performed under sterile, controlled temperature and atmospheric conditions in a bioreactor. A bioreactor is a chamber used to culture cells in which environmental conditions such as temperature, atmosphere, agitation and/or pH can be monitored. In one embodiment, said bioreactor is a stainless steel chamber. In another embodiment, said bioreactor is a pre-sterilized plastic bag (e.g. Cellbag®, Wave Biotech, Bridgewater, N.J.). In other embodiment, said pre-sterilized plastic bags are about 50 L to 1000 L bags.

The VLPs are then isolated using methods that preserve the integrity thereof, such as by gradient centrifugation, e.g., cesium chloride, sucrose and iodixanol, as well as standard purification techniques including, e.g., ion exchange and gel filtration chromatography.

Figure 26:
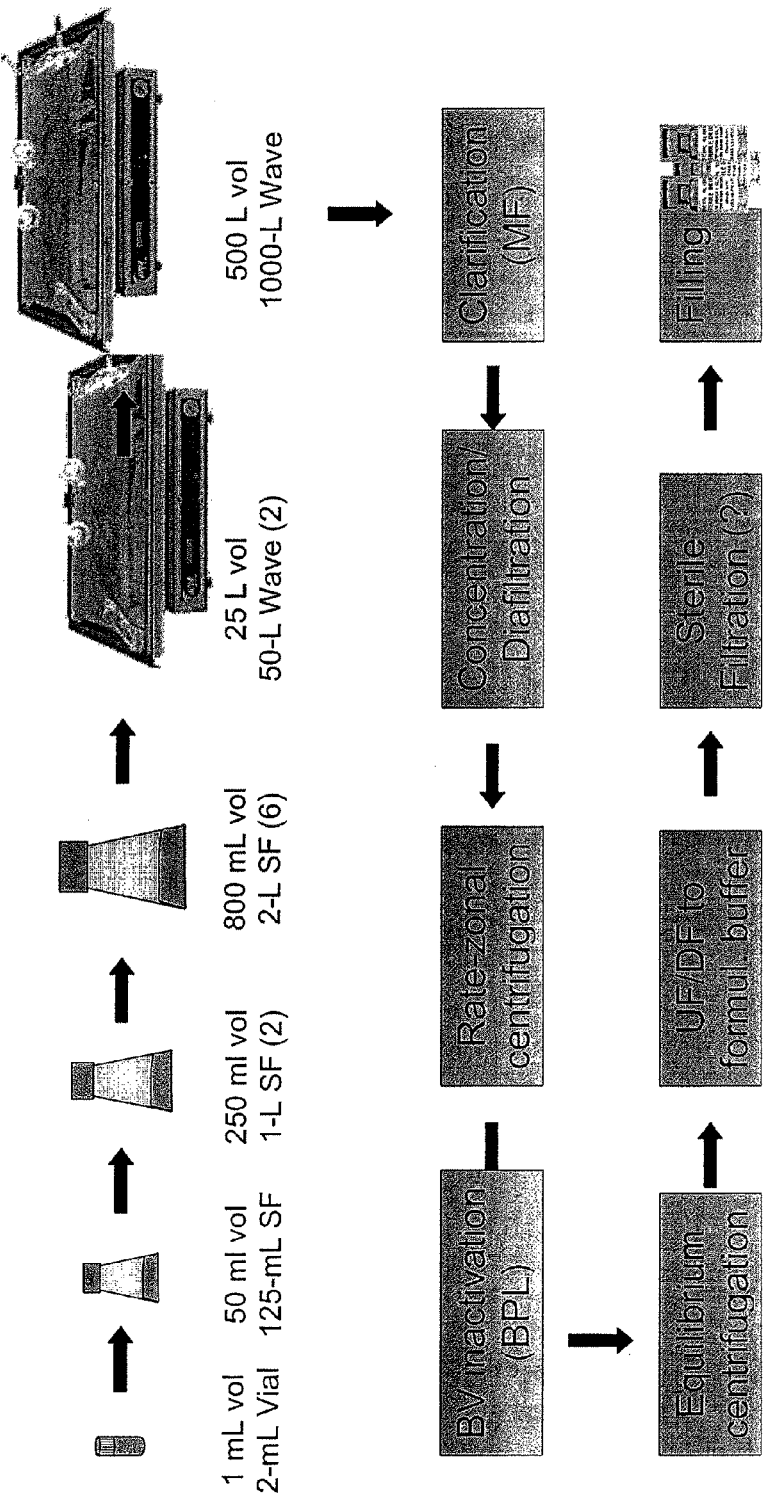
FIG. 26 depicts an example for manufacturing, isolating and purifying VLPs of the invention.

The following is an example of how VLPs of the invention can be made, isolated and purified. Usually VLPs are produced from recombinant cell lines engineered to create a VLP when said cells are grown in cell culture (see above). Production of VLPs may be accomplished by the scheme illustrated in FIG. 26. A person of skill in the art would understand that there are additional methods that can be utilized to make and purify VLPs of the invention, thus the invention is not limited to the method described.

Production of VLPs of the invention can start by seeding Sf9 cells (non-infected) into shaker flasks, allowing the cells to expand and scaling up as the cells grow and multiply (for example from a 125-ml flask to a 50 L Wave bag). The medium used to grow the cell is formulated for the appropriate cell line (preferably serum free media, e.g. insect medium ExCell-420, JRH). Next, said cells are infected with recombinant baculovirus at the most efficient multiplicity of infection (e.g. from about 1 to about 3 plaque forming units per cell). Once infection has occurred, the influenza HA, NA and M1 proteins are expressed from the virus genome, self assemble into VLPs and are secreted from the cells approximately 24 to 72 hours post infection. Usually, infection is most efficient when the cells are in mid-log phase of growth ($4-8 \times 10^6$ cells/ml) and are at least about 90% viable.

VLPs of the invention can be harvested approximately 48 to 96 hours post infection, when the levels of VLPs in the cell culture medium are near the maximum but before extensive cell lysis. The Sf9 cell density and viability at the time of harvest can be about $0.5 \times 10^6$ cells/ml to about $1.5 \times 10^6$ cells/ml with at least 20% viability, as shown by dye exclusion assay. Next, the medium is removed and clarified. NaCl can be added to the medium to a concentration of about 0.4 to about 1.0 M, preferably to about 0.5 M, to avoid VLP aggregation. The removal of cell and cellular debris from the cell culture medium containing VLPs of the invention can be accomplished by tangential flow filtration (TFF) with a single use, pre-sterilized hollow fiber 0.5 or 1.00 µm filter cartridge or a similar device.

Next, VLPs in the clarified culture medium can be concentrated by ultrafiltration using a disposable, pre-sterilized 500,000 molecular weight cut off hollow fiber cartridge. The concentrated VLPs can be diafiltrated against 10 volumes pH 7.0 to 8.0 phosphate-buffered saline (PBS) containing 0.5 M NaCl to remove residual medium components.

The concentrated, diafiltered VLPs can be furthered purified on a 20% to 60% discontinuous sucrose gradient in pH 7.2 PBS buffer with 0.5 M NaCl by centrifugation at 6,500×g for 18 hours at about 4° C. to about 10° C. Usually VLPs will form a distinctive visible band between about 30% to about 40% sucrose or at the interface (in a 20% and 60% step gradient) that can be collected from the gradient and stored. This product can be diluted to comprise 200 mM of NaCl in preparation for the next step in the purification process. This product contains VLPs and may contain intact baculovirus particles.

Further purification of VLPs can be achieved by anion exchange chromatography, or 44% isopycnic sucrose cushion centrifugation. In anion exchange chromatography, the sample from the sucrose gradient (see above) is loaded into column containing a medium with an anion (e.g. Matrix Fractogel EMD TMAE) and eluded via a salt gradient (from about 0.2 M to about 1.0 M of NaCl) that can separate the VLP from other contaminates (e.g. baculovirus and DNA/RNA). In the sucrose cushion method, the sample comprising the VLPs is added to a 44% sucrose cushion and centrifuged for about 18 hours at 30,000 g. VLPs form a band at the top of 44% sucrose, while baculovirus precipitates at the bottom and other contaminating proteins stay in the 0% sucrose layer at the top. The VLP peak or band is collected.

The intact baculovirus can be inactivated, if desired. Inactivation can be accomplished by chemical methods, for example, formalin or β-propyl lactone (BPL). Removal and/or inactivation of intact baculovirus can also be largely accomplished by using selective precipitation and chromatographic methods known in the art, as exemplified above. Methods of inactivation comprise incubating the sample containing the VLPs in 0.2% of BPL for 3 hours at about 25° C. to about 27° C. The baculovirus can also be inactivated by incubating the sample containing the VLPs at 0.05% BPL at 4° C. for 3 days, then at 37° C. for one hour.

After the inactivation/removal step, the product comprising VLPs can be run through another diafiltration step to remove any reagent from the inactivation step and/or any residual sucrose, and to place the VLPs into the desired buffer (e.g. PBS). The solution Comprising VLPs can be sterilized by methods known in the art (e.g. sterile filtration) and stored in the refrigerator or freezer.

The above techniques can be practiced across a variety of scales. For example, T-flasks, shake-flasks, spinner bottles, up to industrial sized bioreactors. The bioreactors can comprise either a stainless steel tank or a pre-sterilized plastic bag (for example, the system sold by Wave Biotech, Bridgewater, N.J.). A person with skill in the art will know what is most desirable for their purposes.

Expansion and production of baculovirus expression vectors and infection of cells with recombinant baculovirus to produce recombinant influenza VLPs can be accomplished in insect cells, for example Sf9 insect cells as previously described. In a preferred embodiment, the cells are SF9 infected with recombinant baculovirus engineered to produce influenza VLPs.

Pharmaceutical or Vaccine Formulations and Administration

The pharmaceutical compositions useful herein contain a pharmaceutically acceptable carrier, including any suitable diluent or excipient, which includes any pharmaceutical agent that does not itself induce the production of an immune response harmful to the vertebrate receiving the composition, and which may be administered without undue toxicity and a VLP of the invention. As used herein, the term "pharmaceutically acceptable" means being approved by a regulatory agency of the Federal or a state government or listed in the U.S. Pharmacopia, European Pharmacopia or other generally recognized pharmacopia for use in vertebrates, and more particularly in humans. These compositions can be useful as a vaccine and/or antigenic compositions for inducing a protective immune response in a vertebrate.

Said pharmaceutical formulations of the invention comprise VLPs comprising an influenza M1, HA and/or NA protein and a pharmaceutically acceptable carrier or excipient. Pharmaceutically acceptable carriers include but are not limited to saline, buffered saline, dextrose, water, glycerol, sterile isotonic aqueous buffer, and combinations thereof. A thorough discussion of pharmaceutically acceptable carriers, diluents, and other excipients is presented in Remington's Pharmaceutical Sciences (Mack Pub. Co. N.J. current edition). The formulation should suit the mode of administration. In a preferred embodiment, the formulation is suitable for administration to humans, preferably is sterile, non-particulate and/or non-pyrogenic.

The composition, if desired, can also contain minor amounts of wetting or emulsifying agents, or pH buffering agents. The composition can be a solid form, such as a lyophilized powder suitable for reconstitution, a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

The invention also provides for a pharmaceutical pack or kit comprising one or more containers filled with one or more of the ingredients of the vaccine formulations of the invention. In a preferred embodiment, the kit comprises two containers, one containing VLPs and the other containing an adjuvant. Associated with such container(s) can be a notice in the form prescribed by a governmental agency regulating the manufacture, use or sale of pharmaceuticals or biological products, which notice reflects approval by the agency of manufacture, use or sale for human administration.

The invention also provides that the VLP formulation be packaged in a hermetically sealed container such as an ampoule or sachette indicating the quantity of composition. In one embodiment, the VLP composition is supplied as a liquid, in another embodiment, as a dry sterilized lyophilized powder or water free concentrate in a hermetically sealed container and can be reconstituted, e.g., with water or saline to the appropriate concentration for administration to a subject. Preferably, the VLP composition is supplied as a dry sterile lyophilized powder in a hermetically sealed container at a unit dosage of preferably, about 1 µg, about 5 µg, about 10 µg, about 20 µg, about 25 µg, about 30 µg, about 50 µg, about 100 µg, about 125 µg, about 150 µg, or about 200 µg. Alternatively, the unit dosage of the VLP composition is less than about 1 µg, (for example about 0.08 µg, about 0.04 µg; about 0.2 µg, about 0.4 µg, about 0.8 µg, about 0.5 µg or less, about 0.25 µg or less, or about 0.1 µg or less), or more than about 125 µg, (for example about 150 µg or more, about 250 µg or more, or about 500 µg or more). These doses may be measured as total VLPs or as µg of HA. The VLP composition should be administered within about 12 hours, preferably within about 6 hours, within about 5 hours, within about 3 hours, or within about 1 hour after being reconstituted from the lyophilized powder.

In an alternative embodiment, a VLP composition is supplied in liquid form in a hermetically sealed container indicating the quantity and concentration of the VLP composition. Preferably, the liquid form of the VLP composition is supplied in a hermetically sealed container at least about 50 µg/ml, more preferably at least about 100 µg/ml, at least about 200 µg/ml, at least 500 µg/ml, or at least 1 mg/ml.

Generally, influenza VLPs of the invention are administered in an effective amount or quantity (as defined above) sufficient to stimulate an immune response against one or more strains of influenza virus. Preferably, administration of the VLP of the invention elicits substantial immunity against at least one influenza virus. Typically, the dose can be adjusted within this range based on, e.g., age, physical condition, body weight, sex, diet, time of administration, and other clinical factors. The prophylactic vaccine formulation is systemically administered, e.g., by subcutaneous or intramuscular injection using a needle and syringe, or a needleless injection device. Alternatively, the vaccine formulation is administered intranasally, either by drops, large particle aerosol (greater than about 10 microns), or spray into the upper respiratory tract. While any of the above routes of delivery results in an immune response, intranasal administration confers the added benefit of eliciting mucosal immunity at the site of entry of the influenza virus.

Thus, the invention also comprises a method of formulating a vaccine or antigenic composition that induces substantial immunity to influenza virus infection or at least one symptom thereof to a subject, comprising adding to said formulation an effective dose of an influenza VLP.

While stimulation of substantial immunity with a single dose is preferred, additional dosages can be administered, by the same or different route, to achieve the desired effect. In neonates and infants, for example, multiple administrations may be required to elicit sufficient levels of immunity. Administration can continue at intervals throughout childhood, as necessary to maintain sufficient levels of protection against influenza infection. Similarly, adults who are particularly susceptible to repeated or serious influenza infection, such as, for example, health care workers, day care workers, family members of young children, the elderly, and individuals with compromised cardiopulmonary function may require multiple immunizations to establish and/or maintain protective immune responses. Levels of induced immunity can be monitored, for example, by measuring amounts of neutralizing secretory and serum antibodies, and dosages adjusted or vaccinations repeated as necessary to elicit and maintain desired levels of protection.

Thus, in one embodiment, a method to induce substantial immunity to influenza virus infection or at least one symptom thereof in a subject, comprises administering at least one effective dose of an influenza VLP, wherein said VLP comprises influenza HA, NA and M1 proteins. In another embodiment, a method of inducing substantial immunity to influenza virus infection or at least one symptom thereof in a subject, comprises administering at least one effective dose of an influenza VLP, wherein said VLP consists essentially of influenza HA, NA and M1. Said VLPs may comprise additional influenza proteins and/or protein contaminates in negligible concentrations. In another embodiment, a method of inducing substantial immunity to influenza virus infection or at least one symptom thereof in a subject, comprises administering at least one effective dose of an influenza VLP, wherein said VLP consists of influenza HA, NA and M1. In another embodiment, said influenza HA, NA and M1 is derived from seasonal influenza and/or avian influenza virus. In another embodiment, a method of inducing substantial immunity to influenza virus infection or at least one symptom thereof in a subject, comprises administering at least one effective dose of an influenza VLP comprises influenza proteins, wherein said influenza proteins consist of HA, NA and M1 proteins. These VLPs contain HA, NA and M1 and may contain additional cellular constituents such as cellular proteins, baculovirus proteins, lipids, carbohydrates etc., but do not contain additional influenza proteins (other than fragments of M1, HA and/or NA). In another embodiment, said HA and/or NA exhibits hemagglutinin activity and/or neuraminidase activity, respectfully. In another embodiment, said subject is a mammal. In another embodiment, said mammal is a human. In another embodiment, the method comprises inducing substantial immunity to influenza virus infection or at least one symptom thereof by administering said formulation in one dose. In another embodiment, the method comprises inducing substantial immunity to influenza virus infection or at least one symptom thereof by administering said formulation in multiple doses.

Methods of administering a composition comprising VLPs (vaccine and/or antigenic formulations) include, but are not limited to, parenteral administration (e.g., intradermal, intramuscular, intravenous and subcutaneous), epidural, and mucosal (e.g., intranasal and oral or pulmonary routes or by suppositories). In a specific embodiment, compositions of the present invention are administered intramuscularly, intravenously, subcutaneously, transdermally or intradermally. The compositions may be administered by any convenient route, for example by infusion or bolus injection, by absorption through epithelial or mucocutaneous linings (e.g., oral mucous, colon, conjunctiva, nasopharynx, oropharynx, vagina, urethra, urinary bladder and intestinal mucosa, etc.) and may be administered together with other biologically active agents. In some embodiments, intranasal or other mucosal routes of administration of a composition comprising VLPs of the invention may induce an antibody or other immune response that is substantially higher than other routes of administration. In another embodiment, intranasal or other mucosal routes of administration of a composition comprising VLPs of the invention may induce an antibody or other immune response that will induce cross protection against other strains of influenza viruses. Administration can be systemic or local.

In yet another embodiment, the vaccine and/or antigenic formulation is administered in such a manner as to target mucosal tissues in order to elicit an immune response at the site of immunization. For example, mucosal tissues such as gut associated lymphoid tissue (GALT) can be targeted for immunization by using oral administration of compositions which contain adjuvants with particular mucosal targeting properties. Additional mucosal tissues can also be targeted, such as nasopharyngeal lymphoid tissue (NALT) and bronchial-associated lymphoid tissue (BALT).

Vaccines and/or antigenic formulations of the invention may also be administered on a dosage schedule, for example, an initial administration of the vaccine composition with subsequent booster administrations. In particular embodiments, a second dose of the composition is administered anywhere from two weeks to one year, preferably from about 1, about 2, about 3, about 4, about 5 to about 6 months, after the initial administration. Additionally, a third dose may be administered after the second dose and from about three months to about two years, or even longer, preferably about 4, about 5, or about 6 months, or about 7 months to about one year after the initial administration. The third dose may be optionally administered when no or low levels of specific immunoglobulins are detected in the serum and/or urine or mucosal secretions of the subject after the second dose. In a preferred embodiment, a second dose is administered about one month after the first administration and a third dose is administered about six months after the first administration. In another embodiment, the second dose is administered about six months after the first administration.

In another embodiment, said VLP of the invention can be administered as part of a combination therapy. For example, VLPs of the invention can be formulated with other immunogenic compositions and/or antivirals (e.g. Amantadine, Rimantadine, Zanamivir and Osteltamivir).

The dosage of the pharmaceutical formulation can be determined readily by the skilled artisan, for example, by first identifying doses effective to elicit a prophylactic or therapeutic immune response, e.g., by measuring the serum titer of virus specific immunoglobulins or by measuring the inhibitory ratio of antibodies in serum samples, or urine samples, or mucosal secretions. Said dosages can be determined from animal studies. A non-limiting list of animals used to study the influenza virus include the guinea pig, Syrian hamster, chinchilla, hedgehog, chicken, rat, mouse and ferret. Most animals are not natural hosts to influenza viruses but can still serve in studies of various aspects of the disease. For example, any of the above animals can be dosed with a vaccine candidate, e.g. VLPs of the invention, to partially characterize the immune response induced, and/or to determine if any neutralizing antibodies have been produced. For example, many studies have been conducted in the mouse model because mice are small size and their low cost allows researchers to conduct studies on a larger scale. Nevertheless, the mouse's small size also increases the difficulty of readily observing any clinical signs of the disease and the mouse is not a predictive model for disease in humans.

There has been extensive use of ferrets for studying various aspects of human influenza viral infection and its course of action. The development of many of the contemporary concepts of immunity to the influenza virus would have been impossible without the use of the ferret (Maher et al. 2004). Ferrets have proven to be a good model for studying influenza for several reasons: influenza infection in the ferret closely resembles that in humans with respect to clinical signs, pathogenesis, and immunity; types A and B of human influenza virus naturally infect the ferret, thus providing an opportunity to study a completely controlled population in which to observe the interplay of transmission of infection, illness, and sequence variation of amino acids in the glycoproteins of the influenza virus; and ferrets have other physical characteristics that make it an ideal model for deciphering the manifestations of the disease. For example, ferrets and humans show very similar clinical signs of influenza infection that seem to depend on the age of the host, the strain of the virus, environmental conditions, the degree of secondary bacterial infection, and many other variables. Thus, one skilled in the art can more easily correlate the efficacy of an influenza vaccine and dosage regiments from a ferret model to humans as compared to a mouse or any other model described above.

In addition, human clinical studies can be performed to determine the preferred effective dose for humans by a skilled artisan. Such clinical studies are routine and well known in the art. The precise dose to be employed will also depend on the route of administration. Effective doses may be extrapolated from dose-response curves derived from in vitro or animal test systems.

As also well known in the art, the immunogenicity of a particular composition can be enhanced by the use of non-specific stimulators of the immune response, known as adjuvants. Adjuvants have been used experimentally to promote a generalized increase in immunity against unknown antigens (e.g., U.S. Pat. No. 4,877,611). Immunization protocols have used adjuvants to stimulate responses for many years, and as such, adjuvants are well known to one of ordinary skill in the art. Some adjuvants affect the way in which antigens are presented. For example, the immune response is increased when protein antigens are precipitated by alum. Emulsification of antigens also prolongs the duration of antigen presentation. The inclusion of any adjuvant described in Vogel et al., "A Compendium of Vaccine Adjuvants and Excipients ($2^{nd}$ Edition)," herein incorporated by reference in its entirety for all purposes, is envisioned within the scope of this invention.

Exemplary, adjuvants include complete Freund's adjuvant (a non-specific stimulator of the immune response containing killed *Mycobacterium tuberculosis*), incomplete Freund's adjuvants and aluminum hydroxide adjuvant. Other adjuvants comprise GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion also is contemplated. MF-59, Novasomes®, MHC antigens may also be used.

In one embodiment of the invention the adjuvant is a paucilamellar lipid vesicle having about two to ten bilayers arranged in the form of substantially spherical shells separated by aqueous layers surrounding a large amorphous central cavity free of lipid bilayers. Paucilamellar lipid vesicles may act to stimulate the immune response several ways, as non-specific stimulators, as carriers for the antigen, as carriers of additional adjuvants, and combinations thereof. Paucilamellar lipid vesicles act as non-specific immune stimulators when, for example, a vaccine is prepared by intermixing the antigen with the preformed vesicles such that the antigen remains extracellular to the vesicles. By encapsulating an antigen within the central cavity of the vesicle, the vesicle acts both as an immune stimulator and a carrier for the antigen. In another embodiment, the vesicles are primarily made of non-phospholipid vesicles. In other embodiment, the vesicles are Novasomes. Novasomes® are paucilamellar nonphospholipid vesicles ranging from about 100 nm to about 500 nm. They comprise Brij 72, cholesterol, oleic acid and squalene. Novasomes have been shown to be an effective adjuvant for influenza antigens (see, U.S. Pat. Nos. 5,629,021, 6,387,373, and 4,911,928, herein incorporated by reference in their entireties for all purposes).

In one aspect, an adjuvant effect is achieved by use of an agent, such as alum, used in about 0.05 to about 0.1% solution in phosphate buffered saline. Alternatively, the VLPs can be made as an admixture with synthetic polymers of sugars (Carbopol®) used as an about 0.25% solution. Some adjuvants, for example, certain organic molecules obtained from bacteria; act on the host rather than on the antigen. An example is muramyl dipeptide (N-acetylmuramyl-L-alanyl-D-isoglutamine [MDP]), a bacterial peptidoglycan. In other embodiments, hemocyanins and hemoerythrins may also be used with VLPs of the invention. The use of hemocyanin from keyhole limpet (KLH) is preferred in certain embodiments, although other molluscan and arthropod hemocyanins and hemoerythrins may be employed.

Various polysaccharide adjuvants may also be used. For example, the use of various pneumococcal polysaccharide adjuvants on the antibody responses of mice has been described (Yin et al., 1989). The doses that produce optimal responses, or that otherwise do not produce suppression, should be employed as indicated (Yin et al., 1989). Polyamine varieties of polysaccharides are particularly preferred, such as chitin and chitosan, including deacetylated chitin. In another embodiment, a lipophilic disaccharide-tripeptide derivative of muramyl dipeptide which is described for use in artificial liposomes formed from phosphatidyl choline and phosphatidyl glycerol.

Amphipathic and surface active agents, e.g., saponin and derivatives such as QS21 (Cambridge Biotech), form yet another group of adjuvants for use with the VLPs of the invention. Nonionic block copolymer surfactants (Rabinovich et al., 1994) may also be employed. Oligonucleotides are another useful group of adjuvants (Yamamoto et al., 1988). Quil A and lentinen are other adjuvants that may be used in certain embodiments of the present invention.

Another group of adjuvants are the detoxified endotoxins, such as the refined detoxified endotoxin of U.S. Pat. No. 4,866,034. These refined detoxified endotoxins are effective in producing adjuvant responses in vertebrates. Of course, the detoxified endotoxins may be combined with other adjuvants to prepare multi-adjuvant formulation. For example, combination of detoxified endotoxins with trehalose dimycolate is particularly contemplated, as described in U.S. Pat. No. 4,435,386. Combinations of detoxified endotoxins with trehalose dimycolate and endotoxic glycolipids is also contemplated (U.S. Pat. No. 4,505,899), as is combination of detoxified endotoxins with cell wall skeleton (CWS) or CWS and trehalose dimycolate, as described in U.S. Pat. Nos. 4,436,727, 4,436,728 and 4,505,900. Combinations of just CWS and trehalose dimycolate, without detoxified endotoxins, is also envisioned to be useful, as described in U.S. Pat. No. 4,520,019.

Those of skill in the art will know the different kinds of adjuvants that can be conjugated to vaccines in accordance with this invention and these include alkyl lysophospholipids (ALP); BCG; and biotin (including biotinylated derivatives) among others. Certain adjuvants particularly contemplated for use are the teichoic acids from Gram-cells. These include the lipoteichoic acids (LTA), ribitol teichoic acids (RTA) and glycerol teichoic acid (GTA). Active forms of their synthetic counterparts may also be employed in connection with the invention (Takada et al., 1995).

Various adjuvants, even those that are not commonly used in humans, may still be employed in other vertebrates, where, for example, one desires to raise antibodies or to subsequently obtain activated T cells. The toxicity or other adverse effects that may result from either the adjuvant or the cells, e.g., as may occur using non-irradiated tumor cells, is irrelevant in such circumstances.

Another method of inducing an immune response can be accomplished by formulating the VLPs of the invention with "immune stimulators." These are the body's own chemical messengers (cytokines) to increase the immune system's response. Immune stimulators include, but not limited to, various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc. The immunostimulatory molecules can be administered in the same formulation as the influenza VLPs, or can be administered separately. Either the protein or an expression vector encoding the protein can be administered to produce an immunostimulatory effect.

Method of Stimulating an Anti-Influenza Immune Response

The VLPs of the invention are useful for preparing compositions that stimulate an immune response that confers immunity or substantial immunity to influenza viruses. Both mucosal and cellular immunity may contribute to immunity to influenza infection and disease. Antibodies secreted locally in the upper respiratory tract are a major factor in resistance to natural infection. Secretory immunoglobulin A (sIgA) is involved in protection of the upper respiratory tract and serum IgG in protection of the lower respiratory tract. The immune response induced by an infection protects against reinfection with the same virus or an antigenically similar viral strain. Influenza virus undergoes frequent and unpredictable changes; therefore, after natural infection, the effective period of protection provided by the host's immunity may only be a few years against the new strains of virus circulating in the community.

VLPs of the invention can induce substantial immunity in a vertebrate (e.g. a human) when administered to said vertebrate. The substantial immunity results from an immune response against the influenza VLP of the invention that protects or ameliorates influenza infection or at least reduces a symptom of influenza virus infection in said vertebrate. In some instances, if the said vertebrate is infected, said infection will be asymptomatic. The response may be not a fully protective response. In this case, if said vertebrate is infected with an influenza virus, the vertebrate will experience reduced symptoms or a shorter duration of symptoms compared to a non-immunized vertebrate.

In one embodiment, the invention comprises a method of inducing substantial immunity to influenza virus infection or at least one symptom thereof in a subject, comprising administering at least one effective dose of an influenza VLP. In another embodiment, said induction of substantial immunity reduces duration of influenza symptoms. In another embodiment, a method to induce substantial immunity to influenza virus infection or at least one symptom thereof in a subject, comprises administering at least one effective dose of an influenza VLP, wherein said VLP comprises influenza HA, NA and M1 proteins. In another embodiment, said influenza VLP comprises influenza proteins, wherein said influenza proteins consist of HA, NA and M1 proteins. These VLPs contain HA, NA and M1 and may contain additional cellular constituents such as cellular proteins, baculovirus proteins, lipids, carbohydrates etc., but do not contain additional influenza proteins (other than fragments of M1, HA and/or NA). In another embodiment, a method of inducing substantial immunity to influenza virus infection or at least one symptom thereof in a subject, comprises administering at least one effective dose of an influenza VLP, wherein said VLP consists essentially of influenza HA, NA and M1. Said VLPs may comprise additional influenza proteins and/or protein contaminates in negligible concentrations. In another embodiment, a method of inducing substantial immunity to influenza virus infection or at least one symptom thereof in a subject, comprises administering at least one effective dose of an influenza VLP, wherein said VLP consists of influenza HA, NA and M1. In another embodiment, said HA and/or NA exhibits hemagglutinin activity and/or neuraminidase activity, respectfully. In another embodiment, said subject is a mammal. In another embodiment, said mammal is a human. In a further embodiment, said VLP is formulated with an adjuvant or immune stimulator.

Recently there has been a concerted effort to create a vaccine against avian influenza virus that has the potential to create a pandemic. That is because a number of avian influenza viruses have crossed the species barrier and directly infected humans resulting in illness and, in some cases, death. These viruses were H5N1, H9N2 and H7N7 (Cox et al., 2004). A recent study examined the potential of using inactivated H5N1 influenza virus as a vaccine. The formulation of the vaccine was similar to the licensed inactivated vaccines currently licensed for marketing. The study concluded that using inactivated H5N1 virus did induce an immune response in humans, however the dose given was very high (90 μg of avian influenza compared to 15 μg of the licensed vaccine) (Treanor et al., 2006). This high amount of avian influenza antigen is impractical for a worldwide vaccination campaign.

As illustrated below, the VLPs of the invention induces an immune response in a vertebrate when administered to said vertebrate.

Thus, the invention encompasses a method of inducing substantial immunity to influenza virus infection or at least one symptom thereof in a subject, comprising administering at least one effective dose of an avian influenza VLP. In another embodiment, said induction of substantial immunity reduces duration of influenza symptoms. In another embodiment, said induction of immunity is from administering at least 0.2 μg of avian HA in VLPs of the invention. In another embodiment, said induction of immunity is from administering about 0.2 μg of avian HA to about 15 μg of avian HA in VLPs of the invention. In another embodiment, said induction of immunity is from administering about 15 μg of avian HA to about 45 μg of avian HA in VLPs of the invention. In another embodiment, said induction of immunity is from administering about 45 μg of avian HA to about 135 μg of avian HA in VLPs of the invention. In another embodiment, said induction of immunity is from administering about 10 μg, about 20 μg, about 30 μg, about 40 μg, about 45 μg, about 50 μg, about 60 μg, about 70 μg, about 80 μg, about 90 μg, about 100 μg, about 110 μg, about 120 μg, about 130 μg, about 140 μg, about 150 μg or higher. Administration may be in one or more doses, but may be advantageously in a single dose. In another embodiment, said VLP avian HA is derived from avian influenza H5N1.

In another embodiment, the invention comprises a method of inducing substantial immunity to avian influenza virus infection or at least one symptom thereof in a subject comprising administering at least one effective dose of an avian influenza VLP, wherein said VLP comprises an avian influenza HA, NA and M1. In another embodiment, said avian influenza VLP comprises avian influenza proteins, wherein said avian influenza proteins consist of HA, NA and M1 proteins. These VLPs contain HA, NA and M1 and may contain additional cellular constituents such as cellular proteins, baculovirus proteins, lipids, carbohydrates etc. but do not contain additional influenza proteins (other than fragments of M1, HA and/or NA). In another embodiment, said method of inducing substantial immunity to avian influenza virus infection or at least one symptom thereof in a subject comprises administering at least one effective dose of an avian influenza VLP, wherein said VIP consists essentially of avian influenza HA, NA and M1. Said VLPs may comprise additional influenza proteins and/or protein contaminates in negligible concentrations. In another embodiment, a method to induce substantial immunity to influenza virus infection or at least one symptom thereof in a subject, comprises administering at least one effective dose of an influenza VLP, wherein said VLP consists of avian influenza HA, NA and M1. In another embodiment, said avian influenza HA and NA are H5N1, respectively. In another embodiment, said avian influenza HA and NA are H9N2, respectively. In another embodiment, said avian influenza HA and NA are H7N7, respectively. In another embodiment, said avian influenza HA and/or NA exhibits hemagglutinin activity and/or neuraminidase activity, respectfully. In another embodiment, said subject is a mammal. In another embodiment, said mammal is a human. In a further embodiment, said VLP is formulated with an adjuvant or immune stimulator.

In another embodiment, said avian influenza VLPs will induce an immune response in a vertebrate that is about 2 fold, about 4 fold, about 8 fold, about 16 fold, about 32 fold about 64 fold, about 128 fold increase (or higher) more potent than a similar avian influenza antigens formulated similarly to the licensed inactivated vaccines currently licensed for marketing. Current formulations comprise whole inactivated virus (e.g. formaldehyde treated), split virus (chemically disrupted), and subunit (purified glycoprotein) vaccines. Methods for determining potency for a vaccine are known and routine in the art. For example, microneutralization assays and hemagglutination inhibition assays can be performed to determine potency of an avian VLP vaccine compared to avian influenza antigens formulated similar to the licensed inactivated vaccines currently licensed for marketing. In one embodiment, said increase in potency is realized when about 0.2 μg, about 0.4 μg, about 0.6 μg about 0.8 μg, about 1 μg, about 2 μg, about 3 μg, about 4 μg, about 5 μg, about 6 μg, about 7 μg, about 9 μg, about 10 μg, about 15 μg, about 20 μg, about 25 μg, about 30 μg, about 35 μg, 40 μg, about 45 μg, about 50 μg, about 60 μg, about 70 μg, about 80 μg, about 90 μg, about 100 μg, about 110 μg, about 120 μg, about 130 μg, about 140 μg, about 150 μg or higher of VLPs and the antigen formulated similarly to the inactivated vaccines currently licensed for marketing is administered to a vertebrate (i.e. equivalent amounts of HA and/or NA in a VLP with equivalent amounts of HA and/or NA formulated in similarly to the licensed inactivated vaccines and/or any other antigen) Amounts can be measured according to HA content. For example, 1 μg of a VLP of the invention is about 1 μg of HA in a solution of VLPs comprising HA or may be measured by weight of VLPs.

Seasonal influenza vaccines are administered to humans every year to reduce the incidence of influenza cases every year. At present, there are two subtypes of influenza A and influenza B circulating in the United States. Current vaccines are, therefore, trivalent to provide protection against the strains currently circulating. Each year a different stain or variation of an influenza viral changes. Thus, for most years a new vaccine composition is manufactured and administered. Inactivated vaccines are produced by propagation of the virus in embryonated hens' eggs. The allantoic fluid is harvested, and the virus is concentrated and purified, then inactivated. Thus, the current licensed influenza virus, vaccines may contain trace amounts of residual egg proteins and, therefore, should not be administered to persons who have anaphylactic hypersensitivity to eggs. In addition, supplies of eggs must be organized and strains for vaccine production must be selected months in advance of the next influenza season, thus limiting the flexibility of this approach and often resulting in delays and shortages in production and distribution. In addition, some influenza strains do not replicate well in embryonated chicken eggs which may limit the influenza strains which can be grown and formulated into vaccines.

As mentioned above, VLP of the invention do not require eggs for production. These VLPs are made via a cell culture system. Thus, the invention encompasses a method of inducing substantial immunity to influenza virus infection or at least one symptom thereof in a subject, comprising administering at least one effective dose of a seasonal influenza VLP. A discussed above, seasonal influenza virus refers to the influenza viral strains that has been determined to be passing within the human population for a given influenza season based on the epidemiological surveys by National Influenza Centers worldwide. Said studies and some isolated influenza viruses are sent to one of four World Health Organization (WHO) reference laboratories, one of which is located at the Centers for Disease Control and Prevention (CDC) in Atlanta, for detailed testing. These laboratories test how well antibodies made to the current vaccine react to the circulating virus and new flu viruses. This information, along with information about flu activity, is summarized and presented to an advisory committee of the U.S. Food and Drug Administration (FDA)

and at a WHO meeting. These meetings result in the selection of three viruses (two subtypes of influenza A viruses and one influenza B virus) to go into flu vaccines for the following fall and winter. The selection occurs in February for the northern hemisphere and in September for the southern hemisphere. Usually, one or two of the three virus strains in the vaccine changes each year. In another embodiment, said induction of substantial immunity reduces duration of influenza symptoms.

In another embodiment, the invention comprises a method of inducing substantial immunity to a seasonal influenza virus infection or at least one symptom thereof in a subject comprising administering at least one effective dose of a seasonal influenza VLP, wherein said VLP comprises a seasonal influenza HA, NA and M1. In another embodiment, said seasonal influenza VLP comprises seasonal influenza proteins, wherein said influenza proteins consist of HA, NA and M1 proteins. These VLPs contain HA, NA and M1 and may contain additional cellular constituents such as cellular proteins, baculovirus proteins, lipids, carbohydrates etc. but do not contain additional influenza proteins (other than fragments of M1, HA and/or NA). In another embodiment, said method of inducing substantial immunity to seasonal influenza virus infection or at least one symptom thereof in a subject comprises administering at least one effective dose of a seasonal influenza VLP, wherein said VLP consists essentially of seasonal influenza HA, NA and M1. Said VLPs may comprise additional influenza proteins and/or protein contaminates in negligible concentrations. In another embodiment, a method to induce substantial immunity to influenza virus infection or at least one symptom thereof in a subject, comprises administering at least one effective dose of an influenza VLP, wherein said VLP consists of seasonal influenza HA, NA and M1. In another embodiment, said avian influenza HA and/or NA exhibits hemagglutinin activity and/or neuraminidase activity, respectfully. In another embodiment, said subject is a mammal. In another embodiment, said mammal is a human. In a further embodiment, said VLP is formulated with an adjuvant or immune stimulator.

Generally, seasonal influenza VLPs of the invention are administered in a quantity sufficient to stimulate substantial immunity for one or more strains of seasonal influenza virus. In one embodiment, the VLPs are blended together with other VLPs comprising different influenza subtypes proteins (as listed above). In another embodiment, the formulation is a trivalent formulation which comprises a mixture of VLPs with seasonal influenza HA and/or NA proteins from at least two influenza A and/or one at least one B subtype. In another embodiment, said B subtype is produced by the same method as described above. In another embodiment, a multivalent formulation comprises one or more of the VLP of the invention as described above.

In another embodiment, VLPs of the invention (avian or seasonal VLPs) may elicit an immune response that will provide protection against more than one strain of influenza virus. This cross-protection of a vertebrate with an influenza VLP constructed from a particular strain, of a particular subgroup, may induce cross-protection against influenza virus of different strains and/or subgroups. The examples below show that VLPs of the invention are capable of inducing cross reactivity with different strains and/or subgroups.

The humoral immune system produces antibodies against different influenza antigens, of which the HA-specific antibody is the most important for neutralization of the virus and thus prevention of illness. The NA-specific antibodies are less effective in preventing infection, but they lessen the release of virus from infected cells. The mucosal tissues are the main portal entry of many pathogens, including influenza, and the mucosal immune system provides the first line of defense against infection apart from innate immunity. SIgA and, to some extent, IgM are the major neutralizing antibodies directed against mucosal pathogens preventing pathogen entry and can function intracellularly to inhibit replication of virus. Nasal secretions contain neutralizing antibodies particularly to influenza HA and NA, which are primarily of the IgA isotype and are produced locally. During primary infection, all three major Ig classes (IgG, IgA and IgM) specific to HA can be detected by enzyme-linked immunosorbent assay in nasal washings, although IgA and IgM are more frequently detected than IgG. Both IgA and, to some extent, IgM are actively secreted locally, whereas IgG is derived as a serum secretion. In subjects who have a local IgA response, a serum IgA response also is observed. The local IgA response stimulated by natural infection lasts for at least 3-5 months, and influenza-specific, IgA-committed memory cells can be detected locally. IgA also is the predominant Ig isotype in local secretions after secondary infection, and an IgA response is detected in the serum upon subsequent infection. The presence of locally produced neutralizing antibodies induced by live virus vaccine correlates with resistance to infection and illness after challenge with wild-type virus.

Resistance to influenza infection or illness is correlated with the level of local and/or serum antibody to HA and NA. Serum anti-HA antibodies are the most commonly measured correlate of protection against influenza (Cox et al., 1999). A protective serum antibody (haemagglutination inhibition (HI) titer≧40) response can be detected in approximately 80% of subjects after natural influenza infection. B cells producing all three major Ig classes are present in the peripheral blood in normal subjects (Cox et al., 1994) and individuals undergoing influenza infection. In humans, serum antibodies play a role in both resistance to and recovery from influenza infection. The level of serum antibody to HA and NA in humans can be correlated with resistance to illness following experimental infection and natural infection. During primary infection, the three major Ig classes can be detected within 10-14 days. IgA and IgM levels peak after 2 weeks and then begin to decline, whereas the level of IgG peaks at 4-6 weeks. Whereas IgG and IgM are dominant in the primary response, IgG and IgA predominate in the secondary immune response.

Thus, the invention encompasses a method of inducing a substantially protective antibody response to influenza virus infection or at least one symptom thereof in a subject, comprising administering at least one effective dose of an influenza VLP. In another embodiment, said induction of substantially protective antibody response reduces duration of influenza symptoms. In another embodiment, a method to induce substantially protective antibody response to influenza virus infection or at least one symptom thereof in a subject, comprises administering at least one effective dose of an influenza VLP, wherein said VLP comprises influenza HA, NA and M1 proteins.

In another embodiment, the invention comprises a method of inducing substantially protective antibody response to influenza virus infection or at least one symptom thereof in a subject, comprises administering at least one effective dose of an influenza VLP, wherein said VLP consists essentially of influenza HA, NA and M1. Said VLPs may comprise additional influenza proteins and/or protein contaminates in negligible concentrations. In another embodiment, said influenza VLP comprises influenza proteins, wherein said influenza proteins consist of HA, NA and M1 proteins. These VLPs contain HA, NA and M1 and may contain additional cellular constituents such as cellular proteins, baculovirus proteins, lipids, carbohydrates etc., but do not contain additional influenza proteins (other than fragments of M1, HA and/or NA). In another embodiment, a method of inducing substantial immunity to influenza virus infection or at least one symptom thereof in a subject, comprises administering at least one effective dose of an influenza VLP, wherein said VLP consists of influenza HA, NA and M1. In another embodiment, wherein said influenza HA, NA and M1 is derived from seasonal influenza and/or avian influenza. In another embodiment, said HA and/or NA exhibits hemagglutinin activity and/or neuraminidase activity, respectfully. In another embodiment, said subject is a mammal. In another embodiment, said mammal is a human. In a further embodiment, said VLP is formulated with an adjuvant or immune stimulator.

As used herein, an "antibody" is a protein comprising one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. Antibodies exist as intact immunoglobulins or as a number of well-characterized fragments produced by digestion with various peptidases.

Cell-mediated immunity also plays a role in recovery from influenza infection and may prevent influenza-associated complications. Influenza-specific cellular lymphocytes have been detected in the blood and the lower respiratory tract secretions of infected subjects. Cytolysis of influenza-infected cells is mediated by CTLs in concert with influenza-specific antibodies and complement. The primary cytotoxic response is detectable in blood after 6-14 days and disappears by day 21 in infected or vaccinated individuals (Ennis et al., 1981). Influenza-specific CTLs exhibit cross-reactive specificities in in vitro cultures; thus, they lyse cells infected with the same type of influenza but not with other types (e.g. influenza A but not influenza B virus). CTLs that recognize the internal nonglycosylated proteins, M, NP and PB2 have been isolated (Fleischer et al., 1985). The CTL response is cross-reactive between influenza A strains (Gerhard et al., 2001) and is important in minimizing viral spread in combination with antibody (Nguyen et al., 2001).

Cell-mediated immunity also plays a role in recovery from influenza infection and may prevent influenza-associated complications. Influenza-specific cellular lymphocytes have been detected in the blood and the lower respiratory tract secretions of infected subjects. Cytolysis of influenza-infected cells is mediated by CTLs in concert with influenza-specific antibodies and complement. The primary cytotoxic response is detectable in blood after 6-14 days and disappears by day 21 in infected or vaccinated individuals (Ennis et al., 1981). Influenza-specific CTLs exhibit cross-reactive specificities in in vitro cultures; thus, they lyse cells infected with the same type of influenza but not with other types (e.g. influenza A but not influenza B virus). CTLs that recognize the internal nonglycosylated proteins, M, NP and PB2 have been isolated (Fleischer et al., (1985). The CTL response is cross-reactive between influenza A strains (Gerhard et al., 2001) and is important in minimizing viral spread in combination with antibody (Nguyen et al., 2001).

Thus, the invention encompasses a method of inducing a substantially protective cellular immune response to influenza virus infection or at least one symptom thereof in a subject, comprising administering at least one effective dose of an influenza VLP. In another embodiment, a method of inducing substantial immunity to influenza virus infection or at least one symptom thereof in a subject, comprises administering at least one effective dose of an influenza VLP, wherein said VLP consists of influenza HA, NA and M1. In another embodiment, said influenza VLP comprises influenza proteins, wherein said influenza proteins consist of HA, NA and M1 proteins. These VLPs contain HA, NA and M1 and may contain additional cellular constituents such as cellular proteins, baculovirus proteins, lipids, carbohydrates etc. but do not contain additional influenza proteins (other than fragments of M1, HA and/or NA). In another embodiment wherein said influenza HA, NA and M1 is derived from seasonal influenza and/or avian influenza virus. In another embodiment, said HA and/or NA exhibits hemagglutinin activity and/or neuraminidase activity, respectfully. In another embodiment, said subject is a mammal. In another embodiment, said mammal is a human. In a further embodiment, said VLP is formulated with an adjuvant or immune stimulator.

As mentioned above, the VLPs of the invention (e.g. avian and/or seasonal influenza VLPs) prevent or reduce at least one symptom of influenza infection in a subject. Symptoms of influenza are well known in the art. They include fever, myalgia, headache, severe malaise, nonproductive cough, sore throat, weight loss and rhinitis. Thus, the method of the invention comprises the prevention or reduction of at least one symptom associated with influenza viral infection. A reduction in a symptom may be determined subjectively or objectively, e.g., self assessment by a subject, by a clinician's assessment or by conducting an appropriate assay or measurement (e.g. body temperature), including, e.g., a quality of life assessment, a slowed progression of an influenza infection or additional symptoms, a reduced severity of a influenza symptoms or a suitable assays (e.g. antibody titer and/or T-cell activation assay). The objective assessment comprises both animal and human assessments.

The principal strategy advocated by the Advisory Committee on Immunization Practices (ACIP) for control of influenza has been the vaccination of persons at risk for serious complications from influenza, in particular, people ≧65 years old. Yearly influenza epidemics, however, continue unabated and are responsible for significant health and financial burden to our society (Glaser et al., 1996). In the last 20 years (1976-1999), a significant increase has occurred in influenza-associated all cause excess deaths. From 1990 to 1999, the annual number of influenza-associated all cause deaths exceeded 50,000 (Thompson et al., 2003). Despite the increase in vaccine coverage of people ≧65 years to 65% during the last decade, a corresponding reduction in influenza-associated all cause excess deaths has not been observed.

Thus, another strategy for the prevention and control of influenza is universal vaccination of healthy children and individuals. Children have high rates of infection, medically attended illness and hospitalization from influenza (Neuzil et al., 2000). Children play an important role in the transmission of influenza within schools, families and communities. Vaccination with current influenza vaccines of approximately 80% of schoolchildren in a community has decreased respiratory illnesses in adults and excess deaths in the elderly (Reichert et al., 2001). This concept is known as community immunity or "herd immunity" and is thought to play an important part of protecting the community against disease. Because vaccinated people have antibodies that neutralize influenza virus, they are much less likely to transmit influenza virus to other people. Thus, even people who have not been vaccinated (and those whose vaccinations have become weakened or whose vaccines are not fully effective) often can be shielded by the herd immunity because vaccinated people around them are not getting sick. Herd immunity is more effective as the percentage of people vaccinated increases. It is thought that approximately 95% of the people in the community must be protected by a vaccine to achieve herd immunity. People who are not immunized increase the chance that they and others will get the disease.

Thus, the invention encompasses a method of inducing a substantially protective immunity to influenza virus infection to a population or a community in order to reduce the incidence of influenza virus infections among immunocompromised individuals or non-vaccinated individual buy administering VLPs of the invention to a population in a community. In one embodiment, most school-aged children are immunized against influenza virus by administering the VLPs of the invention. In another embodiment, most healthy individuals in a community to are immunized against influenza virus by administering the VLPs of the invention. In another embodiment VLPs of the invention are part of a "dynamic vaccination" strategy. Dynamic vaccination is the steady production of a low-efficacy vaccine that is related to an emerging pandemic strain, but due to an antigentic drift may not provide complete protection in a mammal (see Germann et al., 2006). Because of the uncertainty about the future identity of a pandemic strain, it is almost impossible to stockpile a well matched pandemic strain. However, vaccination with a poorly matched but potentially efficacious vaccine may slow the spread of the pandemic virus and/or reduce the severity of symptoms of a pandemic strain of influenza virus.

The invention also encompasses a vaccine comprising an influenza VLP, wherein said vaccine induces substantial immunity to influenza virus infection or at least one symptom thereof when administered to a subject. In another embodiment, said induction of substantial immunity reduces duration of influenza symptoms. In another embodiment, a said vaccine induces substantial immunity to influenza virus infection or at least one symptom thereof in a subject, comprises a VLP which comprises influenza HA, NA and M1 proteins. In another embodiment, a said vaccine induces substantial immunity to influenza virus infection or at least one symptom thereof in a subject, comprises a VLP which consists essentially of influenza HA, NA and M1 proteins. Said VLPs may comprise additional influenza proteins and/or protein contaminates in negligible concentrations. In another embodiment, a said vaccine induces substantial immunity to influenza virus infection or at least one symptom thereof in a subject, comprises a VLP which consists of influenza HA, NA and M1 proteins. In another embodiment, a said vaccine induces substantial immunity to influenza virus infection or at least one symptom thereof in a subject, comprises a VLP comprises influenza proteins, wherein said influenza proteins consist of HA, NA and M1 proteins. These VLPs contain HA, NA and M1 and may contain additional cellular constituents such as cellular proteins, baculovirus proteins, lipids, carbohydrates etc., but do not contain additional influenza proteins (other than fragments of M1, HA and/or NA). In another embodiment, said influenza HA, NA and M1 proteins are derived from an avian and/or seasonal influenza virus. In another embodiment, said HA and/or NA exhibits hemagglutinin activity and/or neuraminidase activity, respectfully. In another embodiment, said subject is a mammal. In another embodiment, said mammal is a human. In a further embodiment, said VLP is formulated with an adjuvant or immune stimulator. In another embodiment, where said vaccine is administered to a mammal. In a further embodiment, said mammal is a human.

This invention is further illustrated by the following examples which should not be construed as limiting. The contents of all references, patents and published patent applications cited throughout this application, as well as the Figures and the Sequence Listing, are incorporated herein by reference.

EXAMPLES

Example 1

Materials and Methods

Avian influenza A/Hong Kong/1073/99 (H9N2) virus HA, NA, and M1 genes were expressed in *Spodoptera frugiperda* cells (Sf-9S cell line; ATCC PTA-4047) using the baculovirus bacmid expression system. The HA, NA, and M1 genes were synthesized by the reverse transcription and polymerase chain reaction (PCR) using RNA isolated from avian influenza A/Hong Kong/1073/99 (H9N2) virus (FIGS. 1, 2, and 3). For reverse transcription and PCR, oligonucleotide primers specific for avian influenza A/Hong Kong/1073/99 (H9N2) virus HA, NA, and M1 genes were used (Table 1). The cDNA copies of these genes were cloned initially into the bacterial subcloning vector, pCR2.1TOPO. From the resulting three pCR2.1TOPO-based plasmids, the HA, NA, and M1 genes were inserted downstream of the AcMNPV polyhedrin promoters in the baculovirus transfer vector, pFastBac1 (InVitrogen), resulting in three pFastBac1-based plasmids: pHA, pNA, and pM1 expressing these influenza virus genes, respectively. Then, a single pFastBac1-based plasmid pHAM was constructed encoding both the HA and M1 genes, each downstream from a separate polyhedrin promoter (FIG. 4). The nucleotide sequence of the NA gene with the adjacent 5'- and 3'-regions within the pNA plasmid was determined (SEQ ID NO:1) (FIG. 1). At the same time, the nucleotide sequences of the HA and M1 genes with the adjacent regions were also determined using the pHAM plasmid (SEQ ID NOS:2 and 3) (FIGS. 2 and 3).

Finally, a restriction DNA fragment from the pHAM plasmid that encoded both the HA and M1 expression cassettes was cloned into the pNA plasmid. This resulted in the plasmid pNAHAM encoding avian influenza A/Hong Kong/1073/99 (H9N2) virus HA, NA, and M1 genes (FIG. 4).

Plasmid pNAHAM was used to construct a recombinant baculovirus containing influenza virus NA, HA, and M1 genes integrated into the genome, each downstream from a separate baculovirus polyhedrin promoter. Infection of permissive Sf-9S insect cells with the resulting recombinant baculovirus resulted in co-expression of these three influenza genes in each Sf-9S cell infected with such recombinant baculovirus.

The expression products in infected Sf-9S cells were characterized at 72 hr postinfection (p.i. by SDS-PAGE analysis, Coomassie blue protein staining, and Western immunoblot analysis using HA- and M1-specific antibodies (FIG. 5). Western immunoblot analysis was carried out using rabbit antibody raised against influenza virus type A/Hong Kong/ 1073/99 (H9N2) (CDC, Atlanta, Ga., USA), or mouse monoclonal antibody to influenza M1 protein (Serotec, UK). The HA, NA, and M1 proteins of the expected molecular weights (64 kd, 60 kd, and 31 kd, respectively) were detected by Western immunoblot analysis. Compared to the amount of HA protein detected in this assay, the NA protein showed lower reactivity with rabbit serum to influenza A/Hong Kong/ 1073/99 (H9N2) virus. Explanations for the amount of detectable NA protein included lower expression levels of the NA protein from Sf-9S cells infected with recombinant baculovirus as compared to the HA protein, lower reactivity of the NA with this serum under denaturing conditions in the Western immunoblot assay (due to the elimination of important NA epitopes during gel electrophoresis of membrane binding), lower NA-antibody avidity as compared to HA-antibody, or a lower abundance of NA-antibodies in the serum.

The culture medium from the Sf-9S cells infected with recombinant baculovirus expressing A/Hong Kong/1073/99 (H9N2) HA, NA, and M1 proteins was also probed for influenza proteins. The clarified culture supernatants were subjected to ultracentrifugation at 27,000 rpm in order to concentrate high-molecular protein complexes of influenza virus, such as subviral particles, VLP, complexes of VLP, and possibly, other self-assembled particulates comprised of influenza HA, NA, and M1 proteins. Pelleted protein products were resuspended in phosphate-buffered saline (PBS, pH 7.2) and further purified by ultracentrifugation on discontinuous 20-60% sucrose step gradients. Fractions from the sucrose gradients were collected and analyzed by SDS-PAGE analysis, Western immunoblot analysis, and electron microscopy.

Influenza HA and M1 proteins of the expected molecular weights were detected in multiple sucrose density gradient fractions by Coomassie blue staining and Western immunoblot analysis (FIG. 6, Table 1). This suggested that influenza viral proteins from infected Sf-9S cells are aggregated in complexes of high-molecular weight, such as capsomers, subviral particles, VLP, and/or VLP complexes. The NA proteins, although inconsistently detected by Coomassie blue staining and Western immunoblot analysis, which was likely due to the inability of the rabbit anti-influenza serum to recognize denatured NA protein in the Western immunoblot assay, were consistently detected in neuraminidase enzyme activity assay (FIG. 10).

TABLE 1

| Fraction#* | Titer |
|---|---|
| 1 | <1:5001 |
| 3 | <1:500 |
| 5 | 1:500 |
| 7 | 1:1000 |
| 9 | 1:2000 |
| 11 | 1:2000 |
| 12 | 1:4000 |
| 14 | 1:500 |
| 16 | <1:500 |
| PBS** | <1:500 |
| A/Shangdong/9/93 | <1:1000 |

| Virus Strain | Gene | RT-PCR Primer | | SEQ ID NO |
|---|---|---|---|---|
| Type A (H3N2) Sydney/5/97 | Hemagglutinin (HA) | Forward | 5'-A GGATCCATG AAGACTATCATTGCTTTGAG-3' | 13 |
| | | Reverse | 5'-A GGTACC TCAAATGCAAATGTTGCACCTAATG-3' | 14 |
| | Neuraminidase (NA) | Forward | 5'-GGGGACAAGTTTGTACAAAAAAGCAGGCTTAGAAG GAGATAGAACC ATG AATCCAAATCAAAAGATAATAAC-3' | 15 |
| | | Reverse | 5'-GGGGACCACTTTGTACAAGAAAGCTGGGTCCTATAT AGGCATGAGATTGATGTCCGC-3' | 16 |
| | Matrix (M1) | Forward | 5'-AAA GAATTC ATG AGTCTTCTAACCGAGGTCGAAACGTA-3' | 17 |
| | | Reverse | 5'-AAA TTCGAA TTACTCCAGCTCTATGCTGACAAAATGAC-3' | 18 |
| | M2 | Forward | 5'-A GAATC ATG AGTCTTCTAACCGAGGTCGAAACGCCT ATCAGAAACGAATGGGGGTGC-3' | 19 |
| | | Reverse | 5'-AAA TTCGAA TTACTCCAGCTCTATGCTGACAAAATGAC-3' | 20 |
| | Nucleoprotein (NP) | Forward | 5'-A GAATTC ATG GCGTCCCAAGGCACCAAACG-3' | 21 |
| | | Reverse | 5'-A GCGGCCGCTTAATTGTCGTACTCCTCTGCATTGTCTCCGAA GAAATAAG-3' | 22 |
| Type B Harbin | Hemagglutinin (HA) | Forward | 5'-A GAATTC ATG AAGGCAATAATTGTACTACTCATGG-3' | 23 |
| | | Reverse | 5'-A GCGGCCGCTTATAGACAGATGGAGCAAGAAACATTGTC TCTGGAGA-3' | 24 |
| | Neuraminidase (NA) | Forward | 5'-A GAATT CATG CTACCTTCAACTATACAAACG-3' | 25 |
| | | Reverse | 5'-A GCGGCCGCTTACAGAGCCATATCAACACCTGTGACAGTG-3' | 26 |

*Fraction from 20-60% sucrose gradient

**Negative Control

***Positive Control

The presence of high-molecular VLPs was confirmed by gel filtration chromatography. An aliquot from sucrose density gradient fractions containing influenza viral proteins was loaded onto a Sepharose CL-4B column for fractionation based on mass. The column was calibrated with dextran blue 2000, dextran yellow, and vitamin B12 (Amersham Pharmacia) with apparent molecular weights of 2,000,000; 20,000; and 1,357 daltons, respectively, and the void volume of the column was determined. As expected, high-molecular influenza viral proteins migrated in the void volume of the column, which was characteristic of macromolecular proteins, such as virus particles. Fractions were analyzed by Western immunoblot analysis to detect influenza and baculovirus proteins. For example, M1 proteins were detected in the void volume fractions, which also contained baculovirus proteins (FIG. 7).

Figure 8:
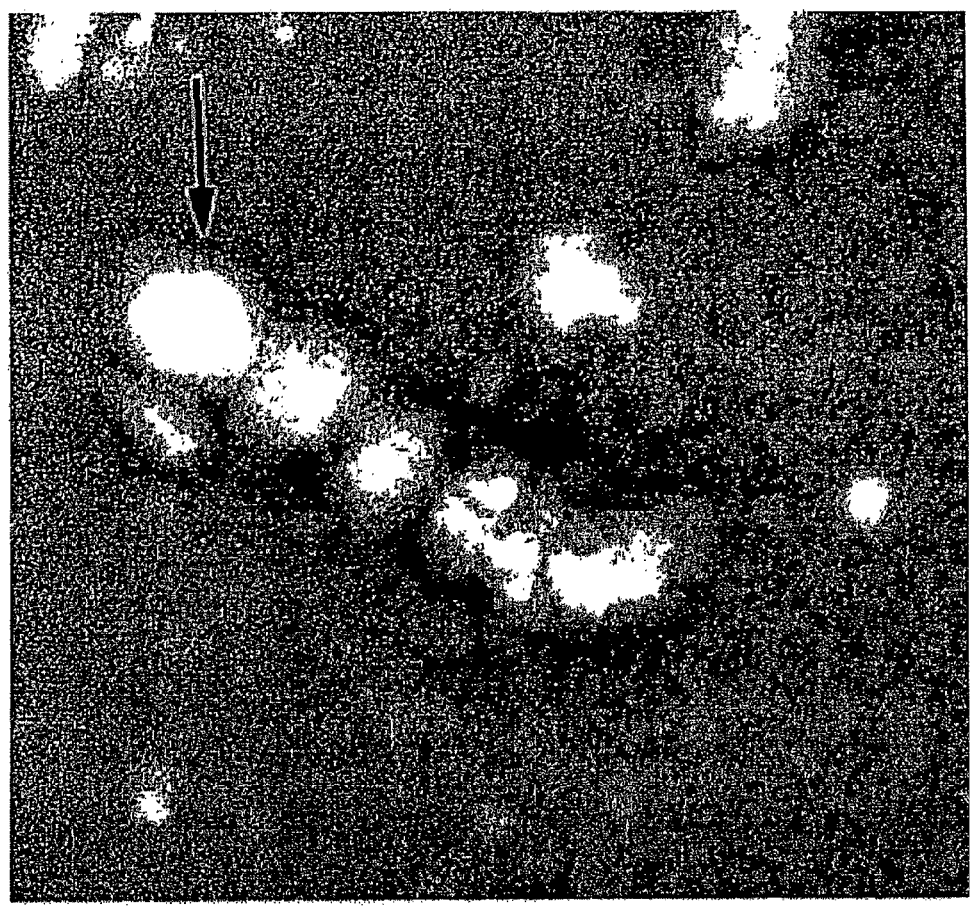
FIG. 8 depicts the detection of avian influenza A/Hong Kong/1073/99 (H9N2) proteins including subviral particles, VLP, and VLP complexes, by electron microscopy.

The morphology of influenza VLPs and proteins in sucrose gradient fractions was elucidated by electron microscopy. For negative-staining electron microscopy, influenza proteins from two sucrose density gradient fractions were fixed with 2% glutaraldehyde in PBS, pH 7.2. Electron microscopic examination of negatively-stained samples revealed the presence of macromolecular protein complexes or VLPs in both fractions. These VLPs displayed different sizes including diameters of approximately 60 and 80 nm and morphologies (spheres). Larger complexes of both types of particles were also detected, as well as rod-shaped particles (FIG. 8). All observed macromolecular structures had spikes (peplomers) on their surfaces, which is characteristic of influenza viruses. Since the size and appearance of 80 nm particles was similar to particles of wild type influenza virus, these structures likely represented VLPs, which have distinct similarities to wild type influenza virions, including similar particle geometry, architecture, triangulation number, symmetry, and other characteristics. The smaller particles of approximately 60 nm may represent subviral particles that differ from VLPs both morphologically and structurally. Similar phenomenon of recombinant macromolecular proteins of different sizes and morphologies was also reported for other viruses. For example, recombinant core antigen (HBcAg) of hepatitis B virus forms particles of different sizes, which have different architecture and triangulation number T=4 and T=3, respectively (Crowther et al., 1994).

Figure 9:
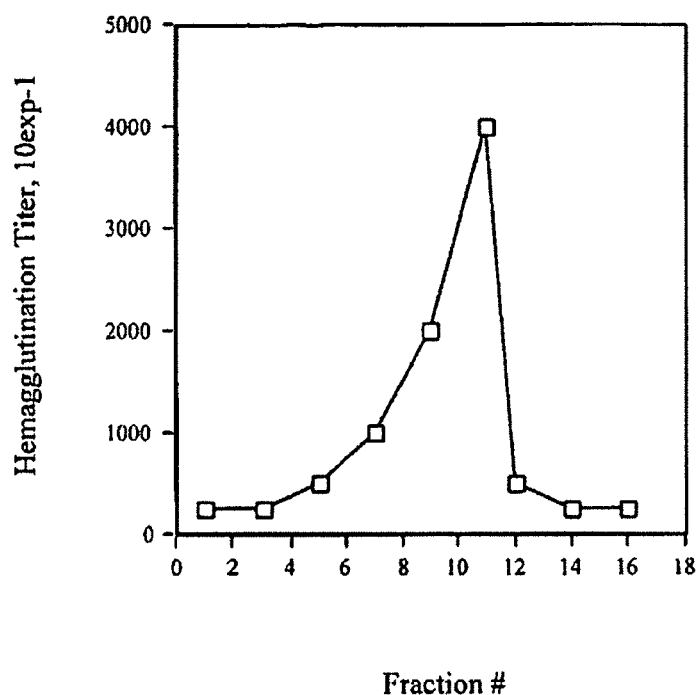
FIG. 9 depicts the hemagglutination activity of purified avian influenza A/Hong Kong/1073/99 (H9N2) VLPs.
Figure 10:
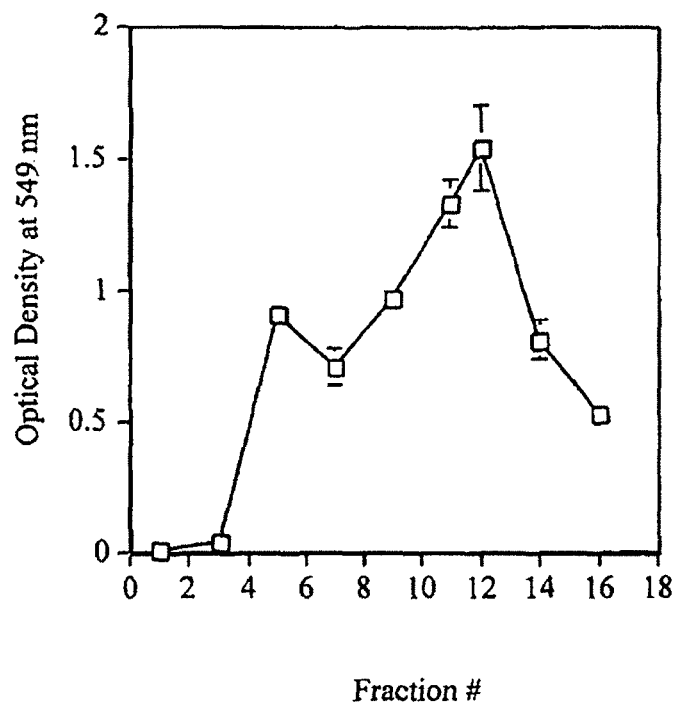
FIG. 10 depicts the neuraminidase activity of purified avian influenza A/Hong Kong/1073/99 (H9N2) VLPs.

To characterize the functional properties of the purified influenza A/Hong Kong/1073/99 (H9N2) VLPs, samples were tested in a hemagglutination assay (FIG. 9) and a neuraminidase enzyme assay (FIG. 10). For the hemagglutination assay, 2-fold dilutions of purified influenza VLPs were mixed with 0.6% guinea pig red blood cells and incubated at 4° C. for 1 hr or 16 hr. The extent of hemagglutination was inspected visually and the highest dilution of recombinant influenza proteins capable of agglutinating red blood cells was determined and recorded (FIG. 9). Again, many fractions from the sucrose density gradient exhibited hemagglutination activity, suggesting that multiple macromolecular and monomeric forms of influenza proteins were present. The highest titer detected was 1:4000. In a control experiment, wild-type influenza A/Shangdong virus demonstrated a titer of 1:2000. The hemagglutination assay revealed that the recombinant VLPs consisting of influenza A/Hong Kong/1073/99 (H9N2) virus HA, NA, and M1 proteins were functionally active. This suggested that the assembly, conformation, and folding of the HA subunit proteins within the VLPs were similar or identical to that of the wild type influenza virus.

Additionally, a neuraminidase enzyme assay was performed on samples of purified H9N2 VLPs. The amount of neuraminidase activity in sucrose density gradient fractions was determined using fetuin as a substrate. In the neuraminidase assay, the neuraminidase cleaved sialic acid from substrate molecules to release sialic acid for measurement. Arsenite reagent was added to stop enzyme activity. The amount of sialic acid liberated was determined chemically with thiobarbituric acid that produces a pink color that was proportional to the amount of free sialic acid. The amount of color (chromophor) was measured spectrophotometrically at wavelength 549 nm. Using this method, neuraminidase activity was demonstrated in sucrose gradient fractions containing influenza VLPs (FIG. 10). As expected, the activity was observed in several fractions, with two peak fractions. As a positive control, wild type influenza virus was used. The wild type influenza virus exhibited neuraminidase enzyme activity comparable to that of purified influenza VLPs. These findings corroborated the HA results with regard to protein conformation and suggested that purified VLPs of influenza A/Hong Kong/1073/99 (H9N2) virus were functionally similar to wild type influenza virus.

The results from the above analyses and assays indicated that expression of influenza A/Hong Kong/1073/99 (H9N2) HA, NA, and M1 proteins was sufficient for the self-assembly and transport of functional VLPs from baculovirus-infected insect cells. Since these influenza VLPs represented self-assembled influenza structural proteins and demonstrated functional and biochemical properties similar to those of wild type influenza virus, these influenza VLPs conserved important structural conformations including surface epitopes necessary for effective influenza vaccines.

Example 2

RT-PCR Cloning of Avian Influenza A/Hong Kong/1073/99 Viral Genes

It is an object of the present invention to provide synthetic nucleic acid sequences capable of directing production of recombinant influenza virus proteins. Such synthetic nucleic acid sequences were obtained by reverse transcription and polymerase chain reaction (PCR) methods using influenza virus natural genomic RNA isolated from the virus. For the purpose of this application, nucleic acid sequence refers to RNA, DNA, cDNA or any synthetic variant thereof which encodes the protein.

Avian influenza A/Hong Kong/1073/99 (H9N2) virus was provided by Dr. K. Subbarao (Centers for Disease Control, Atlanta, Ga., USA). Viral genomic RNA was isolated by the acid phenol RNA extraction method under Biosafety Level 3 (BSL3) containment conditions at CDC using Trizol LS reagent (Invitrogen, Carlsbad, Calif. USA). cDNA molecules of the viral RNAs were obtained by reverse transcription using MuLV reverse transcriptase (InVitrogen) and PCR using oligonucleotide primers specific for HA, NA, and M1 proteins and Taq I DNA polymerase (InVitrogen) (Table 1). The PCR fragments were cloned into the bacterial subcloning vector, pCR2.1TOPO (InVitrogen), between Eco RI sites that resulted in three recombinant plasmids, containing the HA, NA, and M1 cDNA clones.

Example 3

RT-PCR Cloning of Human Influenza A/Sydney/5/94 (H3N2) Viral Genes

Influenza A/Sydney/5/97 (H3N2) Virus was obtained from Dr. M. Massare (Novavax, Inc., Rockville, Md.). Viral genomic RNA was isolated by the RNA acid phenol extraction method under BSL2 containment conditions at Novavax, Inc. using Trizol LS reagent (Invitrogen). cDNA molecules of the viral RNAs were obtained by reverse transcription and PCR using oligonucleotide primers specific for HA, NA, M1, M2, and NP proteins (Table 1). The PCR fragments were cloned into the bacterial subcloning vector, pCR2.1TOPO, between Eco RI sites that resulted in five recombinant plasmids, containing the HA, NA, M1, M2, and NP cDNA clones.

Example 4

Cloning of Avian Influenza A/Hong Kong/1073/99 Viral cDNAs into Baculovirus Transfer Vectors From the pCR2.1TOPO-based plasmids, the HA, NA, or M1 genes were subcloned into pFastBac1 baculovirus transfer vector (InVitrogen) within the polyhedron locus and Tn7 att sites and downstream of the baculovirus polyhedrin promoter and upstream of the polyadenylation signal sequence. The viral genes were ligated with T4 DNA ligase. For the HA gene, a Bam HI-Kpn I DNA fragment from pCR2.1TOPO-HA was inserted into BamHI-KpnI digested pFastBac1 plasmid DNA. For the NA gene, an EcoRI DNA fragment from pCR2.1TOPO-NA was inserted into EcoRI digested pFastBac1 plasmid DNA. For the M1 gene, an Eco RI DNA fragment from pCR2.1TOPO-M1 was inserted into Eco RI digested pFastBac1 plasmid DNA. Competent *E. coli* DH5α bacteria (InVitrogen) were transformed with these DNA ligation reactions, transformed colonies resulted, and bacterial clones isolated. The resulting pFastBac1-based plasmids, pFastBac1-HA, pFastBac1-NA, and pFastBac1-M1 were characterized by restriction enzyme mapping on agarose gels (FIG. 4A). The nucleotide sequences as shown on FIGS. 1-3 of the cloned genes were determined by automated DNA sequencing. DNA sequence analysis showed that the cloned influenza HA, NA, and M1 genes were identical to the nucleotide sequences for these genes as published previously [NA, HA, and M1 genes of influenza A/Hong Kong/1073/99 (H9N2) (GenBank accession numbers AJ404629, AJ404626, and AJ278646, respectively)].

Example 5

Cloning of Human Influenza A/Sydney/5/97 Viral cDNAs into Baculovirus Transfer Vectors From the pCR2.1TOPO-based plasmids, the HA, NA, M1, M2, and NP genes were subcloned into pFastBac1 baculovirus transfer vector within the polyhedron locus and Tn7 att sites and downstream of the baculovirus polyhedrin promoter and upstream of the polyadenylation signal sequence. The viral genes were ligated with T4 DNA ligase. For the HA gene, a Bam HI-Kpn I DNA fragment from pCR2.1TOPO-hHA3 was inserted into BamHI-KpnI digested pFastBac1 plasmid DNA. For the NA gene, an Eco RI DNA fragment from pCR2.1TOPO-hNA was inserted into EcoRI digested pFastBac1 plasmid DNA. For the M1 gene, an Eco RI DNA fragment from pCR2.1TOPO-hM1 was inserted into EcoRI digested pFastBac1 plasmid DNA. For the M2 gene, an EcoRI DNA fragment from pCR2.1TOPO-hM2 was inserted into EcoRI digested pFastBac1 plasmid DNA. For the NP gene, an EcoRI DNA fragment from pCR2.1TOPO-hNP was inserted into EcoRI digested pFastBac1 plasmid DNA. Competent *E. coli* DH5α bacteria were transformed with these DNA ligation reactions, transformed colonies resulted, and bacterial clones isolated. The resulting pFastBac1-based plasmids, pFastBac1-hHA3, pFastBac1-hNA2, pFastBac1-hM1, pFASTBAC1-hM2, and pFASTBAC1-hNP were characterized by restriction enzyme mapping on agarose gels. The nucleotide sequences of the cloned genes were determined by automated DNA sequencing. DNA sequence analysis showed that the cloned influenza HA, NA, M1, M2, and NP genes were identical to the nucleotide sequences for these genes as published previously.

Example 6

Construction of Multigenic Baculovirus Transfer Vectors Encoding Multiple Avian Influenza A/Hong Kong/1073/99 Viral Genes In order to construct pFastBac1-based bacmid transfer vectors expressing multiple influenza A/Hong Kong/1073/99 (H9N2) virus genes, initially a Sna BI-Hpa I DNA fragment from pFastBac1-M1 plasmid containing the M1 gene was cloned into Hpa I site of pFastBac1-HA. This resulted in pFastBac1-HAM plasmid encoding both HA and M1 genes within independent expression cassettes and expressed under the control of separate polyhedrin promoters.

Finally, a SnaBI-AvrII DNA fragment from pFastBac1-HAM containing the HA and M1 expression cassettes, was transferred into Hpa I-Avr II digested pFastBac1-NA plasmid DNA. This resulted in the plasmid pFastBac1-NAHAM encoding three independent expression cassettes for expression of influenza HA, NA, and M1 genes and expressed under the control of separate polyhedrin promoters (FIG. 4B).

In another example, the H3 gene from pFASTBAC1-hHA3 (see Example 5) was cloned into pFASTBAC1-NAHAM as a fourth influenza viral gene for the expression and production of heterotypic influenza VLPs.

Example 7

Generation of Multigenic Recombinant Baculovirus Encoding NA, HA, and M1 Genes of Avian Influenza A/Hong Kong/1073/99 Virus in Insect Cells The resulting multigenic bacmid transfer vector pFastBac1-NAHAM was used to generate a multigenic recombinant baculovirus encoding avian influenza A/Hong Kong/1073/99 (H9N2) HA, NA, and M1 genes for expression in insect cells. Recombinant bacmid DNAs were produced by site-specific recombination at polyhedrin and Tn7 att DNA sequences between pFastBac1-NAHAM DNA and the AcMNPC baculovirus genome harbored in competent *E. coli* DH10BAC cells (InVitrogen) (FIG. 4B). Recombinant bacmid DNA was isolated by the mini-prep plasmid DNA method and transfected into Sf-9s cells using the cationic lipid CELLFECTIN (InVitrogen). Following transfection, recombinant baculoviruses were isolated, plaque purified, and amplified in Sf-9S insect cells. Virus stocks were prepared in Sf-9S insect cells and characterized for expression of avian influenza viral HA, NA, and M1 gene products. The resulting recombinant baculovirus was designated bNA-HAM-H9N2.

Example 8

Expression of Recombinant Avian Influenza A/Hong Kong/1073/99 Proteins in Insect Cells Sf-9S insect cells maintained as suspension cultures in shaker flasks at 28° C. in serum-free medium (HyQ SFM, HyClone, Ogden, Utah) were infected at a cell density of 2×10⁶ cells/ml with the recombinant baculovirus, bNAHAM-H9N2, at a multiplicity of infection (MOI) of 3 pfu/cell. The virus infection proceeded for 72 hrs. to allow expression of influenza proteins. Expression of avian influenza A/Hong Kong/1073/99 (H9N2) HA and M1 proteins in infected insect cells was confirmed by SDS-PAGE and Western immunoblot analyses. SDS-PAGE analysis was performed on 4-12% linear gradient NuPAGE gels (Invitrogen) under reduced and denaturing conditions. Primary antibodies in Western immunoblot analysis were polyclonal rabbit antiserum raised against avian influenza A/Hong Kong/1073/99 (H9N2) obtained from CDC and monoclonal murine antiserum to influenza M1 protein (Serotec, UK). Secondary antibodies for Western immunoblot analysis were alkaline phosphatase conjugated goat IgG antisera raised against rabbit or mouse IgG (H+ L) (Kirkegaard and Perry Laboratories, Gaithersburg, Md., USA). Results of these analyses (FIG. 5) indicated that the HA and M1 proteins were expressed in the baculovirus-infected insect cells.

Example 9

Purification of Recombinant Avian Influenza H9N2 Virus-Like Particles and Macromolecular Protein Complexes Culture supernatants (200 ml) from Sf-9S insect cells infected with the recombinant baculovirus bNAHAM-H9N2 that expressed avian influenza A/Hong Kong/1073/99 (H9N2) HA, NA, and M1 gene products were harvested by low speed centrifugation. Culture supernatants were clarified by centrifugation in a Sorval RC-5B superspeed centrifuge for 1 hr at 10,000×g and 4° C. using a GS-3 rotor. Virus and VLPs were isolated from clarified culture supernatants by centrifugation in a Sorval OTD-65 ultracentrifuge for 3 hr at 27,000 rpm and 4° C. using a Sorval TH-641 swinging bucket rotor. The virus pellet was resuspended in 1 ml of PBS (pH 7.2), loaded onto a 20-60% (w/v) discontinuous sucrose step gradient, and resolved by centrifugation in a Sorval OTD-65 ultracentrifuge for 16 hr at 27,000 rpm and 4° C. using a Sorval TH-641 rotor. Fractions (0.5 ml) were collected from the top of the sucrose gradient.

Figure 6:
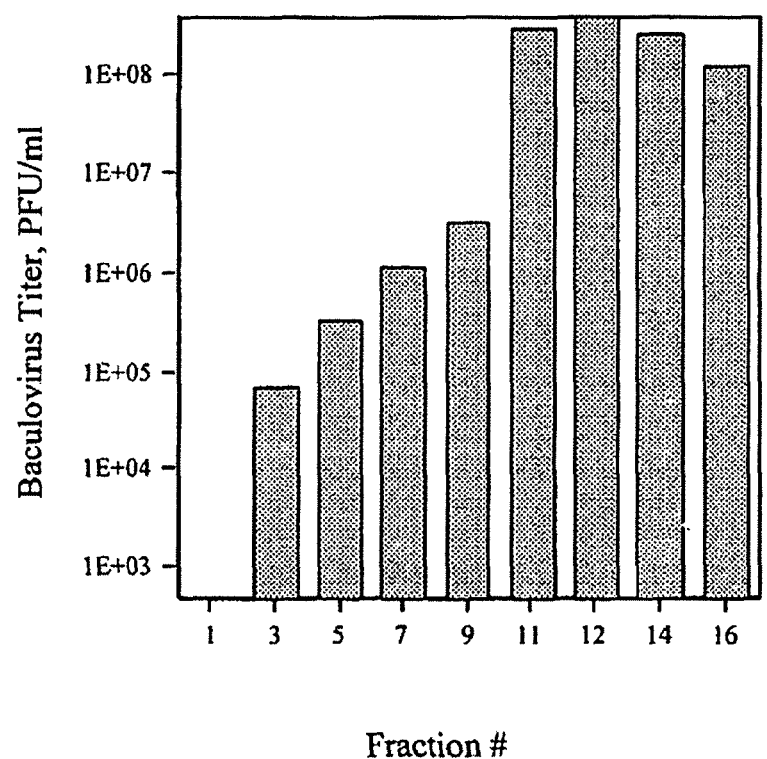
FIG. 6 depicts the purification of avian influenza A/Hong Kong/1073/99 (H9N2) VLPs by the sucrose density gradient method.

Influenza proteins in the sucrose gradient fractions were analyzed by SDS-PAGE and Western immunoblot analyses as described above in Example 6. The HA and M1 proteins were found in the same sucrose gradient fractions (FIG. 6) as shown by Western blot analysis and suggested that the HA and M1 proteins were associated as macromolecular protein complexes. Also the HA and M1 proteins were found in fractions throughout the sucrose gradient suggesting that these recombinant viral proteins were associated with macromolecular protein complexes of different densities and compositions.

Example 10

Analysis of Recombinant Avian Influenza H9N2 VLPs and Proteins by Gel Filtration Chromatography Protein macromolecules such as VLPs and monomeric proteins migrate differently on gel filtration or size exclusion chromatographic columns based on their mass size and shape. To determine whether the recombinant influenza proteins from sucrose gradient fractions were monomeric proteins or macromolecular protein complexes such as VLPs, a chromatography column (7 mm×140 mm) with a resin bed volume of 14 ml of Sepharose CL-4B (Amersham) was prepared. The size exclusion column was equilibrated with PBS and calibrated with Dextran Blue 2000, Dextran Yellow, and Vitamin B12 (Amersham Pharmacia) with apparent molecular weights of 2,000,000; 20,000; and 1,357, respectively, to ascertain the column void volume. Dextran Blue 2000 eluted from the column in the void volume (6 ml fraction) also. As expected, the recombinant influenza protein complexes eluted from the column in the void volume (6 ml fraction). This result was characteristic of a high molecular weight macromolecular protein complex such as VLPs. Viral proteins in the column fractions were detected by Western immunoblot analysis as described above in Example 6. The M1 proteins were detected in the void volume fractions (FIG. 7). As expected baculovirus proteins were also in the void volume.

Example 11

Electron Microscopy of Recombinant Influenza VLPs

To determine whether the macromolecular protein complexes isolated on sucrose gradients and containing recombinant avian influenza proteins had morphologies similar to influenza virions, electron microscopic examination of negatively stained samples was performed. Recombinant avian influenza A/Hong Kong/1073/99 (H9N2) protein complexes were concentrated and purified from culture supernatants by ultracentrifugation on discontinuous sucrose gradients as described in Example 7. Aliquots of the sucrose gradient fractions were treated with a 2% glutaraldehyde in PBS, pH7.2, absorbed onto fresh discharged plastic/carbon-coated grids, and washed with distilled water. The samples were stained with 2% sodium phosphotungstate, pH 6.5, and observed using a transmission electron microscope (Philips). Electron micrographs of negatively-stained samples of recombinant avian influenza H9N2 protein complexes from two sucrose gradient fractions showed spherical and rod-shaped particles (FIG. 8) from two sucrose gradient fractions. The particles had different sizes (60 and 80 nm) and morphologies. Larger complexes of both types of particles were also detected, as well as rod-shaped particles (FIG. 8). All observed protein complex structures exhibited spike like surface projections resembling influenza virus HA and NA peplomers. Since the size and appearance of the 80 nm particles was similar to that of wild type influenza virus particles, these structures likely represented enveloped influenza VLPs. The smaller particles of approximately 60 nm probably represented subviral particles that differed from the above VLPs both morphologically and structurally.

Example 12

Analysis of Functional Characteristics of Influenza Proteins by Hemagglutination Assay To determine whether the purified influenza VLPs and proteins possessed functional activities, such as hemagglutination and neuraminidase activity, which were characteristic for influenza virus, the purified influenza VLPs and proteins were tested in hemagglutination and neuraminidase assays.

For the hemagglutination assay, a series of 2-fold dilutions of sucrose gradient fractions containing influenza VLPs or positive control wild type influenza virus type A were prepared. Then they were mixed with 0.6% guinea pig red blood cells in PBS (pH 7.2) and incubated at 4° C. for 1 to 16 hr. As a negative control, PBS was used. The extent of hemagglutination was determined visually, and the highest dilution of fraction capable of agglutinating guinea pig red blood cells was determined (FIG. 9). The highest hemagglutination titer observed for the purified influenza VLPs and proteins was 1:4000, which was higher than the titer shown by the wild type influenza control, which was 1:2000.

Example 13

Analysis of Functional Characteristics of Influenza Proteins by Neuraminidase Assay The amount of neuraminidase activity in influenza VLP-containing sucrose gradient fractions was determined by the neuraminidase assay. In this assay the NA (an enzyme) acted on the substrate (fetuin) and released sialic acid. Arsenite reagent was added to stop enzyme activity. The amount of sialic acid liberated was determined chemically with the thiobarbituric acid that produced a pink color in proportion to free sialic acid. The amount of color (chromophor) was measured in a spectrophotometer at wavelength 594 nm. The data, as depicted in FIG. 8, showed that a significant amount of sialic acid was produced by VLP-containing fractions of the sucrose gradients and that these fractions corresponded to those fractions exhibiting hemagglutination activity.

Example 14

Figure 11:
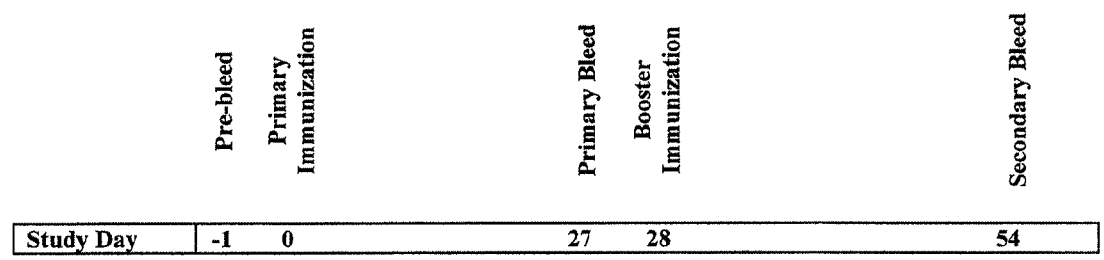
FIG. 11 depicts the immunization and bleed schedule for the immunogenicity study of recombinant influenza with purified avian influenza A/Hong Kong/1073/99 (H9N2) VLPs in mice.

Immunization of BALB/c Mice with Functional Homotypic Recombinant Influenza H9N2 VLPs The immunogenicity of the recombinant influenza VLPs was ascertained by immunization of mice followed by Western blot analysis of immune sera. Recombinant VLPs (1 µg/injection) comprised of viral HA, NA, and M1 proteins from avian influenza virus type A/Honk Kong/1073/99 and purified on sucrose gradients were inoculated subcutaneously into the deltoid region of ten (10) female BALB/c mice at day 0 and day 28 (FIG. 11). PBS (pH 7.2) was administered similarly as a negative control into five (5) mice. The mice were bled from the supraorbital cavity at day-1 (pre-bleed), day 27 (primary bleed), and day 54 (secondary bleed). Sera were collected from blood samples following overnight clotting and centrifugation.

For Western blot analysis, 200 ng of inactivated avian influenza virus type A H9N2 or cold-adapted avian influenza virus type A H9N2, as well as See Blue Plus 2 pre-stained protein standards (InVitrogen), was denatured (95° C., 5 minutes) and subjected to electrophoresis under reduced conditions (10 mM 3-mercaptoethanol) on 4-12% polyacrylamide gradient NuPAGE gels (InVitrogen) in MES buffer at 172 volts until the bromophenol blue tracking dye disappeared. For protein gels, the electrophoreses proteins were visualized by staining with Colloidal Coomassie Blue reagent (InVitrogen). Proteins were transferred from the gel to nitrocellulose membranes in methanol by the standard Western blot procedure. Sera from VLP-immunized mice and rabbits immunized with inactivated avian influenza virus H9N2 (positive control sera) were diluted 1:25 and 1:100, respectively, in PBS solution (pH 7.2) and used as primary antibody. Protein bound membranes, which were blocked with 5% casein, were reacted with primary antisera for 60 minutes at room temperature with constant shaking. Following washing of primary antibody membranes with phosphate buffered saline solution containing Tween 20, secondary antisera [goat anti-murine IgG—alkaline phosphatase conjugate (1:10,000) or goat anti-rabbit IgG—alkaline phosphatase conjugate (1:10, 000)] were reacted 60 minutes with the membrane. Following washing of secondary antibody membranes with phosphate buffered saline solution containing Tween 20, antibody-binding proteins on the membranes were visualized by development with the chromogenic substrate such as NBT/BCIP (InVitrogen).

Figure 12:
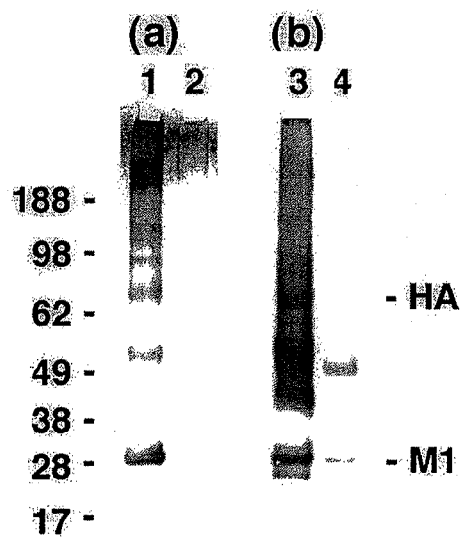
FIG. 12 depicts the results of an immunogenicity study in mice immunized with recombinant influenza H9N2 VLPs.

The results of Western blot analysis (FIG. 12) were that proteins with molecular weights similar to viral HA and M1 proteins (75 and 30 kd, respectively) bound to positive control sera (FIG. 12B) and sera from mice immunized with the recombinant influenza H9N2 VLPs (FIG. 12A). These results indicated that the recombinant influenza H9N2 VLPs alone were immunogenic in mice by this route of administration.

Example 15

Kong/1073/99 (H9N2) VLP Immunogenicity And Challenge Study in BALB/c Mice

BALB/C mice were immunized with H9N2 VLPs (1 µg HA or 10 ng HA/dose), with or without 100 µg Novasome adjuvant, on day 0 and day 21 and challenged with homologous infectious virus IN on day 57. Mice were bled on days 0, 27 and 57 with the serum assayed for anti-HA antibodies by the hemagglutination inhibition assay (HI) using turkey RBCs, and influenza by ELISA. Results of this study are shown in FIG. 13 through FIG. 16.

Figure 13:
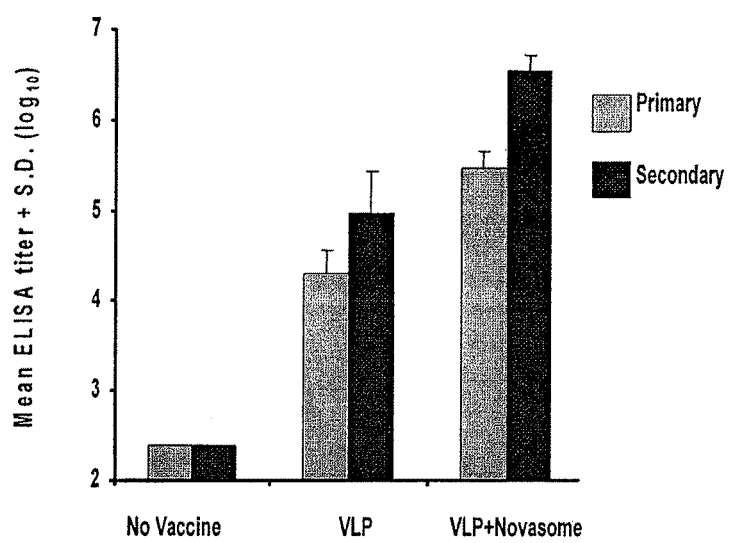
FIG. 13 depicts the geometric mean antibody responses in BALB/c mice after a primary and secondary immunization.

High titers of H9N2 antibodies were induced after a single immunization (primary) with H9N2 VLP vaccine without or with Novasomes and a dose of 10 µg VLPs containing 1 µg HA (FIG. 13). Specific antibody titers were increased about half to one log following a booster immunization.

Figure 14:
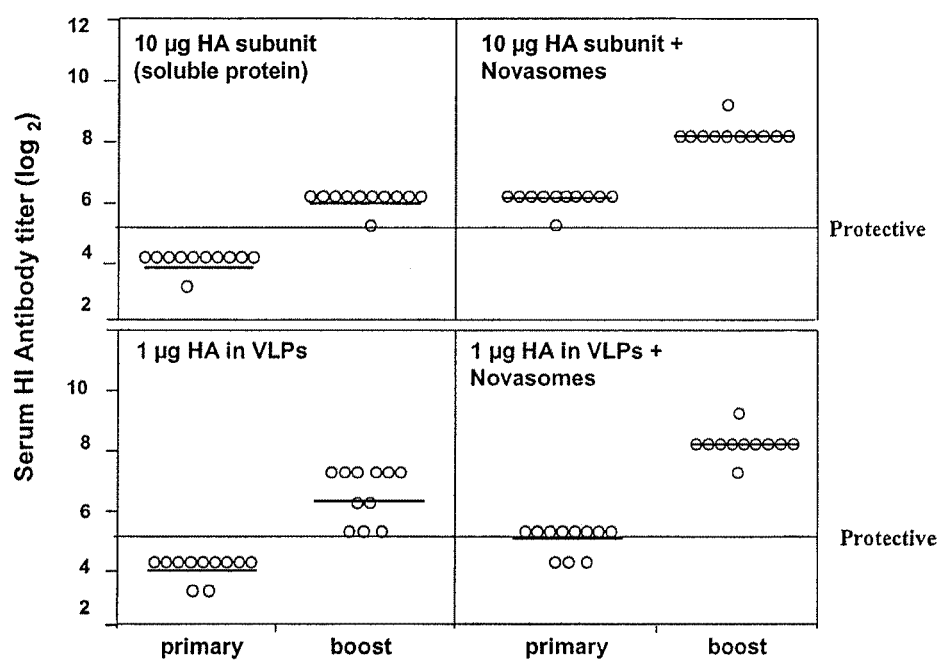
FIG. 14 depicts serum hemagglutinin inhibition (HI) responses in BALB/c mice.

After immunization and a boost with 1 µg of HA in the form of H9N2 VLPs the serum HI levels were at or above the level generally considered protective (log 2=5) in all animals (FIG. 14, lower left panel). H9N2 VLPs formulated with Novasome adjuvant increased HI responses about 2 fold following primary immunization and about 4 fold after the booster (FIG. 14, lower right panel). Purified subunit H9N2 hemagglutinin also induced protective levels of HI antibodies after boosting and Novasomes again increased HI antibody responses by about 2 fold after the primary and 4 fold after the booster immunizations (FIG. 14, upper panels). The level of HI antibody induced with 10 µg of HA given as a subunit vaccine was equivalent to 1 µg of HA presented in the form of a VLP.

Figure 15:
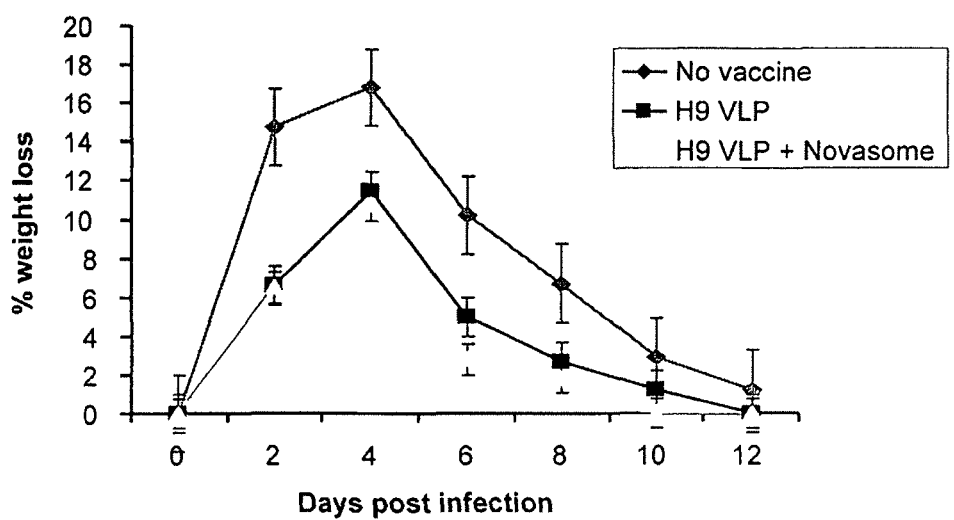
FIG. 15 depicts weight loss (%) in BALB/c mice challenged with H9N2 influenza.

In addition, weight loss was significantly less in the mice immunized with H9N2 VLPs or with VLPs plus adjuvant compared to unvaccinated control animals (FIG. 15). There was no statistical difference in weight loss in the groups immunized with H9N2 VLPs and H9N2 VLPs plus Novasome adjuvant.

Figure 16:
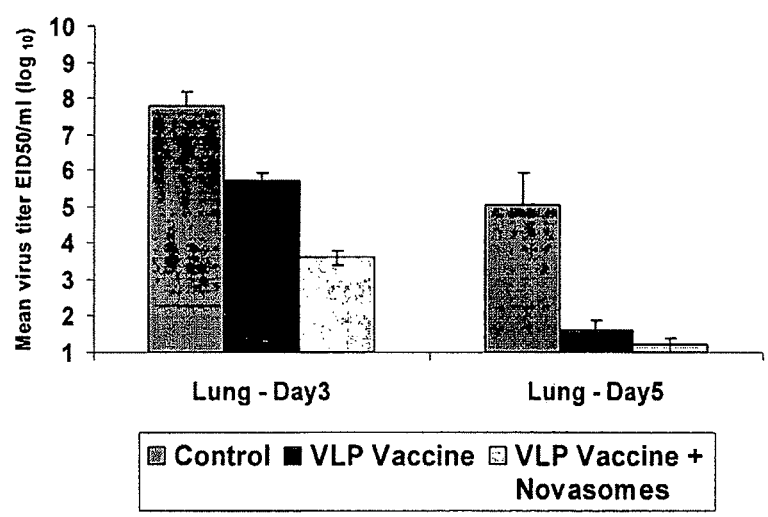
FIG. 16 depicts lung virus titers at 3 and 5 days post challenge with H9N2.

Likewise, lung virus titers at 3 and 5 days post challenge with H9N2 virus were significantly reduced in mice immunized with H9N2 VLPs (FIG. 16). At day 3 when the influenza virus titers peak in the lung tissues, mice immunized with H9N2 VLPs plus Novasomes® had a significantly greater reduction in virus titer compared to mice immunized with VLPs alone and the unvaccinated control mice.

Example 16

A/Fujian/411/2002 (H3N2) VLP Immunogenicity and Cross Reactivity Between Several Influenza Strains BALB/c mice were immunized with A/Fujian/411/2002 VLPs (3.0, 0.6, 0.12 and 0.24 µg HA/dose), twice IM and IN.

Figure 17:
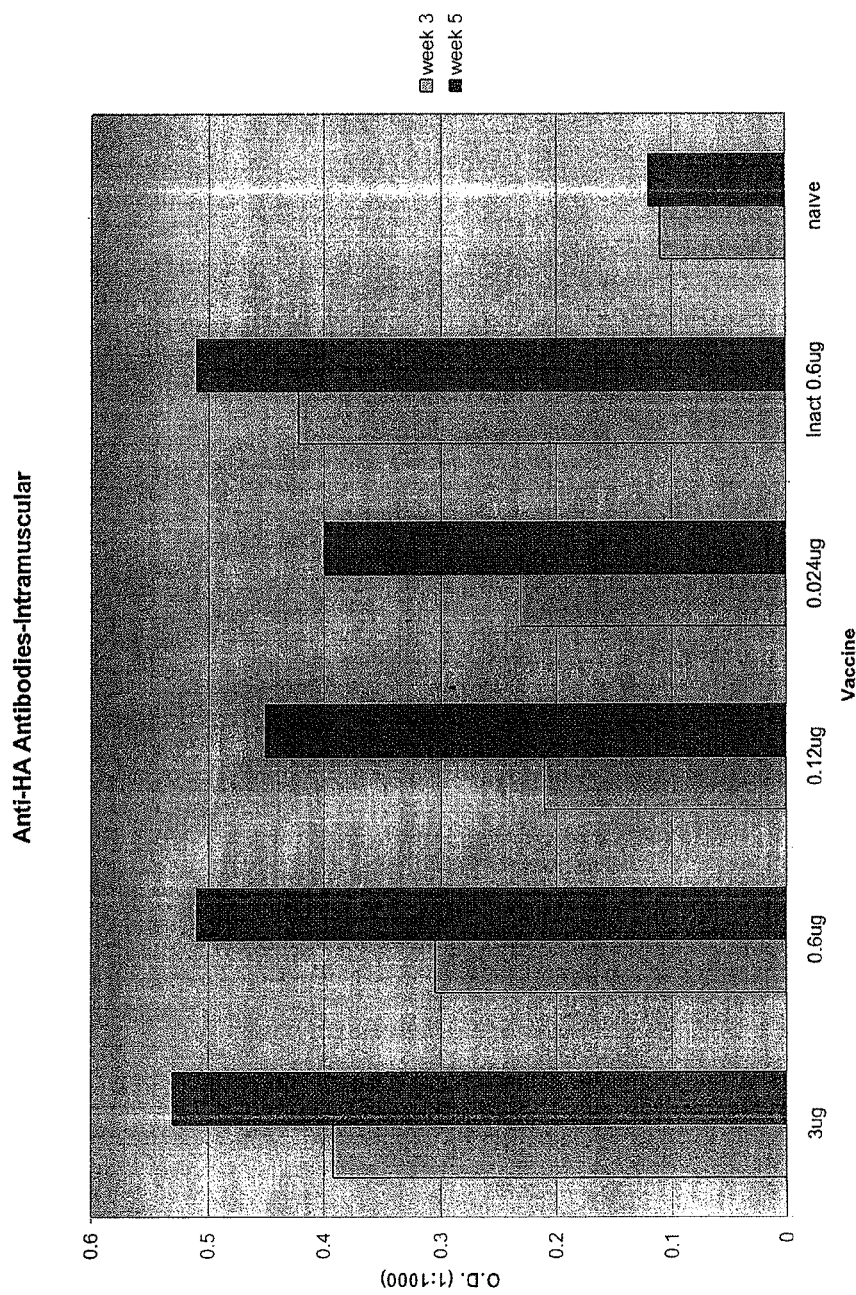
FIGS. 17A, 17B and 17C depict mice antibody response to A/Fujian/411/2002 when immunized with H3N2 VLP.
Figure 17:
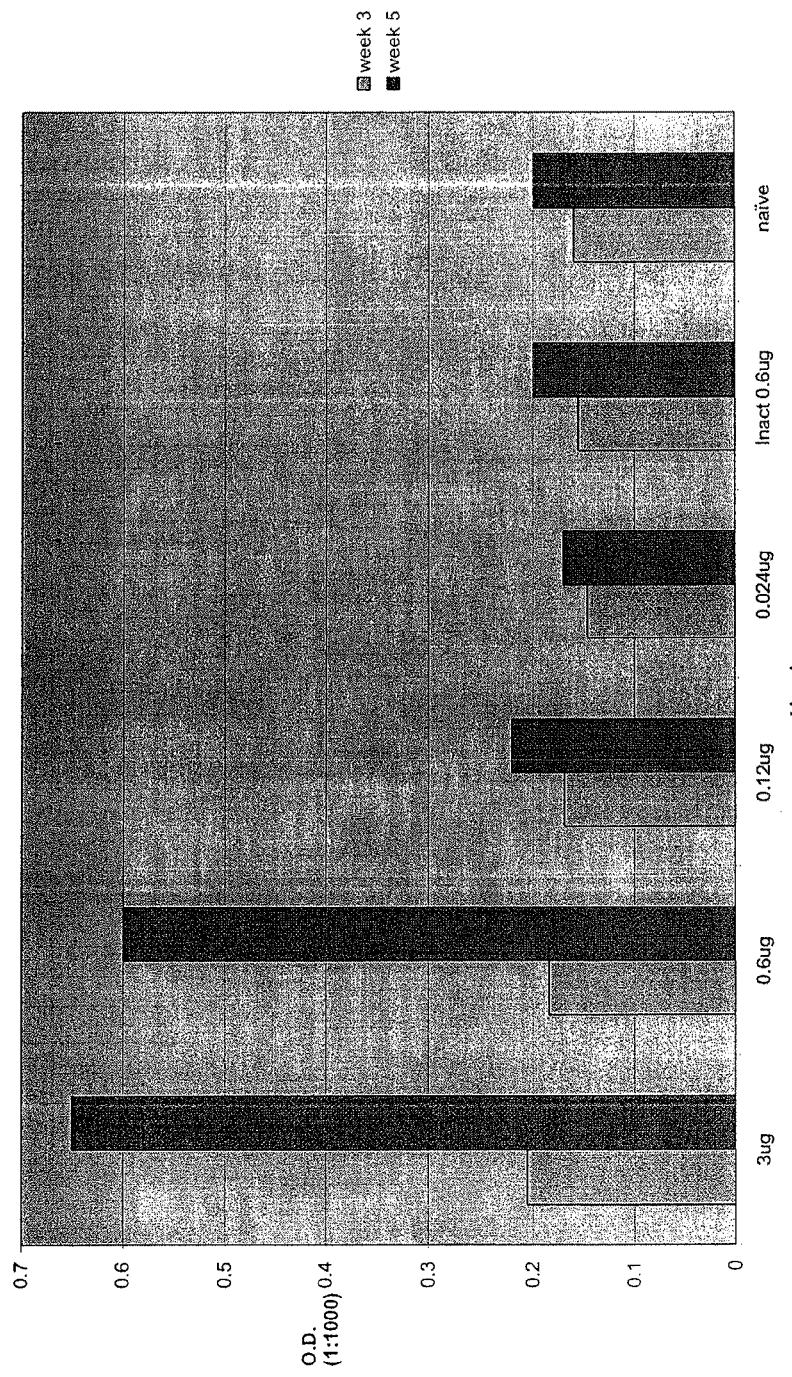
Figure 17:
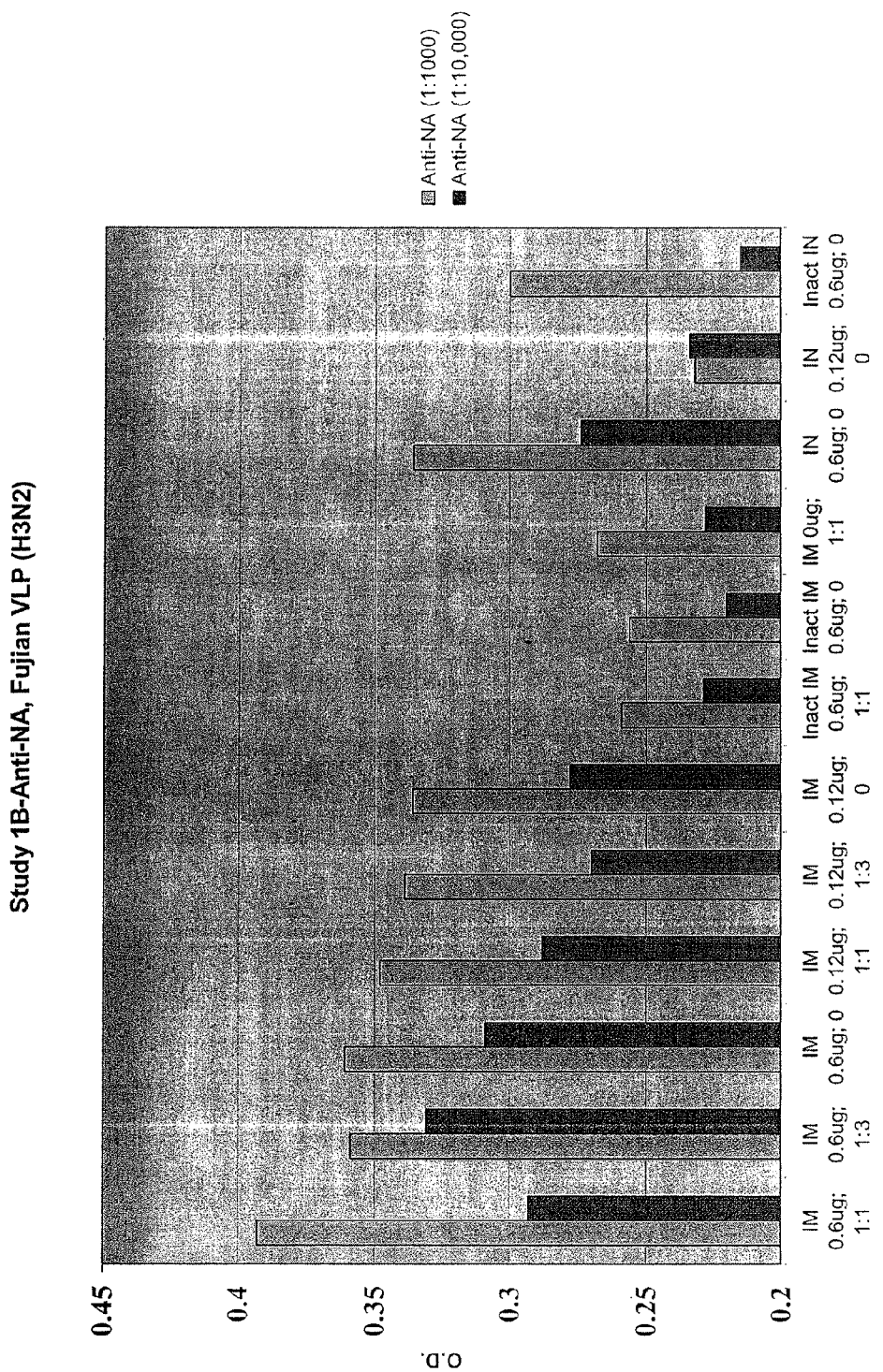

Mice were bled on days 0 and 35. The serum was then assayed for anti-HA antibodies by the hemagglutination inhibition assay (HI) using turkey RBCs, and for anti-influenza antibodies by ELISA. Results of this study are shown on FIGS. 17A, 17B and 17C. These results indicate that an immune response was mounted both IM and IN against HA and NA.

Example 17

Determination of the IgG Isotypes in Mouse after Inoculation with H3N2 VLPs

Mice were inoculated with VLPs intramuscularly and intranasal. At week 5 sera was collected and assayed to distinguish between IgG isotypes.

Figure 18:
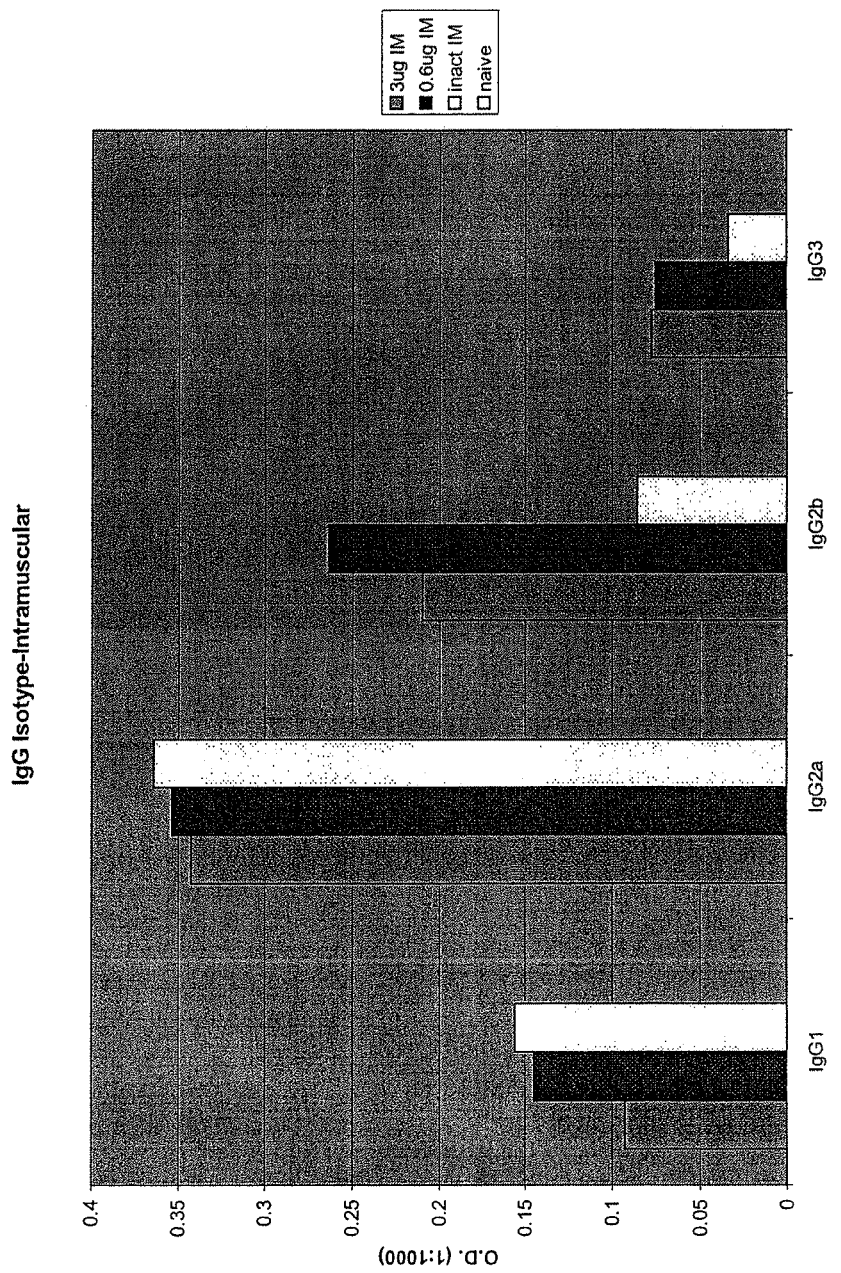
FIGS. 18 A and B depict mice IgG antibody isotypes
Figure 18:
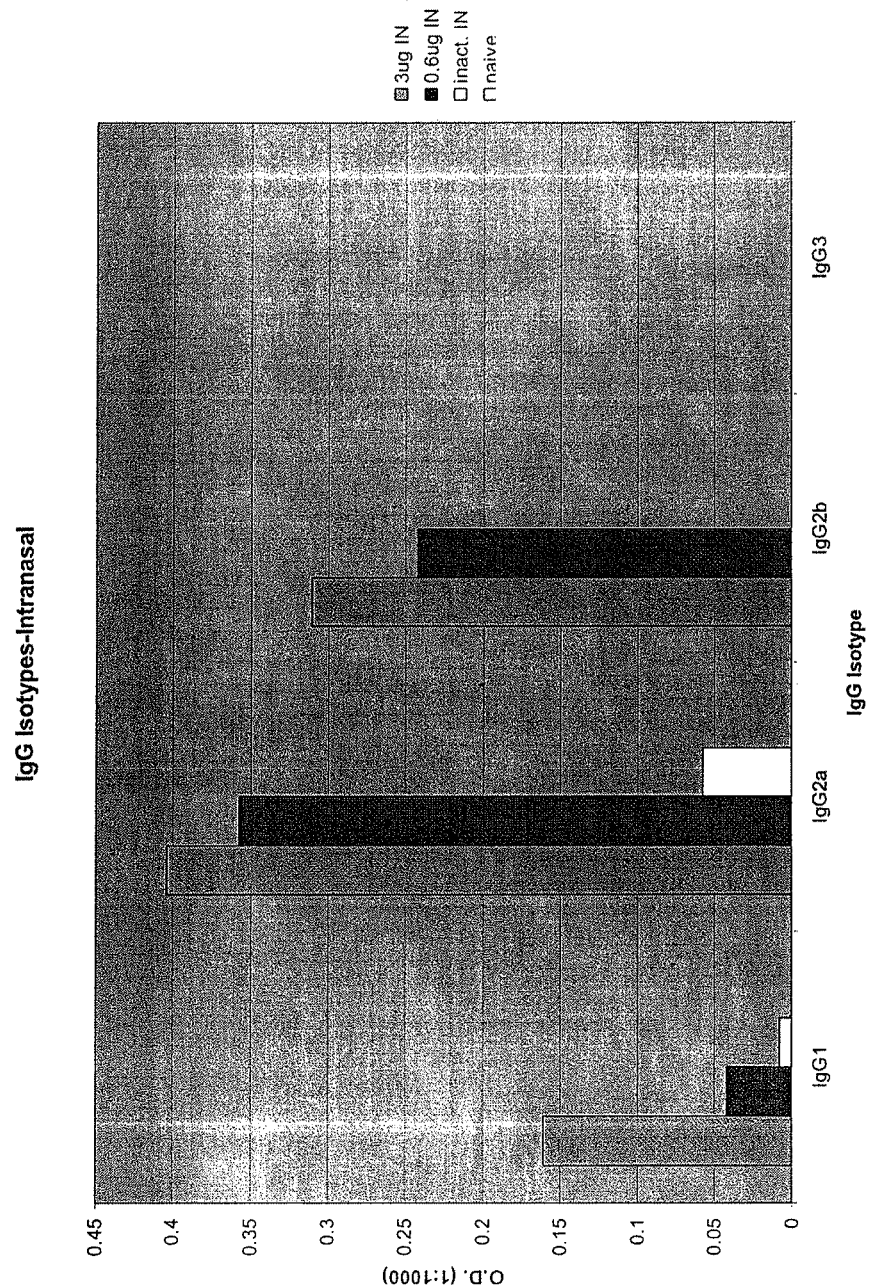

Sera was tested on plates coated with purified HA (Protein Sciences) A/Wyoming/3/2003 using an ELISA assay. Serial five-fold dilutions of sera was added to the wells and the plates were incubated. Next, the biotinylated goat anti-mouse Ig, or anti-mouse IgG1, anti-mouse IgG2a, anti-mouse IgG2b and anti-mouse IgG3. Then, streptavidine-peroxidase was added to the wells. Bound conjugates were detected. Results are illustrated on FIGS. 18A and B. These results illustrate that IgG2a are the most abundant isotype in an immune response against VLPs in mouse.

Example 18

A/Hong Kong/1073/99 (H9N2) VLP Dose-Ranging Study in SD Rats

Figure 19:
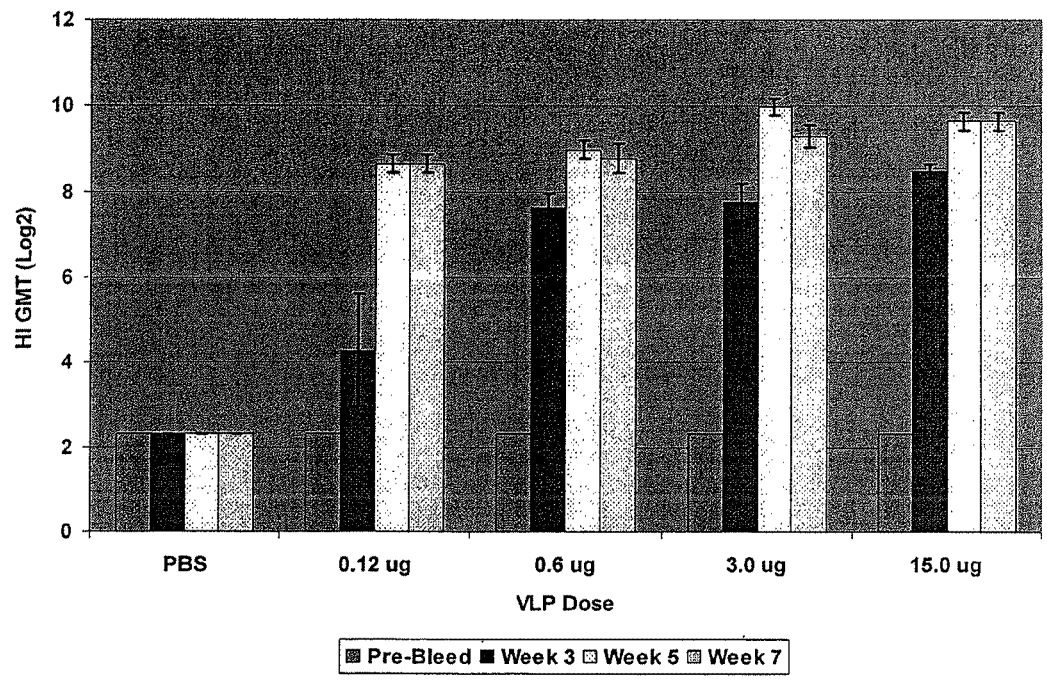
FIG. 19 hemagglutinin inhibition (HI) antibody responses in SD Rats immunized with H9N2 VLP vaccine.

SD rats (n=6 per dose) were immunized on day 0 and day 21 with purified A/Hong Kong/1073/99 (H9N2) VLPs diluted with PBS at neutral pH to 0.12, 0.6, 3.0, and 15.0 μg HA or with PBS alone. Blood samples were taken from the animals on day 0, day 21, day 35 and day 49 and the serum assayed for hemagglutination inhibition assay (HI) to detect functional antibodies able to inhibit the binding function of the HA. The dosage was based on HA content as measured using SDS-PAGE and scanning densitometry of purified H9N2 VLPs. Hemagglutinin inhibition assay titer results are depicted in FIG. 19. A single 0.6 μg HA dose of H9N2 VLPs or two doses of 0.12 μg HA produced protective levels of HI antibodies in rats. These data indicate that a lower amount of HA can induce a protective response when said HA is part of a VLP.

Example 19

Kong/1073/99 (H9N2) VLP Immunogenicity

Figure 20:
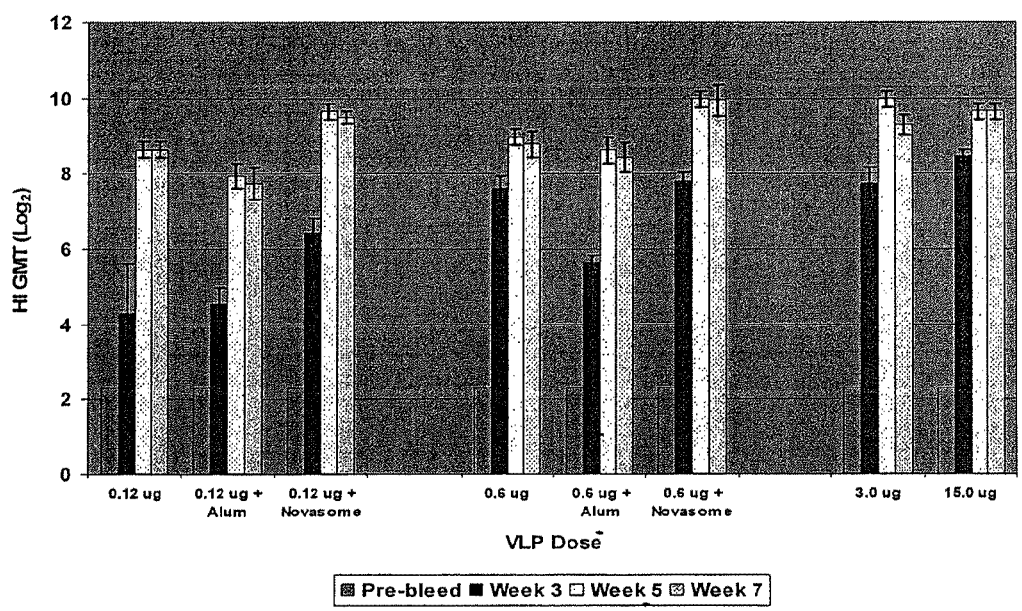
FIGS. 20A and 20B depict hemagglutinin inhibition (HI) antibody responses to different doses of H9N2 VLPs with and without adjuvant in BALB/c mice.
Figure 20:
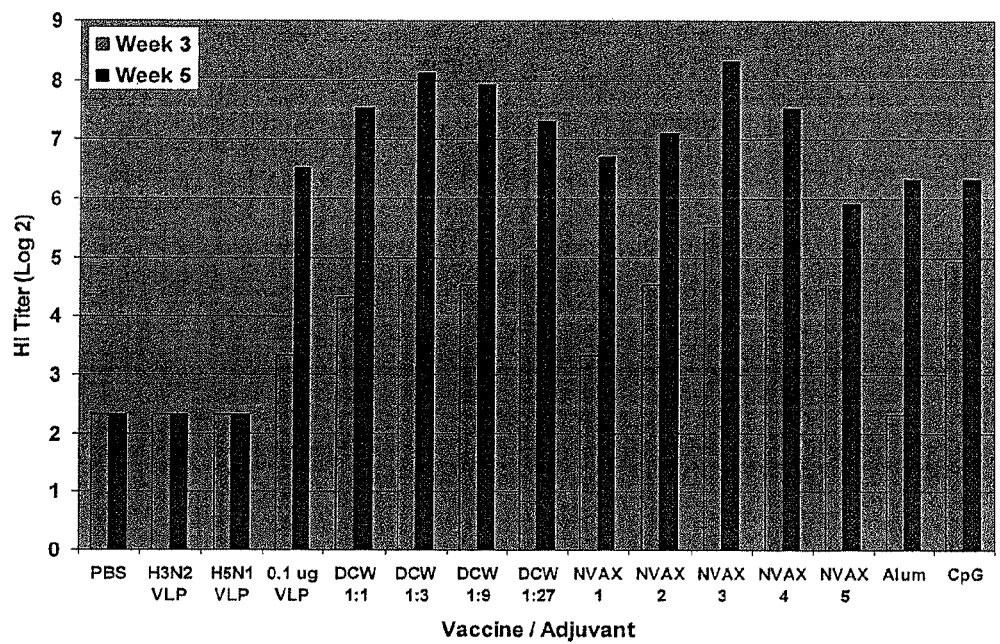

BALB/C mice were immunized with H9N2 VLPs (0.12, 0.6 μg HA/dose), with or without 100 μg Novasome and Alum adjuvant, on day 0 and day 21 and challenged with homologous infectious virus IN on day 57. Mice were also immunized with 3.0 and 15.0 μg HA/dose (no adjuvant). Mice were bled on days 0, 21, 35 and 49 with the serum assayed for anti-HA antibodies by the hemagglutination inhibition assay (HI) using turkey RBCs, and influenza by ELISA. Results of this study are shown in FIGS. 20 A and B.

The results indicate that a more robust overall immune response was observed when the VLPs were administered with an adjuvant. However, a protective response was elicited with 0.12 μg HA/dose at week 3 when compared to the VLPs formulation with Alum and VLPs with no adjuvant. Also in week 7, the VLPs comprising Novasomes had about 2 log increase in HI titer as compared to the VLP with Alum. The robustness of the response was similar to VLPs administered at 3.0 and 15.0 μg HA/dose without an adjuvant. These results indicate that Novasomes elicit a more robust response as compared to Alum. In addition, a protective immune response can be achieved with 25× less VLPs when said VLPs are administered in a formulation comprising Novasomes.

Also, in the 0.6 μg HA/dose data, the Novasome formulation had an about 1.5 log greater response than compared to Alum. The immune responses were similar in magnitude to VLPs administered in 3.0 and 15.0 μg HA/dose without adjuvant. These results indicate that with an adjuvant, approximately 5× less VLPs are needed to be administered to achieve a protective response.

Also, FIG. 20B depicts the HI titer of H9N2 VLPs using different formulations of Novasomes. The following are the formulas used in the experiment:

Group 1: H9N2 VLP (0.1 μg) (n = 5)
Group 2: H9N2 VLP (0.1 μg) w/DCW neat) (n = 5)
Group 3: H9N2 VLP (0.1 μg) w/DCW 1:3) (n = 5)
Group 4: H9N2 VLP (0.1 μg) w/DCW 1:9) (n = 5)
Group 5: H9N2 VLP (0.1 μg) w/DCW 1:27) (n = 5)
Group 6: H9N2 VLP (0.1 μg) w/NVAX 1) (n = 5)
Group 7: H9N2 VLP (0.1 μg) w/NVAX 2) (n = 5)
Group 8: H9N2 VLP (0.1 μg) w/NVAX 3) (n = 5)
Group 9: H9N2 VLP (0.1 μg) w/NVAX 4) (n = 5)
Group 10: H9N2 VLP (0.1 μg) w/NVAX 5) (n = 5)
Group 11: H9N2 VLP (0.1 μg) w/Alum-OH) (n = 5)
Group 12: H9N2 VLP (0.1 μg) w/CpG) (n = 5)
Group 13: PBS (0.6 μg) (n = 5)
Group 14: H3 VLPs (0.6 μg) (n = 5)
Group 15: H5 VLPs (0.6 μg) (n = 8)

H9: (Lot# 11005)
DCW: Novasomes (Lot# 121505-2, Polyoxyethylene-2-cetyl ether, Cholesterol, Superfined soybean oil, and Cetylpridinium chloride)
NVAX 1: B35P83, MF-59 replica (Squalene, Polysorbate, and Span)
NVAX 2: B35P87 (Soybean Oil, Brij, Cholesterol, Pluronic F-68)
NVAX 3: B35P88 (Soybean Oil, Brij, Cholesterol, Pluronic F-68, and Polyethyleneimine)
NVAX 4: B31P60 (Squalene, Brij, Cholesterol, Oleic acid)
NVAX 5: B31P63 (Soybean oil, Glyceryl monostearate, Cholesterol, Polysorbate)
CpG: (Lot# 1026004)
H5: (Lot# 22406)

Figure 21:
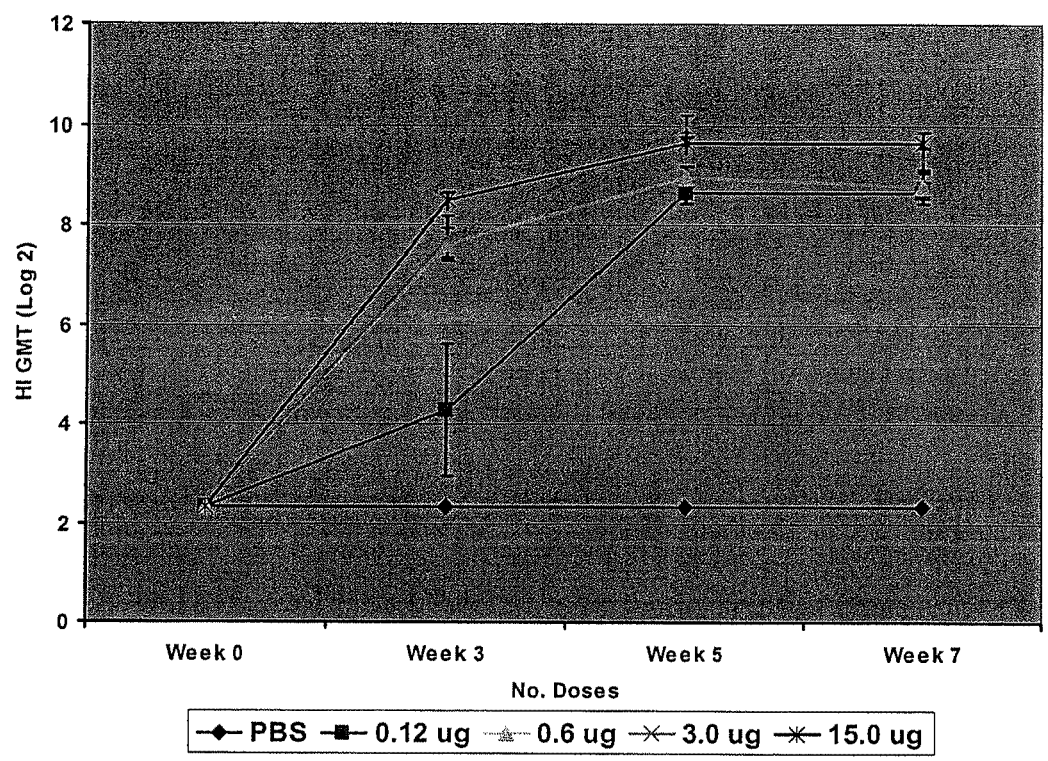
FIG. 21 depicts serum hemagglutinin inhibition (HI) responses in BALB/c mice between different doses of VLPs.

FIG. 21 depicts and H9N2 VLP dose response curve. This data indicates that a dose of VLPs at 0.6 μg HA/dose is the minimum to elicit a protective immune response in mice after 3 weeks.

Example 20

Materials and Methods for Ferret Studies

Ferrets were purchased from Triple F Farms (FFF, Sayre, Pa.). All ferrets purchased has an HAI titer of less that 10 hemagglutination units. Approximately two days prior to vaccination, animals were implanted with a temperature transponder (BioMedic Data Systems, Inc.). Animal (6 animals/group) were vaccinated on day 0 either with (1) PBS (negative control, group one), (2) H3N2 influenza VLPs @ 15 μg of H3 (group 2), (3) H3N2 influenza VLPs @ 3 μg of H3 (group 2), (4) H3N2 influenza VLPs @ 0.6 μg of H3 (group 3), (5) H3N2 influenza VLPs @ 0.12 μg of H3 (group 5), or (6) rH3HA @ 15 μg (group 6). On day 21 animals were boosted with vaccine. Animals were bled on days 0 (prior to vaccination), day 21 (prior to vaccine boost), and day 42. Animals were assessed for clinical signs of adverse vaccine effects once weekly throughout the study period. Similar studies were performed with other influenza VLPs.

HAI Levels in Ferret Sera

Ferret sera were obtained from FFF, treated with Receptor Destroying Enzyme (RDE) and tested in a hemagglutination inhibition (HAI) assay by standard procedures (Kendal et al. (1982)). All ferrets that were chosen for the study tested negative (HAI=10) for pre-existing antibodies to currently circulating human influenza virus (A/New Caledonia/20/99 (H1N1), A panama/2007/99 (H3N2), A/Wellington/01/04 (H2N3) and B/Sichuan/379/99 and H5N1).

Ferrets

Approximately 8 month-old, influenza naïve, castrated and descented, male Fitch ferrets (*Mustela putorius furo*) were purchased form FFF. Animals were housed in stainless steel rabbit cages (Shor-line, KS) containing Sani-chips Laboratory Animal Bedding (P.J. Murphy Forest Products, NJ). Ferrets were provided with Teklad Global Ferret Diet (Harlan Teklad, Wis.) and fresh water ad libitum. Pans were changed three times each week, and cages were cleaned biweekly.

Vaccinations and Blood Collection of Ferrets

The vaccine, H3N2 influenza VLPs or H9N2 influenza VLPs and controls, for example, rH3NA (A/Wyoming/3/2003) and PBS (negative control) were stored at 4° C. prior to use. For most studies, six groups of ferrets (N-6/group) were vaccinated intramuscularly with either concentration of vaccine or control in a volume of 0.5 ml.

Prior to blood collection and vaccination, animals were anesthetized by intramuscular injection into the inner thigh with a solution of Katamine (25 mg/kg, Atropine (0.05 mg/kg) and Xylazine (2.0 mg/kg) "KAX." Once under anesthesia, ferrets were positioned in dorsal recumbency and blood was collected (volume between 0.5 and 1.0 ml) from the anterior vena cava using a 23 gauge 1" needle connected to a 1 cc tuberculin syringe. Blood was transferred to a tube containing a serum separator and clot activator and allowed to clot at room temperature. Tubes were centrifuged and sera was removed and frozen at –80° C. Blood was collected prior to vaccination (day 0), prior to boost (day 21) and day 42 and tested by HAI assay.

Monitoring of Ferrets

Temperatures were measured weekly at approximately the same time throughout the study period. Pre-vaccination values were averaged to obtain a baseline temperature for each ferret. The change in temperature (in degrees Fahrenheit) was calculated at each time point for each animal. Ferrets were examined weekly for clinical signs of adverse vaccine effects, including temperature, weight loss, loss of activity, nasal discharge, sneezing and diarrhea. A scoring system bases on that described by Reuman et al. (1989) was used to assess activity level where 0=alert and playful; 1=alert but playful only when stimulated; 2=alert by not playful when stimulated; 3=neither alert not playful when stimulated. Based on the scores for each animal in a group, a relative inactivity index was calculated as $\Sigma(day0-Day 42)[activity score+1]/\Sigma$ (day0–Day 42), where n equals the total number of observations. A value of 1 was added to each base score so that a score of "0" could be divided by a denominator, resulting in an index value of 1.0.

Serum Preparations

Sera generally have low levels of non-specific inhibitors on hemagglutination. To inactivate these non-specific inhibitors, sera were treated with (RDE) prior to being tested. Briefly, three part RDE was added to one part sera and incubated overnight at 37° C. RDE was inactivated by incubation at 56° C. for approximately 30 minutes. Following inactivation of RDE, PBS was added to the sample for a final serum dilution of 1:10 (RDE-Tx). The diluted RDE-Tx sera was stored at 4° C. prior to testing (for 7 days) or stored at –20° C.

Preparation Turkey Erythrocytes:

Human influenza viruses bind to sialic acid receptors containing N-acetylneuraminic acid α 2,6-galactose linkages. Avian influenza viruses bind to sialic acid receptors containing N-acetylneuraminic acid α 2,3 galactose (α 2,3 linkages) and express both α 2,3 and α 2,6 linkages. Turkey erythocytes (TRBC) are used for the HAI assay since A/Fujian is a human influenza virus. The TRBCs adjusted with PBS to achieve a 0.5% vol/vol suspension. The cells are kept at 4° C. and used within 72 hours of preparation.

HAI Assay

The HAI assay was adapted from the CDC laboratory-based influenza surveillance manual (Kendal et al. (1982) Concepts and procedures for laboratory based influenza surveillance, U.S. Department of Health and Human Services, Public Health Service, Centers for Disease Control, Atlanta, Ga., herein incorporated by reference in its entirety for all purposes). RDE-Tx sera was serially two-fold diluted in v-bottom microtiter plates. An equal volume of virus adjusted, adjusted to approximately 8 HAU/50 ul was added to each well. The plates were covered and incubated at room temperature for 15 minutes followed by the addition of 0.5% TRBC. The plates were mixed by agitation, covered, and the TRBC were allowed to settle for 30 minutes at room temperature. The HAI titer was determined by the reciprocal dilution of the last row which contained non-agglutinated TRBC. Positive and negative serum controls were included for each plate.

Example 21

A/Hong Kong/1073/99 (H9N2) VLP Dose-Ranging Study in Ferrets

Figure 22:
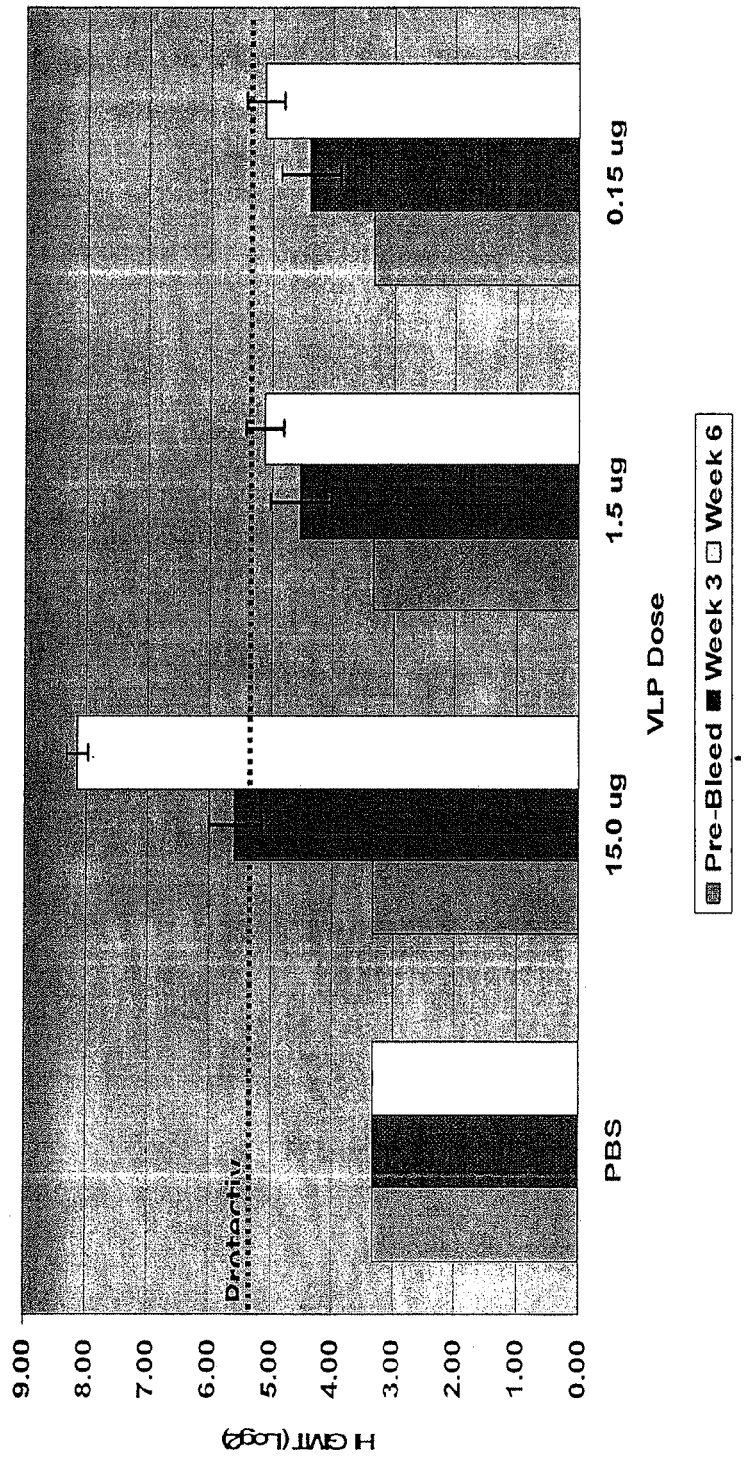
FIG. 22 depicts serum hemagglutinin inhibition (HI) responses in ferrets.

Ferrets, serologically negative by hemagglutination inhibition for influenza viruses, were used to assess the antibody and HI titer after an inoculation with 1-19N2 VLPs. Ferrets were bled on days 0, and 21 days with the serum assayed for anti-HA antibodies by the hemagglutination inhibition assay (HI) using turkey RBCs, and for anti-influenza antibodies by ELISA. Results are illustrated in FIG. 22. These results show HI titers corresponding to protective antibody levels at VLP doses of 1.5 and 15 μg.

Example 21

Vaccination of H3N2 VLPs in Ferrets

Ferrets were vaccinated at day 0, and given a boost on day 21 with different strains of H3N2 VLPs at different dosages (HA dosages of 0.12, 0.6, 3.0, 15.0 μg). The positive control was rH3HA at 15 μg and PBS alone is the negative control. Sera, as described above, were taken from the ferrets on day 0 prior to vaccination, day 21 (prior to boost) and day 42. An HI assay was conducted on the serum samples to determine if there was an immune response against the VLPs. These data are illustration on FIG. 23. These data indicate that H3N2 VLPs, when introduced into ferrets, do induce an immune response. Thus, the H3N2 VLPs are immunogenic in ferrets.

Example 22

RT-PCR and Cloning of HA, NA, and M1 Genes of Influenza A/Indonesia/5/05 (H5N1) Virus Clade 2 influenza virus, strain A/Indonesia/5/05 (H5N1) viral RNA was extracted using Trizol LS (Invitrogen, Carlsbad, Calif.) under BSL-3 containment conditions. Reverse transcription (RT) and PCR were performed on extracted viral RNA using the One-Step RT-PCR system (Invitrogen)

with gene-specific oligonucleotide primers. The following primer pairs were used for the synthesis of the H5N1 hemagglutinin (HA), neuraminidase (NA), and matrix (M1) genes, respectively:

```
                                                     (SEQ ID. 4)
5'-AACGGTCCGATGGAGAAAATAGTGCTTCTTC-3'
and (SEQ ID. 5)
5'-AAAGCTTTTAAATGCAAATTCTGCATTGTAACG-3'
(HA);

(SEQ ID. 6)
5'-AACGGTCCGATGAATCCAAATCAGAAGATAAT-3'
and (SEQ ID. 7)
5'-AAAGCTTCTACTTGTCAATGGTGAATGGCAAC-3'
(NA);
and (SEQ ID. 8)
5'-AACGGTCCGATGAGTCTTCTAACCGAGGTC-3'
and (SEQ ID. 9)
5'-AAAGCTTTCACTTGAATCGCTGCATCTGCAC-3'
(M1) (ATG codons are underlined).
```

Following RT-PCR, cDNA fragments containing influenza HA, NA, and M1 genes with molecular weights of 1.7, 1.4, and 0.7 kB, respectively, were cloned into the pCR2.1-TOPO vector (Invitrogen). The nucleotide sequences of the HA, NA, and M1 genes were determined by DNA sequencing. A similar strategy was followed for cloning a Glade I H5N1 influenza virus from Vietnam/1203/2003.

Example 23

Generation of Recombinant Baculoviruses Comprising H5N1

The HA gene was cloned as a RsrII-HindIII DNA fragment (1.7 kb) downstream of the AcMNPV polyhedrin promoter within pFastBac1 bacmid transfer vector (Invitrogen) digested with RsrII and HindIII. Similarly, the NA and M1 genes were cloned as EcoRI-HindIII DNA fragments (1.4 and 0.8 kb, respectively) into EcoRI-HindIII-digested pFastBac1 plasmid DNA. The three resulting baculovirus transfer plasmids pHA, pNA, and pM1 containing influenza A/Indonesia/5/05 (H5N1) virus HA, NA, and M1 genes, respectively, were used to generate recombinant bacmids.

Bacmids were produced by site-specific homologous recombination following transformation of bacmid transfer plasmids containing influenza genes into *E. coli* DH10Bac competent cells, which contained the AcMNPV baculovirus genome (Invitrogen). The recombinant bacmid DNA was transfected into the Sf9 insect cells.

Nucleotide sequences of the Indonesia/5/05 HA, NA, and M1 genes.

```
HA
                                                    (SEQ ID. 10)
ATGGAGAAAATAGTGCTTCTTCTTGCAATAGTCAGTCTTGTTAAAAGTGATCAGATTTGC

ATTGGTTACCATGCAAACAATTCAACAGAGCAGGTTGACACAATCATGGAAAAGAACGTT

ACTGTTACACATGCCCAAGACATACTGGAAAAGACACACAACGGGAAGCTCTGCGATCTA

GATGGAGTGAAGCCTCTAATTTTAAGAGATTGTAGTGTAGCTGGATGGCTCCTCGGGAAC

CCAATGTGTGACGAATTCATCAATGTACCGGAATGGTCTTACATAGTGGAGAAGGCCAAT

CCAACCAATGACCTCTGTTACCCAGGGAGTTTCAACGACTATGAAGAACTGAAACACCTA

TTGAGCAGAATAAACCATTTTGAGAAAATTCAAATCATCCCCAAAAGTTCTTGGTCCGAT

CATGAAGCCTCATCAGGAGTGAGCTCAGCATGTCCATACCTGGGAAGTCCCTCCTTTTTT

AGAAATGTGGTATGGCTTATCAAAAGAACAGTACATACCCAACAATAAAGAAAAGCTAC

AATAATACCAACCAAGAAGATCTTTTGGTACTGTGGGGAATTCACCATCCTAATGATGCG

GCAGAGCAGACAAGGCTATATCAAAACCCAACCACCTATATTTCCATTGGGACATCAACA

CTAAACCAGAGATTGGTACCAAAAATAGCTACTAGATCCAAAGTAAACGGGCAAAGTGGA

AGGATGGAGTTCTTCTGGACAATTTTAAAACCTAATGATGCAATCAACTTCGAGAGTAAT

GGAAATTTCATTGCTCCAGAATATGCATACAAAATTGTCAAGAAGGGGACTCAGCAATT

ATGAAAAGTGAATTGGAATATGGTAACTGCAACACCAAGTGTCAAACTCCAATGGGGGCG

ATAAACTCTAGTATGCCATTCCACAACATACACCCTCTCACCATCGGGGAATGCCCCAAA

TATGTGAAATCAAACAGATTAGTCCTTGCAACAGGGCTCAGAAATAGCCCTCAAAGAGAG

AGCAGAAGAAAAAGAGAGGACTATTTGGAGCTATAGCAGGTTTTATAGAGGGAGGATGG

CAGGGAATGGTAGATGGTTGGTATGGGTACCACCATAGCAATGAGCAGGGGAGTGGGTAC

GCTGCAGACAAAGAATCCACTCAAAAGGCAATAGATGGAGTCACCAATAAGGTCAACTCA

ATCATTGACAAAATGAACACTCAGTTTGAGGCCGTTGGAAGGGAATTTAATAACTTAGAA
```

-continued

AGGAGAATAGAGAATTTAAACAAGAAGATGGAAGACGGGTTTCTAGATGTCTGGACTTAT

AATGCCGAACTTCTGGTTCTCATGGAAAATGAGAGAACTCTAGACTTTCATGACTCAAAT

GTTAAGAACCTCTACGACAAGGTCCGACTACAGCTTAGGGATAATGCAAAGGAGCTGGGT

AACGGTTGTTTCGAGTTCTATCACAAATGTGATAATGAATGTATGGAAAGTATAAGAAAC

GGAACGTACAACTATCCGCAGTATTCAGAAGAAGCAAGATTAAAAAGAGAGGAAATAAGT

GGGGTAAAATTGGAATCAATAGGAACTTACCAAATACTGTCAATTTATTCAACAGTGGCG

AGTTCCCTAGCACTGGCAATCATGATGGCTGGTCTATCTTTATGGATGTGCTCCAATGGA

TCGTTACAATGCAGAATTTGCATTTAA

NA
(SEQ ID. 11)
ATGAATCCAAATCAGAAGATAATAACCATTGGATCAATCTGTATGGTAATTGGAATAGTT

AGCTTAATGTTACAAATTGGGAACATGATCTCAATATGGGTCAGTCATTCAATTCAGACA

GGGAATCAACACCAAGCTGAATCAATCAGCAATACTAACCCTCTTACTGAGAAAGCTGTG

GCTTCAGTAACATTAGCGGGCAATTCATCTCTTTGCCCCATTAGAGGATGGGCTGTACAC

AGTAAGGACAACAATATAAGGATCGGTTCCAAGGGGGATGTGTTTGTTATTAGAGAGCCG

TTCATCTCATGCTCCCACCTGGAATGCAGAACTTTCTTCTTGACTCAGGGAGCCTTGCTG

AATGACAAGCACTCCAACGGGACTGTCAAAGACAGAAGCCCTCACAGAACATTAATGAGT

TGTCCTGTGGGTGAGGCTCCCTCTCCATATAACTCAAGGTTTGAGTCTGTTGCTTGGTCA

GCAAGTGCTTGCCATGATGGCACCAGTTGGTTGACAATTGGAATTTCTGGCCCAGACAAT

GAGGCTGTGGCTGTATTGAAATACAATGGCATAATAACAGACACTATCAAGAGTTGGAGG

AACAACATACTGAGAACTCAAGAGTCTGAATGTGCATGTGTAAATGGCTCTTGCTTTACT

GTAATGACTGATGGACCAAGTGATGGGCAGGCATCATATAAGATCTTCAAAATGGAAAAA

GGAAAAGTGGTCAAATCAGTCGAATTGGATGCTCCTAATTATCACTATGAGGAATGCTCC

TGTTATCCTGATGCCGGCGAAATCACATGTGTTTGCAGGGATAATTGGCATGGCTCAAAT

AGGCCATGGGTATCTTTCAATCAAAATTTGGAGTATCAAATAGGATATATATGCAGTGGA

GTTTTCGGAGACAATCCACGCCCCAATGATGGAACAGGTAGTTGTGGCCCGATGTCCCCT

AACGGGGCATATGGGGTAAAAGGGTTTTCATTTAAATACGGCAATGGTGTTTGGATCGGG

AGAACCAAAAGCACTAATTCCAGGAGCGGCTTTGAAATGATTTGGGATCCAAATGGGTGG

ACTGGAACGGACAGTAGCTTTTCAGTGAAACAAGATATAGTAGCAATAACTGATTGGTCA

GGATATAGCGGGAGTTTTGTCCAGCATCCAGAACTGACAGGATTAGATTGCATAAGACCT

TGTTTCTGGGTTGAGTTAATCAGAGGGCGGCCCAAAGAGAGCACAATTTGGACTAGTGGG

AGCAGCATATCTTTTTGTGGTGTAAATAGTGACACTGTGAGTTGGTCTTGGCCAGACGGT

GCTGAGTTGCCATTCACCATTGACAAGTAG

M1
(SEQ ID. 12)
ATGAGTCTTCTAACCGAGGTCGAAACGTACGTTCTCTCTATCATCCCGTCAGGCCCCCTC

AAAGCCGAGATCGCGCAGAAACTTGAAGATGTCTTTGCAGGAAAGAACACCGATCTCGAG

GCTCTCATGGAGTGGCTAAAGACAAGACCAATCCTGTCACCTCTGACTAAAGGGATTTTG

GGATTTGTATTCACGCTCACCGTGCCCAGTGAGCGAGGACTGCAGCGTAGACGCTTTGTC

CAGAATGCCCTAAATGGAAATGGAGATCCAAATAATATGGATAGGGCAGTTAAGCTATAT

AAGAAGCTGAAAAGAGAAATAACATTCCATGGGGCTAAAGAGGTTTCACTCAGCTACTCA

ACCGGTGCACTTGCCAGTTGCATGGGTCTCATATACAACAGGATGGGAACGGTGACTACG

GAAGTGGCTTTTGGCCTAGTGTGTGCCACTTGTGAGCAGATTGCAGATTCACAGCATCGG

-continued

TCTCACAGGCAGATGGCAACTATCACCAACCCACTAATCAGGCATGAAAACAGAATGGTG

CTGGCCAGCACTACAGCTAAGGCTATGGAGCAGATGGCGGGATCAAGTGAGCAGGCAGCG

GAAGCCATGGAGGTCGCTAATCAGGCTAGGCAGATGGTGCAGGCAATGAGGACAATTGGA

ACTCATCCTAACTCTAGTGCTGGTCTGAGAGATAATCTTCTTGAAAATTTGCAGGCCTAC

CAGAAACGAATGGGAGTGCAGATGCAGCGATTCAAGTGA

One cloned HA gene, pHA5, contained two nucleotide changes, nt #1172 and nt #1508 (in the wt), as compared to the wild-type HA gene sequence. A similar strategy was followed for constructing and creating Glade 1 H5N1 influenza virus from Vietnam/1203/2003 VLPs (see below). The alignments of pHA5 nucleotide and amino acid sequences follow.

```
wt      1 ................ATGGAGAAAATAGTGCTTCTTCTTGCAATAG  31   seq id 10
                          ||||||||||||||||||||||||||||||
pHA5   51 ATTCGCCCTTAACGGTCCGATGGAGAAAATAGTGCTTCTTCTTGCAATAG 100   seq id 56

32 TCAGTCTTGTTAAAAGTGATCAGATTTGCATTGGTTACCATGCAAACAAT  81
          ||||||||||||||||||||||||||||||||||||||||||||||||||
      101 TCAGTCTTGTTAAAAGTGATCAGATTTGCATTGGTTACCATGCAAACAAT 150

82 TCAACAGAGCAGGTTGACACAATCATGGAAAAGAACGTTACTGTTACACA 131
          ||||||||||||||||||||||||||||||||||||||||||||||||||
      151 TCAACAGAGCAGGTTGACACAATCATGGAAAAGAACGTTACTGTTACACA 200

132 TGCCCAAGACATACTGGAAAAGACACACAACGGGAAGCTCTGCGATCTAG 181
          ||||||||||||||||||||||||||||||||||||||||||||||||||
      201 TGCCCAAGACATACTGGAAAAGACACACAACGGGAAGCTCTGCGATCTAG 250

182 ATGGAGTGAAGCCTCTAATTTTAAGAGATTGTAGTGTAGCTGGATGGCTC 231
          ||||||||||||||||||||||||||||||||||||||||||||||||||
      251 ATGGAGTGAAGCCTCTAATTTTAAGAGATTGTAGTGTAGCTGGATGGCTC 300

232 CTCGGGAACCCAATGTGTGACGAATTCATCAATGTACCGGAATGGTCTTA 281
          ||||||||||||||||||||||||||||||||||||||||||||||||||
      301 CTCGGGAACCCAATGTGTGACGAATTCATCAATGTACCGGAATGGTCTTA 350

282 CATAGTGGAGAAGGCCAATCCAACCAATGACCTCTGTTACCCAGGGAGTT 331
          ||||||||||||||||||||||||||||||||||||||||||||||||||
      351 CATAGTGGAGAAGGCCAATCCAACCAATGACCTCTGTTACCCAGGGAGTT 400

332 TCAACGACTATGAAGAACTGAAACACCTATTGAGCAGAATAAACCATTTT 381
          ||||||||||||||||||||||||||||||||||||||||||||||||||
      401 TCAACGACTATGAAGAACTGAAACACCTATTGAGCAGAATAAACCATTTT 450

382 GAGAAAATTCAAATCATCCCCAAAAGTTCTTGGTCCGATCATGAAGCCTC 431
          ||||||||||||||||||||||||||||||||||||||||||||||||||
      451 GAGAAAATTCAAATCATCCCCAAAAGTTCTTGGTCCGATCATGAAGCCTC 500

432 ATCAGGAGTGAGCTCAGCATGTCCATACCTGGGAAGTCCCTCCTTTTTTA 481
          ||||||||||||||||||||||||||||||||||||||||||||||||||
      501 ATCAGGAGTGAGCTCAGCATGTCCATACCTGGGAAGTCCCTCCTTTTTTA 550

482 GAAATGTGGTATGGCTTATCAAAAAGAACAGTACATACCCAACAATAAAG 531
          ||||||||||||||||||||||||||||||||||||||||||||||||||
      551 GAAATGTGGTATGGCTTATCAAAAAGAACAGTACATACCCAACAATAAAG 600

532 AAAAGCTACAATAATACCAACCAAGAAGATCTTTTGGTACTGTGGGAAT  581
          ||||||||||||||||||||||||||||||||||||||||||||||||||
      601 AAAAGCTACAATAATACCAACCAAGAAGATCTTTTGGTACTGTGGGAAT  650

632 CCACCTATATTTCCATTGGGACATCAACACTAAACCAGAGATTGGTACCA 681
          ||||||||||||||||||||||||||||||||||||||||||||||||||
      701 CCACCTATATTTCCATTGGGACATCAACACTAAACCAGAGATTGGTACCA 750

682 AAAATAGCTACTAGATCCAAAGTAAACGGGCAAAGTGGAAGGATGGAGTT 731
          ||||||||||||||||||||||||||||||||||||||||||||||||||
      751 AAAATAGCTACTAGATCCAAAGTAAACGGGCAAAGTGGAAGGATGGAGTT 800

732 CTTCTGGACAATTTTAAAACCTAATGATGCAATCAACTTCGAGAGTAATG 781
          ||||||||||||||||||||||||||||||||||||||||||||||||||
      801 CTTCTGGACAATTTTAAAACCTAATGATGCAATCAACTTCGAGAGTAATG 850
```

```
 782 GAAATTTCATTGCTCCAGAATATGCATACAAAATTGTCAAGAAAGGGGAC  831
     ||||||||||||||||||||||||||||||||||||||||||||||||||
 851 GAAATTTCATTGCTCCAGAATATGCATACAAAATTGTCAAGAAAGGGGAC  900

832 TCAGCAATTATGAAAAGTGAATTGGAATATGGTAACTGCAACACCAAGTG  881
     ||||||||||||||||||||||||||||||||||||||||||||||||||
 901 TCAGCAATTATGAAAAGTGAATTGGAATATGGTAACTGCAACACCAAGTG  950

882 TCAAACTCCAATGGGGGCGATAAACTCTAGTATGCCATTCCACAACATAC  931
     ||||||||||||||||||||||||||||||||||||||||||||||||||
 951 TCAAACTCCAATGGGGGCGATAAACTCTAGTATGCCATTCCACAACATAC 1000

932 ACCCTCTCACCATCGGGGAATGCCCCAAATATGTGAAATCAAACAGATTA  981
     ||||||||||||||||||||||||||||||||||||||||||||||||||
1001 ACCCTCTCACCATCGGGGAATGCCCCAAATATGTGAAATCAAACAGATTA 1050

982 GTCCTTGCAACAGGGCTCAGAAATAGCCCTCAAAGAGAGAGCAGAAGAAA 1031
     ||||||||||||||||||||||||||||||||||||||||||||||||||
1051 GTCCTTGCAACAGGGCTCAGAAATAGCCCTCAAAGAGAGAGCAGAAGAAA 1100

1032 AAAGAGAGGACTATTTGGAGCTATAGCAGGTTTTATAGAGGGAGGATGGC 1081
     ||||||||||||||||||||||||||||||||||||||||||||||||||
1101 AAAGAGAGGACTATTTGGAGCTATAGCAGGTTTTATAGAGGGAGGATGGC 1150

1082 AGGGAATGGTAGATGGTTGGTATGGGTACCACCATAGCAATGAGCAGGGG 1131
     ||||||||||||||||||||||||||||||||||||||||||||||||||
1151 AGGGAATGGTAGATGGTTGGTATGGGTACCACCATAGCAATGAGCAGGGG 1200

1132 AGTGGGTACGCTGCAGACAAAGAATCCACTCAAAAGGCAATAGATGGAGT 1181
     |||||||||||||||||||||||||||||||||||||||| |||||||||
1201 AGTGGGTACGCTGCAGACAAAGAATCCACTCAAAAGGCAATGGATGGAGT 1250

1182 CACCAATAAGGTCAACTCAATCATTGACAAAATGAACACTCAGTTTGAGG 1231
     ||||||||||||||||||||||||||||||||||||||||||||||||||
1251 CACCAATAAGGTCAACTCAATCATTGACAAAATGAACACTCAGTTTGAGG 1300

1232 CCGTTGGAAGGGAATTTAATAACTTAGAAAGGAGAATAGAGAATTTAAAC 1281
     ||||||||||||||||||||||||||||||||||||||||||||||||||
1301 CCGTTGGAAGGGAATTTAATAACTTAGAAAGGAGAATAGAGAATTTAAAC 1350

1282 AAGAAGATGGAAGACGGGTTTCTAGATGTCTGGACTTATAATGCCGAACT 1331
     ||||||||||||||||||||||||||||||||||||||||||||||||||
1351 AAGAAGATGGAAGACGGGTTTCTAGATGTCTGGACTTATAATGCCGAACT 1400

1332 TCTGGTTCTCATGGAAAATGAGAGAACTCTAGACTTTCATGACTCAAATG 1381
     ||||||||||||||||||||||||||||||||||||||||||||||||||
1401 TCTGGTTCTCATGGAAAATGAGAGAACTCTAGACTTTCATGACTCAAATG 1450

1382 TTAAGAACCTCTACGACAAGGTCCGACTACAGCTTAGGGATAATGCAAAG 1431
     ||||||||||||||||||||||||||||||||||||||||||||||||||
1451 TTAAGAACCTCTACGACAAGGTCCGACTACAGCTTAGGGATAATGCAAAG 1500

1432 GAGCTGGGTAACGGTTGTTTCGAGTTCTATCACAAATGTGATAATGAATG 1481
     ||||||||||||||||||||||||||||||||||||||||||||||||||
1501 GAGCTGGGTAACGGTTGTTTCGAGTTCTATCACAAATGTGATAATGAATG 1550

1482 TATGGAAAGTATAAGAAACGGAACGTACAACTATCCGCAGTATTCAGAAG 1531
     ||||||||||||||||||||||||||||||||||| ||||||||||||||
1551 TATGGAAAGTATAAGAAACGGAACGTGCAACTATCCGCAGTATTCAGAAG 1600

1532 AAGCAAGATTAAAAAGAGAGGAAATAAGTGGGGTAAAATTGGAATCAATA 1581
     ||||||||||||||||||||||||||||||||||||||||||||||||||
1601 AAGCAAGATTAAAAAGAGAGGAAATAAGTGGGGTAAAATTGGAATCAATA 1650

1582 GGAACTTACCAAATACTGTCAATTTATTCAACAGTGGCGAGTTCCCTAGC 1631
     ||||||||||||||||||||||||||||||||||||||||||||||||||
1651 GGAACTTACCAAATACTGTCAATTTATTCAACAGTGGCGAGTTCCCTAGC 1700

1632 ACTGGCAATCATGATGGCTGGTCTATCTTTATGGATGTGCTCCAATGGAT 1681
     ||||||||||||||||||||||||||||||||||||||||||||||||||
1701 ACTGGCAATCATGATGGCTGGTCTATCTTTATGGATGTGCTCCAATGGAT 1750

1682 CGTTACAATGCAGAATTTGCATtTAA........................ 1707
     ||||||||||||||||||||||||
1751 CGTTACAATGCAGAATTTGCATTTAAAAGCTTTAAGGGCGAATTCCAGCA 1800
```

Amino Acid Sequence Alignment of Hemagglutinin

```
pHA5    1  MEKIVLLLAIVSLVKSDQICIGYHANNSTEQVDTIMEKNVTVTHAQDILE  50    seq id 57
           ||||||||||||||||||||||||||||||||||||||||||||||||||
wt      1  MEKIVLLLAIVSLVKSDQICIGYHANNSTEQVDTIMEKNVTVTHAQDILE  50    seq id 58

51  KTHNGKLCDLDGVKPLILRDCSVAGWLLGNPMCDEFINVPEWSYIVEKAN  100
           ||||||||||||||||||||||||||||||||||||||||||||||||||
       51  KTHNGKLCDLDGVKPLILRDCSVAGWLLGNPMCDEFINVPEWSYIVEKAN  100

101  PTNDLCYPGSFNDYEELKHLLSRINHFEKIQIIPKSSWSDHEASSGVSSA  150
           ||||||||||||||||||||||||||||||||||||||||||||||||||
      101  PTNDLCYPGSFNDYEELKHLLSRINHFEKIQIIPKSSWSDHEASSGVSSA  150

151  CPYLGSPSFFRNVVWLIKKNSTYPTIKKSYNNTNQEDLLVLWGIHHPNDA  200
           ||||||||||||||||||||||||||||||||||||||||||||||||||
      151  CPYLGSPSFFRNVVWLIKKNSTYPTIKKSYNNTNQEDLLVLWGIHHPNDA  200

201  AEQTRLYQNPTTYISIGTSTLNQRLVPKIATRSKVNGQSGRMEFFWTILK  250
           ||||||||||||||||||||||||||||||||||||||||||||||||||
      201  AEQTRLYQNPTTYISIGTSTLNQRLVPKIATRSKVNGQSGRMEFFWTILK  250

251  PNDAINFESNGNFIAPEYAYKIVKKGDSAIMKSELEYGNCNTKCQTPMGA  300
           ||||||||||||||||||||||||||||||||||||||||||||||||||
      251  PNDAINFESNGNFIAPEYAYKIVKKGDSAIMKSELEYGNCNTKCQTPMGA  300

301  INSSMPFHNIHPLTIGECPKYVKSNRLVLATGLRNSPQRESRRKKRGLFG  350
           ||||||||||||||||||||||||||||||||||||||||||||||||||
      301  INSSMPFHNIHPLTIGECPKYVKSNRLVLATGLRNSPQRESRRKKRGLFG  350

351  AIAGFIEGGWQGMVDGWYGYHHSNEQGSGYAADKESTQKAMDGVTNKVNS  400
           |||||||||||||||||||||||||||||||||||||||||| |||||||
      351  AIAGFIEGGWQGMVDGWYGYHHSNEQGSGYAADKESTQKAIDGVTNKVNS  400

401  IIDKMNTQFEAVGREFNNLERRIENLNKKMEDGFLDVWTYNAELLVLMEN  450
           ||||||||||||||||||||||||||||||||||||||||||||||||||
      401  IIDKMNTQFEAVGREFNNLERRIENLNKKMEDGFLDVWTYNAELLVLMEN  450

451  ERTLDFHDSNVKNLYDKVRLQLRDNAKELGNGCFEFYHKCDNECMESIRN  500
           ||||||||||||||||||||||||||||||||||||||||||||||||||
      451  ERTLDFHDSNVKNLYDKVRLQLRDNAKELGNGCFEFYHKCDNECMESIRN  500

501  GTCNYPQYSEEARLKREEISGVKLESIGTYQILSIYSTVASSLALAIMMA  550
           || |||||||||||||||||||||||||||||||||||||||||||||||
      501  GTYNYPQYSEEARLKREEISGVKLESIGTYQILSIYSTVASSLALAIMMA  550

551  GLSLWMCSNGSLQCRICI.                                568
           |||||||||||||||||||
      551  GLSLWMCSNGSLQCRICI*                                569
```

Example 26

Generation of Influenza A/Indonesia/5/05 HA, NA, and M1 Genes Optimized for Efficient Expression in Sf9 Cells The following polypeptides were derived from codon-optimized nucleotides corresponding to the Indonesia/5/05 HA gene (see example 31). The codon-optimized nucleotides were designed and produced (Geneart GMBH, Regensburg, FRG) according to the methods disclosed in US patent publication 2005/0118191, herein incorporated by reference in its entirety for all proposes. See Example 31 for nucleic acid sequences

```
Vac2-hac-opt (unmodified aa sequence)
                                                              (SEQ ID 27)
MEKIVLLLAI VSLVKSDQIC IGYHANNSTE QVDTIMEKNV TVTHAQDILE

KTHNGKLCDL DGVKPLILRD CSVAGWLLGN PMCEEFINVP EWSYIVEKAN

PTNDLCYPGS FNDYEELKHL LSRINHFEKI QIIPKSSWSD HEASSGVSSA

CPYLGSPSFF RNVVWLIKKN STYPTIKKSY NNTNQEDLLV LWGIHHPNDA

AEQTRLYQNP TTYISIGTST LNQRLVPKIA TRSKVNGQSG RMEFFWTILK

PNDAINFESN GNFIAPEYAY KIVKKGDSAI MKSELEYGNC NTKCQTPMGA

INSSMPFHNI HPLTIGECPK YVKSNRLVLA TGLRNSPQRE SRRKKRGLFG

AIAGFIEGGW QGMVDGWYGY HHSNEQGSGY AADKESTQKA IDGVTNKVNS

IIDKMNTQFE AVGREFNNLE RRIENLNKKM EDGFLDVWTY NAELLVLMEN
```

```
ERTLDFHDSN VKNLYDKVRL QLRDNAKELG NGCFEFYHKC DNECMESIRN

GTYNYPQYSE EARLKREEIS GVKLESIGTY QILSIYSTVA SSLALAIMMA

GLSLWMCSNG SLQCRICI*

Vac2-hac-spc-opt
(modified, signal peptide from Chitinase, underlined)
                                                    (SEQ ID 28)
Mplykllnvlwlvavsnaip DQICIGYHANNSTE QVDTIMEKNV TVTHAQDILE

KTHNGKLCDL DGVKPLILRD CSVAGWLLGN PMCDEFINVP EWSYIVEKAN

PTNDLCYPGS FNDYEELKHL LSRINHFEKI QIIPKSSWSD HEASSGVSSA

CPYLGSPSFF RNVVWLIKKN STYPTIKKSY NNTNQEDLLV LWGIHHPNDA

AEQTRLYQNP TTYISIGTST LNQRLVPKIA TRSKVNGQSG RMEFFWTILK

PNDAINFESN GNFIAPEYAY KIVKKGDSAI MKSELEYGNC NTKCQTPMGA

INSSMPFHNI HPLTIGECPK YVKSNRLVLA TGLRNSPQRE SRRKKRGLFG

AIAGFIEGGW QGMVDGWYGY HHSNEQGSGY AADKESTQKA IDGVTNKVNS

IIDKMNTQFE AVGREFNNLE RRIENLNKKM EDGFLDVWTY NAELLVLMEN

ERTLDFHDSN VKNLYDKVRL QLRDNAKELG NGCFEFYHKC DNECMESIRN

GTYNYPQYSE EARLKREEIS GVKLESIGTY QILSIYSTVA SSLALAIMMA

GLSLWMCSNG SLQCRICI*

Vac2-hac-sph9-opt (modified, signal peptide from H9, underlined)
                                                    (SEQ ID 29)
METISLITIL LVVTASNA DQICIGYHANNSTE QVDTIMEKNV TVTHAQDILE

KTHNGKLCDL DGVKPLILRD CSVAGWLLGN PMCDEFINVP EWSYIVEKAN

PTNDLCYPGS FNDYEELKHL LSRINHFEKI QIIPKSSWSD HEASSGVSSA

CPYLGSPSFF RNVVWLIKKN STYPTIKKSY NNTNQEDLLV LWGIHHPNDA

AEQTRLYQNP TTYISIGTST LNQRLVPKIA TRSKVNGQSG RMEFFWTILK

PNDAINFESN GNFIAPEYAY KIVKKGDSAI MKSELEYGNC NTKCQTPMGA

INSSMPFHNI HPLTIGECPK YVKSNRLVLA TGLRNSPQRE SRRKKRGLFG

AIAGFIEGGW QGMVDGWYGY HHSNEQGSGY AADKESTQKA IDGVTNKVNS

IIDKMNTQFE AVGREFNNLE RRIENLNKKM EDGFLDVWTY NAELLVLMEN

ERTLDFHDSN VKNLYDKVRL QLRDNAKELG NGCFEFYHKC DNECMESIRN

GTYNYPQYSE EARLKREEIS GVKLESIGTY QILSIYSTVA SSLALAIMMA

GLSLWMCSNG SLQCRICI*

Vac2-hac-cs-opt (- is the modified cleavage site)
                                                    (SEQ ID 30)
MEKIVLLLAI VSLVKSDQIC IGYHANNSTE QVDTIMEKNV TVTHAQDILE

KTHNGKLCDL DGVKPLILRD CSVAGWLLGN PMCDEFINVP EWSYIVEKAN

PTNDLCYPGS FNDYEELKHL LSRINHFEKI QIIPKSSWSD HEASSGVSSA

CPYLGSPSFF RNVVWLIKKN STYPTIKKSY NNTNQEDLLV LWGIHHPNDA

AEQTRLYQNP TTYISIGTST LNQRLVPKIA TRSKVNGQSG RMEFFWTILK

PNDAINFESN GNFIAPEYAY KIVKKGDSAI MKSELEYGNC NTKCQTPMGA

INSSMPFHNI HPLTIGECPK YVKSNRLVLA TGLRNSPQRE S----RGLFG

AIAGFIEGGW QGMVDGWYGY HHSNEQGSGY AADKESTQKA IDGVTNKVNS
```

```
IIDKMNTQFE AVGREFNNLE RRIENLNKKM EDGFLDVWTY NAELLVLMEN

ERTLDFHDSN VKNLYDKVRL QLRDNAKELG NGCFEFYHKC DNECMESIRN

GTYNYPQYSE EARLKREEIS GVKLESIGTY QILSIYSTVA SSLALAIMMA

GLSLWMCSNG SLQCRICI*
```

The following polypeptides corresponding to unmodified, codon-optimized NA and M1 genes where also synthesized.

```
Vac2-naj-opt (neuraminidase)
                                              (SEQ ID 31)
MNPNQKIITI GSICMVIGIV SLMLQIGNMI SIWVSHSIQT

GNQHQAESIS NTNPLTEKAV ASVTLAGNSS LCPIRGWAVH

SKDNNIRIGS KGDVFVIREP FISCSHLECR TFFLTQGALL

NDKHSNGTVK DRSPHRTLMS CPVGEAPSPY NSRFESVAWS

ASACHDGTSW LTIGISGPDN EAVAVLKYNG IITDTIKSWR

NNILRTQESE CACVNGSCFT VMTDGPSDGQ ASYKIFKMEK

GKVVKSVELD APNYHYEECS CYPDAGEITC VCRDNWHGSN

RPWVSFNQNL EYQIGYICSG VFGDNPRPND GTGSCGPMSP

NGAYGVKGFS FKYGNGVWIG RTKSTNSRSG FEMIWDPNGW

TGTDSSFSVK QDIVAITDWS GYSGSFVQHP ELTGLDCIRP

CFWVELIRGR PKESTIWTSG SSISFCGVNS DTVSWSWPDG

AELPFTIDK*

Vac2-mc-opt (matrix)
                                              (SEQ ID 32)
MSLLTEVETY VLSIIPSGPL KAEIAQKLED VFAGKNTDLE

ALMEWLKTRP ILSPLTKGIL GFVFTLTVPS ERGLQRRRFV

QNALNGNGDP NNMDRAVKLY KKLKREITFH GAKEVSLSYS

TGALASCMGL IYNRMGTVTT EVAFGLVCAT CEQIADSQHR

SHRQMATITN PLIRHENRMV LASTTAKAME QMAGSSEQAA

EAMEVANQAR QMVQAMRTIG THPNSSAGLR DNLLENLQAY

QKRMGVQMQR FK*
```

The synthetic, codon-optimized HA, NA, and M1 genes were subcloned into pFastBac1 transfer plasmid using BamHI and HindIII sites, as described above. Recombinant bacmids for expression in Sf9 cells of synthetic HA, NA, M1 genes were generated as described above, using *E. coli* strain DH10Bac (Invitrogen).

Example 24

Cloning of Clade 1 A/Viet Nam/1203/04 (H5N1) Influenza Virus by RT-PCR

The HA, NA and M1 genes were cloned by RT-PCR according to the above describes method. The below sequences are comparisons of the published gene compared to the cloned genes.

The HA gene for Clade 1 A/Viet Nam/1203/04 (H5N1)

```
Upper Lane: Acc # AY818135 HA gene                      (SEQ ID 36)
Lower Lane: Novavax's A/Vietnam/1203/2004 (H5N1) HA gene (SEQ ID 37)

1 ........................................ATGGAGAAAA  10
                                               ||||||||||
 301 AGTGTGATGGATATCTGCAGAATTCGCCCTTAGGCGCGCCATGGAGAAAA  350

11 TAGTGCTTCTTTTTGCAATAGTCAGTCTTGTTAAAAGTGATCAGATTTGC   60
     ||||||||||||||||||||||||||||||||||||||||||||||||||
 351 TAGTGCTTCTTTTTGCAATAGTCAGTCTTGTTAAAAGTGATCAGATTTGC  400

61 ATTGGTTACCATGCAAACAACTCGACAGAGCAGGTTGACACAATAATGGA  110
     ||||||||||||||||||||||||||||||||||||||||||||||||||
 401 ATTGGTTACCATGCAAACAACTCGACAGAGCAGGTTGACACAATAATGGA  450

111 AAAGAACGTTACTGTTACACATGCCCAAGACATACTGGAAAAGAAACACA  160
     ||||||||||||||||||||||||||||||||||||||||||||||||||
 451 AAAGAACGTTACTGTTACACATGCCCAAGACATACTGGAAAAGAAACACA  500

161 ACGGGAAGCTCTGCGATCTAGATGGAGTGAAGCCTCTAATTTTGAGAGAT  210
     ||||||||||||||||||||||||||||||||||||||||||||||||||
 501 ACGGGAAGCTCTGCGATCTAGATGGAGTGAAGCCTCTAATTTTGAGAGAT  550

211 TGTAGCGTAGCTGGATGGCTCCTCGGAAACCCAATGTGTGACGAATTCAT  260
     ||||||||||||||||||||||||||||||||||||||||||||||||||
 551 TGTAGCGTAGCTGGATGGCTCCTCGGAAACCCAATGTGTGACGAATTCAT  600

261 CAATGTGCCGGAATGGTCTTACATAGTGGAGAAGGCCAATCCAGTCAATG  310
     ||||||||||||||||||||||||||||||||||||||||||||||||||
 601 CAATGTGCCGGAATGGTCTTACATAGTGGAGAAGGCCAATCCAGTCAATG  650
```

```
 311 ACCTCTGTTACCCAGGGGATTTCAATGACTATGAAGAATTGAAACACCTA  360
     ||||||||||||||||||||||||||||||||||||||||||||||||||
 651 ACCTCTGTTACCCAGGGGATTTCAATGACTATGAAGAATTGAAACACCTA  700

361 TTGAGCAGAATAAACCATTTTGAGAAAATTCAGATCATCCCCAAAAGTTC  410
     ||||||||||||||||||||||||||||||||||||||||||||||||||
 701 TTGAGCAGAATAAACCATTTTGAGAAAATTCAGATCATCCCCAAAAGTTC  750

411 TTGGTCCAGTCATGAAGCCTCATTAGGGGTGAGCTCAGCATGTCCATACC  460
     ||||||||||||||||||||||||||||||||||||||||||||||||||
 751 TTGGTCCAGTCATGAAGCCTCATTAGGGGTGAGCTCAGCATGTCCATACC  800

461 AGGGAAAGTCCTCCTTTTTCAGAAATGTGGTATGGCTTATCAAAAAGAAC  510
     ||||||||||||||||||||||||||||||||||||||||||||||||||
 801 AGGGAAAGTCCTCCTTTTTCAGAAATGTGGTATGGCTTATCAAAAAGAAC  850

511 AGTACATACCCAACAATAAAGAGGAGCTACAATAATACCAACCAAGAAGA  560
     ||||||||||||||||||||||||||||||||||||||||||||||||||
 851 AGTACATACCCAACAATAAAGAGGAGCTACAATAATACCAACCAAGAAGA  900

561 TCTTTTGGTACTGTGGGGGATTCACCATCCTAATGATGCGGCAGAGCAGA  610
     ||||||||||||||||||||||||||||||||||||||||||||||||||
 901 TCTTTTGGTACTGTGGGGGATTCACCATCCTAATGATGCGGCAGAGCAGA  950

611 CAAAGCTCTATCAAAACCCAACCACCTATATTTCCGTTGGGACATCAACA  660
     ||||||||||||||||||||||||||||||||||||||||||||||||||
 951 CAAAGCTCTATCAAAACCCAACCACCTATATTTCCGTTGGGACATCAACA 1000

661 CTAAACCAGAGATTGGTACCAAGAATAGCTACTAGATCCAAAGTAAACGG  710
     ||||||||||||||||||||||||||||||||||||||||||||||||||
1001 CTAAACCAGAGATTGGTACCAAGAATAGCTACTAGATCCAAAGTAAACGG 1050

711 GCAAAGTGGAAGGATGGAGTTCTTCTGGACAATTTTAAAGCCGAATGATG  760
     ||||||||||||||||||||||||||||||||||||||||||||||||||
1051 GCAAAGTGGAAGGATGGAGTTCTTCTGGACAATTTTAAAGCCGAATGATG 1100

761 CAATCAACTTCGAGAGTAATGGAAATTTCATTGCTCCAGAATATGCATAC  810
     ||||||||||||||||||||||||||||||||||||||||||||||||||
1101 CAATCAACTTCGAGAGTAATGGAAATTTCATTGCTCCAGAATATGCATAC 1150

811 AAAATTGTCAAGAAGGGGACTCAACAATTATGAAAAGTGAATTGGAATA  860
     ||||||||||||||||||||||||||||||||||||||||||||||||||
1151 AAAATTGTCAAGAAGGGGACTCAACAATTATGAAAAGTGAATTGGAATA 1200

861 TGGTAACTGCAACACCAAGTGTCAAACTCCAATGGGGGCGATAAACTCTA  910
     ||||||||||||||||||||||||||||||||||||||||||||||||||
1201 TGGTAACTGCAACACCAAGTGTCAAACTCCAATGGGGGCGATAAACTCTA 1250

911 GCATGCCATTCCACAATATACACCCTCTCACCATTGGGAATGCCCCAAA  960
     ||||||||||||||||||||||||||||||||||||||||||||||||||
1251 GCATGCCATTCCACAATATACACCCTCTCACCATTGGGAATGCCCCAAA 1300

961 TATGTGAAATCAAACAGATTAGTCCTTGCGACTGGGCTCAGAAATAGCCC 1010
     ||||||||||||||||||||||||||||||||||||||||||||||||||
1301 TATGTGAAATCAAACAGATTAGTCCTTGCGACTGGGCTCAGAAATAGCCC 1350
```

```
1011 TCAAAGAGAGAAGAAGAAAAAAGAGAGGATTATTTGGAGCTATAGCAG 1060
     ||||||||||||||||||||||||||||||||||||||||||||||||
1351 TCAAAGAGAGAAGAAGAAAAAAGAGAGGATTATTTGGAGCTATAGCAG 1400

1061 GTTTTATAGAGGGAGGATGGCAGGGAATGGTAGATGGTTGGTATGGGTAC 1110
     |||||||||||||||||||||||||||||||||||||||||||||||||
1401 GTTTTATAGAGGGAGGATGGCAGGGAATGGTAGATGGTTGGTATGGGTAC 1450

1111 CACCATAGCAATGAGCAGGGGAGTGGGTACGCTGCAGACAAAGAATCCAC 1160
     |||||||||||||||||||||||||||||||||||||||||||||||||
1451 CACCATAGCAATGAGCAGGGGAGTGGGTACGCTGCAGACAAAGAATCCAC 1500

1161 TCAAAGGCAATAGATGGAGTCACCAATAAGGTCAACTCGATCATTGACA 1210
     |||||||||||||||||||||||||||||||||||||||||||||||||
1501 TCAAAGGCAATAGATGGAGTCACCAATAAGGTCAACTCGATCATTGACA 1550

1211 AAATGAACACTCAGTTTGAGGCCGTTGGAAGGGAATTTAACAACTTAGAA 1260
     |||||||||||||||||||||||||||||||||||||||||||||||||
1551 AAATGAACACTCAGTTTGAGGCCGTTGGAAGGGAATTTAACAACTTAGAA 1600

1261 AGGAGAATAGAGAATTTAAACAAGAAGATGGAAGACGGGTTCCTAGATGT 1310
     |||||||||||||||||||||||||||||||||||||||||||||||||
1601 AGGAGAATAGAGAATTTAAACAAGAAGATGGAAGACGGGTTCCTAGATGT 1650

1311 CTGGACTTATAATGCTGAACTTCTGGTTCTCATGGAAAATGAGAGAACTC 1360
     |||||||||||||||||||||||||||||||||||||||||||||||||
1651 CTGGACTTATAATGCTGAACTTCTGGTTCTCATGGAAAATGAGAGAACTC 1700

1361 TAGACTTTCATGACTCAAATGTCAAGAACCTTTACGACAAGGTCCGACTA 1410
     |||||||||||||||||||||||||||||||||||||||||||||||||
1701 TAGACTTTCATGACTCAAATGTCAAGAACCTTTACGACAAGGTCCGACTA 1750

1411 CAGCTTAGGGATAATGCAAAGGAGCTGGGTAACGGTTGTTTCGAGTTCTA 1460
     |||||||||||||||||||||||||||||||||||||||||||||||||
1751 CAGCTTAGGGATAATGCAAAGGAGCTGGGTAACGGTTGTTTCGAGTTCTA 1800

1461 TCATAAATGTGATAATGAATGTATGGAAAGTGTAAGAAATGGAACGTATG 1510
     |||||||||||||||||||||||||||||||||||||||||||||||||
1801 TCATAAATGTGATAATGAATGTATGGAAAGTGTAAGAAATGGAACGTATG 1850

1511 ACTACCCGCAGTATTCAGAAGAAGCGAGACTAAAAAGAGAGGAAATAAGT 1560
     |||||||||||||||||||||||||||||||||||||||||||||||||
1851 ACTACCCGCAGTATTCAGAAGAAGCGAGACTAAAAAGAGAGGAAATAAGT 1900

1561 GGAGTAAAATTGGAATCAATAGGAATTTACCAAATACTGTCAATTTATTC 1610
     |||||||||||||||||||||||||||||||||||||||||||||||||
1901 GGAGTAAAATTGGAATCAATAGGAATTTACCAAATACTGTCAATTTATTC 1950

1611 TACAGTGGCGAGTTCCCTAGCACTGGCAATCATGGTAGCTGGTCTATCCT 1660
     |||||||||||||||||||||||||||||||||||||||||||||||||
1951 TACAGTGGCGAGTTCCCTAGCACTGGCAATCATGGTAGCTGGTCTATCCT 2000

1661 TATGGATGTGCTCCAATGGATCGTTACAATGCAGAATTTGCATTTAA... 1707
     |||||||||||||||||||||||||||||| ||||||||||||||||
2001 TATGGATGTGCTCCAATGGGTCGTTACAATGCAGAATTTGCATTTAAGCG 2050
```

Comparison of the NA Genes.

```
The NA gene for Clade 1 A/Viet Nam/1203/04 (H5N1)           (SEQ ID 39)
H5N1naLANL ISDN 38704 x NA_Viet1203_Lark (NVAX)             (SEQ ID 38)

1 .....ATGAATCCAAATCAGAAGATAATAACCATCGGATCAATCTGTATG    45
          |||||||||||||||||||||||||||||||||||||||||||||
  451 CCGGGATGAATCCAAATCAGAAGATAATAACCATCGGATCAATCTGTATG   500

46 GTAACTGGAATAGTTAGCTTAATGTTACAAATTGGGAACATGATCTCAAT    95
      ||||||||||||||||||||||||||||||||||||||||||||||||||
  501 GTAACTGGAATAGTTAGCTTAATGTTACAAATTGGGAACATGATCTCAAT   550

96 ATGGGTCAGTCATTCAATTCACACAGGGAATCAACACCAATCTGAACCAA   145
      ||||||||||||||||||||||||||||||||||||||||||||||||||
  551 ATGGGTCAGTCATTCAATTCACACAGGGAATCAACACCAATCTGAACCAA   600

146 TCAGCAATACTAATTTTCTTACTGAGAAAGCTGTGGCTTCAGTAAAATTA   195
      ||||||||||||||||||||||||||||||||||||||||||||||||||
  601 TCAGCAATACTAATTTTCTTACTGAGAAAGCTGTGGCTTCAGTAAAATTA   650

196 GCGGGCAATTCATCTCTTTGCCCCATTAACGGATGGGCTGTATACAGTAA   245
      ||||||||||||||||||||||||||||||||||||||||||||||||||
  651 GCGGGCAATTCATCTCTTTGCCCCATTAACGGATGGGCTGTATACAGTAA   700

246 GGACAACAGTATAAGGATCGGTTCCAAGGGGGATGTGTTTGTTATAAGAG   295
      ||||||||||||||||||||||||||||||||||||||||||||||||||
  701 GGACAACAGTATAAGGATCGGTTCCAAGGGGGATGTGTTTGTTATAAGAG   750

296 AGCCGTTCATCTCATGCTCCCACTTGGAATGCAGAACTTTCTTTTTGACT   345
      ||||||||||||||||||||||||||||||||||||||||||||||||||
  751 AGCCGTTCATCTCATGCTCCCACTTGGAATGCAGAACTTTCTTTTTGACT   800

346 CAGGGAGCCTTGCTGAATGACAAGCACTCCAATGGGACTGTCAAAGACAG   395
      ||||||||||| ||||||||||||||||||||||||||||||||||||||
  801 CAGGGAGCCTCGCTGAATGACAAGCACTCCAATGGGACTGTCAAAGACAG   850

396 AAGCCCTCACAGAACATTAATGAGTTGTCCTGTGGGTGAGGCTCCCTCCC   445
      ||||||||||||||||||||||||||||||||||||||||||||||||||
  851 AAGCCCTCACAGAACATTAATGAGTTGTCCTGTGGGTGAGGCTCCCTCCC   900

446 CATATAACTCAAGGTTTGAGTCTGTTGCTTGGTCAGCAAGTGCTTGCCAT   495
      ||||||||||||||||||||||||||||||||||||||||||||||||||
  901 CATATAACTCAAGGTTTGAGTCTGTTGCTTGGTCAGCAAGTGCTTGCCAT   950

496 GATGGCACCAGTTGGTTGACGATTGGAATTTCTGGCCCAGACAATGGGGC   545
      ||||||||||||||||||||||||||||||||||||||||||||||||||
  951 GATGGCACCAGTTGGTTGACGATTGGAATTTCTGGCCCAGACAATGGGGC  1000

546 TGTGGCTGTATTGAAATACAATGGCATAATAACAGACACTATCAAGAGTT   595
      ||||||||||||||||||||||||||||||||||||||||||||||||||
 1001 TGTGGCTGTATTGAAATACAATGGCATAATAACAGACACTATCAAGAGTT  1050

596 GGAGGAACAACATACTGAGAACTCAAGAGTCTGAATGTGCATGTGTAAAT   645
      ||||||||||||||||||||||||||||||||||||||||||||||||||
 1051 GGAGGAACAACATACTGAGAACTCAAGAGTCTGAATGTGCATGTGTAAAT  1100

646 GGCTCTTGCTTTACTGTAATGACTGACGGACCAAGTAATGGTCAGGCATC   695
      ||||||||||||||||||||||||||||||||||||||||||||||||||
 1101 GGCTCTTGCTTTACTGTAATGACTGACGGACCAAGTAATGGTCAGGCATC  1150

696 ACATAAGATCTTCAAAATGGAAAAAGGGAAAGTGGTTAAATCAGTCGAAT   745
      ||||||||||||||||||||||||||||||||||||||||||||||||||
 1151 ACATAAGATCTTCAAAATGGAAAAAGGGAAAGTGGTTAAATCAGTCGAAT  1200

746 TGGATGCTCCTAATTATCACTATGAGGAATGCTCCTGTTATCCTAATGCC   795
      ||||||||||||||||||||||||||||||||||||||||||||||||||
 1201 TGGATGCTCCTAATTATCACTATGAGGAATGCTCCTGTTATCCTAATGCC  1250
```

-continued

```
 796 GGAGAAATCACATGTGTGTGCAGGGATAATTGGCATGGCTCAAATCGGCC   845
     ||||||||||||||||||||||||||||||||||||||||||||||||||
1251 GGAGAAATCACATGTGTGTGCAGGGATAATTGGCATGGCTCAAATCGGCC  1300

846 ATGGGTATCTTTCAATCAAAATTTGGAGTATCAAATAGGATATATATGCA   895
     ||||||||||||||||||||||||||||||||||||||||||||||||||
1301 ATGGGTATCTTTCAATCAAAATTTGGAGTATCAAATAGGATATATATGCA  1350

896 GTGGAGTTTTCGGAGACAATCCACGCCCCAATGATGGAACAGGTAGTTGT   945
     ||||||||||||||||||||||||||||||||||||||||||||||||||
1351 GTGGAGTTTTCGGAGACAATCCACGCCCCAATGATGGAACAGGTAGTTGT  1400

946 GGTCCGGTGTCCTCTAACGGGGCATATGGGTAAAAGGGTTTTCATTTAA   995
     |||||||||||||||||||||||||||||||||||||||||||||||||
1401 GGTCCGGTGTCCTCTAACGGGGCATATGGGTAAAAGGGTTTTCATTTAA  1450

996 ATACGGCAATGGTGTCTGGATCGGGAGAACCAAAAGCACTAATTCCAGGA  1045
     ||||||||||||||||||||||||||||||||||||||||||||||||||
1451 ATACGGCAATGGTGTCTGGATCGGGAGAACCAAAAGCACTAATTCCAGGA  1500

1046 GCGGCTTTGAAATGATTTGGGATCCAAATGGGTGGACTGAAACGGACAGT  1095
     ||||||||||||||||||||||||||||||||||||||||||||||||||
1501 GCGGCTTTGAAATGATTTGGGATCCAAATGGGTGGACTGAAACGGACAGT  1550

1096 AGCTTTTCAGTGAAACAAGATATCGTAGCAATAACTGATTGGTCAGGATA  1145
     ||||||||||||||||||||||||||||||||||||||||||||||||||
1551 AGCTTTTCAGTGAAACAAGATATCGTAGCAATAACTGATTGGTCAGGATA  1600

1146 TAGCGGGAGTTTTGTCCAGCATCCAGAACTGACAGGACTAGATTGCATAA  1195
     ||||||||||||||||||||||||||||||||||||||||||||||||||
1601 TAGCGGGAGTTTTGTCCAGCATCCAGAACTGACAGGACTAGATTGCATAA  1650

1196 GACCTTGTTTCTGGGTTGAGTTGATCAGAGGGCGGCCCAAAGAGAGCACA  1245
     ||||||||||||||||||||||||||||||||||||||||||||||||||
1651 GACCTTGTTTCTGGGTTGAGTTGATCAGAGGGCGGCCCAAAGAGAGCACA  1700

1246 ATTTGGACTAGTGGGAGCAGCATATCTTTTTGTGGTGTAAATAGTGACAC  1295
     ||||||||||||||||||||||||||||||||||||||||||||||||||
1701 ATTTGGACTAGTGGGAGCAGCATATCTTTTTGTGGTGTAAATAGTGACAC  1750

1296 TGTGGGTTGGTCTTGGCCAGACGGTGCCGAGTTGCCATTCACCATTGACA  1345
     |||||||||||||||||||||||||||| |||||||||||||||||||||
1751 TGTGGGTTGGTCTTGGCCAGACGGTGCTGAGTTGCCATTCACCATTGACA  1800

1346 AGTAG.............................................  1350
     |||||
1801 AGTAGGGGCCCTCGAGTAAGGGCGAATTCCAGCACACTGGCGGCCGTTAC  1850
```

Comparisons of the M1 Genes.

```
The M1 gene for Clade 1 A/Viet Nam/1203/04 (H5N1)       (SEQ ID 40)
H5N1m1Lan1 ISDN9958 x M1_Viet1203_Lark (NVAX)           (SEQ ID 41)

1 ...............................ATGAGTCTTCTAACCG   16
                                    ||||||||||||||||
301 ATATCTGCAGAATTCGCCCTTAGAATTCGACGTCATGAGTCTTCTAACCG  350

17 AGGTCGAAACGTACGTTCTCTCTATCATCCCGTCAGGCCCCCTCAAAGCC   66
    ||||||||||||||||||||||||||||||||||||||||||||||||||
351 AGGTCGAAACGTACGTTCTCTCTATCATCCCGTCAGGCCCCCTCAAAGCC  400

67 GAGATCGCACAGAAACTTGAAGATGTCTTTGCAGGAAAGAACACCGATCT  116
    ||||||||||||||||||||||||||||||||||||||||||||||||||
401 GAGATCGCACAGAAACTTGAAGATGTCTTTGCAGGAAAGAACACCGATCT  450
```

-continued

```
117  CGAGGCTCTCATGGAGTGGCTAAAGACAAGACCAATCCTGTCACCTCTGA  166
     ||||||||||||||||||||||||||||||||||||||||||||||||||
451  CGAGGCTCTCATGGAGTGGCTAAAGACAAGACCAATCCTGTCACCTCTGA  500

167  CTAAAGGGATTTTGGGATTTGTATTCACGCTCACCGTGCCCAGTGAGCGA  216
     ||||||||||||||||||||||||||||||||||||||||||||||||||
501  CTAAAGGGATTTTGGGATTTGTATTCACGCTCACCGTGCCCAGTGAGCGA  550

217  GGACTGCAGCGTAGACGCTTTGTCCAGAATGCCCTAAATGGAAATGGAGA  266
     ||||||||||||||||||||||||||||||||||||||||||||||||||
551  GGACTGCAGCGTAGACGCTTTGTCCAGAATGCCCTAAATGGAAATGGAGA  600

267  TCCAAATAATATGGATAGGGCAGTTAAGCTATATAAGAAGCTGAAAAGAG  316
     ||||||||||||||||||||||||||||||||||||||||||||||||||
601  TCCAAATAATATGGATAGGGCAGTTAAGCTATATAAGAAGCTGAAAAGAG  650

317  AAATAACATTCCATGGGCTAAGGAGGTCGCACTCAGCTACTCAACCGGT   366
     ||||||||||||||||||||||||||||||||||||||||||||||||||
651  AAATAACATTCCATGGGCTAAGGAGGTCGCACTCAGCTACTCAACCGGT   700

367  GCACTTGCCAGTTGCATGGGTCTCATATACAACAGGATGGGAACGGTGAC  416
     ||||||||||||||||||||||||||||||||||||||||||||||||||
701  GCACTTGCCAGTTGCATGGGTCTCATATACAACAGGATGGGAACGGTGAC  750

417  TACGGAAGTGGCTTTTGGCCTAGTGTGTGCCACTTGTGAGCAGATTGCAG  466
     ||||||||||||||||||||||||||||||||||||||||||||||||||
751  TACGGAAGTGGCTTTTGGCCTAGTGTGTGCCACTTGTGAGCAGATTGCAG  800

467  ATTCACAGCATCGGTCTCACAGACAGATGGCAACTATCACCAACCCACTA  516
     ||||||||||||||||||||||||||||||||||||||||||||||||||
801  ATTCACAGCATCGGTCTCACAGACAGATGGCAACTATCACCAACCCACTA  850

517  ATCAGACATGAGAACAGAATGGTGCTGGCCAGCACTACAGCTAAGGCTAT  566
     ||||||||||||||||||||||||||||||||||||||||||||||||||
851  ATCAGACATGAGAACAGAATGGTGCTGGCCAGCACTACAGCTAAGGCTAT  900

567  GGAGCAGATGGCGGGATCAAGTGAGCAGGCAGCGGAAGCCATGGAGATCG  616
     ||||||||||||||||||||||||||||||||||||||||||||||||||
901  GGAGCAGATGGCGGGATCAAGTGAGCAGGCAGCGGAAGCCATGGAGATCG  950

617  CTAATCAGGCTAGGCAGATGGTGCAGGCAATGAGGACAATTGGGACTCAT  666
     ||||||||||||||||||||||||||||||||||||||||||||||||||
951  CTAATCAGGCTAGGCAGATGGTGCAGGCAATGAGGACAATTGGGACTCAT  1000

667  CCTAACTCTAGTGCTGGTCTGAGAGATAATCTTCTTGAAAATTTGCAGGC  716
     ||||||||||||||||||||||||||||||||||||||||||||||||||
1001 CCTAACTCTAGTGCTGGTCTGAGAGATAATCTTCTTGAAAATTTGCAGGC  1050

717  CTACCAGAAACGAATGGGAGTGCAGATGCAGCGATTCAAGTGA
     |||||||||||||||||||||||||||||||||||||||||||
1051 CTACCAGAAACGAATGGGAGTGCAGATGCAGCGATTCAAGTGA
```

All the sequences were cloned and analyzed according to the disclosed methods above.

Example 25

Generation of Clade 1 H5N1 influenza A/Viet Nam/1203/04 HA, NA, and M1 Genes Optimized for Efficient Expression in Sf9 Cells The following polypeptides were derived from codon-optimized nucleotides corresponding to A/Viet Nam/1203/04. The nucleotides were designed and synthesized (Geneart GMBH, Regensburg, FRG) as disclosed above (see Example 24).

VN1203-ha-cs-opt (modified cleavage site, underlined)
(SEQ ID 33)
MEKIVLLFAIVSLVKSDQICIGYHANNSTEQVDTIMEKNVTVTH

AQDILEKTHNGKLCDLDGVKPLILRDCSVAGWLLGNPMCDEFINVPEWSYIVEKANPA

-continued

NDLCYPGDFNDYEELKHLLSRINHFEKIQIIPKNSWSSHEASLGVSSACPYQGKSSFF

RNVVWLIKKNNAYPTIKRSYNNTNQEDLLVLWGIHHPNDAAEQTRLYQNPTTYISVGT

STLNQRLVPKIATRSKVNGQNGRMEFFWTILKPNDAINFESNGNFIAPEYAYKIVKKG

DSAIMKSELEYGNCNTKCQTPMGAINSSMPFHNIHPLTIGECPKYVKSNRLVLATGLR

NSPQRET----RGLFGAIAGFIEGGWQGMVDGWYGYHHSNEQGSGYAADKESTQKAID

GVTNKVNSIIDKMNTQFEAVGREFNNLERRIENLNKKMEDGFLDVWTYNAELLVLMEN

ERTLDFHDSNVKNLYDKVRLQLRDNAKELGNGCFEFYHKCDNECMESVRNGTYDYPQY

SEEARLKREEISGVKLESIGTYQILSIYSTVASSLALAIMVAGLSLWMCSNGSLQCRI

CI*

VN1203-ha-spc-opt (modified signal peptide, underlined)
(SEQ ID 34)

Mplykllnvlwlvavsnaip DQICIGYHANNSTEQVDTIMEKNVTVTH

AQDILEKTHNGKLCDLDGVKPLILRDCSVAGWLLGNPMCDEFINVPEWSYIVEKANPA

NDLCYPGDFNDYEELKHLLSRINHFEKIQIIPKNSWSSHEASLGVSSACPYQGKSSFF

RNVVWLIKKNNAYPTIKRSYNNTNQEDLLVLWGIHHPNDAAEQTRLYQNPTTYISVGT

STLNQRLVPKIATRSKVNGQNGRMEFFWTILKPNDAINFESNGNFIAPEYAYKIVKKG

DSAIMKSELEYGNCNTKCQTPMGAINSSMPFHNIHPLTIGECPKYVKSNRLVLATGLR

NSPQRERRRKKRGLFGAIAGFIEGGWQGMVDGWYGYHHSNEQGSGYAADKESTQKAID

GVTNKVNSIIDKMNTQFEAVGREFNNLERRIENLNKKMEDGFLDVWTYNAELLVLMEN

ERTLDFHDSNVKNLYDKVRLQLRDNAKELGNGCFEFYHKCDNECMESVRNGTYDYPQY

SEEARLKREEISGVKLESIGTYQILSIYSTVASSLALAIMVAGLSLWMCSNGSLQCRI

CI*

VN1203-ha-sph9-opt (The signal peptide and cleavage site are shaded)
(SEQ ID 35)
METISLITIL LVVTASNA DQICIGYHANNSTEQVDTIMEKNVTVTH

AQDILEKTHNGKLCDLDGVKPLILRDCSVAGWLLGNPMCDEFINVPEWSYIVEKANPA

NDLCYPGDFNDYEELKHLLSRINHFEKIQIIPKNSWSSHEASLGVSSACPYQGKSSFF

RNVVWLIKKNNAYPTIKRSYNNTNQEDLLVLWGIHHPNDAAEQTRLYQNPTTYISVGT

STLNQRLVPKIATRSKVNGQNGRMEFFWTILKPNDAINFESNGNFIAPEYAYKIVKKG

DSAIMKSELEYGNCNTKCQTPMGAINSSMPFHNIHPLTIGECPKYVKSNRLVLATGLR

NSPQRERRRKKRGLFGAIAGFIEGGWQGMVDGWYGYHHSNEQGSGYAADKESTQKAID

GVTNKVNSIIDKMNTQFEAVGREFNNLERRIENLNKKMEDGFLDVWTYNAELLVLMEN

ERTLDFHDSNVKNLYDKVRLQLRDNAKELGNGCFEFYHKCDWECMESVRNGTYDYPQY

SEEARLKREEISGVKLESIGTYQILSIYSTVASSLALAIMVAGLSLWMCSNGSLQCRI

CI*

Example 26

H5N1 Vietnam/1203/2003 VLP Immunogenicity (Extreme Dose Sparing)

Figure 25:
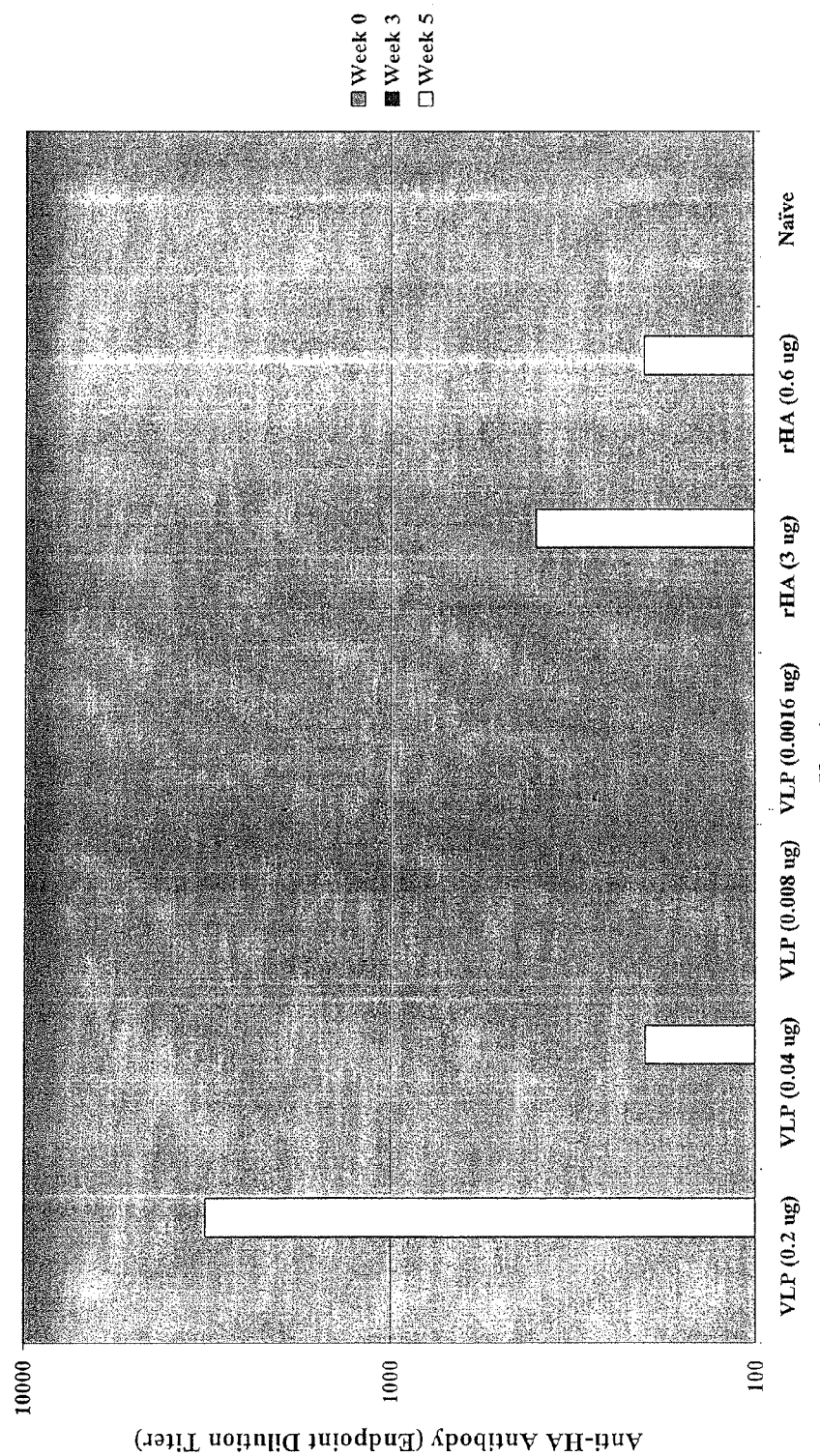
FIG. 25 depicts anti-HA Antibody (Endpoint Dilution Titer) of mice inoculated intranasally with H5N1 (Vietnam/1203/2003) VLPs at low doses.

BALB/C mice were immunized intramuscularly and intranasally with H5N1 VLPs at very low doses of VLPs (0.2, 0.04, 0.008, 0.0016 μg HA/dose), Mice were bled on days 0, 21 and 35. The mice were given a boost on day 21. The serum was assayed for anti-HA antibodies by the hemagglutination inhibition assay (HI) using turkey RBCs and influenza virus using an ELISA. Results of this study are shown in FIGS. 24 and 25.

The results indicate that a robust overall immune response was observed when the VLPs were administered intramuscularly at very lose doses. The robustness of the response was similar to control at 3.0 and 0.6 μg HA/dose. These data show see a true dose response and the antibody response to 0.2 μg of VLP is greater than 3.0 μg of rHA protein. Although the response was not as robust for the intranasal administration, a dose of VLPs at 0.2 μg HA/dose did induce a robust response. The ELISA titer with the 0.2 μg dose in this experiment is similar to the 0.12 μg dose of the H3N2 VLP vaccine in previous experiments, see above.

Example 27

Challenge Studies

Figure 27:
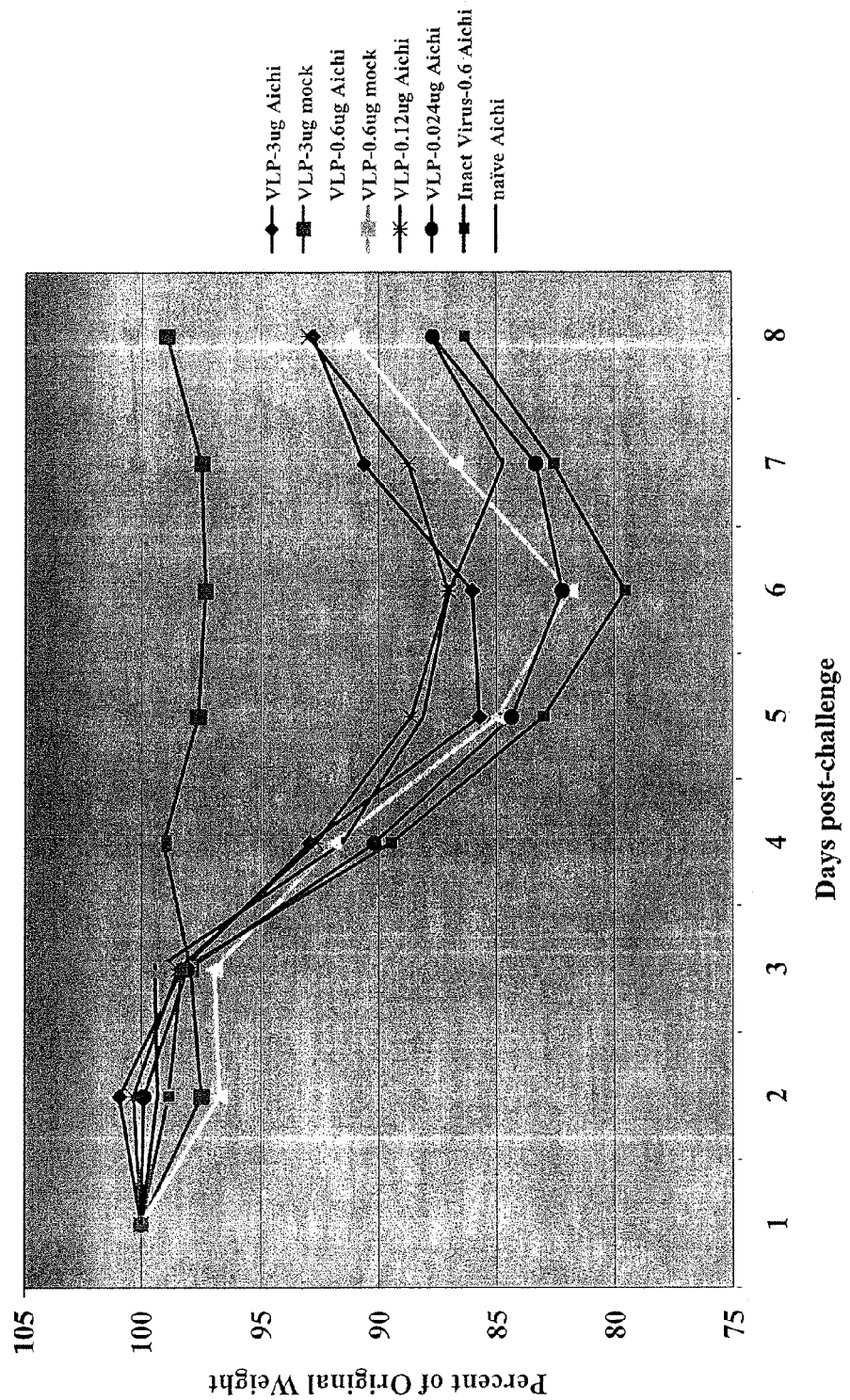
FIG. 27 depicts mice inoculated with H3N2 VLPs given intramuscularly and subsequently challenged intranasally with A/Aichi/2/68x31 (H3N2) virus.
Figure 28:
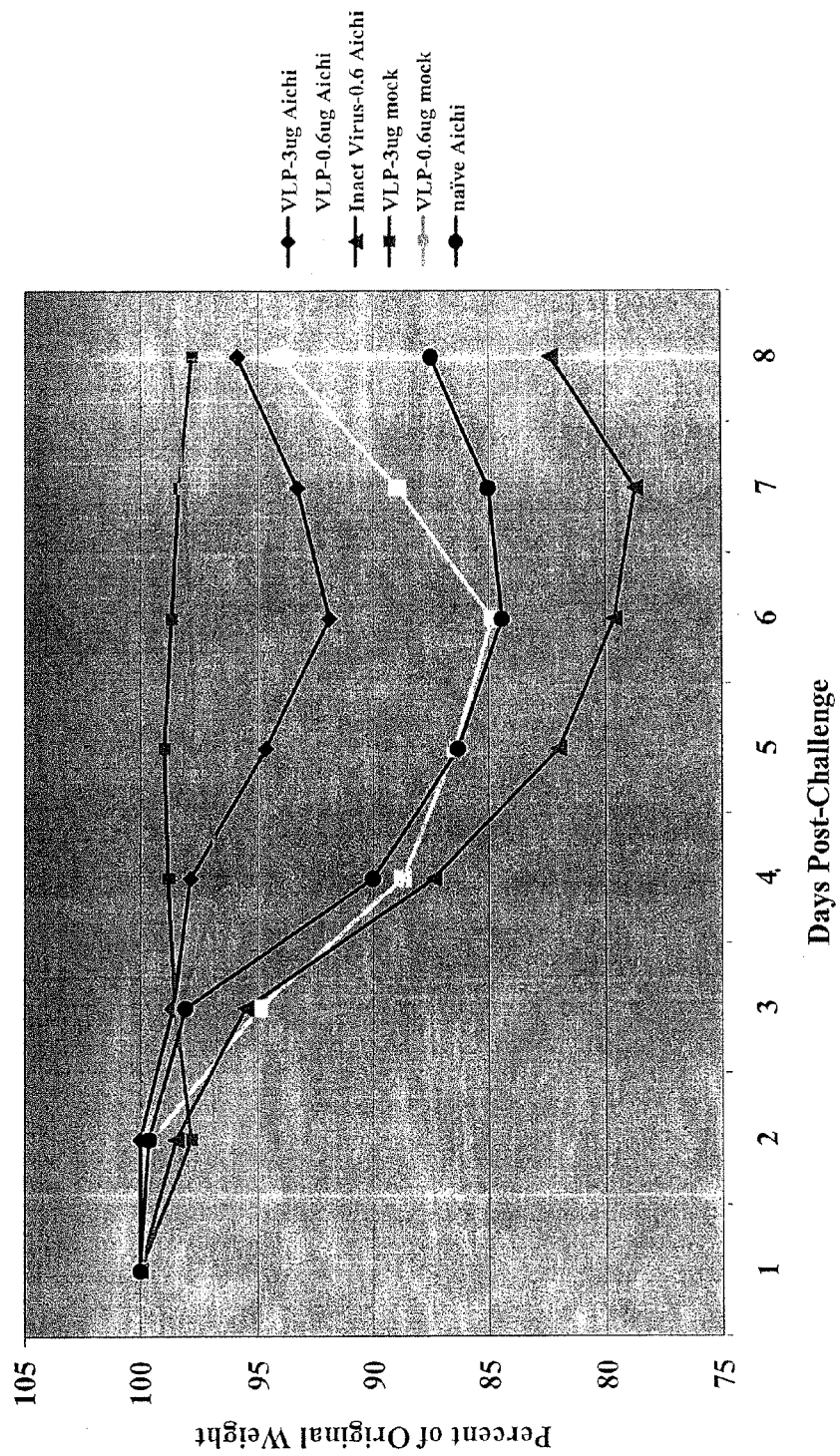
FIG. 28 depicts mice inoculated with H3N2 VLPs given intranasally and subsequently challenged intranasally with A/Aichi/2/68x31 (H3N2) virus.

The results indic After inoculating BALB/c mice with VLPs at concentrations of 3 µg, 0.6 µg 0.12 µg and 0.02 µg of H3N2 VLPs intramuscularly and intranasally (total HA dose), mice were challenged with influenza virus A/Aichi/268×31. The results of this study are shown on FIGS. 27 and 28. These data show that there is a decrease in weight in all vaccinated animals, however the animals that were vaccinated with 3.0 µg and 0.12 µg of VLPs recovered quicker than the other animals in both intramuscular and intranasal vaccinations. The intranasal doses provided enhanced protection.

Example 29

Challenge Studies (Ferrets)

In this study, ferrets were vaccinated with H9N2 VLPs. There were a total of 18 ferrets in the challenge study: 6 mock vaccinated, 6 vaccinated with medium dose (1.5 µg), and 6 vaccinated with high dose (15.0 µg) intramuscularly. Next, ferrets were challenged with $10^6$ $EID_{50}$ of A/HK/1073/99 intranasally. Nasal washes were collected on days 1, 3, 5 and 7. The virus in the nasal washes was titered on days 3, 5 and 7 for all animals. These data are represented on Table 2 and in FIG. 29. These data show that by day 7, all of the vaccinated animals had no detectable virus in nasal washes while the mock group had detectable viral titers.

TABLE 2

Wild Type Virus Titers (log 10/ml) in Ferrets after viral challenge

| Ferret | Day 3 | Day 5 | Day 7 |
|---|---|---|---|
| Group: Placebo Mock Control (n = 6) | | | |
| 4512 | 7 | 5.5 | 3.5 |
| 4524 | 6.5 | 6.75 | 1.98 |
| 4525 | 7.5 | 6.5 | 6.75 |
| 4526 | 7.5 | 7.25 | 3.5 |
| 4527 | 6.75 | 7.25 | 2.5 |
| 4528 | 7.5 | 6.25 | 2.75 |
| Mean | 7.125 | 6.583333 | 3.496667 |
| Std. Dev. | 0.44017 | 0.66458 | 1.699137 |
| Group: Low Dose | | | |
| 3916 | 6.75 | 2.75 | 1.5 |
| 3917 | 7.5 | 5.5 | 1.5 |
| 3918 | 7.5 | 6.5 | 1.5 |
| 3919 | 5.5 | 3 | 1.5 |
| 3920 | 6.75 | 2.25 | 1.5 |
| 3921 | 6.5 | 3.5 | 1.5 |
| Avg | 6.75 | 3.916667 | 1.5 |
| Std Dev | 0.74162 | 1.693123 | 0 |
| Group: High Dose | | | |
| 3922 | 6.5 | 2.75 | 1.5 |
| 3923 | 6.25 | 3.75 | 1.5 |

TABLE 2-continued

Wild Type Virus Titers (log 10/ml) in Ferrets after viral challenge

| Ferret | Day 3 | Day 5 | Day 7 |
|---|---|---|---|
| 3924 | 5.75 | 1.5 | 1.5 |
| 3925 | 6.5 | 4.75 | 1.5 |
| 3926 | 6.25 | 3.5 | 1.5 |
| 3927 | 5.75 | 1.5 | 1.5 |
| Avg. | 6.166667 | 2.958333 | 1.5 |
| Std Dev | 0.341565 | 1.298236 | 0 |

Example 30

Mice Intramuscular and Intranasal Inoculation Studies

Figure 30:
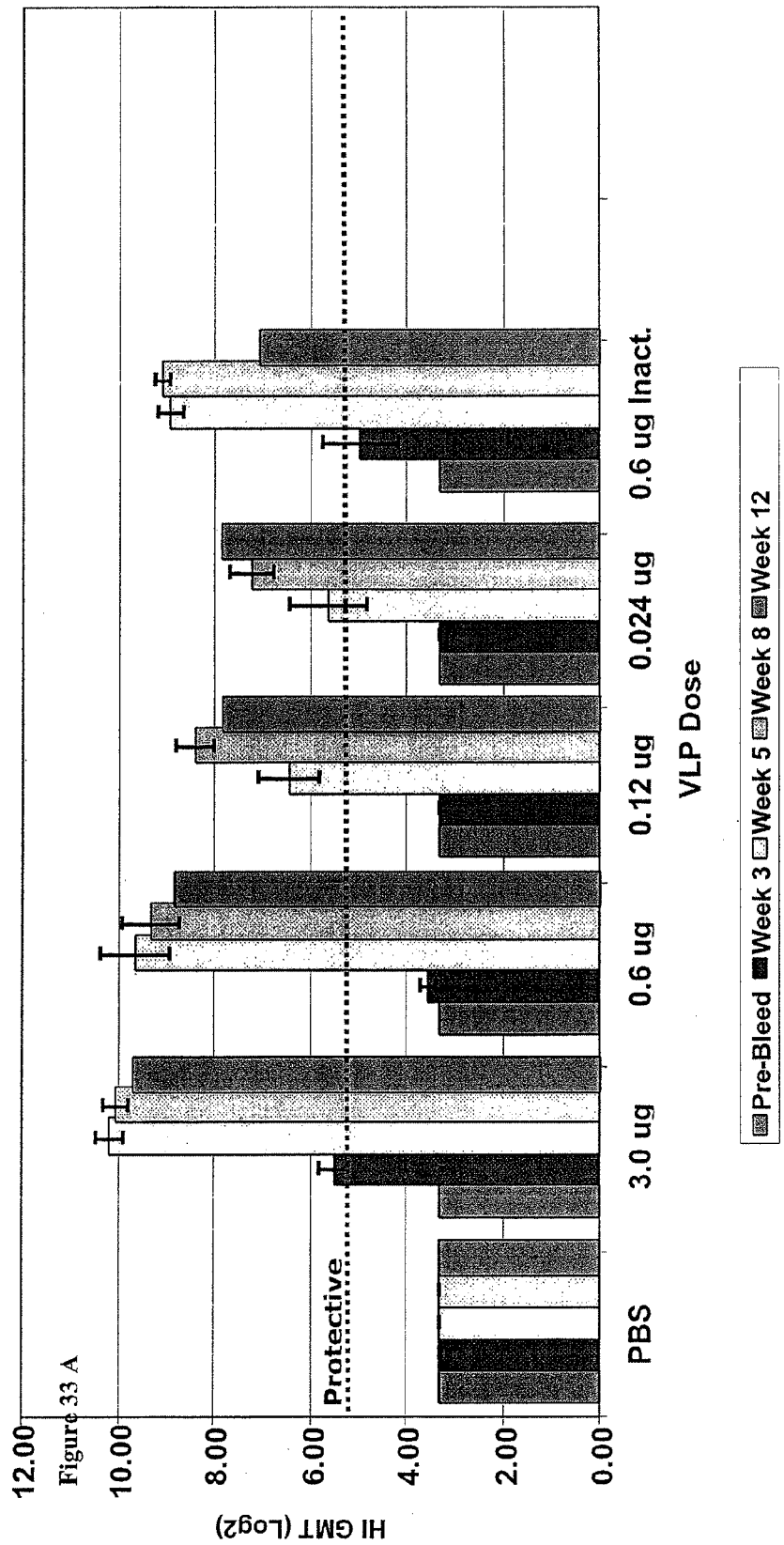
FIGS. 30A, 30B, 30C, 30D, 30E, 30F, 30G, 30H depicts hemagglutinin inhibition (HI) antibody responses in mice after inoculation with different doses of A/Fujian/411/2002 (H3N2) VLPs intramuscularly or intranasally tested against different H3N2 strains of influenza viruses.
Figure 30:
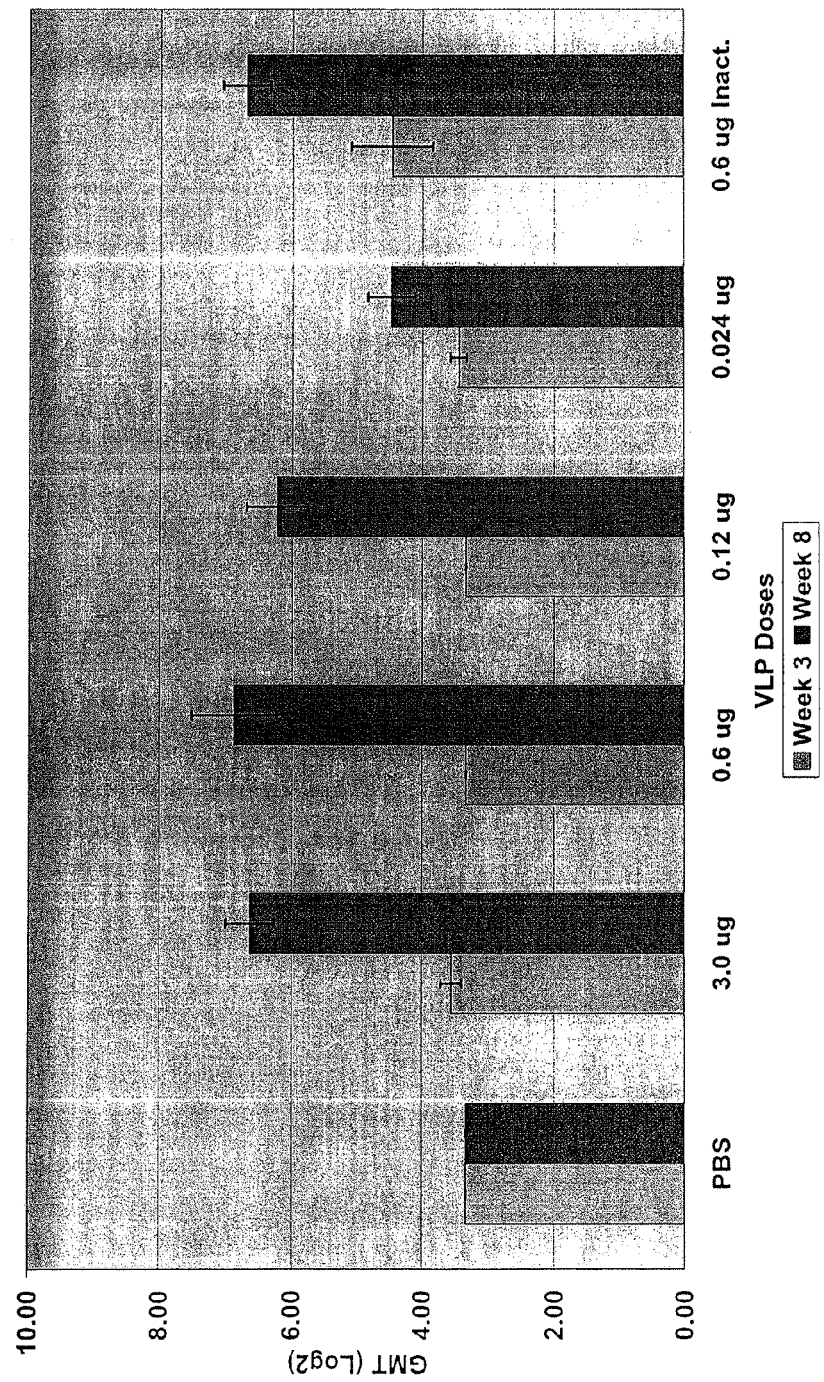

Mice were inoculated with A/Fujian/411/2002 (H3N2) VLPs at concentrations of 3 µg, 0.6 µg 0.12 µg or 0.024 µg (total HA dose) intramuscularly or intranasally at day 0 and were boosted 3 weeks later. Control mice were inoculated with formalin inactivated A/Wyoming (Fujian-Like, vaccine strain) or PBS. Sera were collected from the inoculated mice at weeks 0, 3, 5 and 8. The collected sera were assayed for anti-HA antibodies by the hemagglutination inhibition assay (HI) for anti-influenza antibodies by ELISA. The assay was conducted using A/Fujian/411/2002, A/Panama/2007/99, A/Wyoming/3/03 and A/New York/55/2004 influenza virus strains of H3N2. Results of this study are shown on FIGS. 30 A-H. These data indicate the H3N2 VLPs induced antibodies against the parent A/Fujian/411/2002 strains of influenza virus and against other H3N2 strains. These data also indicate that the titers in intranasally inoculated mice rise later than intramuscularly inoculated mice. However, the intranasal titers are higher than intramuscular titers after about 8 weeks. In addition, titers to the inactivated virus antigen appear to be comparable to the VLP at equivalent doses following intramuscular inoculation. However, the inactivated antigen does not appear to be as immunogenic following intranasal inoculation, nor is it as broadly protective following intranasal inoculation.

Example 31

Generation of Clade 2 H5N1 Influenza HA, NA, and M1 Genes Optimized for Efficient Expression in SD Cells The following optimized nucleotides and polypeptides corresponding to HA, NA and M1 of Clade 2 H5N1 viruses, A A/Indonesia/5/05, A/Bar headed goose/Qinghai/1A/2005 and A/Anhui/1/2005, were designed and synthesized (Geneart GMBH, Regensburg, FRG) as disclosed above. The optimized nucleotides and polypeptides are listed below. In order to make VLPs, A/Anhui HA can be expressed with A/Indonesia NA and M1. For VLPs comprising A/Quinghai HA and NA, A/Indonesia M1 gene can be co-expressed with A/Quinghai HA and NA.

```
A/INDONESIA/5/05
A/INDONESIA/Optimized HA (Start and stop codon are underlined)
                                                              (SEQ ID 42)
GGTACCGGATCCGCCACCATGGAGAAGATCGTGCTGCTGCTGGCTATCGTGTCCCTGGTG

AAGTCCGACCAGATCTGCATCGGTTACCACGCTAACAACTCCACCGAGCAGGTGGACACC

ATCATGGAGAAGAACGTCACCGTGACCCACGCTCAGGACATCCTCGAAAAGACCCACAAC

GGCAAGCTGTGCGACCTGGACGGTGTCAAGCCCCTGATCCTGCGTGACTGCTCCGTGGCT
```

-continued

```
GGTTGGCTGCTGGGTAACCCCATGTGCGACGAGTTCATCAACGTGCCCGAGTGGTCCTAC

ATCGTGGAGAAGGCTAACCCCACCAACGACCTGTGCTACCCCGGTTCCTTCAACGACTAC

GAGGAGCTGAAGCACCTGCTGTCCCGTATCAACCACTTCGAGAAGATCCAGATCATCCCC

AAGTCCTCTTGGTCCGACCACGAGGCTTCCTCCGGTGTCTCCTCCGCTTGCCCCTACCTG

GGTTCCCCCTCCTTCTTCCGTAACGTGGTGTGGCTGATCAACAAGAACTCCACCTACCCC

ACCATCAAGAAGTCCTACAACAACACCAACCAGGAGGACCTGCTGGTCCTGTGGGGTATC

CACCACCCCAACGACGCTGCCGAGCAGACCCGTCTGTACCAGAACCCCACCACCTACATC

TCCATCGGCACCTCCACCCTGAACCAGCGTCTGGTGCCCAAGATCGCTACCCGTTCCAAG

GTGAACGGCCAGTCCGGTCGTATGGAGTTCTTCTGGACCATCCTGAAGCCTAACGACGCT

ATCAACTTCGAGTCCAACGGCAACTTCATCGCTCCCGAGTACGCTTACAAGATCGTGAAG

AAGGGCGACTCCGCTATCATGAAGTCCGAGCTGGAGTACGGTAACTGCAACACCAAGTGC

CAGACCCCCATGGGTGCTATCAACTCCTCCATGCCCTTCCACAACATCCACCCCCTGACC

ATCGGCGAGTGCCCCAAGTACGTGAAGTCCAACCGTCTGGTGCTGGCTACCGGTCTGCGT

AACTCCCCCCAGCGCGAGTCCCGTCGTAAGAAGCGTGGTCTGTTCGGCGCTATCGCTGGT

TTCATCGAGGGCGGTTGGCAGGGCATGGTGGACGGATGGTACGGTTACCACCACTCTAAC

GAGCAGGGTTCCGGTTACGCTGCTGACAAGGAGTCCACCCAGAAGGCTATCGACGGCGTC

ACCAACAAGGTGAACTCCATCATCGACAAGATGAACACCCAGTTCGAGGCTGTGGGTCGT

GAGTTCAACAACCTCGAGCGTCGTATCGAGAACCTGAACAAGAAGATGGAGGACGGTTTC

CTGGACGTGTGGACCTACAACGCCGAGCTGCTGGTGCTGATGGAGAACGAGCGTACCCTG

GACTTCCACGACTCCAACGTGAAGAACCTGTACGACAAGGTCCGCCTGCAGCTGCGTGAC

AACGCTAAGGAGCTGGGTAACGGTTGCTTCGAGTTCTACCACAAGTGCGACAACGAGTGC

ATGGAGTCCATCCGTAACGGCACCTACAACTACCCCCAGTACTCCGAGGAGGCTCGTCTG

AAGCGTGAGGAGATCTCCGGCGTGAAGCTCGAGTCCATCGGAACCTACCAGATCCTGTCC

ATCTACTCCACCGTGGCTTCCTCCCTGGCTCTGGCTATCATGATGGCTGGTCTGTCCCTG

TGGATGTGCTCCAACGGTTCCCTGCAGTGCCGTATCTGCATCTAATGAAAGCTTGAGCTC
```

A/INDONESIA HA Protein Sequence                                    (SEQ ID 43)

```
MEKIVLLLAI VSLVKSDQIC IGYHANNSTE QVDTIMEKNV TVTHAQDILE

KTHNGKLCDL DGVKPLILRD CSVAGWLLGN PMCDEFINVP EWSYIVEKAN

PTNDLCYPGS FNDYEELKHL LSRINHFEKI QIIPKSSWSD HEASSGVSSA

CPYLGSPSFF RNVVWLIKKN STYPTIKKSY NNTNQEDLLV LWGIHHPNDA

AEQTRLYQNP TTYISIGTST LNQRLVPKIA TRSKVNGQSG RMEFFWTILK

PNDAINFESN GNFIAPEYAY KIVKKGDSAI MKSELEYGNC NTKCQTPMGA

INSSMPFHNI HPLTIGECPK YVKSNRLVLA TGLRNSPQRE SRRKKRGLFG

AIAGFIEGGW QGMVDGWYGY HHSNEQGSGY AADKESTQKA IDGVTNKVNS

IIDKMNTQFE AVGREFNNLE RRIENLNKKM EDGFLDVWTY NAELLVLMEN

ERTLDFHDSN VKNLYDKVRL QLRDNAKELG NGCFEFYHKC DNECMESIRN

GTYNYPQYSE EARLKREEIS GVKLESIGTY QILSIYSTVA SSLALAIMMA

GLSLWMCSNG SLQCRICI
```

A/INDONESIA Optimized HA (cleavage site deleted)
(Start and stop codon are underlined)

-continued (SEQ ID 44)
```
GGATCCGCCACCATGGAGAAGATCGTGCTGCTGCTGGCTATCGTGTCCCTGGTGAAGTCC

GACCAGATCTGCATCGGTTACCACGCTAACAACTCCACCGAGCAGGTGGACACCATCATG

GAGAAGAACGTCACCGTGACCCACGCTCAGGACATCCTCGAAAAGACCCACAACGGCAAG

CTGTGCGACCTGGACGGTGTCAAGCCCCTGATCCTGCGTGACTGCTCCGTGGCTGGTTGG

CTGCTGGGTAACCCCATGTGCGACGAGTTCATCAACGTGCCCGAGTGGTCCTACATCGTG

GAGAAGGCTAACCCCACCAACGACCTGTGCTACCCCGGTTCCTTCAACGACTACGAGGAG

CTGAAGCACCTGCTGTCCCGTATCAACCACTTCGAGAAGATCCAGATCATCCCCAAGTCC

TCTTGGTCCGACCACGAGGCTTCCTCCGGTGTCTCCTCCGCTTGCCCCTACCTGGGTTCC

CCCTCCTTCTTCCGTAACGTGGTGTGGCTGATCAAGAAGAACTCCACCTACCCCACCATC

AAGAAGTCCTACAACAACACCAACCAGGAGGACCTGCTGGTCCTGTGGGGTATCCACCAC

CCCAACGACGCTGCCGAGCAGACCCGTCTGTACCAGAACCCCACCACCTACATCTCCATC

GGCACCTCCACCCTGAACCAGCGTCTGGTGCCCAAGATCGCTACCCGTTCCAAGGTGAAC

GGCCAGTCCGGTCGTATGGAGTTCTTCTGGACCATCCTGAAGCCTAACGACGCTATCAAC

TTCGAGTCCAACGGCAACTTCATCGCTCCCGAGTACGCTTACAAGATCGTGAAGAAGGGC

GACTCCGCTATCATGAAGTCCGAGCTGGAGTACGGTAACTGCAACACCAAGTGCCAGACC

CCCATGGGTGCTATCAACTCCTCCATGCCCTTCCACAACATCCACCCCCTGACCATCGGC

GAGTGCCCCAAGTACGTGAAGTCCAACCGTCTGGTGCTGGCTACCGGTCTGCGTAACTCC

CCCCAGCGCGAGTCCCGTGGTCTGTTCGGCGCTATCGCTGGTTTCATCGAGGGCGGTTGG

CAGGGCATGGTGGACGGATGGTACGGTTACCACCACTCTAACGAGCAGGGTTCCGGTTAC

GCTGCTGACAAGGAGTCCACCCAGAAGGCTATCGACGGCGTCACCAACAAGGTGAACTCC

ATCATCGACAAGATGAACACCCAGTTCGAGGCTGTGGGTCGTGAGTTCAACAACCTCGAG

CGTCGTATCGAGAACCTGAACAAGAAGATGGAGGACGGTTTCCTGGACGTGTGGACCTAC

AACGCCGAGCTGCTGGTGCTGATGGAGAACGAGCGTACCCTGGACTTCCACGACTCCAAC

GTGAAGAACCTGTACGACAAGGTCCGCCTGCAGCTGCGTGACAACGCTAAGGAGCTGGGT

AACGGTTGCTTCGAGTTCTACCACAAGTGCGACAACGAGTGCATGGAGTCCATCCGTAAC

GGCACCTACAACTACCCCCAGTACTCCGAGGAGGCTCGTCTGAAGCGTGAGGAGATCTCC

GGCGTGAAGCTCGAGTCCATCGGAACCTACCAGATCCTGTCCATCTACTCCACCGTGGCT

TCCTCCCTGGCTCTGGCTATCATGATGGCTGGTCTGTCCCTGTGGATGTGCTCCAACGGT

TCCCTGCAGTGCCGTATCTGCATCTAATGAAAGCTT
```

A/INDONESIA HA Protein sequence (SEQ ID 45)
```
MEKIVLLLAI VSLVKSDQIC IGYHANNSTE QVDTIMEKNV TVTHAQDILE

KTHNGKLCDL DGVKPLILRD CSVAGWLLGN PMCDEFINVP EWSYIVEKAN

PTNDLCYPGS FNDYEELKHL LSRINHFEKI QIIPKSSWSD HEASSGVSSA

CPYLGSPSFF RNVVWLIKKN STYPTIKKSY NNTNQEDLLV LWGIHHPNDA

AEQTRLYQNP TTYISIGTST LNQRLVPKIA TRSKVNGQSG RMEFFWTILK

PNDAINFESN GNFIAPEYAY KIVKKGDSAI MKSELEYGNC NTKCQTPMGA

INSSMPFHNI HPLTIGECPK YVKSNRLVLA TGLRNSPQRE SRGLFGAIAG

FIEGGWQGMV DGWYGYHHSN EQGSGYAADK ESTQKAIDGV TNKVNSIIDK

MNTQFEAVGR EFNNLERRIE NLNKKMEDGF LDVWTYNAEL LVLMENERTL

DFHDSNVKNL YDKVRLQLRD NAKELGNGCF EFYHKCDNEC MESIRNGTYN
```

YPQYSEEARL KREEISGVKL ESIGTYQILS IYSTVASSLA LAIMMAGLSL

WMCSNGSLQC RICI

A/INDONESIA Optimized NA (Start and stop codon are underlined)    (SEQ ID 46)

GGTACCGGATCCGCCACC<u>ATG</u>AACCCCAACCAGAAGATCATCACCATCGGCTCCATCTGC

ATGGTGATCGGTATCGTGTCCCTGATGCTGCAGATCGGTAACATGATCTCCATCTGGGTG

TCCCACTCCATCCAGACCGGTAACCAGCACCAGGCTGAGTCCATCTCCAACACCAACCCC

CTGACCGAGAAGGCTGTGGCTTCCGTGACCCTGGCTGGTAACTCCTCCCTGTGCCCCATC

CGTGGTTGGGCTGTGCACTCCAAGGACAACAACATCCGCATCGGTTCCAAGGGTGACGTG

TTCGTGATCCGTGAGCCCTTCATCTCCTGCTCCCACCTCGAGTGCCGTACCTTCTTCCTG

ACCCAAGGTGCTCTGCTGAACGACAAGCACTCCAACGGCACCGTGAAGGACCGTTCCCCC

CACCGTACCCTGATGTCCTGCCCCGTGGGCGAGGCTCCCTCCCCCTACAACTCCCGTTTC

GAGTCCGTGGCTTGGTCCGCTTCCGCTTGCCACGACGGCACCTCTTGGCTGACCATCGGT

ATCTCCGGTCCCGACAACGAGGCTGTCGCTGTGCTGAAGTACAACGGCATCATCACCGAC

ACCATCAAGTCCTGGCGTAACAACATCCTGCGTACCCAGGAGTCCGAGTGCGCTTGCGTG

AACGGTTCCTGCTTCACCGTGATGACCGACGGTCCCTCCGACGGCCAGGCTTCCTACAAG

ATCTTCAAGATGGAGAAGGGCAAGGTGGTGAAGTCCGTGGAGCTGGACGCTCCCAACTAC

CACTACGAGGAGTGCTCTTGCTACCCCGACGCTGGCGAGATCACCTGCGTGTGCCGTGAC

AACTGGCACGGTTCCAACCGTCCCTGGGTGTCCTTCAACCAGAACCTCGAGTACCAGATC

GGTTACATCTGCTCCGGCGTGTTCGGTGACAACCCCGTCCCAACGACGGAACCGGTTCC

TGCGGTCCCATGTCCCCCAACGGTGCTTACGGTGTCAAGGGCTTCTCCTTCAAGTACGGT

AACGGTGTCTGGATCGGTCGTACCAAGTCCACCAACTCCCGCTCCGGTTTCGAGATGATC

TGGGACCCCAACGGTTGGACCGGCACCGACTCTTCCTTCTCCGTGAAGCAGGACATCGTG

GCTATCACCGACTGGTCCGGTTACTCCGGTTCCTTCGTGCAGCACCCCGAGCTGACCGGT

CTGGACTGCATTCGTCCCTGCTTCTGGGTGGAGCTGATCCGTGGTCGTCCCAAGGAGTCC

ACCATCTGGACCTCCGGCTCCTCCATCTCTTTCTGCGGTGTGAACTCCGACACCGTGTCC

TGGTCCTGGCCCGACGGTGCCGAGCTGCCCTTCACCATCGACAAG<u>TAA</u>TGAAAGCTTGAG

CTC

A/INDONESIA NA Protein sequence    (SEQ ID 47)

MNPNQKIITI GSICMVIGIV SLMLQIGNMI SIWVSHSIQT GNQHQAESIS

NTNPLTEKAV ASVTLAGNSS LCPIRGWAVH SKDNNIRIGS KGDVFVIREP

FISCSHLECR TFFLTQGALL NDKHSNGTVK DRSPHRTLMS CPVGEAPSPY

NSRFESVAWS ASACHDGTSW LTIGISGPDN EAVAVLKYNG IITDTIKSWR

NNILRTQESE CACVNGSCFT VMTDGPSDGQ ASYKIFKMEK GKVVKSVELD

APNYHYEECS CYPDAGEITC VCRDNWHGSN RPWVSFNQNL EYQIGYICSG

VFGDNPRPND GTGSCGPMSP NGAYGVKGFS FKYGNGVWIG RTKSTNSRSG

FEMIWDPNGW TGTDSSFSVK QDIVAITDWS GYSGSFVQHP ELTGLDCIRP

CFWVELIRGR PKESTIWTSG SSISFCGVNS DTVSWSWPDG AELPFTIDK

A/INDONESIA Optimized M1    (SEQ ID 48)

GGTACCGGATCCGCCACC<u>ATG</u>TCCCTGCTGACCGAGGTGGAGACCTACGTGCTGTCCATC

ATCCCCTCCGGTCCTCTGAAGGCTGAGATCGCTCAGAAGCTCGAGGACGTTTTCGCTGGC

AAGAACACCGACCTCGAGGCTCTGATGGAGTGGCTCAAGACCCGTCCCATCCTGTCCCCC

-continued

CTGACCAAGGGTATCCTGGGTTTCGTGTTCACCCTGACCGTGCCCTCCGAGCGTGGTCTG

CAGCGTCGTCGTTTCGTGCAGAACGCTCTGAACGGTAACGGTGACCCCAACAACATGGAC

CGTGCTGTGAAGCTGTACAAGAAGCTGAAGCGCGAGATCACCTTCCACGGTGCTAAGGAG

GTGTCCCTGTCCTACTCCACCGGTGCTCTGGCTAGCTGCATGGGCCTGATCTACAACCGT

ATGGGCACCGTGACCACCGAGGTGGCCTTCGGTCTGGTCTGCGCTACCTGCGAGCAGATC

GCTGACTCCCAGCACCGTTCCCACCGTCAGATGGCTACCATCACCAACCCCCTGATCCGT

CACGAGAACCGTATGGTGCTGGCTTCCACCACCGCTAAGGCTATGGAGCAGATGGCTGGT

TCCTCCGAGCAGGCTGCTGAGGCCATGGAGGTGGCCAACCAGGCTCGTCAGATGGTGCAG

GCTATGCGTACCATCGGCACCCACCCCAACTCCTCCGCTGGTCTGCGTGACAACCTGCTC

GAGAACCTGCAGGCTTACCAGAAGCGTATGGGAGTCCAGATGCAGCGCTTCAAGTAATGA

AAGCTTGAGCTC

A/INDONESIA M1 Protein sequence (SEQ ID 49)

MSLLTEVETY VLSIIPSGPL KAEIAQKLED VFAGKNTDLE ALMEWLKTRP

ILSPLTKGIL GFVFTLTVPS ERGLQRRRFV QNALNGNGDP NNMDRAVKLY

KKLKREITFH GAKEVSLSYS TGALASCMGL IYNRMGTVTT EVAFGLVCAT

CEQIADSQHR SHRQMATITN PLIRHENRMV LASTTAKAME QMAGSSEQAA

EAMEVANQAR QMVQAMRTIG THPNSSAGLR DNLLENLQAY QKRMGVQMQR

FK

A/Anhui/1/2005

A/Anhui Optimized HA (Start and stop codon are underlined)

(SEQ ID 50)

GGTACCGGATCCCTCGAGATGGAGAAGATCGTGCTGCTGCTGGCTATCGTGTCCCTGGTG

AAGTCCGACCAGATCTGCATCGGTTACCACGCTAACAACTCCACCGAGCAGGTGGACACC

ATCATGGAGAAGAACGTCACCGTGACCCACGCTCAGGACATCCTGGAAAAGACCCACAAC

GGCAAGCTGTGCGACCTGGACGGTGTCAAGCCCCTGATCCTGCGTGACTGCTCCGTGGCT

GGTTGGCTGCTGGGTAACCCCATGTGCGACGAGTTCATCAACGTGCCCGAGTGGTCCTAC

ATCGTGGAGAAGGCTAACCCCGCTAACGACCTGTGCTACCCCGGTAACTTCAACGACTAC

GAGGAGCTGAAGCACCTGCTGTCCCGTATCAACCACTTCGAGAAGATCCAGATCATCCCC

AAGTCCTCTTGGTCCGACCACGAGGCTTCCTCCGGTGTCTCCTCCGCTTGCCCATACCAG

GGCACCCCATCTTTCTTCCGTAACGTGGTGTGGCTGATCAAGAAGAACAACACCTACCCC

ACCATCAAGCGTTCCTACAACAACACCAACCAGGAGGACCTGCTGATCCTGTGGGGTATC

CACCACTCCAACGACGCTGCCGAGCAGACCAAGCTGTACCAGAACCCCACCACCTACATC

TCCGTGGGCACCTCCACCCTGAACCAGCGTCTGGTGCCCAAGATCGCTACCCGTTCCAAG

GTGAACGGCCAGTCCGGTCGTATGGACTTCTTCTGGACCATCCTGAAGCCTAACGACGCT

ATCAACTTCGAGTCCAACGGCAACTTCATCGCTCCCGAGTACGCTTACAAGATCGTGAAG

AAGGGCGACTCCGCTATCGTCAAGTCCGAGGTGGAGTACGGTAACTGCAACACCAAGTGC

CAGACCCCCATCGGTGCTATCAACTCCTCCATGCCCTTCCACAACATCCACCCCCTGACC

ATCGGCGAGTGCCCCAAGTACGTGAAGTCCAACAAGCTGGTGCTGGCTACCGGTCTGCGT

AACTCCCCCCTGCGTGAGCGTGGTCTGTTCGGCGCTATCGCTGGTTTCATCGAGGGCGGT

TGGCAGGGCATGGTGGACGGTTGGTACGGTTACCACCACAGCAACGAGCAGGGTTCCGGT

TACGCTGCTGACAAGGAGTCCACCCAGAAGGCTATCGACGGCGTCACCAACAAGGTGAAC

TCCATCATCGACAAGATGAACACCCAGTTCGAGGCTGTGGGTCGTGAGTTCAACAACCTG

-continued

GAGCGTCGTATCGAGAACCTGAACAAGAAGATGGAGGACGGTTTCCTGGACGTGTGGACC

TACAACGCCGAGCTGCTGGTGCTGATGGAGAACGAGCGTACCCTGGACTTCCACGACTCT

AACGTGAAGAACCTGTACGACAAGGTCCGCCTGCAGCTGCGTGACAACGCTAAGGAGCTG

GGTAACGGTTGCTTCGAGTTCTACCACAAGTGCGACAACGAGTGCATGGAGTCCGTGCGT

AACGGCACCTACGACTACCCCCAGTACTCCGAGGAGGCTCGTCTGAAGCGTGAGGAGATC

TCCGGCGTGAAGCTGGAGTCCATCGGCACCTACCAGATCCTGTCCATCTACTCCACCGTG

GCTTCCTCCCTGGCTCTGGCTATCATGGTGGCTGGTCTGTCCCTGTGGATGTGCTCCAAC

GGTTCCCTGCAGTGCCGTATCTGCATCTAATAATGAGGCGCGCCAAGCTTGAGCTC

A/Anhui HA Protein sequence (SEQ ID 51)

MEKIVLLLAI VSLVKSDQIC IGYHANNSTE QVDTIMEKNV TVTHAQDILE

KTHNGKLCDL DGVKPLILRD CSVAGWLLGN PMCDEFINVP EWSYIVEKAN

PANDLCYPGN FNDYEELKHL LSRINHFEKI QIIPKSSWSD HEASSGVSSA

CPYQGTPSFF RNVVWLIKKN NTYPTIKRSY NNTNQEDLLI LWGIHHSNDA

AEQTKLYQNP TTYISVGTST LNQRLVPKIA TRSKVNGQSG RMDFFWTILK

PNDAINFESN GNFIAPEYAY KIVKKGDSAI VKSEVEYGNC NTKCQTPIGA

INSSMPFHNI HPLTIGECPK YVKSNKLVLA TGLRNSPLRE RGLFGAIAGF

IEGGWQGMVD GWYGYHHSNE QGSGYAADKE STQKAIDGVT NKVNSIIDKM

NTQFEAVGRE FNNLERRIEN LNKKMEDGFL DVWTYNAELL VLMENERTLD

FHDSNVKNLY DKVRLQLRDN AKELGNGCFE FYHKCDNECM ESVRNGTYDY

PQYSEEARLK REEISGVKLE SIGTYQILSI YSTVASSLAL AIMVAGLSLW

MCSNGSLQCR ICI

A/Bar headed goose/Qinghai/1A/2005
A/Qinghai Optimized HA (Start and stop codon are underlined)

(SEQ ID 52)

CGGGCGCGGAGCGGCCGCATGGAGAAGATCGTGCTGCTGCTGGCTATCGTGTCTCTGGTCAAGTCCGACCAGAT

CTGCATCGGTTACCACGCTAACAACTCCACCGAGCAGGTGGACACCATCATGGAGAAGAACGTCACCGTGACCC

ACGCTCAGGACATCCTCGAAAAGACCCACAACGGCAAGCTGTGCGACCTGGACGGCGTGAAGCCCCTGATCCTG

CGTGACTGCTCCGTGGCTGGTTGGCTGCTGGGTAACCCCATGTGCGACGAGTTCCTCAACGTGCCCGAGTGGTC

CTACATCGTGGAGAAGATCAACCCCGCTAACGACCTGTGCTACCCCGGTAACTTCAACGACTACGAGGAGCTGA

AGCACCTGCTGTCCCGTATCAACCACTTCGAGAAGATCCACATCATCCCCAAGTCCTCTTGGTCCGACCACGAG

GCTTCCTCCGGTGTCTCCTCCGCTTGCCCATACCAGGGCCGTTCTTCCTTCTTCCGCAACGTGGTGTGGCTGAT

CAAGAAGAACAACGCCTACCCCACCATCAAGCGTTCCTACAACAACACCAACCAGGAGGACCTGCTGGTCCTGT

GGGGTATCCACCACCCCAACGACGCTGCCGAGCAGACCCGTCTGTACCAGAACCCCACCACCTACATCTCCGTG

GGCACCTCTACCCTGAACCAGCGTCTGGTGCCCAAGATCGCTACCCGTTCCAAGGTGAACGGCCAGTCCGGTCG

TATGGAGTTCTTCTGGACCATCCTGAAGCCTAACGACGCTATCAACTTCGAGTCCAACGGCAACTTCATCGCTC

CCGAGAACGCTTACAAGATCGTGAAGAAGGGCGACTCCACCATCATGAAGTCCGAGCTGGAGTACGGCAACTGC

AACACTAAGTGCCAGACCCCCATCGGTGCTATCAACTCCTCCATGCCCTTCCACAACATCCACCCCCTGACTAT

CGGCGAGTGCCCCAAGTACGTGAAGTCCAACCGTCTGGTGCTGGCTACCGGTCTGCGTAACTCCCCCCAGATCG

AGACTCGTGGTCTGTTCGGCGCTATCGCTGGTTTCATCGAGGGCGGTTGGCAGGGCATGGTGGACGGTTGGTAC

GGTTACCACCACTCTAACGAGCAGGGTTCCGGTTACGCTGCTGACAAGGAGTCTACCCAGAAGGCTATCGACGG

CGTCACCAACAAGGTGAACTCCATCATCGACAAGATGAACACCCAGTTCGAGGCTGTGGGTCGTGAGTTCAACA

ACCTCGAACGTCGTATCGAGAACCTGAACAAGAAGATGGAGGACGGTTTCCTGGACGTGTGGACCTACAACGCC

-continued

GAGCTGCTGGTGCTGATGGAGAACGAGCGTACCCTGGACTTCCACGACTCCAACGTGAAGAACCTGTACGACAA

GGTCCGCCTGCAGCTGCGTGACAACGCTAAGGAGCTGGGTAACGGTTGCTTCGAGTTCTACCACCGTTGCGACA

ACGAGTGCATGGAGTCCGTGCGTAACGGCACCTACGACTACCCCCAGTACTCCGAGGAGGCTCGTCTGAAGCGT

GAGGAGATCTCCGGTGTCAAGCTCGAATCCATCGGAACCTACCAGATCCTGTCCATCTACTCCACCGTGGCTTC

CTCCCTGGCTCTGGCTATCATGGTGGCTGGTCTGTCCCTGTGGATGTGCTCCAACGGTTCCCTGCAGTGCCGTA

TCTGCATC<u>TAA</u>TAATGAGGCGCGCCAAGCTTGTCGA

A/Qinghai HA Protein sequence (SEQ ID 53)

MEKIVLLLAI VSLVKSDQIC IGYHANNSTE QVDTIMEKNV TVTHAQDILE

KTHNGKLCDL DGVKPLILRD CSVAGWLLGN PMCDEFLNVP EWSYIVEKIN

PANDLCYPGN FNDYEELKHL LSRINHFEKI QIIPKSSWSD HEASSGVSSA

CPYQGRSSFF RNVVWLIKKN NAYPTIKRSY NNTNQEDLLV LWGIHHPNDA

AEQTRLYQNP TTYISVGTST LNQRLVPKIA TRSKVNGQSG RMEFFWTILK

PNDAINFESN GNFIAPENAY KIVKKGDSTI MKSELEYGNC NTKCQTPIGA

INSSMPFHNI HPLTIGECPK YVKSNRLVLA TGLRNSPQIE TRGLFGAIAG

FIEGGWQGMV DGWYGYHHSN EQGSGYAADK ESTQKAIDGV TNKVNSIIDK

MNTQFEAVGR EFNNLERRIE NLNKKMEDGF LDVWTYNAEL LVLMENERTL

DFHDSNVKNL YDKVRLQLRD NAKELGNGCF EFYHRCDNEC MESVRNGTYD

YPQYSEEARL KREEISGVKL ESIGTYQILS IYSTVASSLA LAIMVAGLSL

WMCSNGSLQC RICI

A/Qinghai Optimized NA (Start and stop codon are underlined)

(SEQ ID 54)

ACCGTCCCACCATCGGGCGCGGATCCCTCGAG<u>ATG</u>AACCCCAACCAGAAGATCATCACCATCGGCTCCATCTGC

ATGGTGATCGGTATCGTGTCCCTGATGCTGCAGATCGGTAACATGATCTCCATCTGGGTGTCCCACTCCATCCA

GACCGGTAACCAGCGTCAGGCCGAGCCCATCTCCAACACCAAGTTCCTCACCGAGAAGGCTGTGGCTTCCGTGA

CCCTGGCTGGTAACTCCTCCCTGTGCCCCATCTCCGGTTGGGCTGTGTACTCCAAGGACAACTCCATCCGTATC

GGTTCCCGTGGTGACGTGTTCGTGATCCGTGAGCCCTTCATCTCCTGCTCCCACCTCGAATGCCGTACCTTCTT

CCTGACCCAGGGTGCTCTGCTGAACGACAAGCACTCCAACGGCACCGTGAAGGACCGTTCCCCCCACCGTACCC

TGATGTCCTGCCCCGTGGGCGAGGCTCCCTCCCCCCTACAACTCCCGTTTCGAGTCCCTGGCTTGGTCCGCTTCC

GCTTGCCACGACGGCACCTCTTGGCTGACCATCGGTATCTCCGGTCCCGACAACGGTGCTGTGGCTGTGCTGAA

GTACAACGGCATCATCACCGACACCATCAAGTCCTGCCGTAACAACATCCTGCGTACCCAAGAGTCCGAGTGCG

CTTGCGTGAACGGTTCCTGCTTCACCGTGATGACCGACGGTCCCTCCAACGGCCAGGCTTCCTACAAGATCTTC

AAGATGGAGAAGGGCAAGGTGGTGAAGTCCGTGGAGCTGGACGCTCCCAACTACCACTACGAGGAGTGCTCTTG

CTACCCCGACGCTGGCGAGATCACCTGCGTGTGCCGTGACAACTGGCACGGTTCCAACCGTCCCTGGGTGTCCT

TCAACCAGAACCTCGAATACCAGATCGGTTACATCTGCTCCGGCGTGTTCGGTGACAACCCCCGTCCCAACGAC

GGAACCGGTTCCTGCGGTCCCGTGTCCCCCAACGGTGCTTACGGTGTCAAGGGCTTCTCCTTCAAGTACGGTAA

CGGTGTCTGGATCGGTCGTACCAAGTCCACCAACTCCCGCTCCGGTTTCGAGATGATCTGGGACCCCAACGGTT

GGACCGGCACCGACTCTTCCTTCTCCGTGAAGCAGGACATCGTGGCTATCACCGACTGGTCCGGTTACTCCGGT

TCCTTCGTGCAGCACCCCGAGCTGACCGGTCTGGACTGTATCCGTCCCTGCTTCTGGGTGGAGCTGATCCGTGG

TCGTCCCAAGGAGTCCACCATCTGGACCTCCGGCTCCTCCATCTCTTTCTGCGGTGTGAACTCCGACACCGTGT

CCTGGTCCTGGCCCGACGGTGCCGAGCTGCCCTTCACCATCGACAAG<u>TAA</u>TAATGAATCGATTTGTCGAGAAGT

ACTAGAGGATCATAAT

```
Protein sequence:
A/Qinghai NA Protein sequence                                              (SEQ ID 55)

MNPNQKIITI GSICMVIGIV SLMLQIGNMI SIWVSHSIQT GNQRQAEPIS

NTKFLTEKAV ASVTLAGNSS LCPISGWAVY SKDNSIRIGS RGDVFVIREP

FISCSHLECR TFFLTQGALL NDKHSNGTVK DRSPHRTLMS CPVGEAPSPY

NSRFESVAWS ASACHDGTSW LTIGISGPDN GAVAVLKYNG IITDTIKSWR

NNILRTQESE CACVNGSCFT VMTDGPSNGQ ASYKIFKMEK GKVVKSVELD

APNYHYEECS CYPDAGEITC VCRDNWHGSN RPWVSFNQNL EYQIGYICSG

VFGDNPRPND GTGSCGPVSP NGAYGVKGFS FKYGNGVWIG RTKSTNSRSG

FEMIWDPNGW TGTDSSFSVK QDIVAITDWS GYSGSFVQHP ELTGLDCIRP

CFWVELIRGR PKESTIWTSG SSISFCGVNS DTVSWSWPDG AELPFTIDK
```

Example 32

Human Administration of H5N1 VLPs Vaccines

The purpose of this double-blind, placebo-controlled study was to evaluate the reactogenicity and immunogenicity of H5N1 VLP influenza vaccine (H5N1 VLP) in healthy adults 18 to 40 years of age. The study design evaluates approximately 230 subjects.

Approximately 70 subjects received two doses of a vaccine comprising H5N1 VLPs at a dosage of either 15 µg or 45 µg (or placebo). Of the 70 subjects who were enrolled in this study, 20 subjects where in the 15 µg arm and 50 subjects were in the 45 µg arm. Dosing commenced at 15 µg, which is approximately one third of the total HA antigen content targeted for most seasonal influenza vaccines. Subjects were randomly assigned to receive either two doses (day 0 and day 28) of vaccine or placebo in a 7:3 ratio.

The H5N1 VLP vaccine (H5N1 VLP) used in this study was comprised of virus-like particles (VLPs) containing the hemagglutinin (HA), neuraminidase (NA), and matrix 1 (M1) proteins derived from A/Indonesia/05/2005 (H5N1) influenza virus, which had been extracted and purified from *Spodoptera frugiperda* (Sf9) insect cells infected with a recombinant baculovirus containing the influenza virus genes for HA, NA, and M1. The 45 µg dosages were packaged in single-dose vials, with 0.5 mL dose of the vaccine formulated to contain 45 µg of HA in phosphate buffered saline with 0.5M NaCl at neutral pH. The 15 µg dose was prepared by the clinical site pharmacist by 5:1 dilution of placebo (phosphate buffered saline with 0.5M NaCl at neutral pH) and 180 µg/ml vaccine according to a standard procedure. The H5N1 VLP vaccine was administered by IM injection in the deltoid muscle.

Blood samples for the evaluation were collected at baseline (pre dose 1), approximately 4 weeks later (post dose 1/pre dose 2), approximately 4 weeks post dose 2 and approximately 6 months post dose two. Hemagglutination-inhibition titers and viral neutralization titers were measured utilizing the assays described above. The viruses used for the neutralization studies were wild type, egg-adapted, A/Indo/5/2005 and A/Vietnam/1203/04. Results from this study are shown in the tables below.

TABLE 3

Subject Accounting for Immunogenicity Analyses

| Status | 15 µg HAI & Neut (N = 14) n (%) | 45 µg HAI (N = 35) n (%) | 45 µg Neut (N = 35) n (%) |
| --- | --- | --- | --- |
| Randomized | 14 (100) | 35 (100) | 35 (100) |
| Discontinued | 1 (7.1) | 2 (5.7) | 2 (5.7) |
| Samples/results missing | 1 (7.1) | 2 (5.7) | 3 (8.6) |
| Evaluable samples | 12 (85.7) | 31 (88.6) | 30 (85.7) |

Table 4 summarizes the data of neutralizing antibody titers against A/Indo/5/2005 among subjects who received two doses of the H5N1 VLP vaccine at a dose of 15 µg. Three values for neutralizing antibody titers were available for each subject.

TABLE 4

Neutralizing Antibody Titers Against A/Indo/5/2005 (15 µg)

| Subject # | Run #1* | Run #2* | Run #3* | GMT |
| --- | --- | --- | --- | --- |
| 1 | 5 | 10 | 10 | 7.9 |
| 2 | 20 | 20 | 10 | 15.9 |
| 3 | 10 | 10 | 10 | 10.0 |
| 4 | 20 | 10 | 10 | 12.6 |
| 5 | 10 | 10 | 10 | 10.0 |
| 6 | 10 | 10 | 10 | 10.0 |
| 7 | 5 | 5 | 5 | 5.0 |
| 8 | 40 | 80 | 40 | 50.4 |
| 9 | 10 | 5 | 10 | 7.9 |
| 10 | 40 | 40 | 20 | 31.7 |
| 11 | 5 | 5 | 5 | 5.0 |
| 12 | 5 | 5 | 5 | 5.0 |
| Group GMT | 11.2 | 11.2 | 10.0 | 10.8 |

*Run 1 - passed; Run 2 - plate failure and TCID$_{50}$ titer for Indonesia virus was outside of set range; Run 3 - controls failed but TCID$_{50}$ titer within range; Results for all 3 runs were consistent (within 2-fold)

Table 5 summarizes hemagglutination inhibition (HAI) from individuals who received two doses of the of the H5N1 VLP vaccine at a dose of 45 µg.

TABLE 5

HAI Responses* (VLP Vaccine at 45 μg)

| | n (%) | |
|---|---|---|
| Immunologic Parameter | HAI against A/Indo/5/05 N = 31 | HAI against A/VN/1203/04 N = 31 |
| Titer ≧ 1:10 | 17 (55) | 4 (13) |
| Titer ≧ 1:20 | 15 (48) | 3 (10) |
| Titer ≧ 1:40 | 10 (32) | 2 (7) |
| 4-fold rise from baseline | 15 (48) | 3 (10) |
| GMT (95% CI) | 14.6 (9.8, 21.9) | 6.4 (4.9, 8.4) |

*No subjects had detectable antibody at baseline
No placebo recipients had detectable antibody Table 6 summarizes neutralizing antibody responses among subjects who received two doses of the H5N1 VLP vaccine at a dose of 45 μg.

TABLE 6

Neutralizing Antibody Responses*

| | n (%) | |
|---|---|---|
| Immunologic Parameter | Neut. Antibody against A/Indo/5/05 N = 30 | Neut. Antibody against A/VN/1203/04 N = 30 |
| Titer ≧ 1:10 | 25 (83) | 5 (17) |
| Titer ≧ 1:20 | 19 (63) | 0 (0) |
| Titer ≧ 1:40 | 14 (47) | 0 (0) |
| 4-fold rise from baseline | 19 (63) | 0 (0) |
| GMT (95% CI) | 32.8 (21.3, 50.6) | 5.7 (5.1, 6.4) |

*No subjects had detectable antibody at baseline.
No placebo recipients had detectable antibody.

These data show that among healthy adults who received two injections of H5N1 VLP influenza vaccine at a dose of 15 μg, there was an induction immunologic activity (neutralizing antibody) against the homologous A/Indo/5/05 influenza strain (Table 4). In addition, a vaccine dose of 45 μg was immunogenic with respect to HAI and neutralizing antibody responses against the homologous A/Indo/5/05 influenza strain (Tables 5 and 6). Moreover, antibody responses against the A/Viet Nam/1203/04 strain were observed in a limited number of subjects. Thus, these data show that administering influenza VLPs of the invention to a human can induce a protective (HAI Titer ≧1:40) immune response.

The following references are incorporated herein by reference:

Berglund, P., Fleeton, M. N., Smerdou, C., and Liljestrom, P. (1999). Immunization with recombinant Semliki Forest virus induces protection against influenza challenge in mice. Vaccine 17, 497-507.

Cox, J. C., and Coulter, A. R. (1997). Adjuvants—a classification and review of their modes of action. Vaccine 15, 248-256.

Crawford, J., Wilkinson, B., Vosnesensky, A., Smith, G., Garcia, M., Stone, H., and Perdue, M. L. (1999). Baculovirus-derived hemagglutinin vaccines protect against lethal influenza infections by avian H5 and H7 subtypes. Vaccine 17, 2265-2274.

Crowther R A, Kiselev N A, Bottcher B, Berriman J A, Borisova G P, Ose V, Pumpens P. (1994). Three-dimensional structure of hepatitis B virus core particles determined by electron cryomicroscopy. Cell 17, 943-50.

Gomez-Puertas, P., Mena, I., Castillo, M., Vivo, A., Perez-Pastrana, E., and Portela, A. (1999). Efficient formation of influenza virus-like particles: dependence on the expression levels of viral proteins. J. Gen. Virol. 80, 1635-1645.

Johansson, B. E. (1999). Immunization with influenza A virus hemagglutinin and neuraminidase produced in recombinant baculovirus results in a balanced and broadened immune response superior to conventional vaccine. Vaccine 17, 2073-2080.

Lakey, D. L., Treanor, J. J., Betts, B. F., Smith, G. E., Thompson, J., Sannella, E., Reed, G., Wilkinson, B. E., and Wright, P. E. (1996) Recombinant baculovirus influenza A hemagglutinin vaccines are well tolerated and immunogenic in healthy adults. J. Infect. Dis. 174, 838-841.

Latham, T., and Galarza, J. M. (2001). Formation of wild-type and chimeric influenza virus-like particles following simultaneous expression of only four structural proteins. J. Virol. 75, 6154-6165.

Mena, I., Vivo, A., Perez, E., and Portela, A (1996). Rescue of a synthetic chloramphenicol acetyltransferase RNA into influenza-like particles obtained from recombinant plasmids. J. Virol. 70, 5016-5024.

Murphy, B. R., and Webster, R. G. (1996). Orthomyxoviruses. In "Virology" (D. M. K. B. N. Fields, P. M. Howley, Eds.) Vol. 1, pp. 1397-1445. Lippincott-Raven, Philadelphia.

Neumann, G., Watanabe, T., and Kawaoka, Y. (2000). Plasmid-driven formation of influenza virus-like particles. J. Virol. 74, 547-551.

Olsen, C. W., McGregor, M. W., Dybdahl-Sissoko, N., Schram, B. R., Nelson, K. M., Lunn, D. P., Macklin, M. D., and Swain, W. F. (1997). Immunogenicity and efficacy of baculovirus-expressed and DNA-based equine influenza virus hemagglutinin vaccines in mice. Vaccine 15, 1149-1156.

Peiris, J. S., Guan, Y., Markwell, D., Ghose, P., Webster, R. G., and Shortridge, K. F. (2001). Cocirculation of avian H9N2 and contemporary "human" H3N2 influenza A viruses in pigs in southwestern China: potential for genetic reassortment? J. Virol. 75, 9679-9686.

Pumpens, P., and Grens, E. (2003). Artificial genes for chimeric virus-like particles. In: "Artificial DNA" (Khudyakov, Y. E, and Fields, H. A., Eds.) pp. 249-327. CRC Press, New York.

Pushko, P., Parker, M., Ludwig, G. V., Davis, N. L., Johnston, R. E., and Smith, J. F. (1997). Replicon-helper systems from attenuated Venezuelan equine encephalitis virus: expression of heterologous genes in vitro and immunization against heterologous pathogens in vivo. Virology 239, 389-401.

Slepushkin, V. A., Katz, J. M., Black, R. A., Gamble, W. C., Rota, P. A., and Cox, N. J. (1995). Protection of mice against influenza A virus challenged by vaccination with baculovirus-expressed M2 protein. Vaccine 13, 1399-1402.

Treanor, J. J., Betts, R. F., Smith, G. E., Anderson, E. L., Hackett, C. S., Wilkinson, B. E., Belshe, R. B., and Powers, D. C. (1996). Evaluation of a recombinant hemagglutinin expressed in insect cells as an influenza vaccine in young and elderly adults. J. Infect. Dis. 173, 1467-1470.

Tsuji, M., et al. (1998). Recombinant Sindbis viruses expressing a cytotoxic T-lymphocyte epitope of a malaria parasite or of influenza virus elicit protection against the corresponding pathogen in mice. J. Virol. 72, 6907-6910.

Ulmer, J. B., et al. (1993). Heterologous protection against influenza by injection of DNA encoding a viral protein. Science 259, 1745-1749.

Ulmer, J. B., et al. (1998). Protective CD4+ and CD8+ T cells against influenza virus induced by vaccination with nucleoprotein DNA. J. Virol. 72, 5648-5653.

Watanabe, T., Watanabe, S., Neumann, G., and Kawaoka, Y. (2002) Immunogenicity and protective efficacy of replication-incompetent influenza virus-like particles. J. Virol. 76, 767-773.

Zhou, X., et al. (1995). Generation of cytotoxic and humoral immune responses by non-replicative recombinant Semliki Forest virus. Proc. Natl. Acad. Sci. USA 92, 3009-3013.

Other Embodiments

Those skilled in the art will recognize, or be able to ascertain using no more than routine experimentation, many equivalents to the specific embodiments of the invention described herein. Such equivalents are intended to be encompassed by the claims provided herein.

We claim:

1. A method of inducing substantial immunity to an influenza virus infection in a human susceptible to influenza, comprising administering to said human at least one effective dose of a vaccine, said vaccine comprising an influenza VLP, wherein said VLP comprises influenza M1, HA and NA proteins and wherein said M1 protein is from an avian influenza virus, and wherein said M1 protein is from a different strain of influenza virus than said influenza HA protein and said influenza NA protein.

2. The method of claim 1, wherein said HA and/or NA exhibits hemagglutinin activity and/or neuraminidase activity, respectively.

3. The method of claim 1, wherein said method comprises administering to a human said vaccine orally, intradermally, intranasally, intramusclarly, intraperitoneally, intravenously, or subcutaneously.

4. The method of claim 1, wherein at least two effective doses of the vaccine are administered.

5. The method of claim 4, wherein said doses are administered at least 2 weeks apart, at least 3 weeks apart, at least 4 weeks apart, at least 5 weeks apart or at least 6 weeks apart.

6. The method of claim 1, wherein said dose comprises at least 10 μg of the influenza VLP.

7. The method of claim 1, wherein said dose comprises from about 10 μg to 150 μg of the influenza VLP.

8. The method of claim 1, wherein said dose comprises from about 15 μg to about 45 μg of the influenza VLP.

9. The method of claim 4, wherein said doses comprise from about 15 μg to about 45 μg of the influenza VLP.

10. The method of claim 1, wherein said dose comprises from about 45 μg to about 135 μg of the influenza VLP.

11. The method of claim 4, wherein said doses comprise from about 45 μg to about 135 μg of the influenza VLP.

12. The method of claim 1, wherein said influenza HA and NA proteins are seasonal influenza virus HA and NA proteins.

13. The method of claim 12, wherein said seasonal influenza virus is a type A influenza virus.

14. The method of claim 12, wherein said seasonal influenza virus is a type B influenza virus.

15. The method of claim 1, wherein said influenza HA and NA proteins are avian influenza virus HA and NA proteins.

16. The method of claim 15, wherein said avian influenza virus HA and NA proteins are derived from H5N1.

17. The method of claim 15, wherein said avian influenza virus HA and NA proteins are derived from H9N2.

18. The method of claim 1, wherein said M1 protein is derived from A/Indonesia/5/05.

19. The method of claim 1, wherein said vaccine further comprises an adjuvant or immune stimulator.

* * * * *